(12) United States Patent
Workman et al.

(10) Patent No.: US 11,383,057 B2
(45) Date of Patent: Jul. 12, 2022

(54) CPAP SYSTEM

(71) Applicant: ResMed Pty Ltd, Bella Vista (AU)

(72) Inventors: Jeremy William Workman, Blue Mountains (AU); Ernie Wei-Chih Tsai, Sydney (AU); Michael James Dent, Sydney (AU); Max William Andrew Kabilafkas, Sydney (AU); Dimitri Marco Maurer, Gosford (AU); Andrew Chan, Sydney (AU); Justin John Formica, Sydney (AU); Hargopal Verma, Sydney (AU); Katarzyna Anna Krol-Mazur, Sydney (AU); Chia Ik Tan, Sydney (AU); Jessie Cindy Maikim, Mountain View, CA (US)

(73) Assignee: ResMed Pty Ltd, Bella Vista (AU)

( * ) Notice: Subject to any disclaimer, the term of this patent is extended or adjusted under 35 U.S.C. 154(b) by 0 days.

(21) Appl. No.: 17/548,874

(22) Filed: Dec. 13, 2021

(65) Prior Publication Data

US 2022/0096783 A1 Mar. 31, 2022

Related U.S. Application Data

(63) Continuation of application No. 17/295,160, filed as application No. PCT/IB2020/053608 on Apr. 16, 2020.

(Continued)

(51) Int. Cl.
*A61M 16/10* (2006.01)
*A61M 16/00* (2006.01)
(Continued)

(52) U.S. Cl.
CPC ...... *A61M 16/108* (2014.02); *A61M 16/0066* (2013.01); *A61M 16/022* (2017.08);
(Continued)

(58) Field of Classification Search
CPC .......... A61M 16/0066; A61M 16/0816; A61M 16/109; A61M 16/16; A61M 16/162
See application file for complete search history.

(56) References Cited

U.S. PATENT DOCUMENTS

| | | | |
|---|---|---|---|
| 4,028,444 A | 6/1977 | Brown et al. | |
| 4,782,832 A | 11/1988 | Trimble et al. | |

(Continued)

FOREIGN PATENT DOCUMENTS

| | | |
|---|---|---|
| CA | 2 424 662 A1 | 8/2002 |
| CN | 1930421 A | 3/2007 |

(Continued)

OTHER PUBLICATIONS

"*Respiratory Physiology*", by John B, West, Lippincott Williams & Wilkins, 9th edition published 2012 (8 pages).

(Continued)

*Primary Examiner* — Joseph D. Boecker
(74) *Attorney, Agent, or Firm* — Nixon & Vanderhye P.C.

(57) ABSTRACT

An apparatus for humidifying a flow of breathable gas includes a water reservoir and a water reservoir dock forming a cavity structured and arranged to receive the water reservoir in an operative position. The water reservoir comprises a reservoir base including a cavity structured to hold a volume of water, the reservoir base including a main body and a thermally conductive portion provided to the main body. The thermally conductive portion comprises a combined layered arrangement including a metal plate and a thin film, the thin film comprising a non-metallic material and including a wall thickness of less than about 1 mm. The thin (Continued)

film is adapted to form at least a bottom interior surface of the water reservoir exposed to the volume of water, and the metal plate is adapted to form a bottom exterior surface of the water reservoir.

24 Claims, 149 Drawing Sheets

Related U.S. Application Data

(60) Provisional application No. 62/897,558, filed on Sep. 9, 2019, provisional application No. 62/835,094, filed on Apr. 17, 2019.

(51) Int. Cl.
  *A61M 16/16* (2006.01)
  *A61M 16/08* (2006.01)

(52) U.S. Cl.
  CPC ...... *A61M 16/0816* (2013.01); *A61M 16/107* (2014.02); *A61M 16/109* (2014.02); *A61M 16/1095* (2014.02); *A61M 16/16* (2013.01); *A61M 16/161* (2014.02); *A61M 16/0875* (2013.01); *A61M 2016/0027* (2013.01); *A61M 2016/0039* (2013.01); *A61M 2205/0233* (2013.01); *A61M 2205/15* (2013.01); *A61M 2205/3653* (2013.01); *A61M 2205/3673* (2013.01); *A61M 2207/00* (2013.01)

(56) References Cited

U.S. PATENT DOCUMENTS

| | | | |
|---|---|---|---|
| 4,944,310 A | 7/1990 | Sullivan | |
| 5,259,370 A | 11/1993 | Howe | |
| 5,932,148 A | 8/1999 | Hansell, Jr. et al. | |
| 6,003,204 A | 12/1999 | Roach et al. | |
| 6,532,959 B1 | 3/2003 | Berthon-Jones | |
| 6,581,594 B1 | 6/2003 | Drew et al. | |
| 6,588,734 B2 | 7/2003 | Redner et al. | |
| 6,718,974 B1 | 4/2004 | Moberg | |
| 6,935,337 B2 | 8/2005 | Virr et al. | |
| 7,111,624 B2 | 9/2006 | Thudor et al. | |
| 7,413,173 B2 | 8/2008 | DiMatteo et al. | |
| 7,673,855 B2 | 3/2010 | Anderson et al. | |
| 7,677,246 B2 | 3/2010 | Kepler et al. | |
| 7,766,310 B2 | 8/2010 | Wolff et al. | |
| 7,866,944 B2 | 1/2011 | Kenyon et al. | |
| 8,240,306 B2 | 8/2012 | Cortez, Jr. et al. | |
| 8,316,848 B2 | 11/2012 | Kwok et al. | |
| 8,333,195 B2 | 12/2012 | Cortez, Jr. et al. | |
| 8,356,593 B2 | 1/2013 | Cortez, Jr. et al. | |
| 8,636,479 B2 | 1/2014 | Kenyon et al. | |
| 8,638,014 B2 | 1/2014 | Sears et al. | |
| 8,677,993 B2 | 3/2014 | Cortez, Jr. et al. | |
| 8,733,349 B2 | 5/2014 | Bath et al. | |
| 8,739,780 B2 | 6/2014 | Tang et al. | |
| 8,905,384 B2 | 12/2014 | Rodrigs et al. | |
| 9,038,629 B2 | 5/2015 | Smith et al. | |
| 9,106,061 B1 | 8/2015 | Shotey et al. | |
| 9,227,035 B2 | 1/2016 | Crumblin et al. | |
| 9,328,962 B2 | 5/2016 | Lee et al. | |
| 9,707,370 B2 | 7/2017 | Smith et al. | |
| 10,238,829 B2 | 3/2019 | Kat | |
| 10,252,019 B2 | 4/2019 | Potharaju et al. | |
| 10,252,837 B2 | 4/2019 | Miller et al. | |
| 10,293,125 B2 | 5/2019 | Jeha et al. | |
| 10,317,098 B2 | 6/2019 | Bayer et al. | |
| 10,342,950 B2 | 7/2019 | Bath et al. | |
| 10,864,343 B2 | 12/2020 | Bath et al. | |
| 2003/0116989 A1 | 6/2003 | Guanzon et al. | |
| 2007/0132117 A1 | 6/2007 | Pujol | |
| 2007/0169776 A1* | 7/2007 | Kepler | A61M 16/024 128/200.14 |
| 2008/0251071 A1 | 10/2008 | Armitstead et al. | |
| 2008/0302361 A1 | 12/2008 | Snow et al. | |
| 2009/0044808 A1 | 2/2009 | Guney et al. | |
| 2009/0050156 A1 | 2/2009 | Ng et al. | |
| 2010/0000534 A1 | 1/2010 | Kooij et al. | |
| 2010/0065051 A1* | 3/2010 | Potharaju | A61M 16/16 128/203.26 |
| 2013/0174843 A1* | 7/2013 | Smith | A61M 16/14 128/203.26 |
| 2014/0137861 A1 | 5/2014 | Feldhahn et al. | |
| 2014/0174442 A1 | 6/2014 | Cortez, Jr. et al. | |
| 2014/0246021 A1 | 9/2014 | Buechi et al. | |
| 2014/0264975 A1* | 9/2014 | Bath | A61M 16/021 261/141 |
| 2014/0290655 A1 | 10/2014 | Snow et al. | |
| 2015/0151074 A1 | 6/2015 | Hermez | |
| 2015/0202402 A1* | 7/2015 | Kat | A61M 16/16 128/203.27 |
| 2015/0258300 A1 | 9/2015 | Lin et al. | |
| 2015/0359989 A1 | 12/2015 | Potharaju et al. | |
| 2016/0008560 A1 | 1/2016 | Kwok | |
| 2016/0022954 A1 | 1/2016 | Bath et al. | |
| 2016/0228671 A1 | 8/2016 | Jackson et al. | |
| 2016/0310691 A1* | 10/2016 | Bath | A61M 16/0066 |
| 2017/0121067 A1 | 5/2017 | Miller et al. | |
| 2017/0151411 A1 | 6/2017 | Osborne et al. | |
| 2017/0173293 A1 | 6/2017 | Osborne et al. | |
| 2017/0252531 A1 | 9/2017 | Hensman et al. | |
| 2017/0348505 A1 | 12/2017 | Doo et al. | |
| 2017/0361053 A1 | 12/2017 | Dimatteo et al. | |
| 2018/0071480 A1 | 3/2018 | Tang et al. | |
| 2018/0127911 A1 | 5/2018 | Chen et al. | |
| 2018/0177967 A1* | 6/2018 | Miller | A61M 16/1095 |
| 2018/0185606 A1* | 7/2018 | Van Schalkwyk | A61M 16/024 |
| 2018/0185607 A1 | 7/2018 | Holley et al. | |
| 2018/0214660 A1 | 8/2018 | Stoks et al. | |
| 2018/0333556 A1 | 11/2018 | Ormrod et al. | |
| 2019/0038865 A1 | 2/2019 | Smith et al. | |
| 2019/0117931 A1 | 4/2019 | Virr et al. | |
| 2019/0209802 A1 | 7/2019 | Virr et al. | |
| 2019/0298964 A1 | 10/2019 | Bayer et al. | |
| 2019/0321580 A1 | 10/2019 | Kirchberger et al. | |
| 2020/0155876 A1 | 5/2020 | Appareti et al. | |
| 2020/0330720 A1 | 10/2020 | Formica et al. | |
| 2021/0370014 A1* | 12/2021 | Van Schalkwyk | A61M 16/16 |
| 2022/0023576 A1* | 1/2022 | Van Schalkwyk | A61M 16/0816 |

FOREIGN PATENT DOCUMENTS

| | | |
|---|---|---|
| CN | 1936442 A | 3/2007 |
| CN | 101220988 B | 9/2010 |
| CN | 201768243 U | 3/2011 |
| CN | 204193230 U | 3/2015 |
| CN | 204293650 U | 4/2015 |
| CN | 204671683 U | 9/2015 |
| CN | 105727404 A | 7/2016 |
| CN | 208927355 U | 6/2019 |
| EP | 3 406 289 A1 | 11/2018 |
| EP | 2 178 590 B1 | 4/2021 |
| GB | 2321668 A | 8/1998 |
| JP | 3464916 B2 | 11/2003 |
| JP | 4489478 B2 | 6/2010 |
| WO | WO 98/004310 A1 | 2/1998 |
| WO | WO 98/034665 A1 | 8/1998 |
| WO | WO 2000/078381 A1 | 12/2000 |
| WO | WO 2004/073778 A1 | 9/2004 |
| WO | WO 2005/063328 A1 | 7/2005 |
| WO | WO 2006/074513 A1 | 7/2006 |
| WO | WO 2006/130903 A1 | 12/2006 |
| WO | WO 2009/052560 A1 | 4/2009 |
| WO | WO 2009/127192 A1 | 10/2009 |
| WO | WO 2010/135785 A1 | 12/2010 |
| WO | WO 2012/171072 A1 | 12/2012 |
| WO | WO 2013/020167 A1 | 2/2013 |
| WO | WO 2015/089582 | 6/2015 |
| WO | WO 2018/094452 A1 | 5/2018 |

(56) References Cited

FOREIGN PATENT DOCUMENTS

| WO | WO 2019/216774 A1 | 11/2019 |
| WO | WO 2020/065581 | 4/2020 |
| WO | WO 2020/121255 A1 | 6/2020 |

OTHER PUBLICATIONS

International Search Report dated Jul. 15, 2020 in International Application No. PCT/IB2020/053608, 35 pages.
Written Opinion of the International Searching Authority dated Jul. 15, 2020 in International Application No. PCT/IB2020/053608, 14 pages.
International Preliminary Report on Patentability dated Mar. 22, 2021 in International Application No. PCT/IB2020/053608, 13 pages.
Skye et al., U.S. Appl. No. 63/011,052, filed Apr. 16, 2020, for "Acoustic Detection in Respiratory Treatment Apparatus."

\* cited by examiner

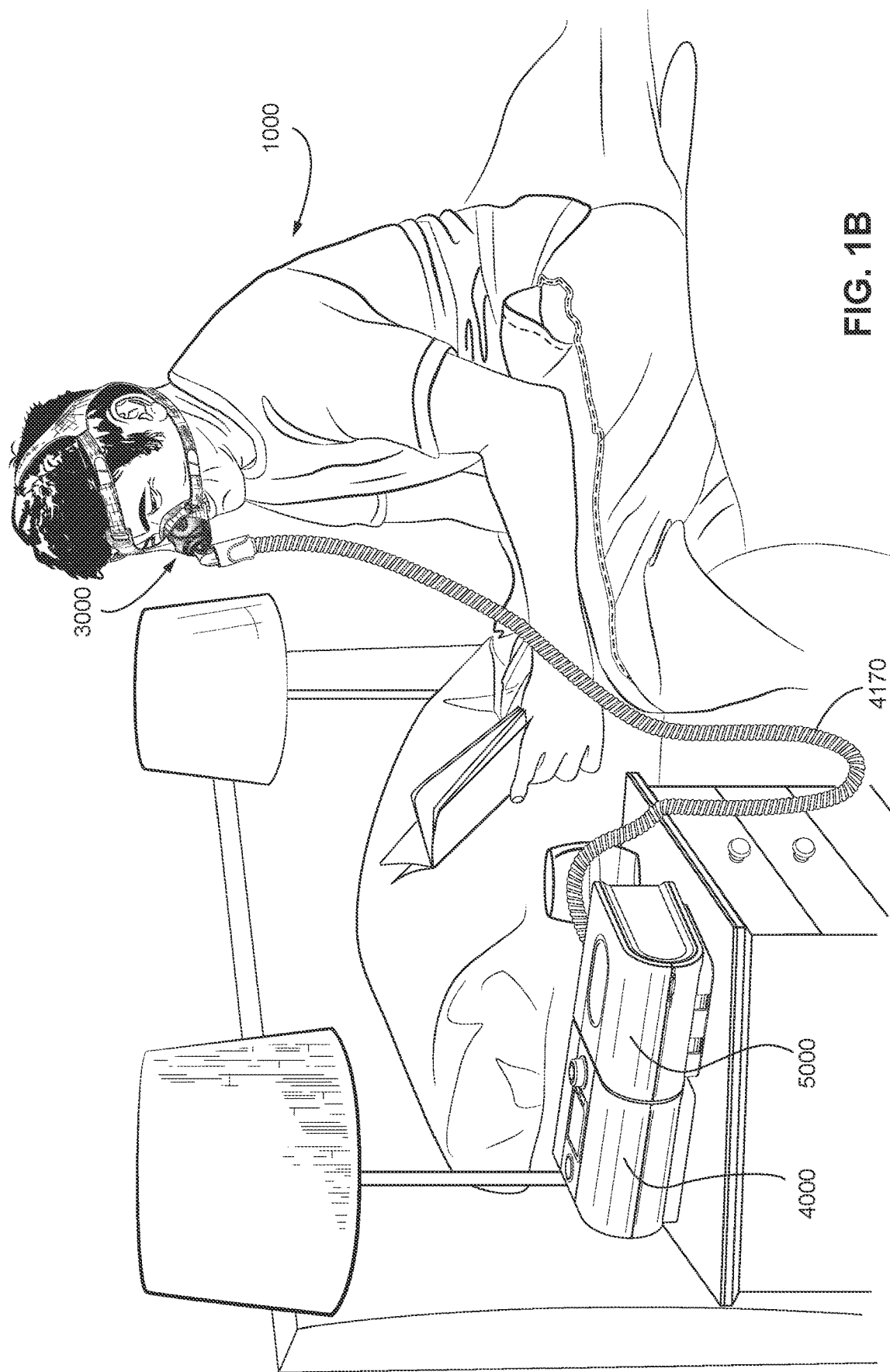

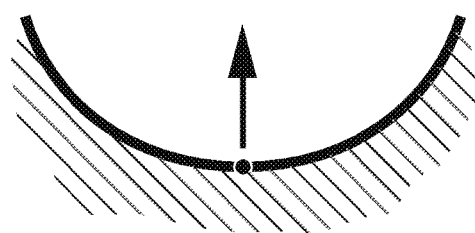
FIG. 3B — Relatively Large Positive Curvature
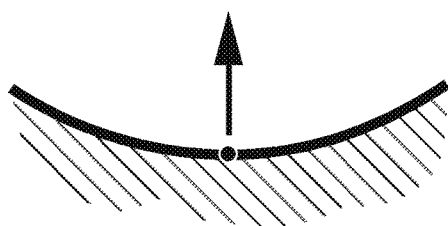
FIG. 3C — Relatively Small Positive Curvature
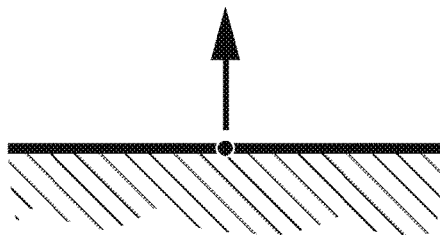
FIG. 3D — Zero Curvature
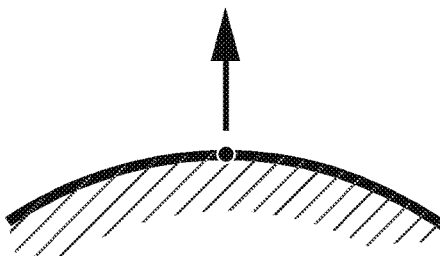
FIG. 3E — Relatively Small Negative Curvature
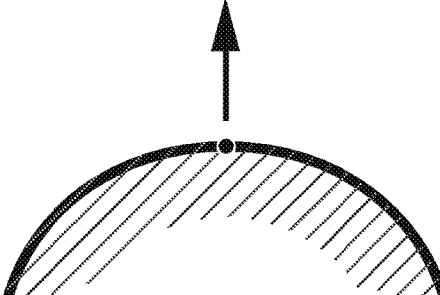
FIG. 3F — Relatively Large Negative Curvature
Copyright 2015 ResMed Limited

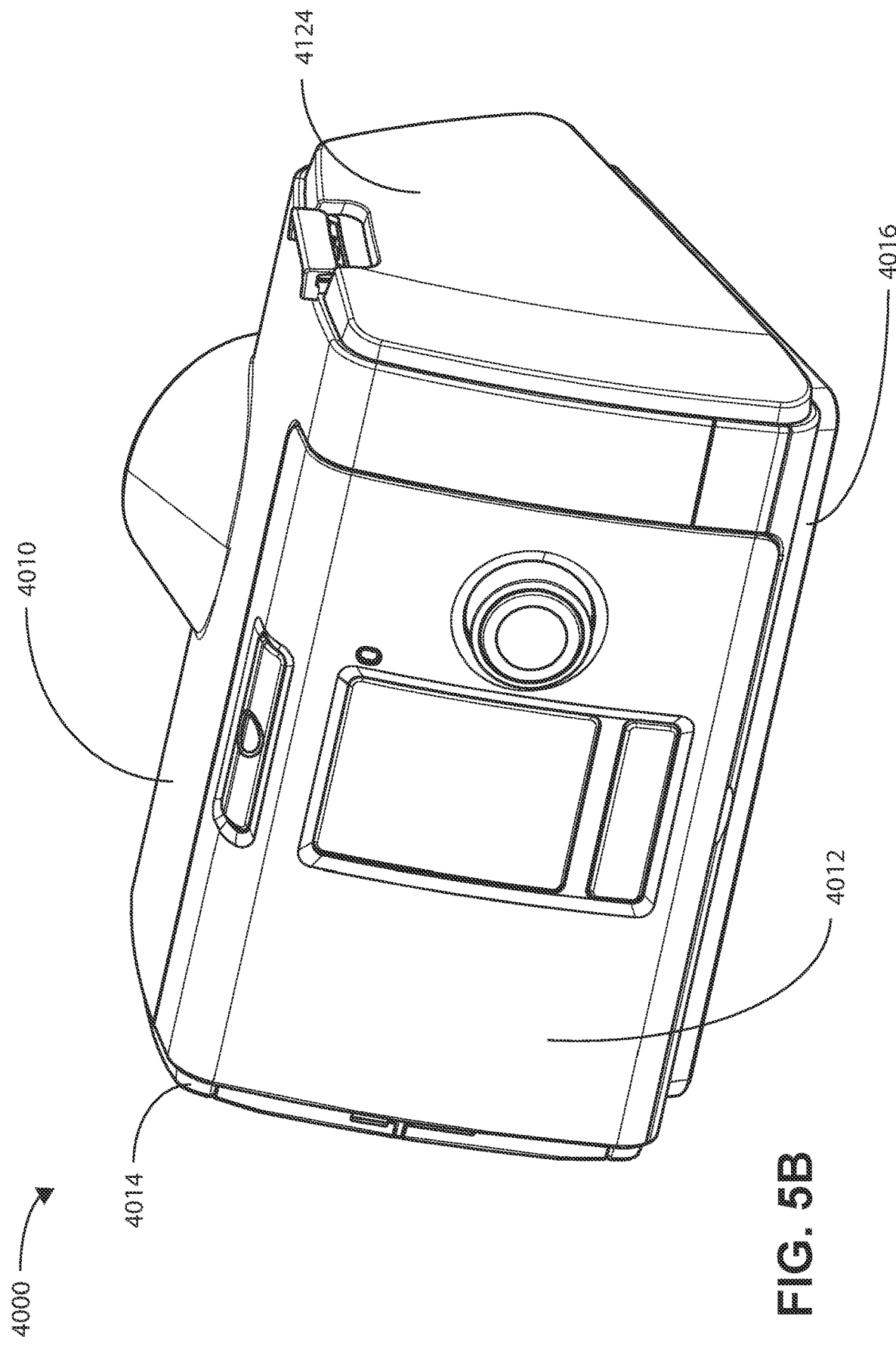

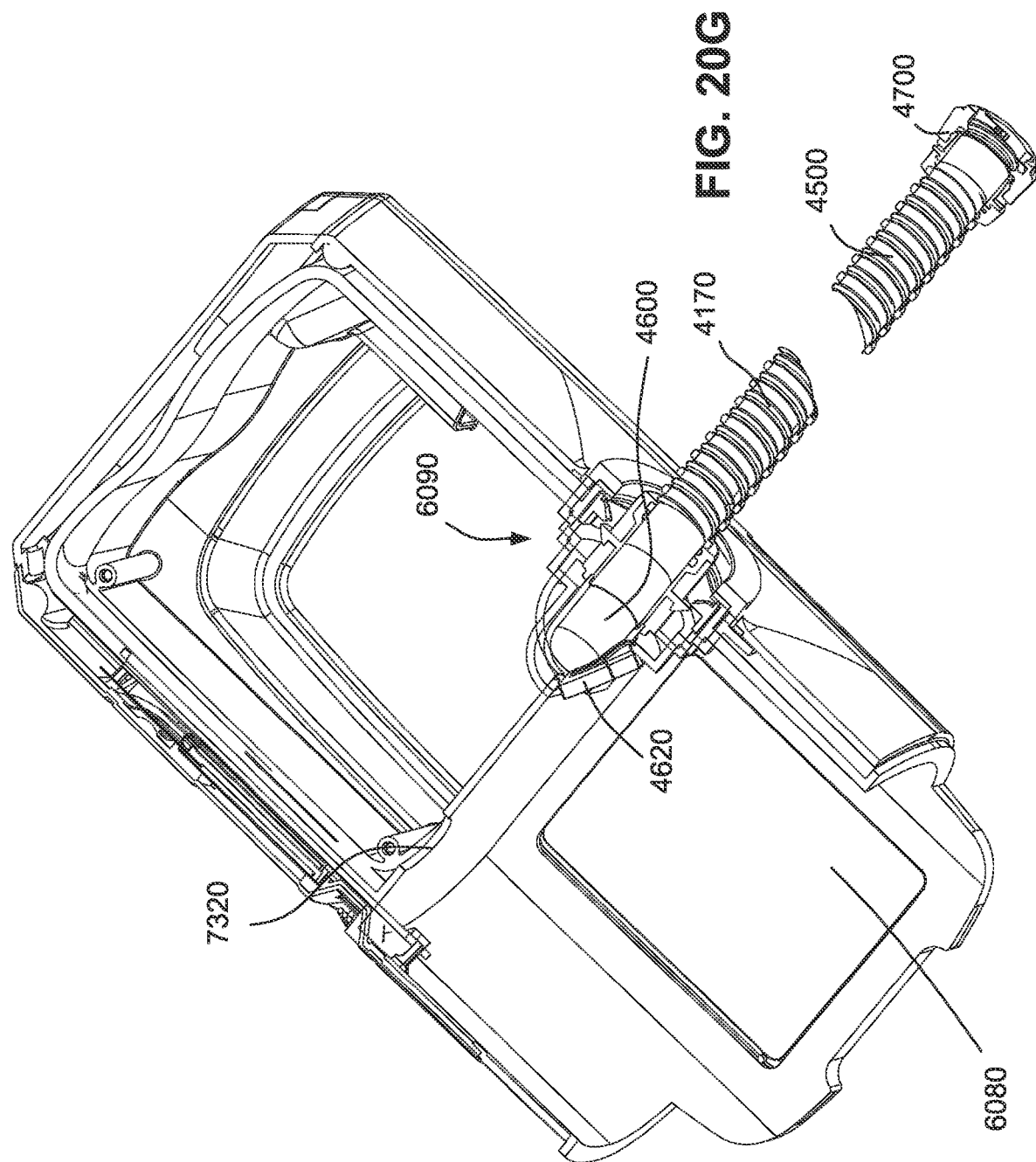

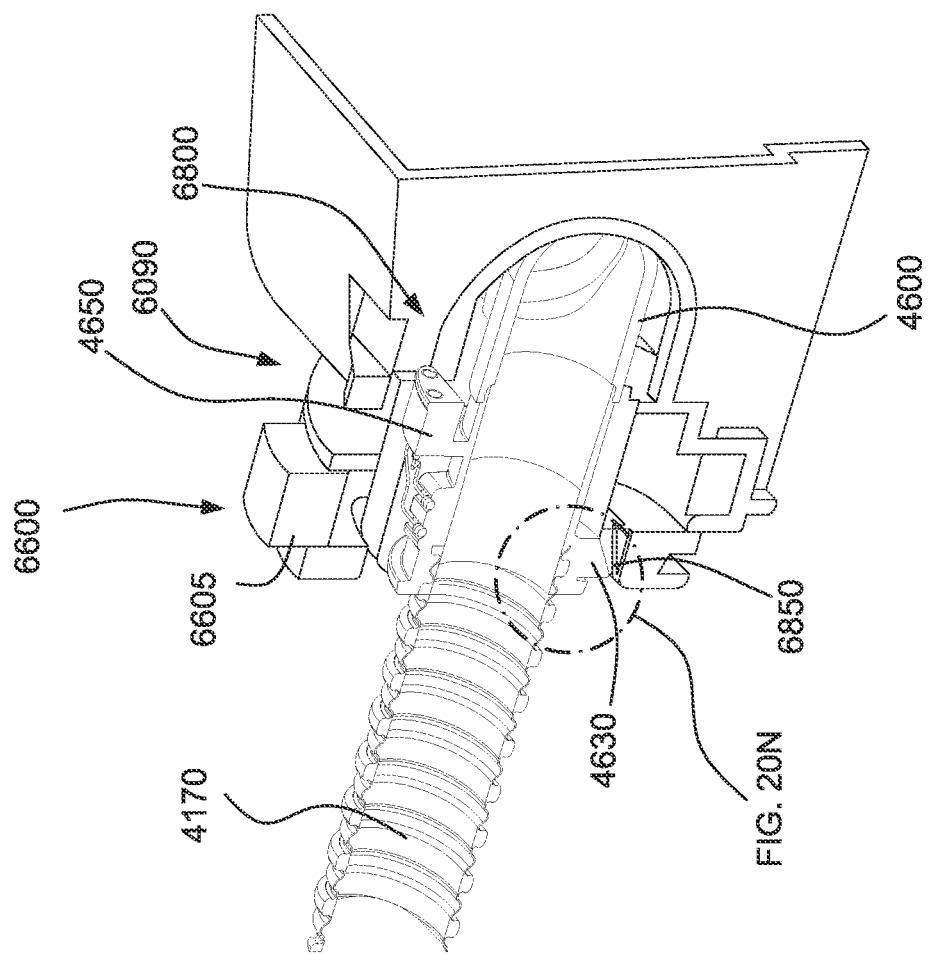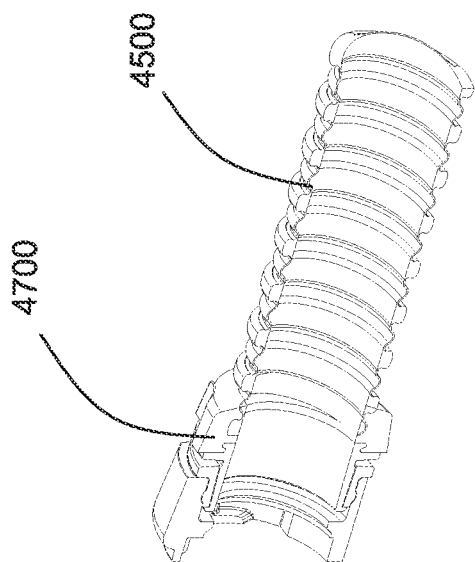

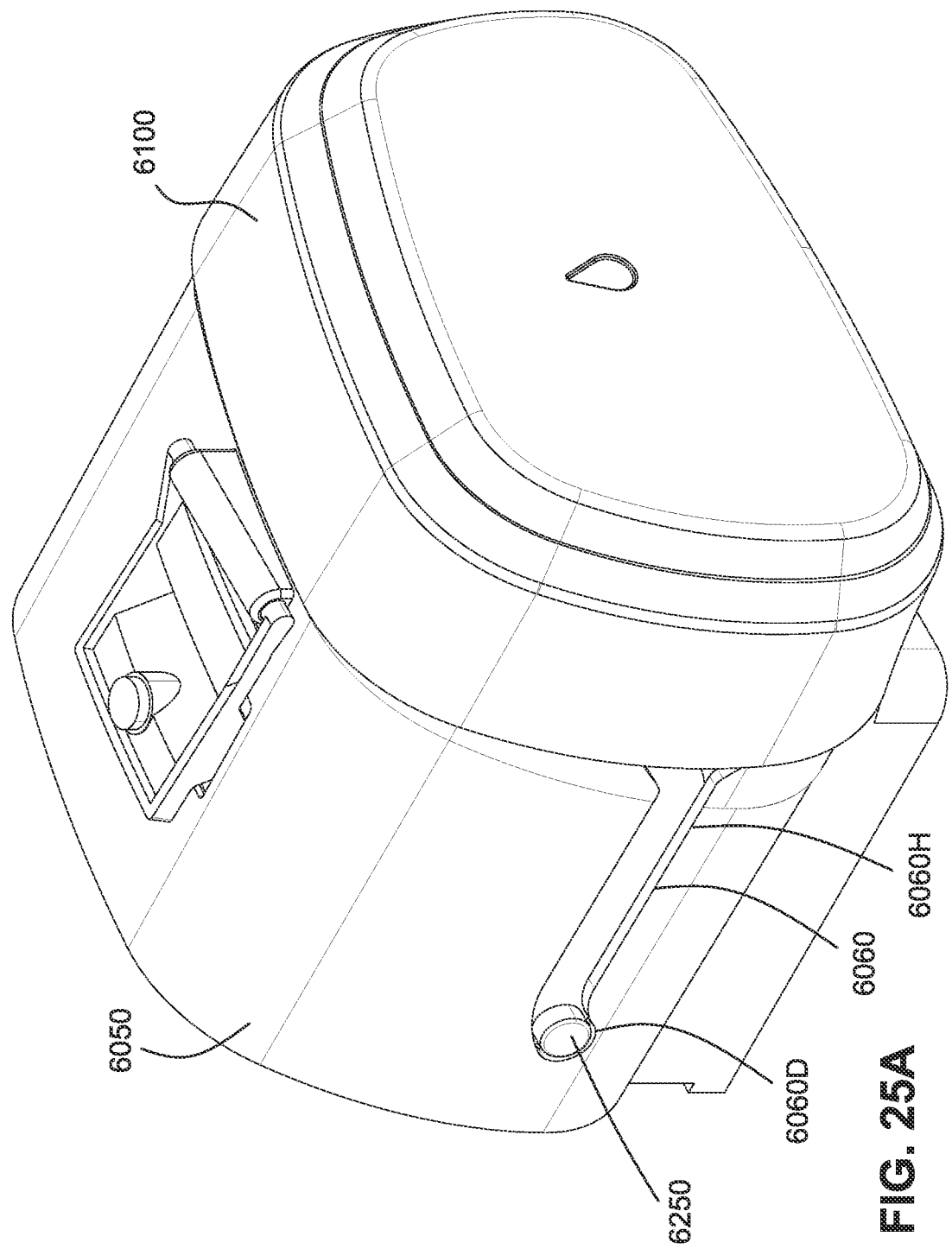

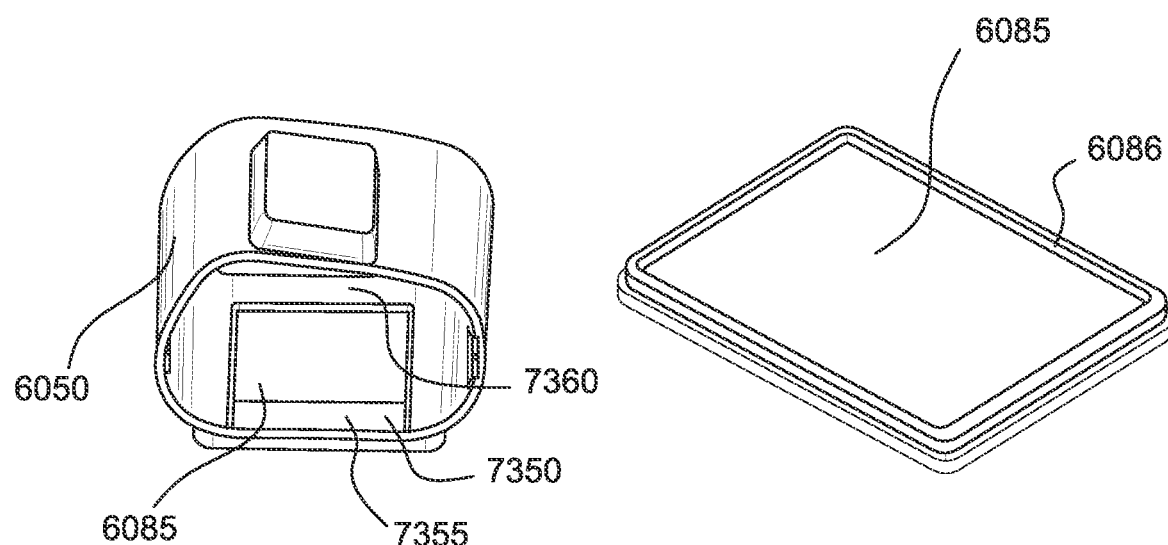
FIG. 28A  FIG. 28B
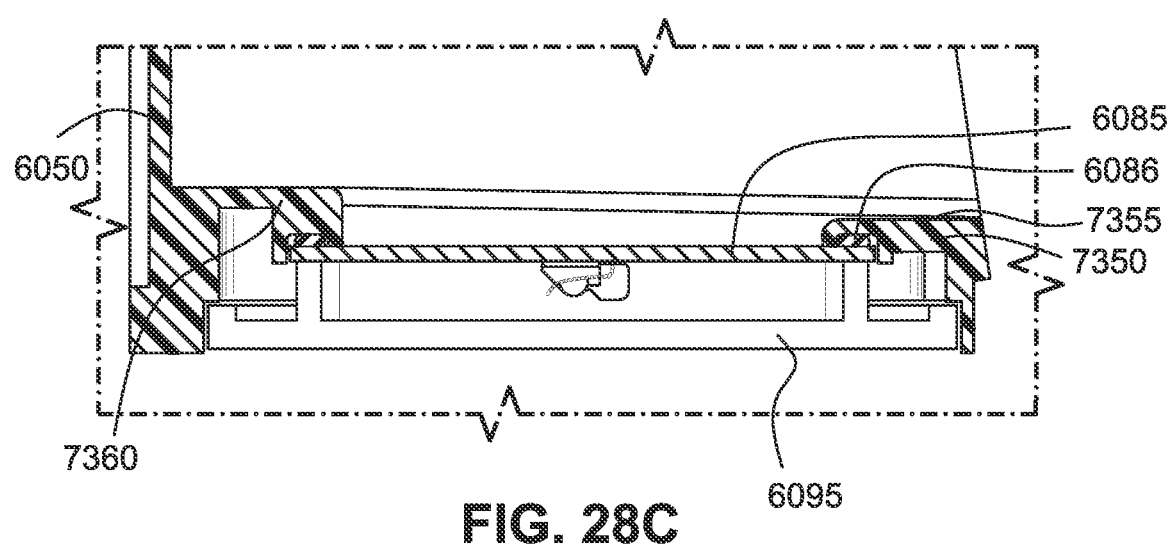
FIG. 28C

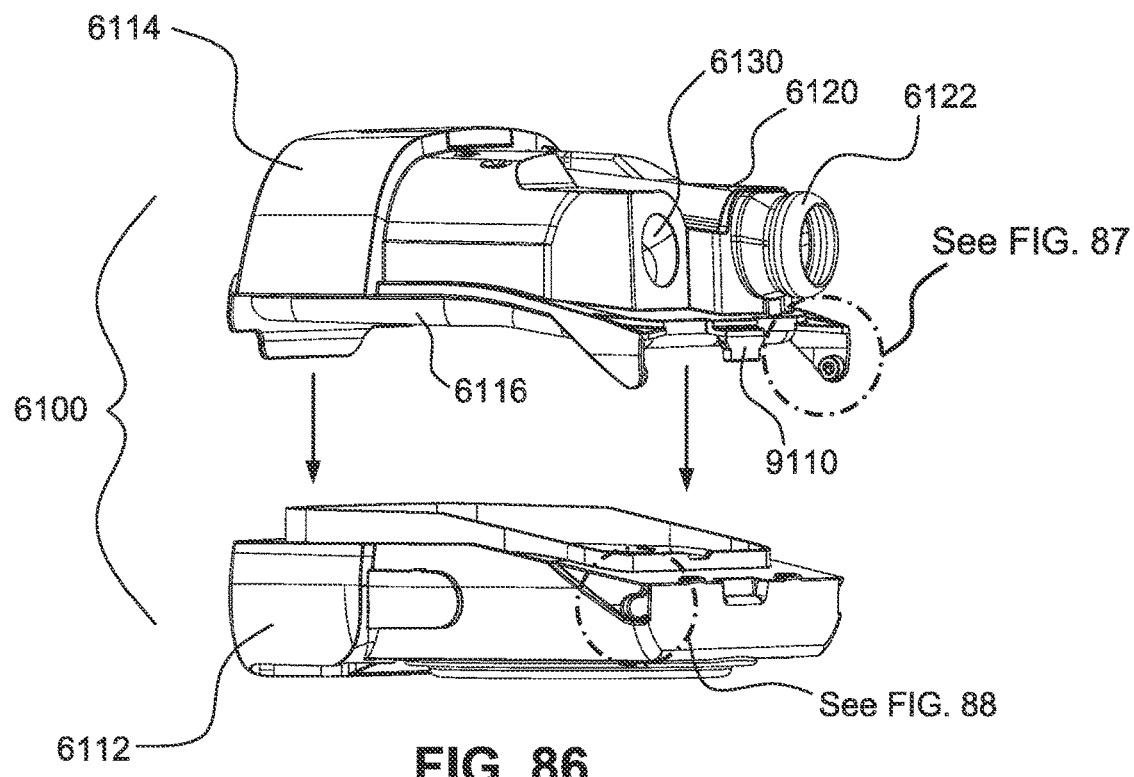
FIG. 86
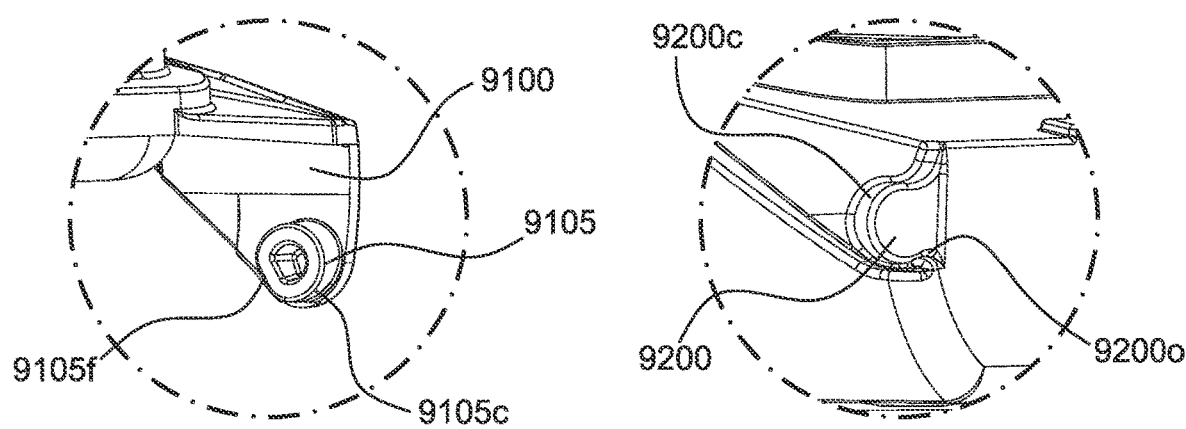
FIG. 87  FIG. 88

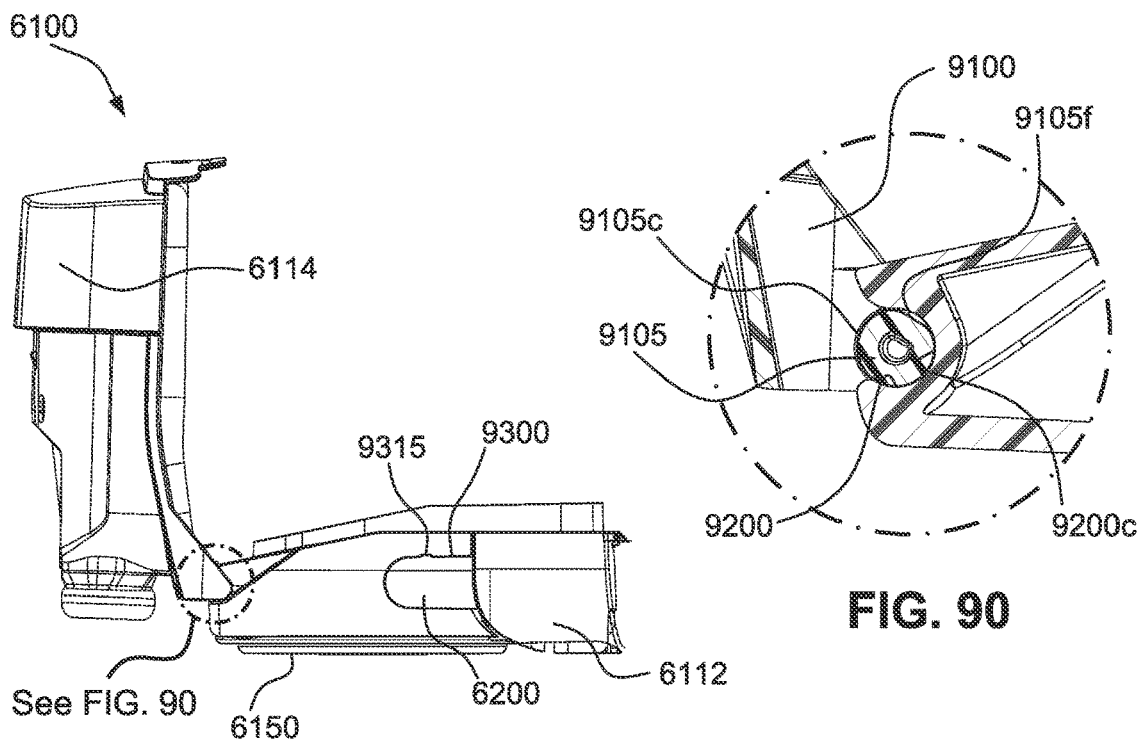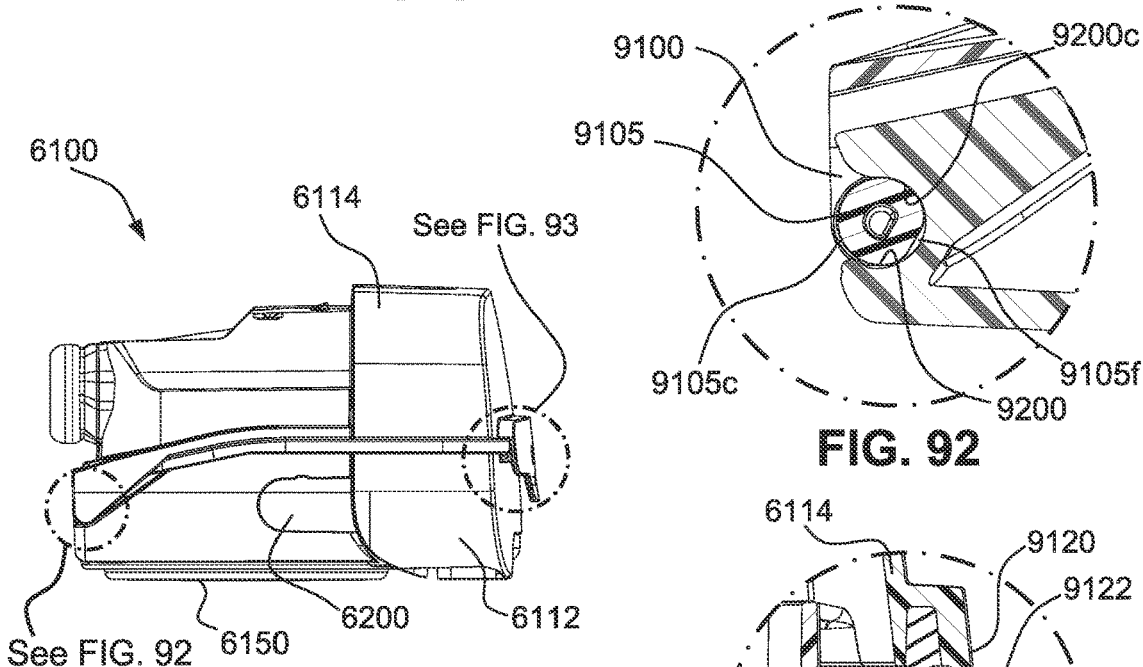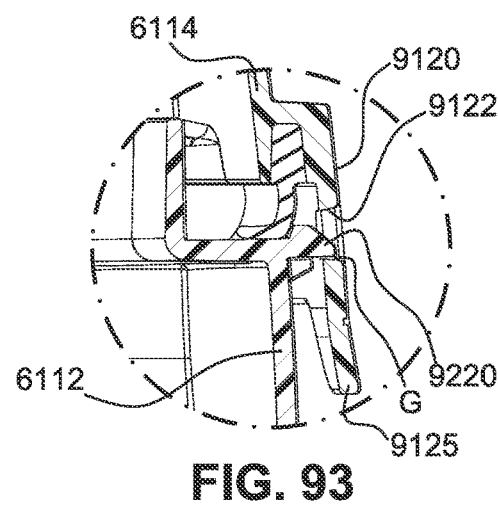

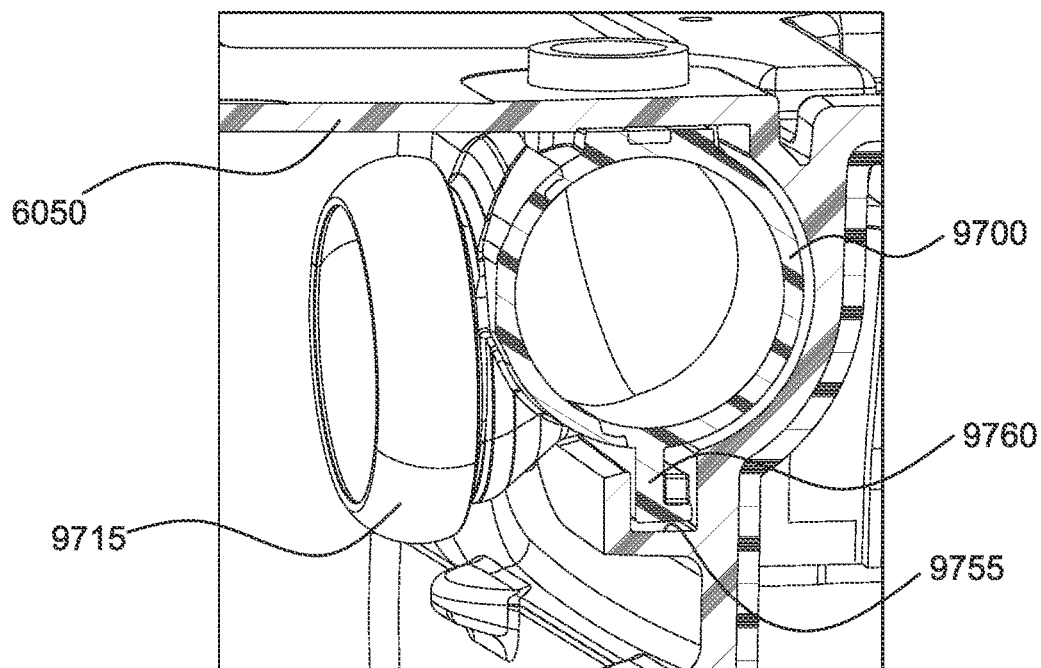
FIG. 115B
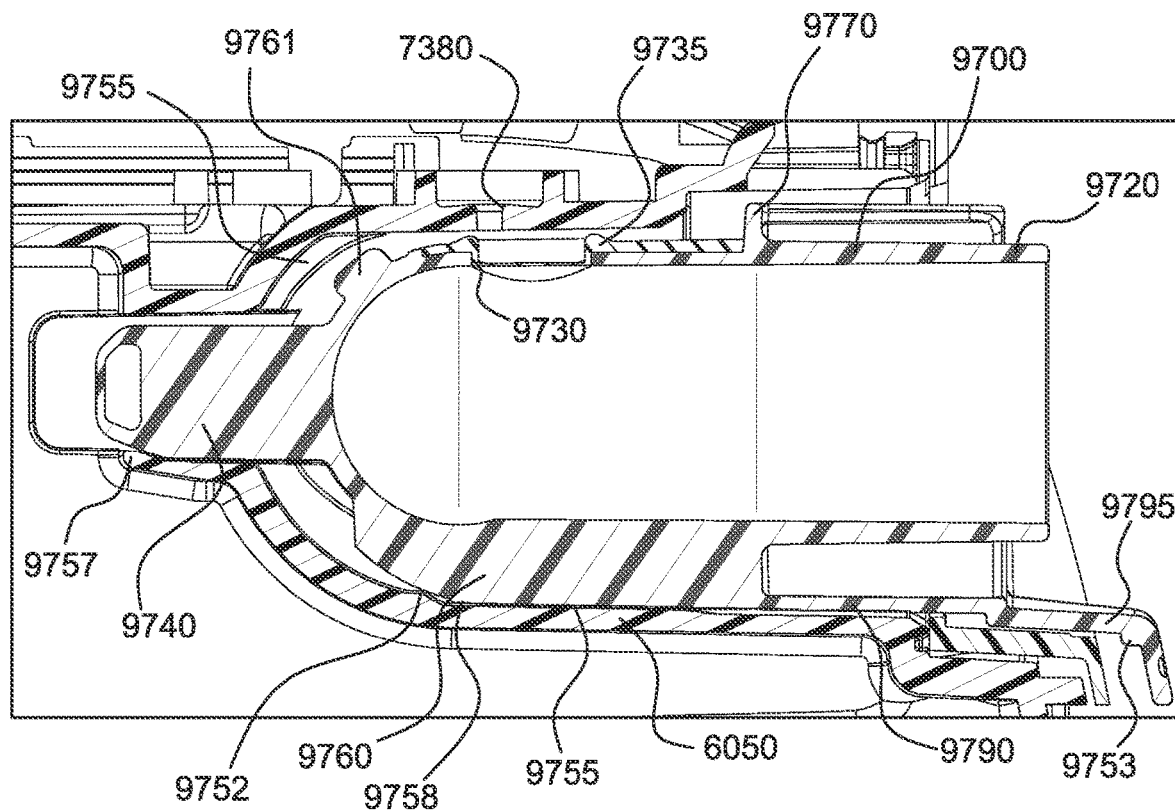
FIG. 115C1

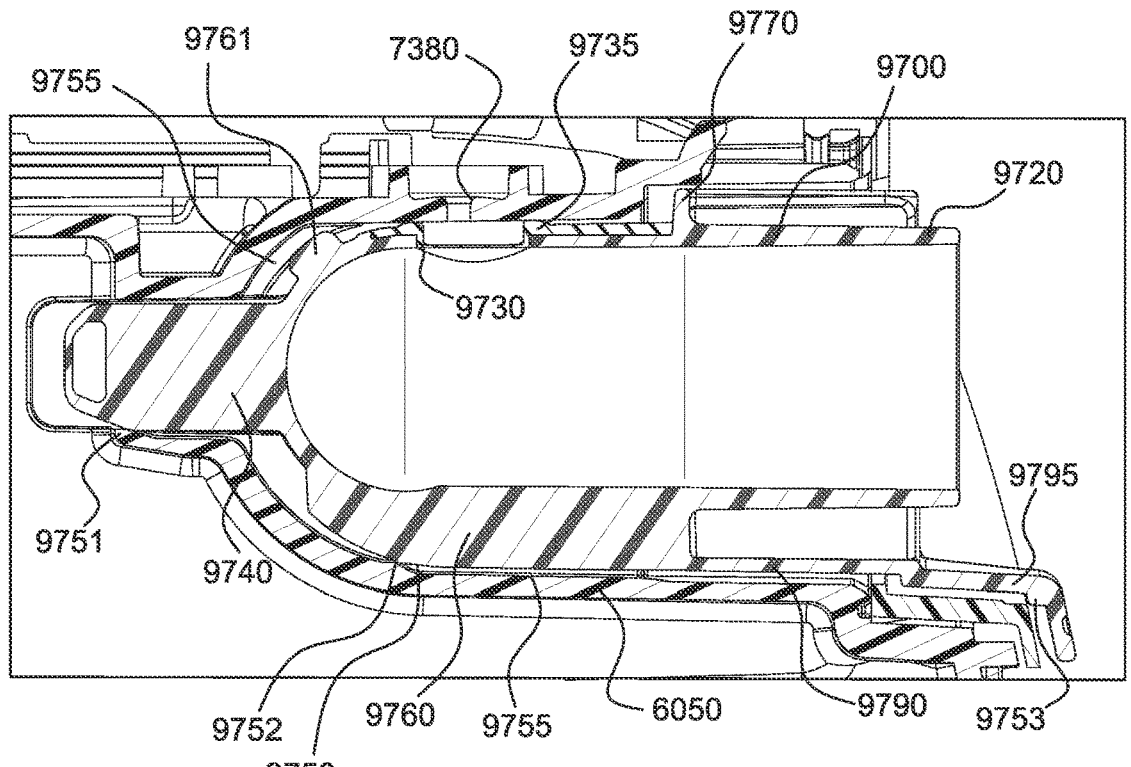
FIG. 115C2
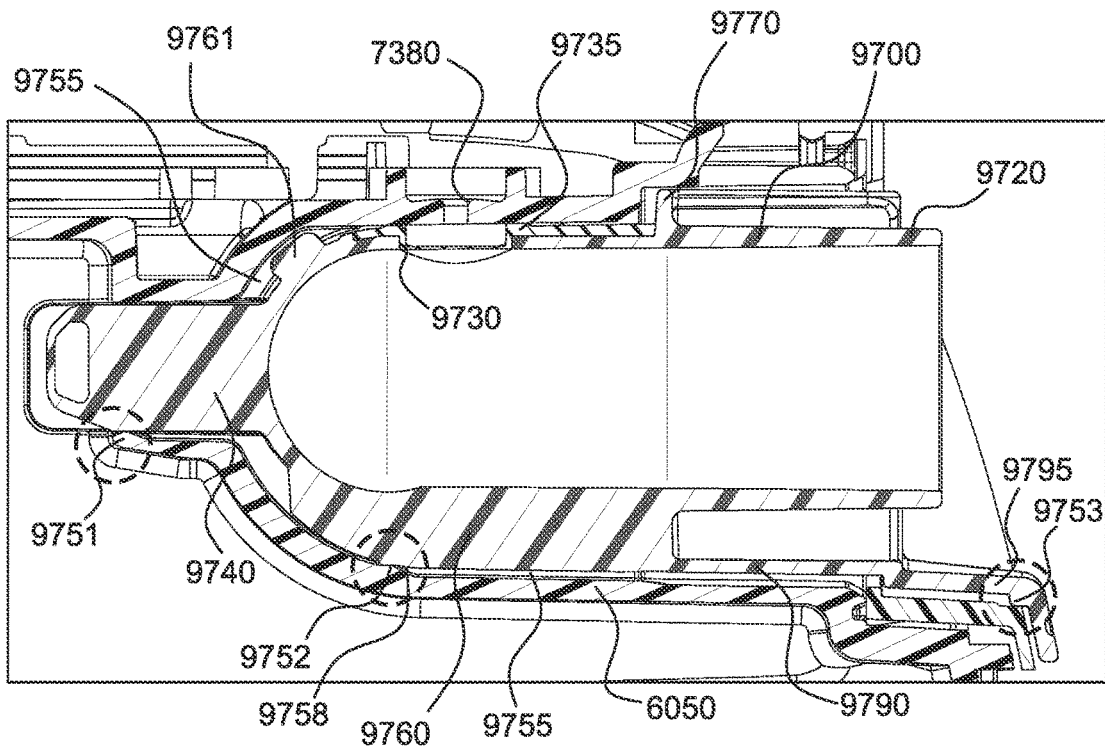
FIG. 115C3

CPAP SYSTEM

1 CROSS-REFERENCE TO RELATED APPLICATIONS

This application is a continuation of U.S. application Ser. No. 17/295,160, filed May 19, 2021, which is the U.S. national phase of International Application No. PCT/IB2020/053608, filed Apr. 16, 2020, which designated the U.S. and claims priority to U.S. Provisional Application No. 62/835,094, filed Apr. 17, 2019, and U.S. Provisional Application No. 62/897,558, filed Sep. 9, 2019, the entire contents of each of which are hereby incorporated by reference.

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use.

2.2 Description of the Related Art

2.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Various therapies, such as Continuous Positive Airway Pressure (CPAP) therapy, Non-invasive ventilation (NIV) and Invasive ventilation (IV) have been used to treat one or more of the above respiratory disorders.

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.3 Treatment Systems

These therapies may be provided by a treatment system or device. Such systems and devices may also be used to screen, diagnose, or monitor a condition without treating it.

A treatment system may comprise a Respiratory Pressure Therapy Device (RPT device), an air circuit, a humidifier, a patient interface, and data management.

Another form of treatment system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressurised. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 cmH$_2$O).

| RPT Device name | A-weighted sound pressure level dB(A) | Year (approx.) |
|---|---|---|
| C-Series Tango ™ | 31.9 | 2007 |
| C-Series Tango ™ with Humidifier | 33.1 | 2007 |
| S8 Escape ™ II | 30.5 | 2005 |
| S8 Escape ™II with H4i ™ Humidifier | 31.1 | 2005 |
| S9 AutoSet ™ | 26.5 | 2010 |
| S9 AutoSetT ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers.

While a number of medical humidifiers are known, they can suffer from one or more shortcomings. Some medical humidifiers may provide inadequate humidification, some are difficult or inconvenient to use by patients.

2.2.3.4 Data Management

There may be clinical reasons to obtain data to determine whether the patient prescribed with respiratory therapy has been "compliant", e.g. that the patient has used their RPT device according to one or more "compliance rules". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

An aspect of one form of the present technology is a method of manufacturing apparatus.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

An aspect of one form of the present technology relates to respiratory treatment apparatus including a source of a flow of air at positive pressure, a chassis or housing constructed and arranged to be fixed in location in use relative to the source, an inlet pneumatic connection structured for connecting to the source to receive sealably the flow of air at positive pressure from the source in use, a container to hold a body of water in use, the container being configured to direct the flow of air so that water vapour may transfer from the body of water to the flow of air in use to increase the absolute humidity of the flow of air, the container including a wall constructed at least in part from a material having a relatively high thermal conductivity, a heating element, a temperature sensor, a controller to control the heating element, and an outlet pneumatic connection structure to receive the flow of air with increased absolute humidity. The chassis or housing is configured to hold the container in location close relative to the heating element so that heat energy may transfer from the heating element to the body of water to increase the absolute humidity of the flow of air. The controller is constructed and arranged to cause the energising of the heating element to heat the water without boiling the water. The respiratory treatment apparatus includes a sealing arrangement so that in use the flow of air with increased absolute humidity received at the outlet pneumatic connection structure has a positive pressure with respect to ambient.

Another aspect of the present technology relates to a CPAP system including a humidifier, a patient interface, and an air delivery tube to deliver humidified air to the patient interface. In an example, the humidifier is integrated with an RPT device structured to produce a flow of air at positive pressure.

Another aspect of the present technology relates to a humidifier including a water reservoir including a cavity structured to hold a volume of water, and a water reservoir dock structured and arranged to receive the water reservoir in an operative position.

Another aspect of the present technology relates to an apparatus for humidifying a flow of breathable gas. The apparatus includes a water reservoir and a water reservoir dock forming a cavity structured and arranged to receive the water reservoir in an operative position. The water reservoir includes a reservoir base including a cavity structured to hold a volume of water. The reservoir base includes a main body and a thermally conductive portion provided to the main body. The thermally conductive portion comprises a combined layered arrangement including a metal plate and a thin film. The thin film comprises a non-metallic material and includes a wall thickness of less than about 1 mm. The thin film is adapted to form at least a bottom interior surface of the water reservoir exposed to the volume of water, and the metal plate is adapted to form a bottom exterior surface of the water reservoir. The water reservoir dock includes a heater plate adapted to thermally contact the metal plate of the water reservoir in the operative position to allow thermal transfer of heat from the heater plate to the volume of water.

Another aspect of the present technology relates to an apparatus for humidifying a flow of breathable gas. The apparatus includes a water reservoir including a cavity structured to hold a volume of water, a water reservoir dock structured and arranged to receive the water reservoir in an operative position, and a guide arrangement structured and arranged to guide the water reservoir into and out of the operative position. The water reservoir includes a conductive portion, and the water reservoir dock includes a heating assembly adapted to thermally engage the conductive portion of the water reservoir in the operative position to allow thermal transfer of heat from the heating assembly to the volume of water. The guide arrangement includes a path extending both in an anterior-posterior direction and in an inferior-superior direction.

Another aspect of the present technology relates to an apparatus for humidifying a flow of breathable gas. The apparatus includes a water reservoir including a cavity structured to hold a volume of water, a water reservoir dock structured and arranged to receive the water reservoir in an operative position, and an air delivery tube configured to pass the flow of breathable gas that has been humidified in the water reservoir to a patient interface. The air delivery tube is structured and arranged to form a direct pneumatic seal with the water reservoir.

Another aspect of the present technology relates to a water reservoir including an inlet tube providing an inlet for receiving a flow of breathable gas and an outlet tube providing an outlet for delivering a humidified flow of breathable gas, wherein the inlet tube includes an inlet seal and the outlet tube includes an outlet seal.

Another aspect of the present technology relates to a water reservoir for an apparatus for humidifying a flow of breathable gas. The water reservoir includes an inlet tube arranged to provide an inlet for receiving a flow of breathable gas into the water reservoir and an outlet tube arranged to provide an outlet for delivering a flow of humidified breathable gas from the water reservoir. At least one of the inlet tube and the outlet tube changes a parameter at least at one point along its length. For example, at least one of the inlet tube and the outlet tube may change direction and/or cross-sectional area at least at one point along its length. In a more specific example, the inlet tube, the outlet tube, or both may curve along its/their length and/or change its cross-section along its length. The change may be abrupt (stepwise) or gradual.

Another aspect of the present technology relates to a water reservoir including a conductive portion adapted to thermally engage with a heating assembly, wherein the conductive portion includes a first portion that extends in a first plane and a second portion that extends in a second plane that is offset in a superior direction from the first plane.

Another aspect of the present technology relates to an apparatus for humidifying a flow of breathable gas. The apparatus includes a water reservoir, a water reservoir dock structured and arranged to receive the water reservoir, and an air delivery tube, wherein insertion/removal of the water reservoir to/from the water reservoir dock is independent from engagement/disengagement of the air delivery tube to/from the water reservoir dock.

Another aspect of the present technology relates to a heating assembly for a water reservoir dock including a heater plate, a heating element, and a thermal pad arranged between the heater plate and the heating element, e.g., to enhance thermal conductivity from the heating element to the heater plate.

Another aspect of the present technology relates to an apparatus for humidifying a flow of breathable gas. The apparatus includes a water reservoir including a cavity structured to hold a volume of water, the water reservoir including a conductive portion, and a water reservoir dock structured and arranged to receive the water reservoir in an operative position, the water reservoir dock including a heating assembly adapted to thermally engage the conductive portion of the water reservoir in the operative position to allow thermal transfer of heat from the heating assembly to the volume of water. The heating assembly includes a heater plate to thermally contact the conductive portion of the water reservoir, a heating element, and a thermal pad arranged between the heater plate and the heating element. The thermal pad comprises a pliable material structured and arranged to engage both the heater plate and the heating element to remove air gaps and spaces between the heater plate and the heating element to enhance thermal conductivity.

Another aspect of the present technology relates to a water reservoir including a conductive portion adapted to thermally engage with a heating assembly, wherein the conductive portion includes one of a metal plate, a thin, non-metallic film, or a combined layered arrangement of a metal plate and a thin, non-metallic film. In an example, the conductive portion may include circular or non-circular shapes.

Another aspect of the present technology relates to including one or more circuit components in an air delivery tube for identifying a type of air delivery tube based on characteristics of the circuit components.

Another aspect of the present technology relates to an apparatus for humidifying a flow of breathable gas. The apparatus includes a water reservoir including a cavity structured to hold a volume of water, a water reservoir dock structured and arranged to receive the water reservoir in an operative position, and an air delivery tube configured to pass the flow of breathable gas that has been humidified in the water reservoir to a patient interface. The air delivery tube includes a dock connector including a contact assembly. The contact assembly includes electrical contacts adapted to, in an operative configuration of the apparatus, engage respective electrical contacts provided to the water reservoir dock. The contact assembly includes an electrical characteristic used as an identifier of one or more parameters of the air delivery tube or the patient interface.

Another aspect of the present technology relates to processing circuitry configured to identify a type of air delivery tube coupled to an apparatus for humidifying a flow of breathable gas based on measured characteristics of a passive circuit component in the air delivery tube.

Another aspect of the present technology relates to processing circuitry configured to identify a type of air delivery tube coupled to an apparatus for humidifying a flow of breathable gas based on measuring characteristics of circuitry in the air delivery tube. The characteristics of the circuitry include a resistance value of one or more heating elements in the air delivery tube and/or a resistance value of one or more sensors in the air delivery tube.

Another aspect of the present technology relates to processing circuitry configured to identify a type of air delivery tube coupled to an apparatus for humidifying a flow of breathable gas based on resistance value of a first resistor and a resistance value of a second resistor provided in the air delivery tube. The first resistor being coupled to a first pair of contacts in the air delivery tube and the second resistor being coupled to a second pair of contacts in the air delivery tube.

Another aspect of the present technology relates to including one or more filters coupled to a sensor circuit at least partially disposed in an air delivery tube for sensing temperature changes in the air delivery tube.

Another aspect of the present technology relates to including low pass filters coupled to a sensor circuit at least partially disposed in an air delivery tube for sensing temperature changes in the air delivery tube. The filters may be configured to filter pulse frequencies of the PWM signal applied to one or more heating elements in the air delivery tube.

Another aspect of the present technology relates to including one or more low pass filters coupled to a sensor circuit at least partially disposed in an air delivery tube for sensing temperature changes in the air delivery tube, wherein a sensing signal is applied periodically to the sensor circuit.

Another aspect of the present technology relates to including a first low pass filter coupled to one end of a sensor included in an air delivery tube and a second low pass filter coupled to a second end of the sensor, wherein a sensing signal is applied at predetermined intervals to the sensor for sensing temperature changes in the air delivery tube.

Another aspect of the present technology relates to including a first low pass filter coupled to a first output of a divider network for detecting operating parameters of a sensor disposed in an air delivery tube and a second low pass filter coupled to a second output of the divider network.

Another aspect of the present technology relates to an apparatus for providing a supply of humidified pressurized breathable gas to a patient interface. The apparatus includes a flow generator configured to pressurize a supply of breathable gas, a humidifier configured to provide water vapour to humidify the supply of pressurized breathable gas, a heated tube configured to be connectable to the humidifier to heat and deliver the humidified supply of breathable gas to the patient interface, a sensor configured to measure a property of the humidified supply of breathable gas in the heated tube, a controller configured to control power provided to the heated tube and control operation of the flow generator, and a set of low pass filters coupled between the sensor and the controller and/or a set of low pass filters coupled between the sensor and ground.

Another aspect of the present technology relates to an apparatus for humidifying a flow of breathable gas including a water reservoir including a cavity structured to hold a volume of water, a water reservoir dock structured and arranged to receive the water reservoir in an operative position, an air delivery tube configured to pass the flow of breathable gas that has been humidified in the water reservoir to a patient interface, and an intermediate component removably and non-rotatably coupled to the water reservoir dock. The intermediate component is configured to pneumatically connect the water reservoir to the air delivery tube. The intermediate component comprises a one-piece construction of a relatively rigid material including an inlet end adapted to interface with the water reservoir and an outlet end adapted to interface with the air delivery tube. The air delivery tube includes a dock connector structured and arranged to form a bayonet-style connection with the water reservoir dock which mechanically and electrically connects the air delivery tube with the water reservoir dock.

Another aspect of the present technology relates to a water reservoir for humidifying a flow of breathable gas including a reservoir base, a reservoir lid, and a hinge joint to hingedly couple the reservoir lid to the reservoir base for hinged movement between an open position and a closed position. The hinge joint includes a pair of hinge pins each configured to engage with a respective one of a pair of slots to provide said hinged movement. Each of the pair of hinge pins comprises a cross-section that represents a major segment of a circle.

Another aspect of the present technology relates to an apparatus for humidifying a flow of breathable gas. The apparatus includes a water reservoir including a cavity structured to hold a volume of water, a water reservoir dock structured and arranged to receive the water reservoir in an operative position, and a guide arrangement structured and arranged to guide the water reservoir into the operative position with the water reservoir dock. The water reservoir includes a heat conductive portion. The water reservoir dock includes a heating assembly adapted to thermally engage the heat conductive portion of the water reservoir in the operative position to allow thermal transfer of heat from the heating assembly to the volume of water. The guide arrangement includes a guiding rail on each side of the water reservoir and a guide slot on each side of the water reservoir dock, each guiding rail configured to engage with a respective guide slot. The guide arrangement further includes one or more biasing edges or tabs provided to a leading edge of the water reservoir configured to engage underneath a respective abutment edge provided to the water reservoir dock when the water reservoir reaches the operative position. The engagement both biases the front of the water reservoir downwardly and locks/prevents its movement in an upward direction.

Another aspect of the present technology relates to an apparatus for humidifying a flow of breathable gas. The apparatus includes a water reservoir including a cavity structured to hold a volume of water and a water reservoir dock structured and arranged to receive the water reservoir in an operative position. The water reservoir includes a heat conductive portion, and the water reservoir dock includes a heating assembly adapted to thermally engage the heat conductive portion of the water reservoir in the operative position to allow thermal transfer of heat from the heating assembly to the volume of water. The heating assembly comprises a heater plate including a base surface to thermally contact the heat conductive portion of the water reservoir and a resilient sealing and/or supporting member to resiliently suspend the heater plate within the water reservoir dock. The resilient sealing and/or supporting member comprises one or more hollow tubes, each of one or more hollow tubes including an axis that is generally perpendicular to the base surface of the heater plate.

Another aspect of the present technology relates to an apparatus for humidifying a flow of breathable gas. The apparatus includes a water reservoir including a cavity structured to hold a volume of water, a water reservoir dock structured and arranged to receive the water reservoir in an operative position, an air delivery tube configured to pass the flow of breathable gas that has been humidified in the water reservoir to a patient interface, and an intermediate component arranged for removably and non-rotatably coupling to the water reservoir dock and the air delivery tube. The intermediate component is configured to, in an operational configuration, pneumatically connect the air delivery tube to the water reservoir.

Another aspect of the present technology relates to a water reservoir for humidifying a flow of breathable gas including a reservoir base including a cavity structured to hold a volume of water. The reservoir base includes a main body and a thermally conductive portion provided to the main body. The thermally conductive portion may comprise a thin film. The thin film comprises a non-metallic material and includes a wall thickness of less than about 1 mm. The main body comprises a plastic material, and the thin film comprises a non-final form that forms an insert molded connection with the main body. The thin film is formed in its final form (e.g. by stamping, vacuum forming or thermal vacuum forming) after it has been insert molded in the main body.

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 Respiratory System and Facial Anatomy

4.3 Patient Interface

Figure 3A:
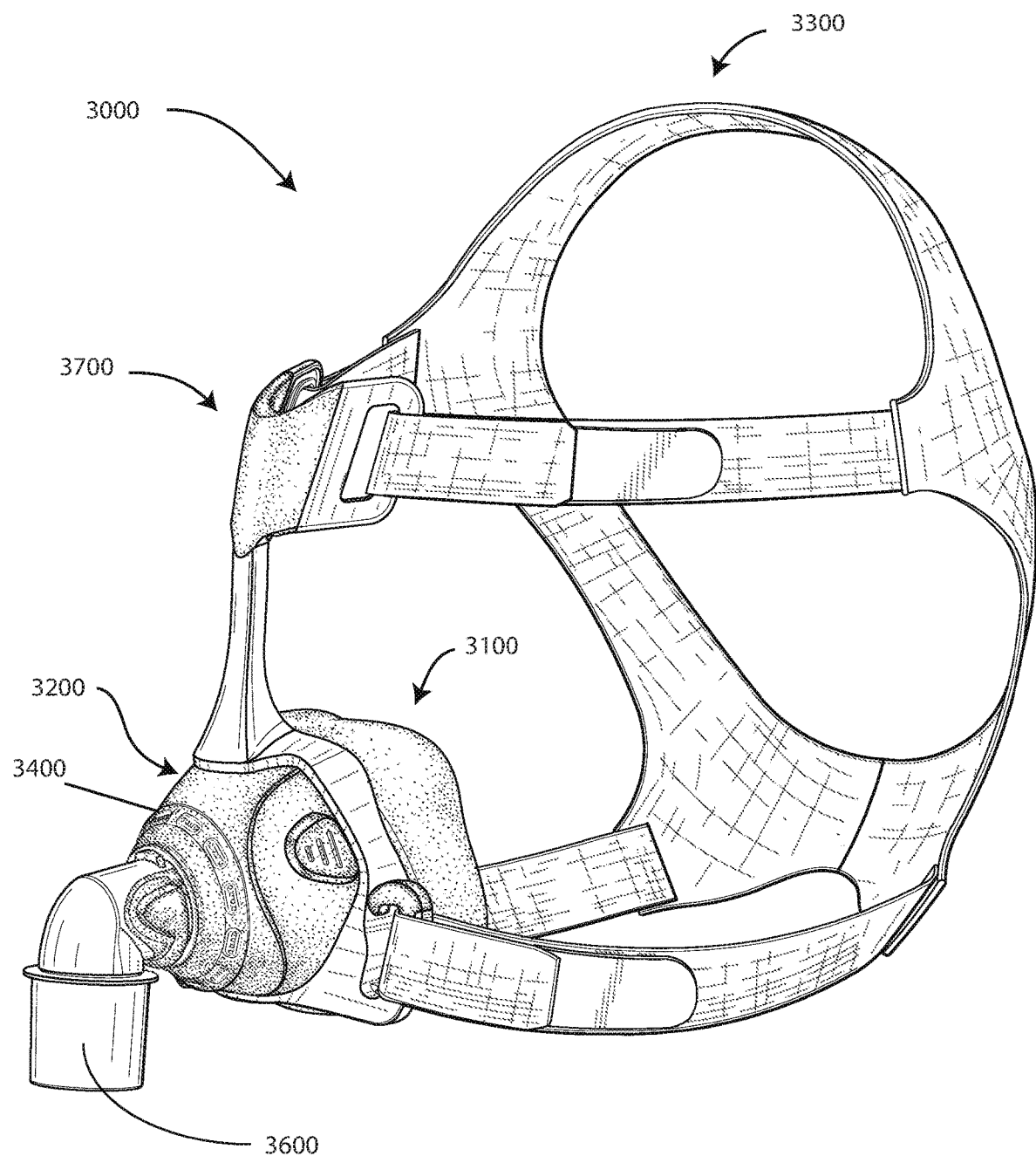

FIG. 3A shows a patient interface in the form of a nasal mask in accordance with one form of the present technology.

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

FIG. 3D shows a schematic of a cross-section through a structure at a point. An outward normal at the point is indicated. The curvature at the point has a value of zero.

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figure 3G:
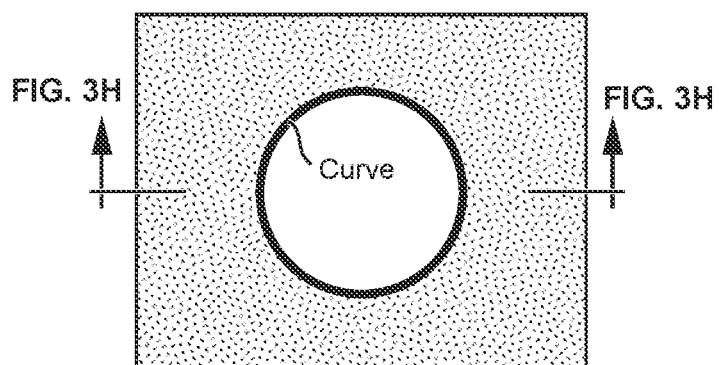

FIG. 3G shows the surface of a structure, with a one dimensional hole in the surface. The illustrated plane curve forms the boundary of a one dimensional hole.

Figure 3H:
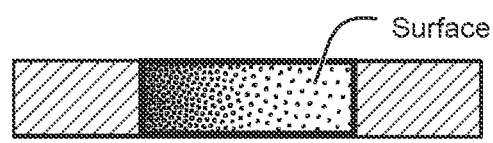

FIG. 3H shows a cross-section through the structure of FIG. 3G. The illustrated surface bounds a two dimensional hole in the structure of FIG. 3G.

Figure 3I:
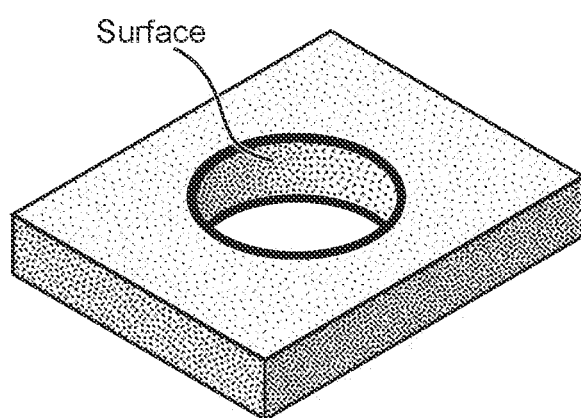

FIG. 3I shows a perspective view of the structure of FIG. 3G, including the two dimensional hole and the one dimensional hole. Also shown is the surface that bounds a two dimensional hole in the structure of FIG. 3G.

4.4 Breathing Waveforms

Figure 4:
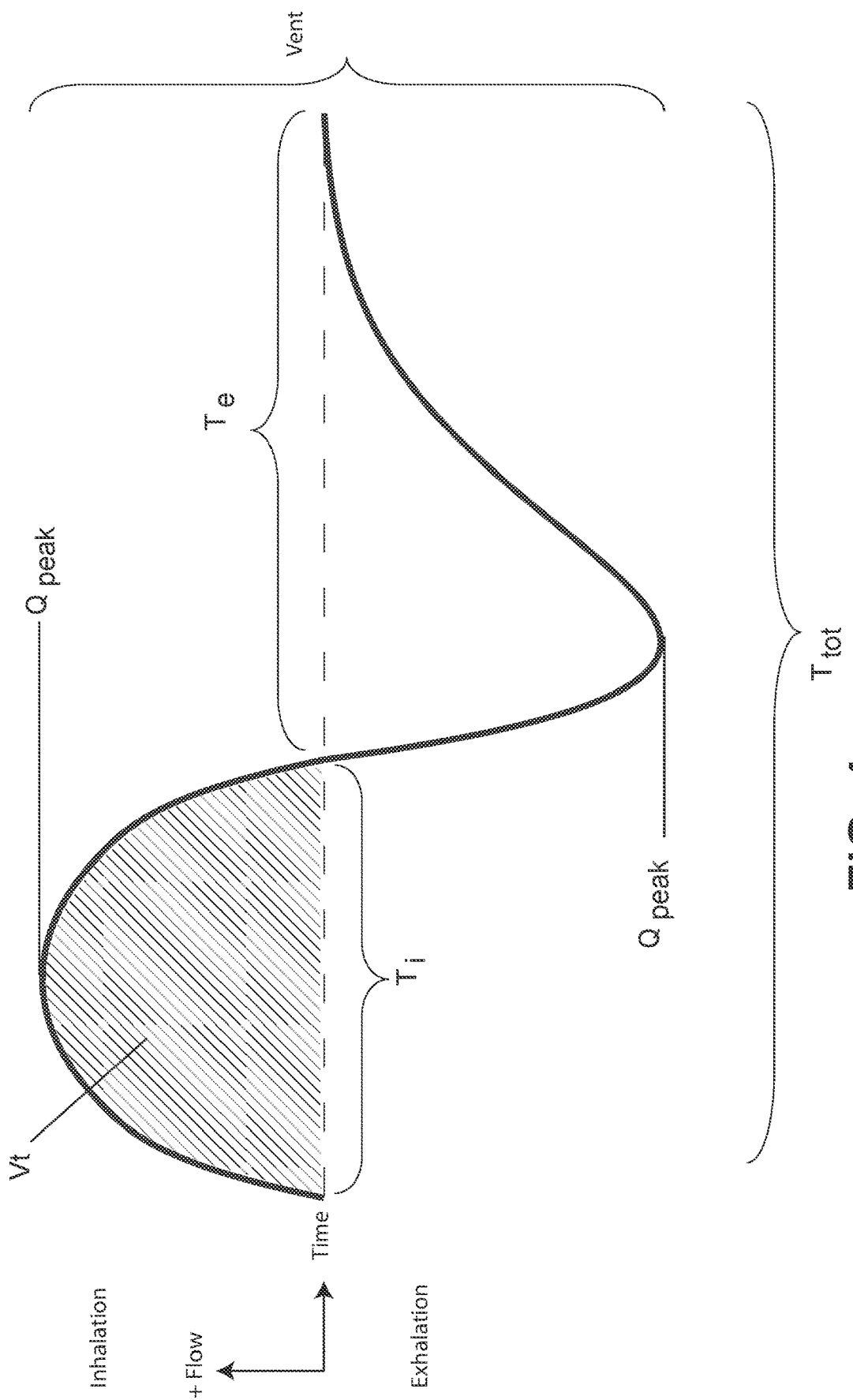

FIG. 4 shows a model typical breath waveform of a person while sleeping.

4.5 RPT Device and Humidifier

Figure 5A:
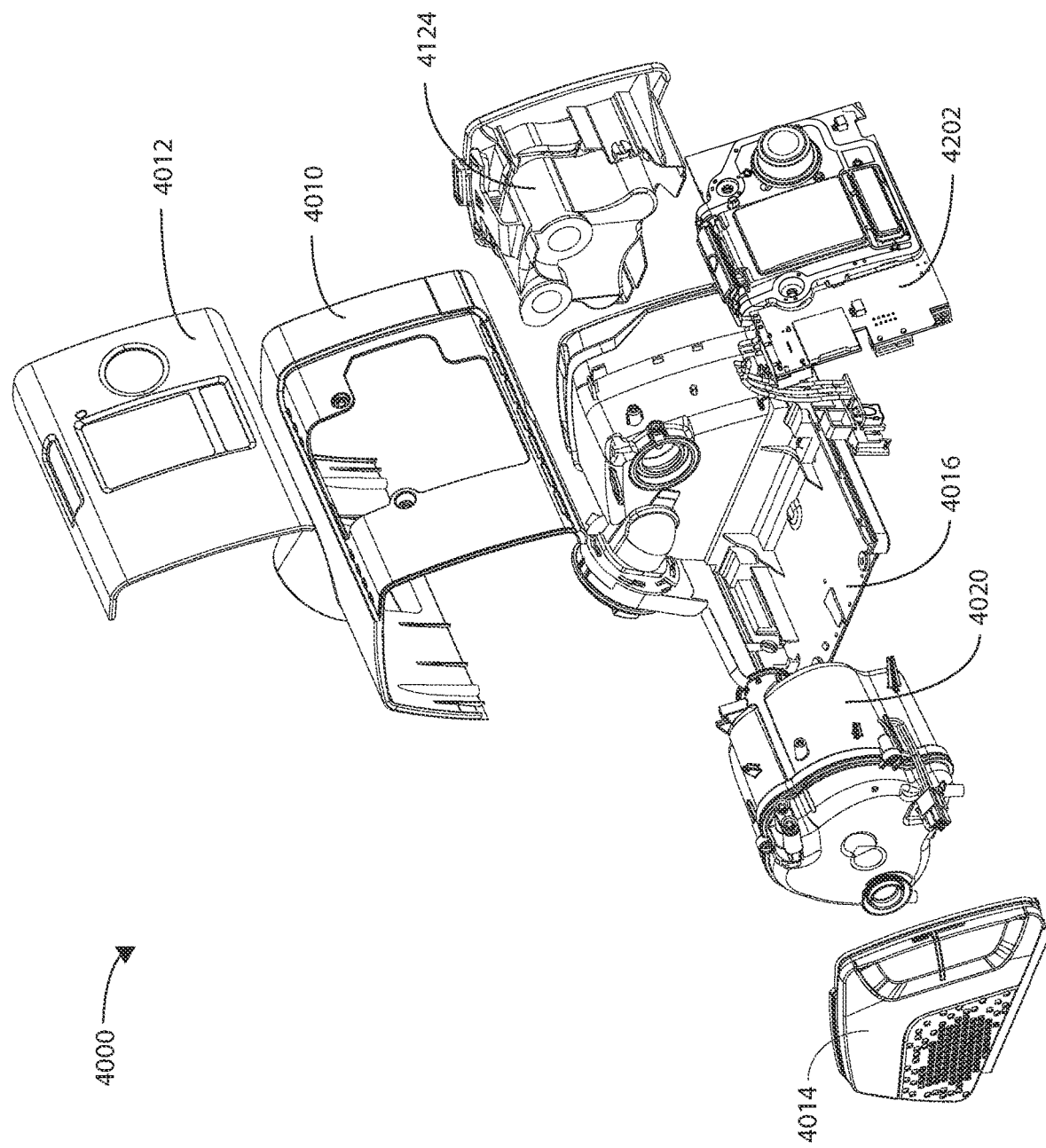

FIG. 5A shows an exploded perspective view of an RPT device 4000 in accordance with one form of the present technology.

FIG. 5B shows a perspective view of an RPT device 4000 comprising an outlet cap with a muffler 4124 in accordance with one form of the present technology.

Figure 5C:
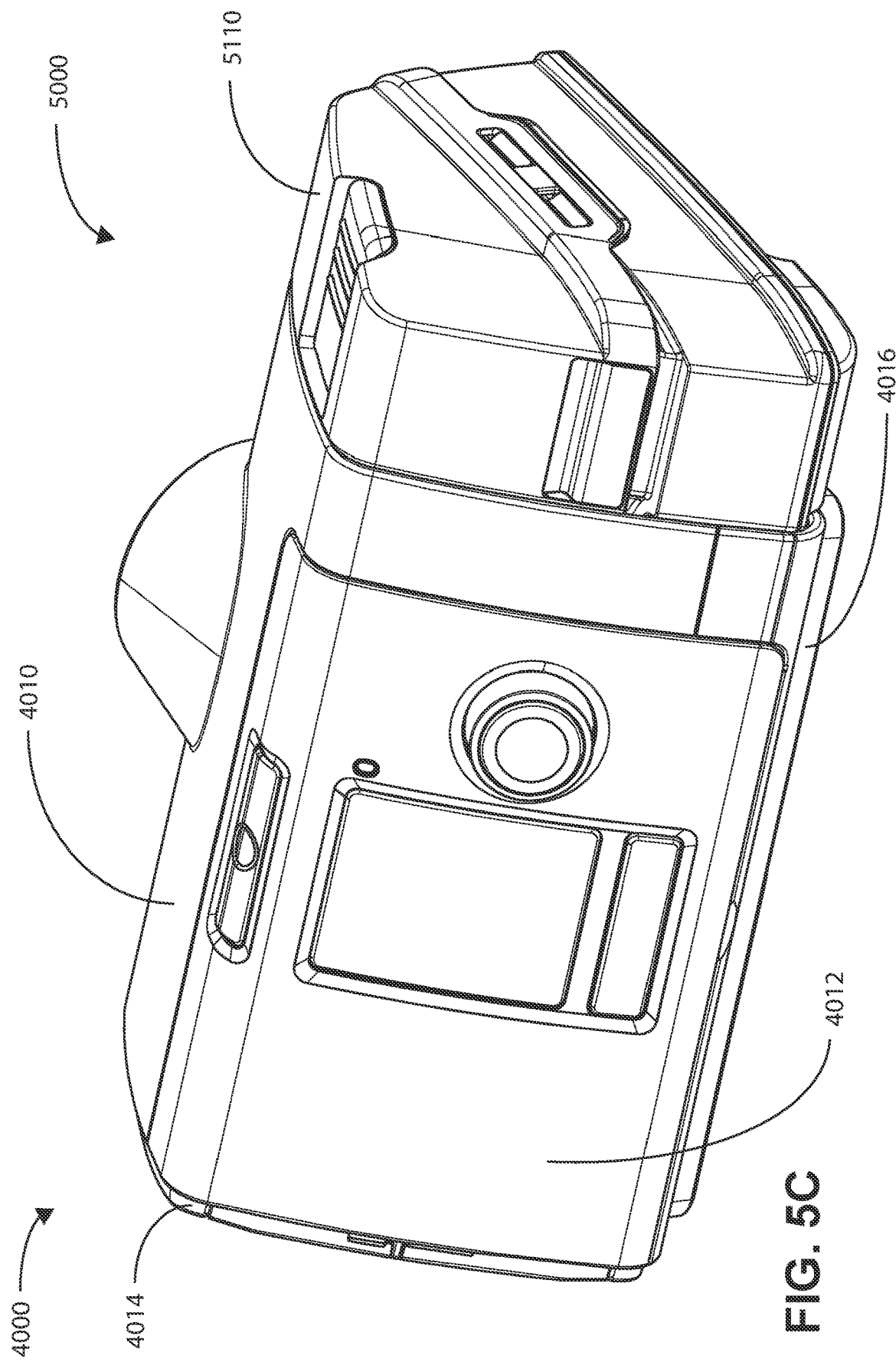

FIG. 5C shows a perspective view of an RPT device 4000 with an integrated humidifier 5000 comprising a water reservoir 5110 in accordance with one form of the present technology.

Figure 5D:
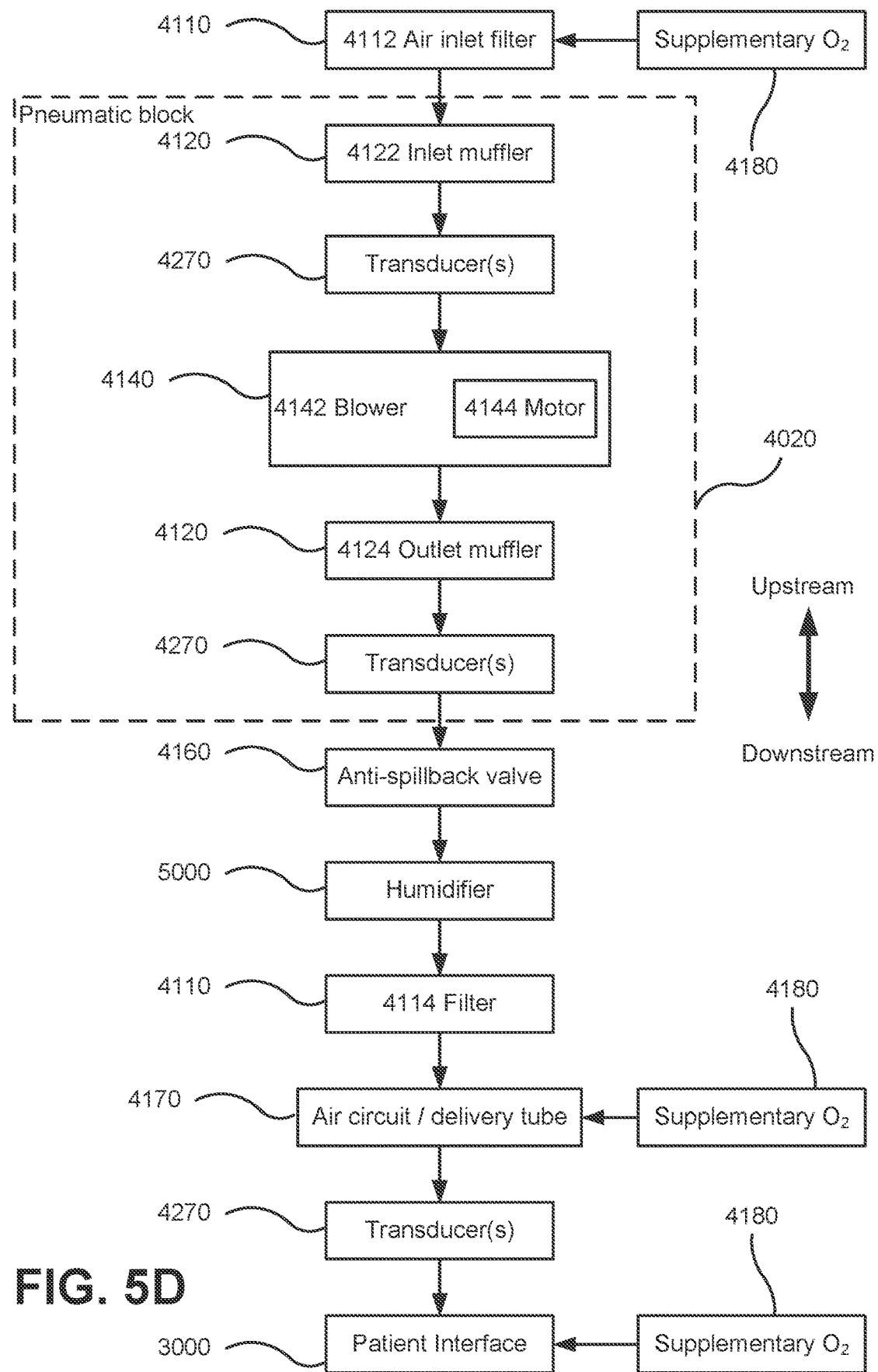

FIG. 5D is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

Figure 5E:
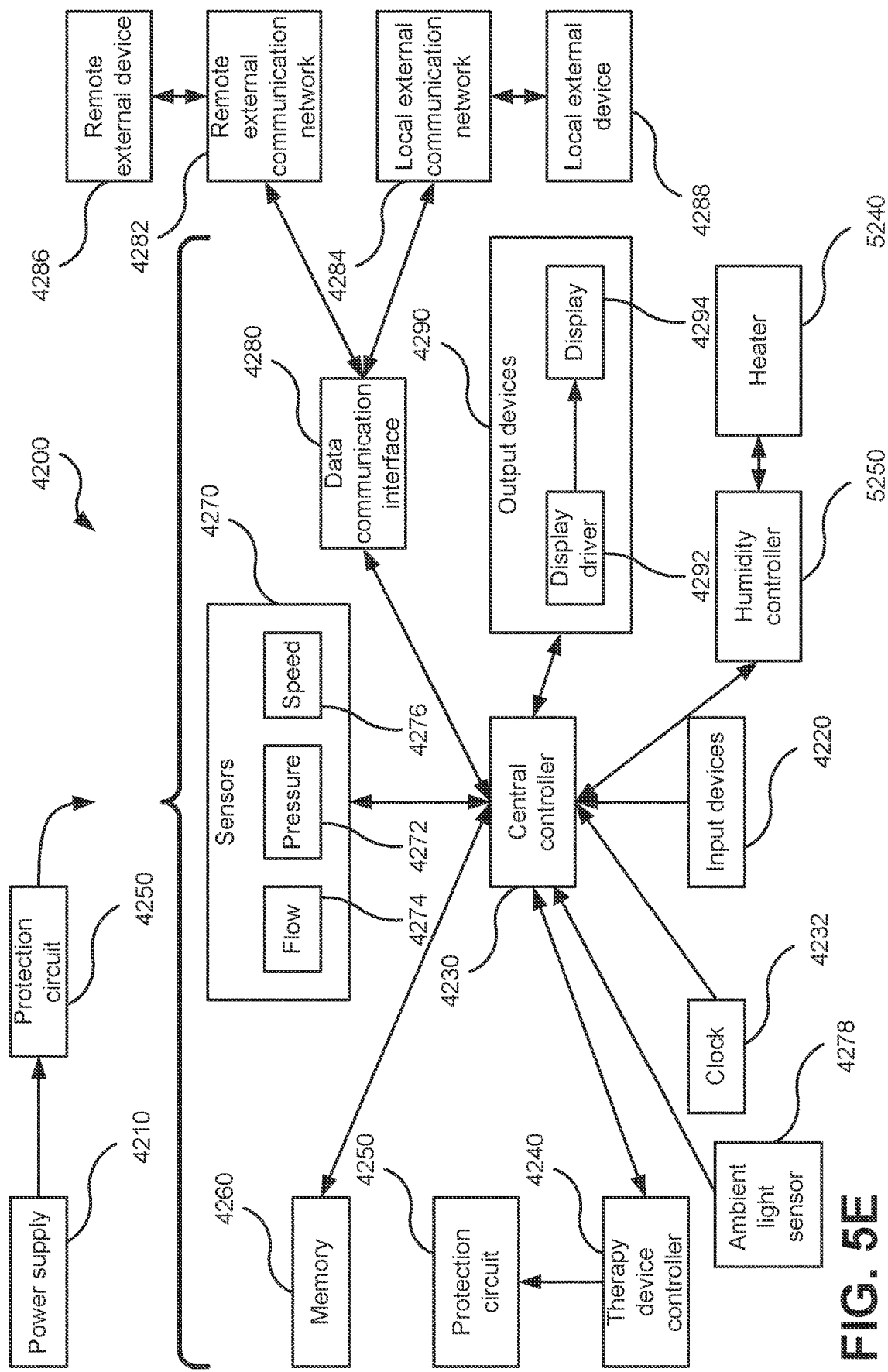

FIG. 5E is a schematic diagram of the electrical components of an RPT device in accordance with one form of the present technology.

Figure 5F:
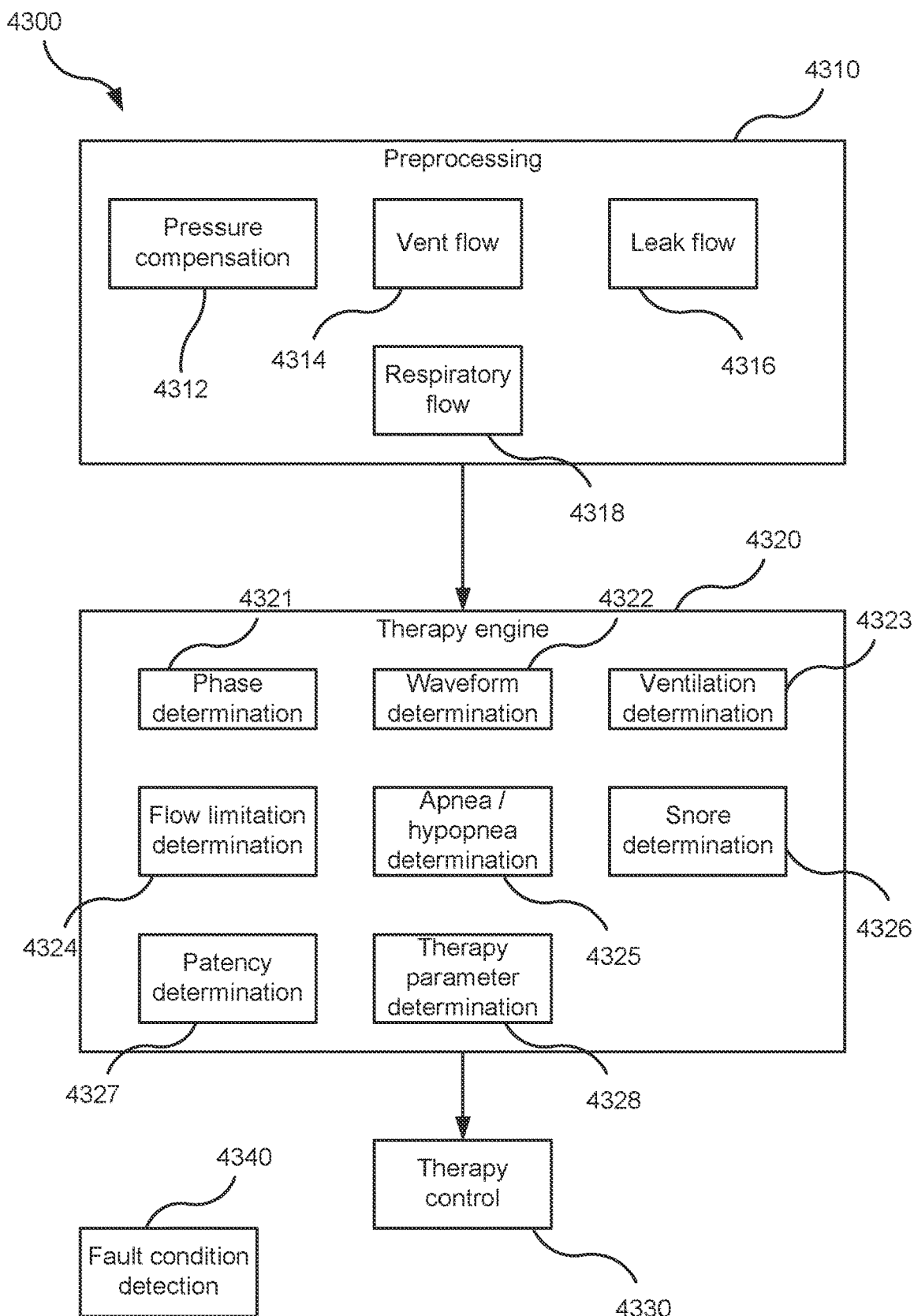

FIG. 5F is a schematic diagram of the algorithms implemented in an RPT device in accordance with one form of the present technology.

Figure 5G:
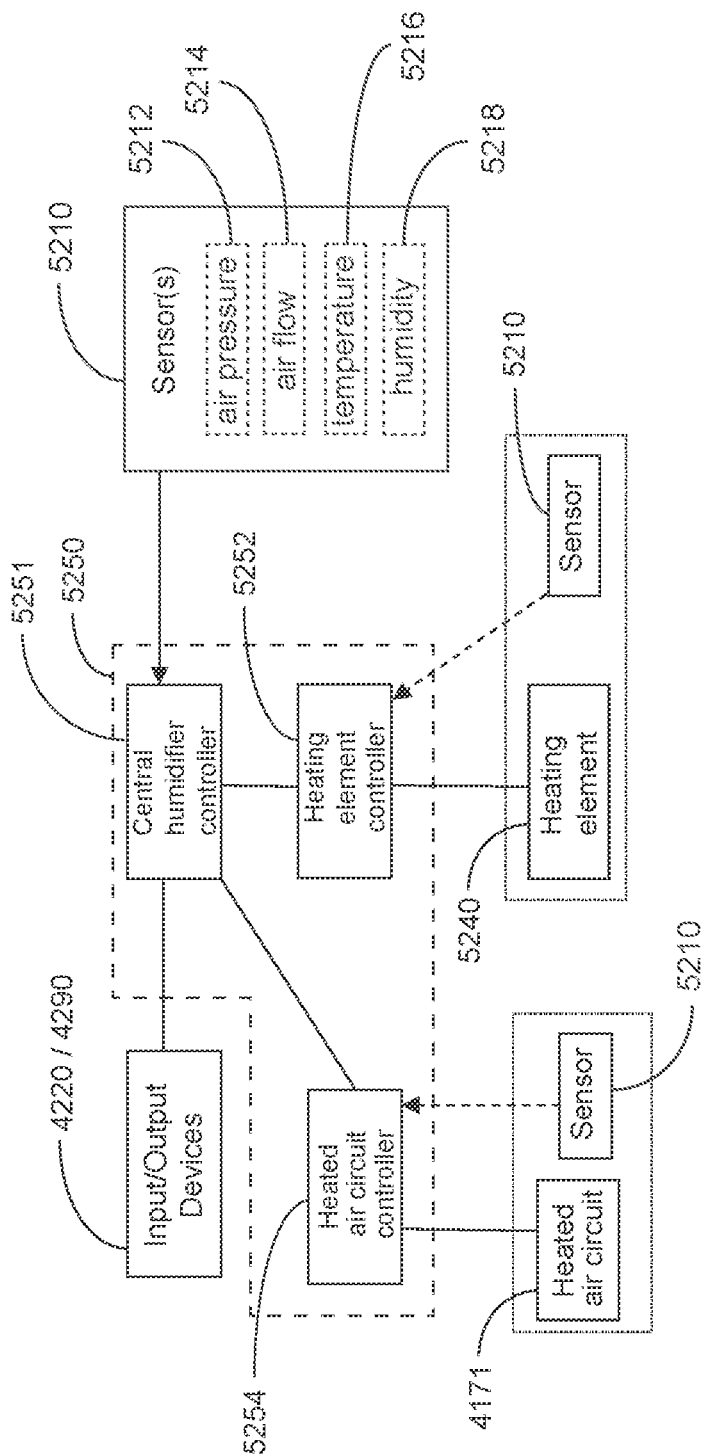

FIG. 5G shows a schematic of a humidifier in accordance with one form of the present technology.

Figure 6A:
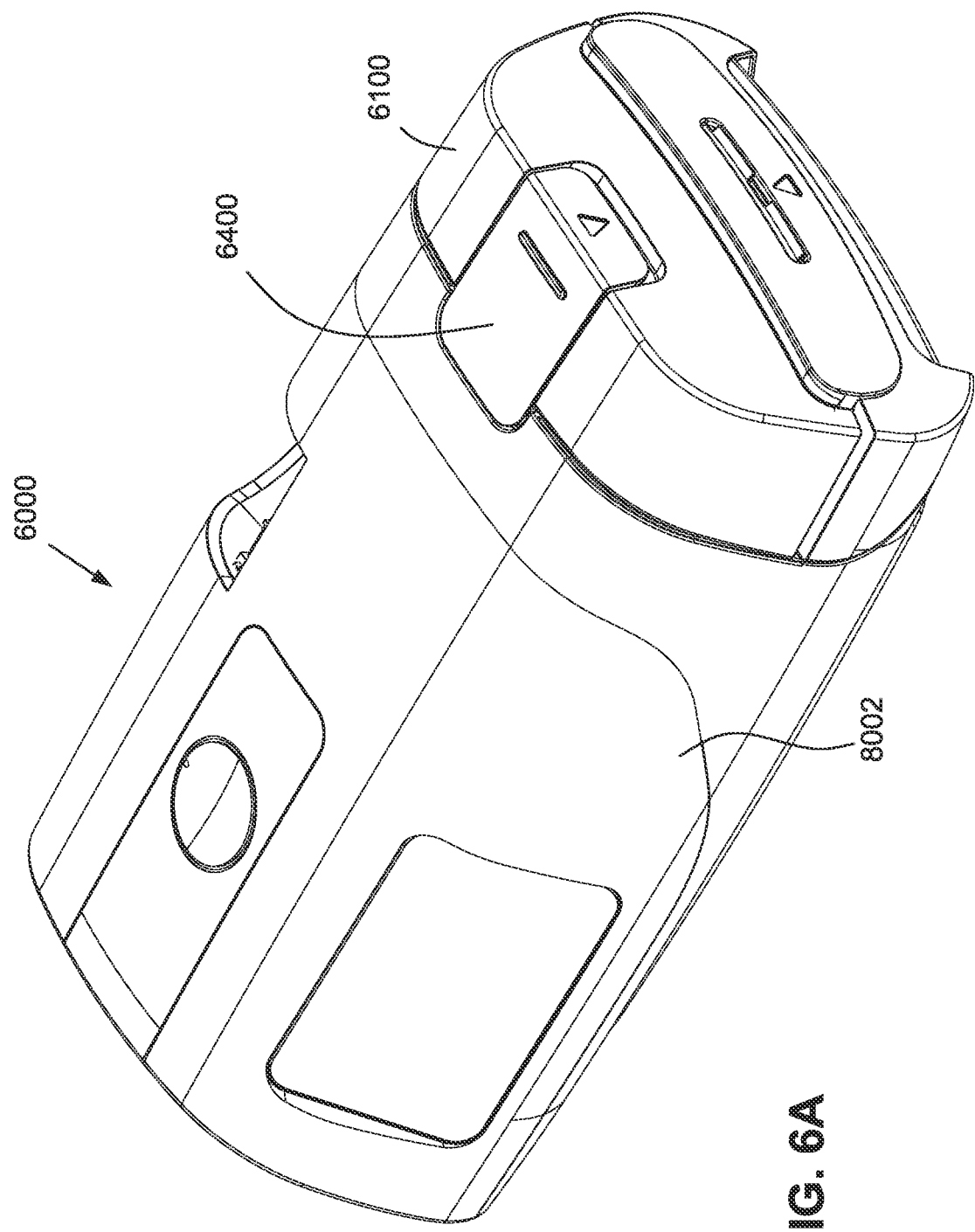

FIG. 6A is a perspective view of an integrated RPT device and humidifier comprising a water reservoir according to an example of the present technology.

Figure 6B:
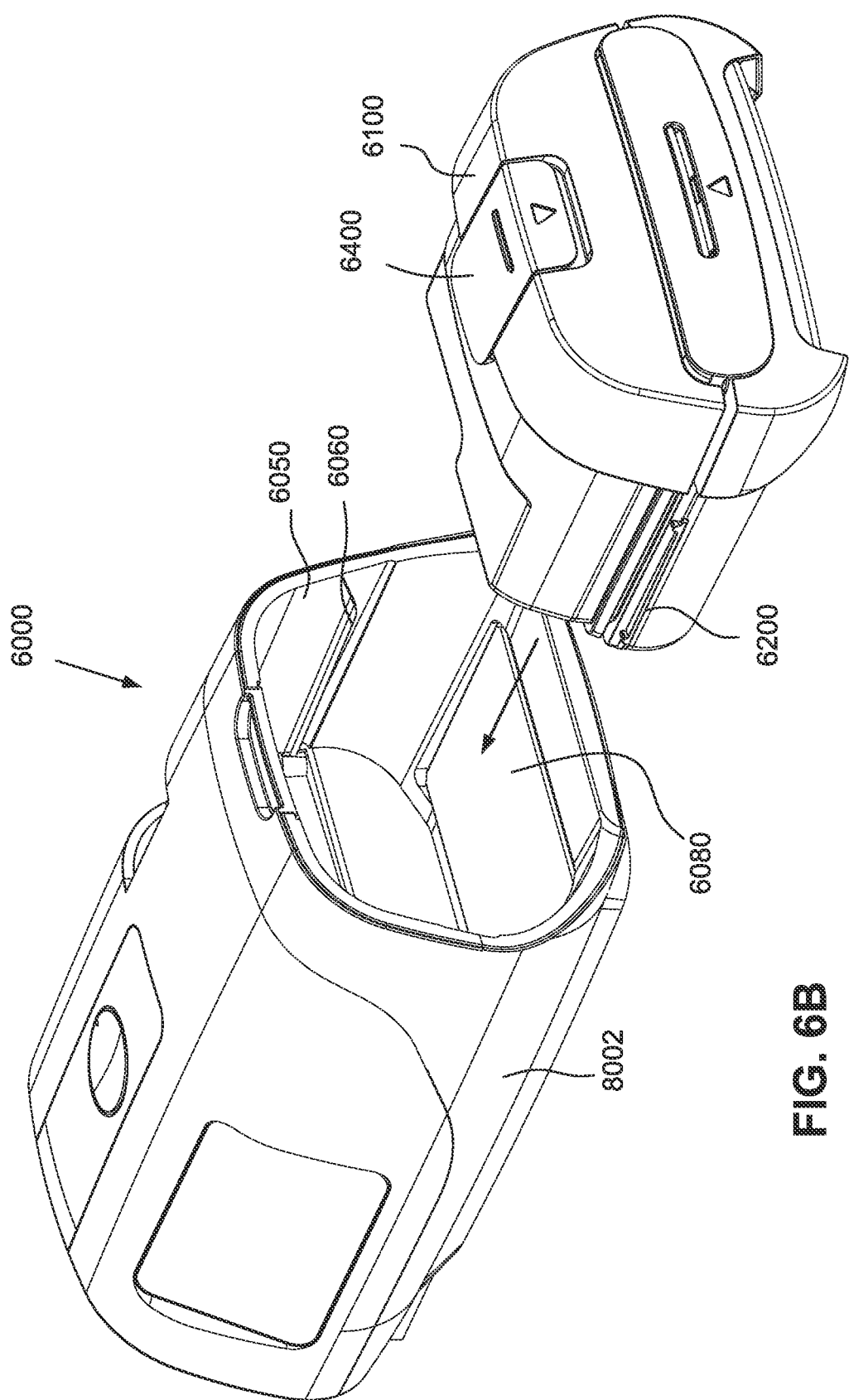

FIG. 6B is a perspective view of the integrated RPT device and humidifier of FIG. 6A with the water reservoir removed from the reservoir dock.

Figure 7:
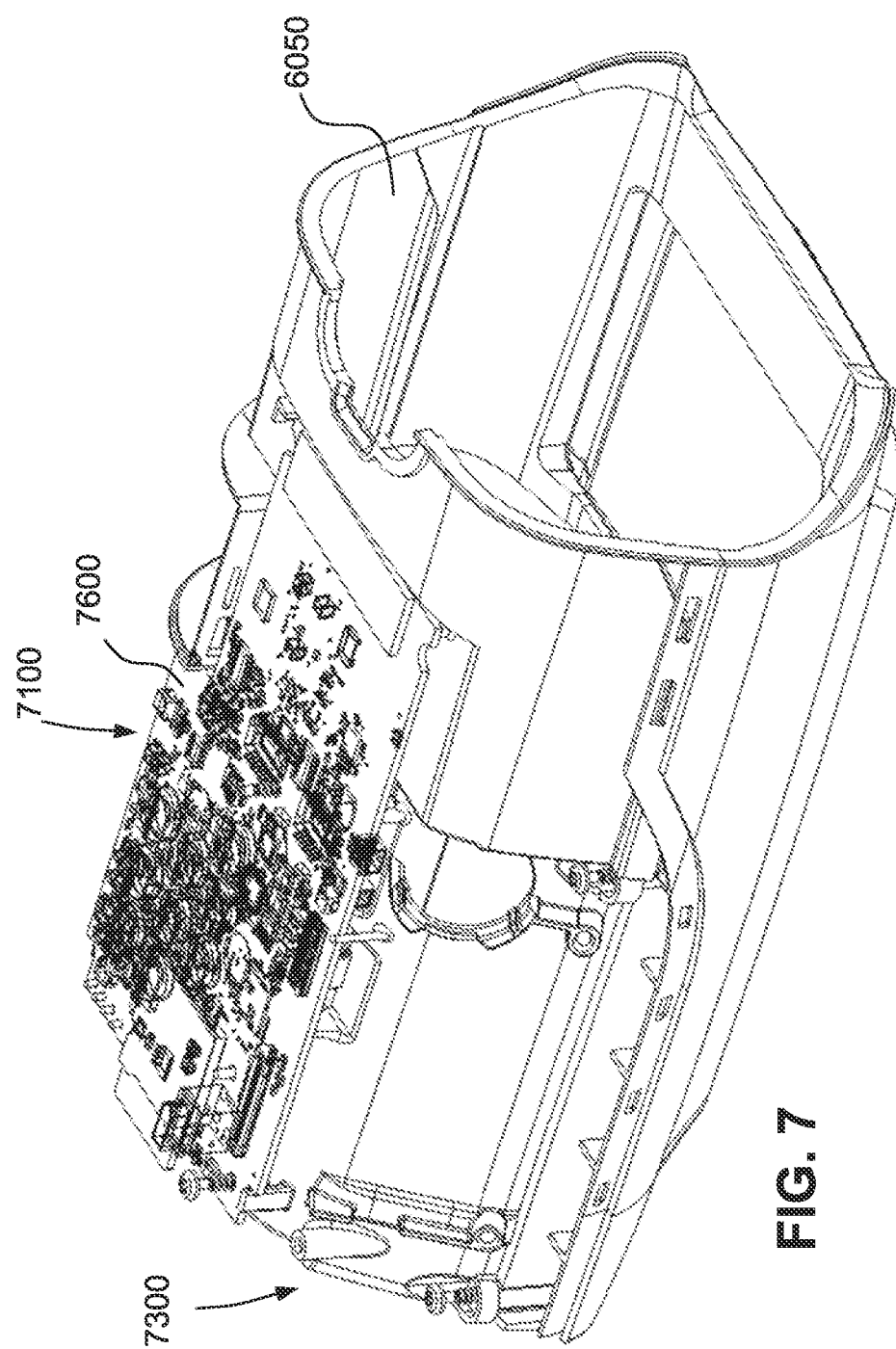

FIG. 7 is a perspective view of a pneumatic block according to an example of the present technology.

Figure 8A:
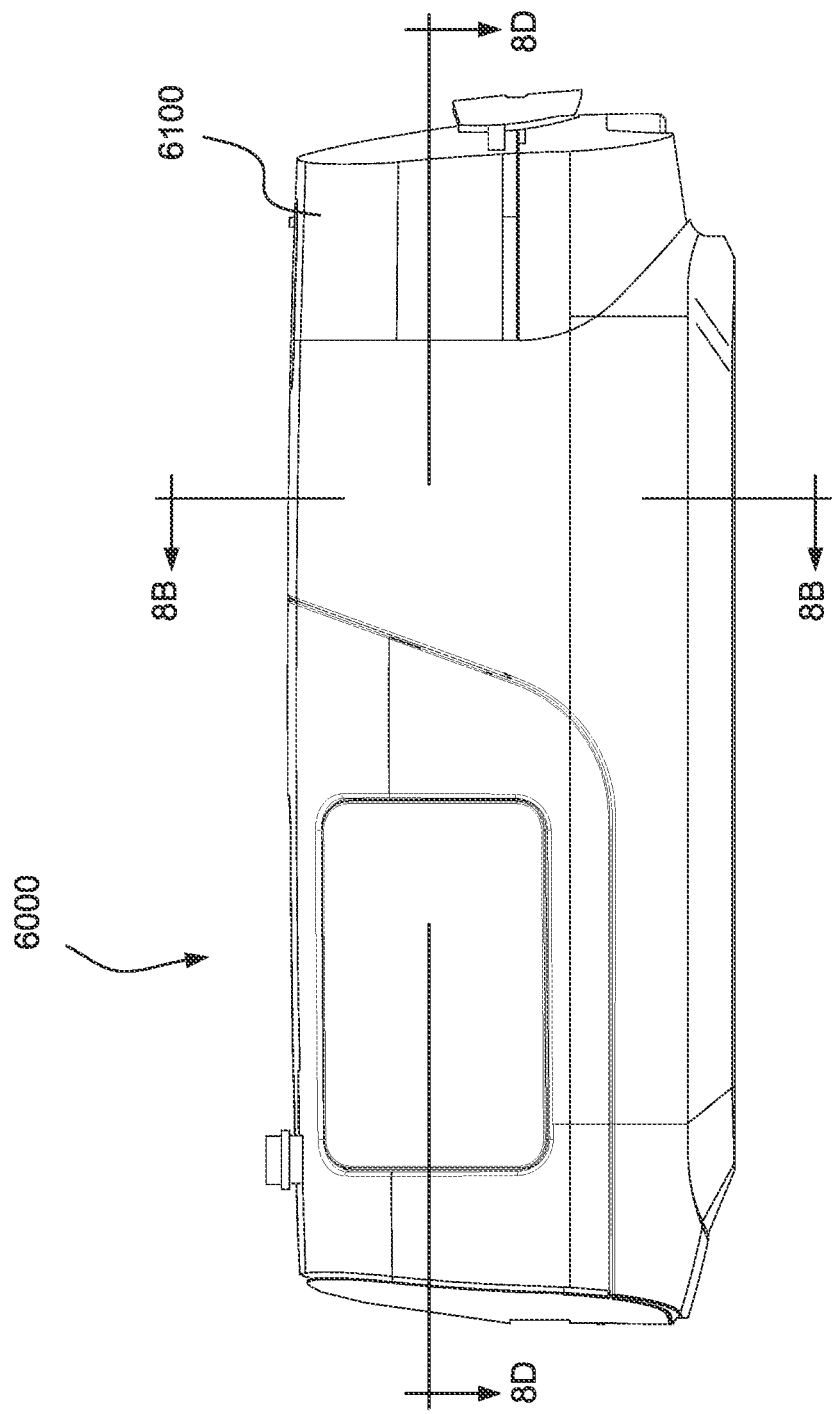

FIG. 8A is a side view of the integrated RPT device and humidifier of FIG. 6A according to an example of the present technology.

Figure 8B:
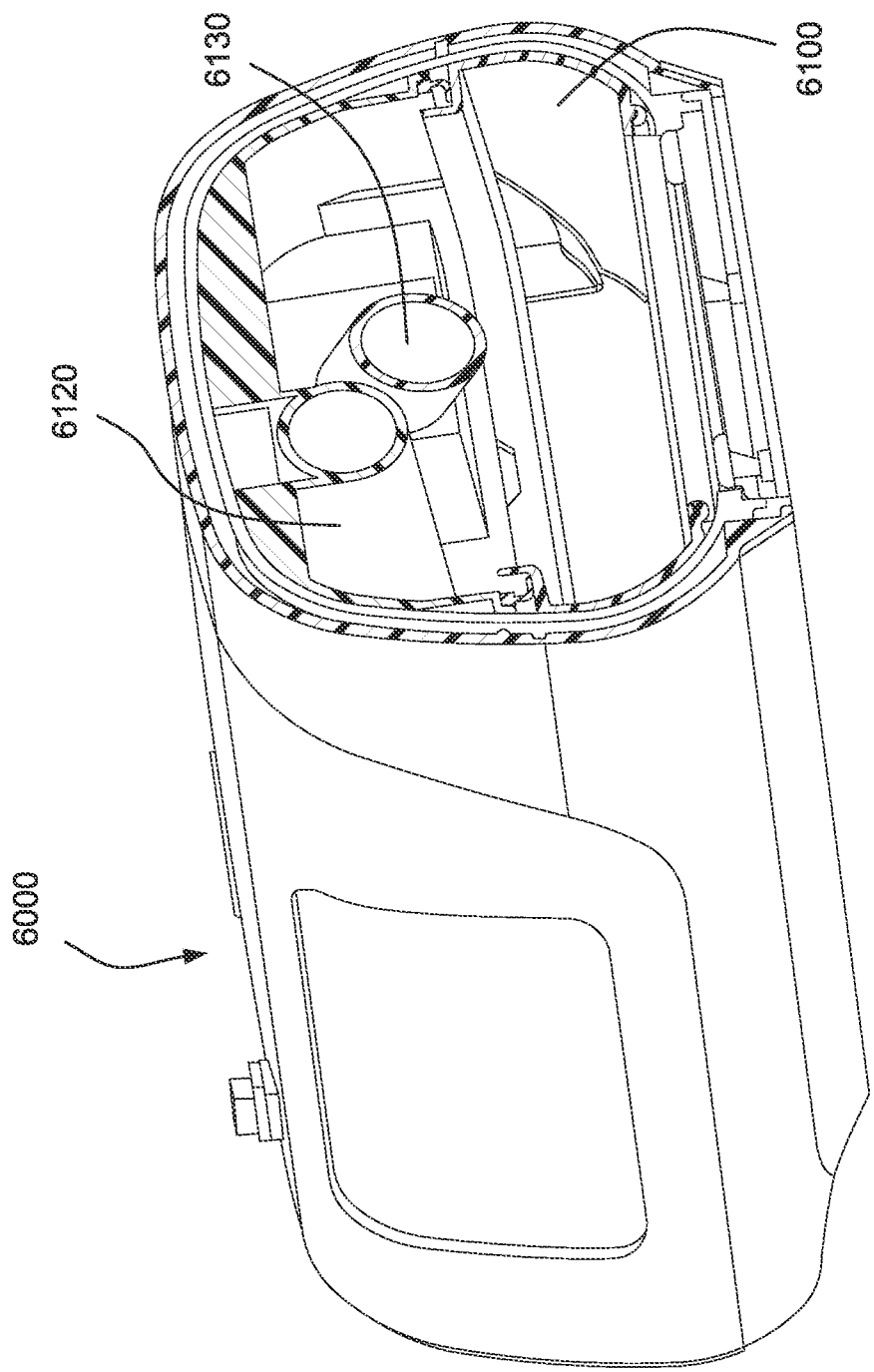

FIG. 8B is a cross-sectional view of the integrated RPT device and humidifier of FIG. 8A, taken along line 8B-8B of FIG. 8A.

Figure 8C:
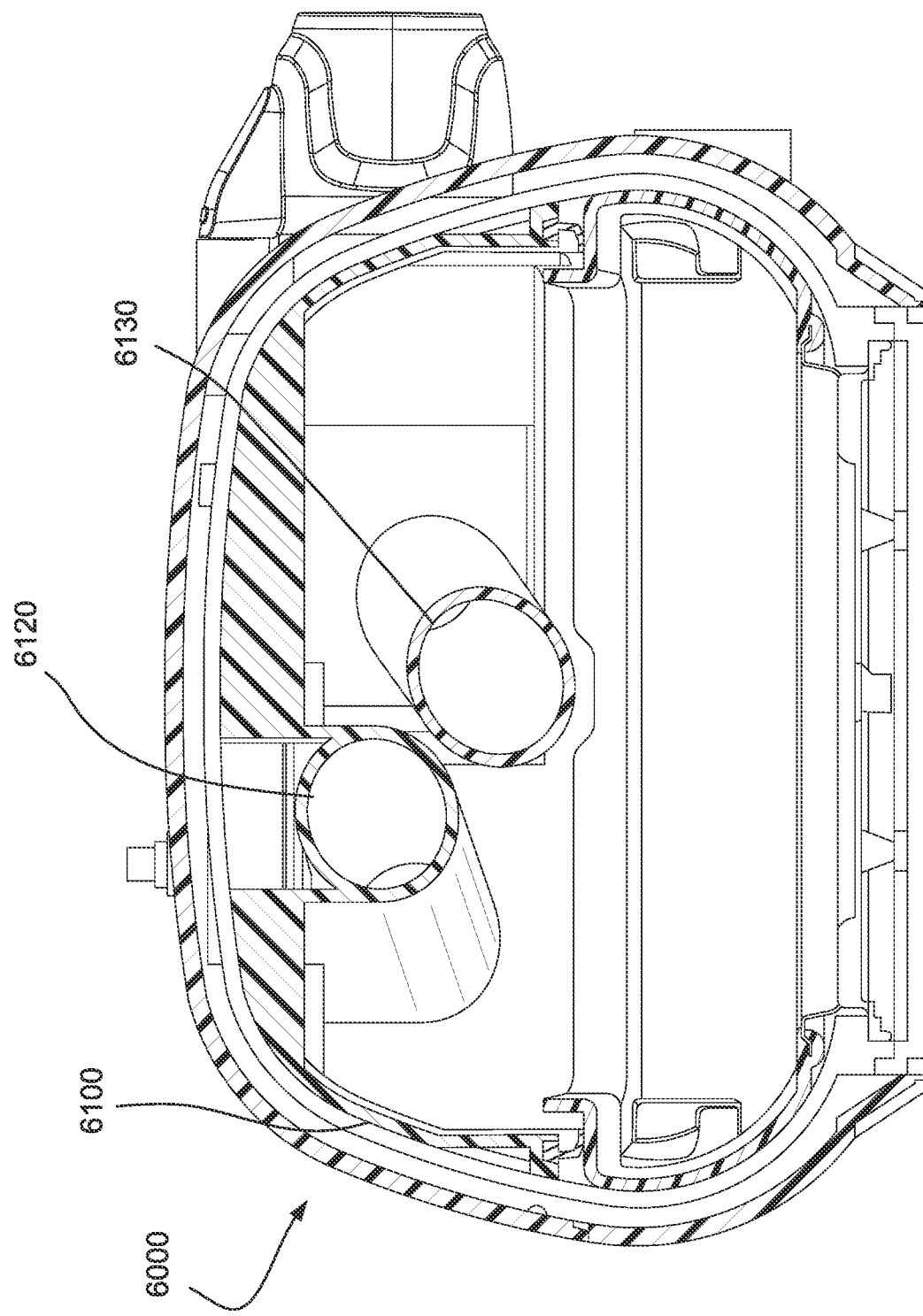

FIG. 8C is a front view of the cross-sectional view shown in FIG. 8B.

Figure 8D:
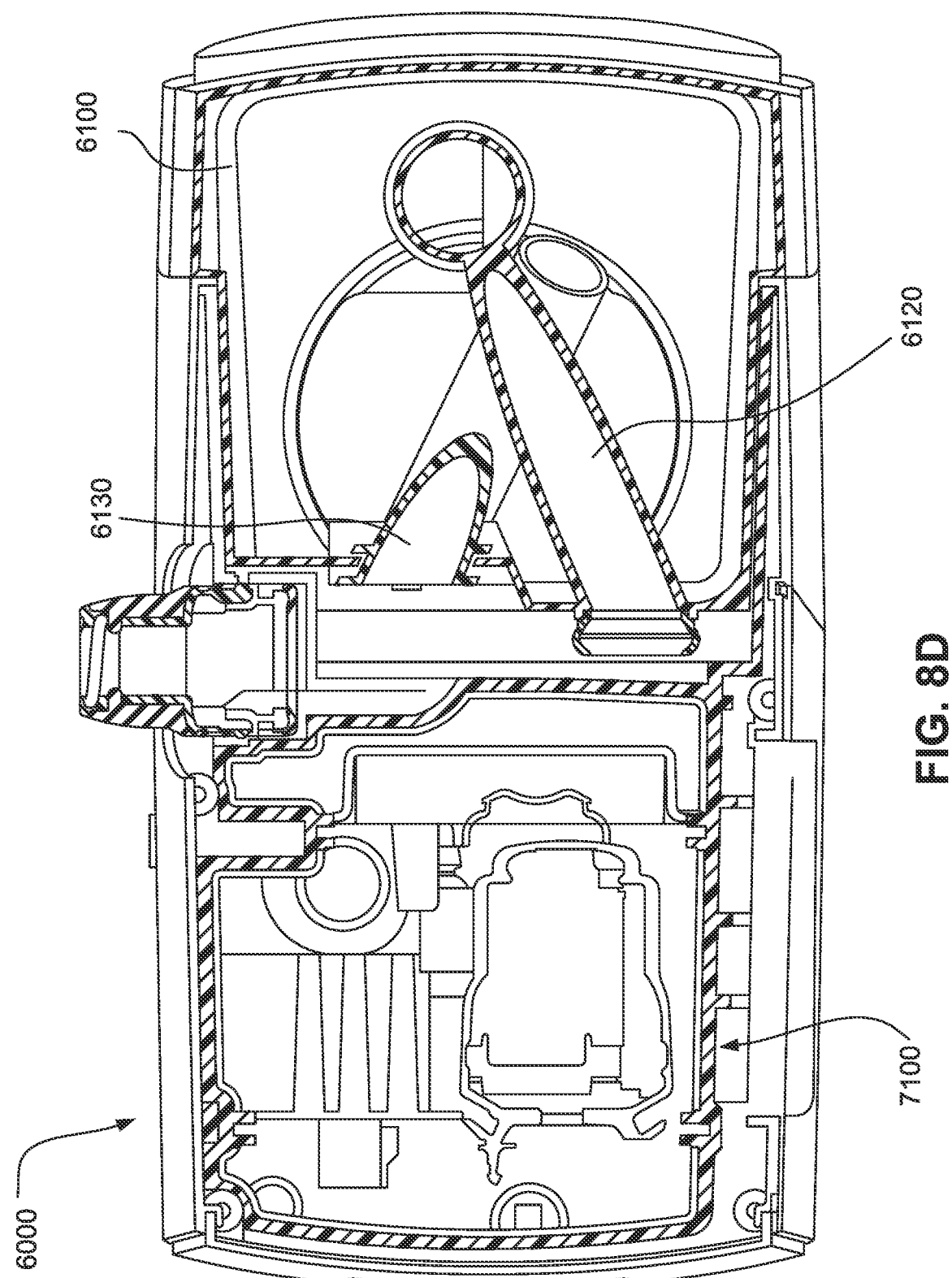

FIG. 8D is a cross-sectional view of the integrated RPT device and humidifier of FIG. 8A, taken along line 8D-8D of FIG. 8A.

Figure 9:
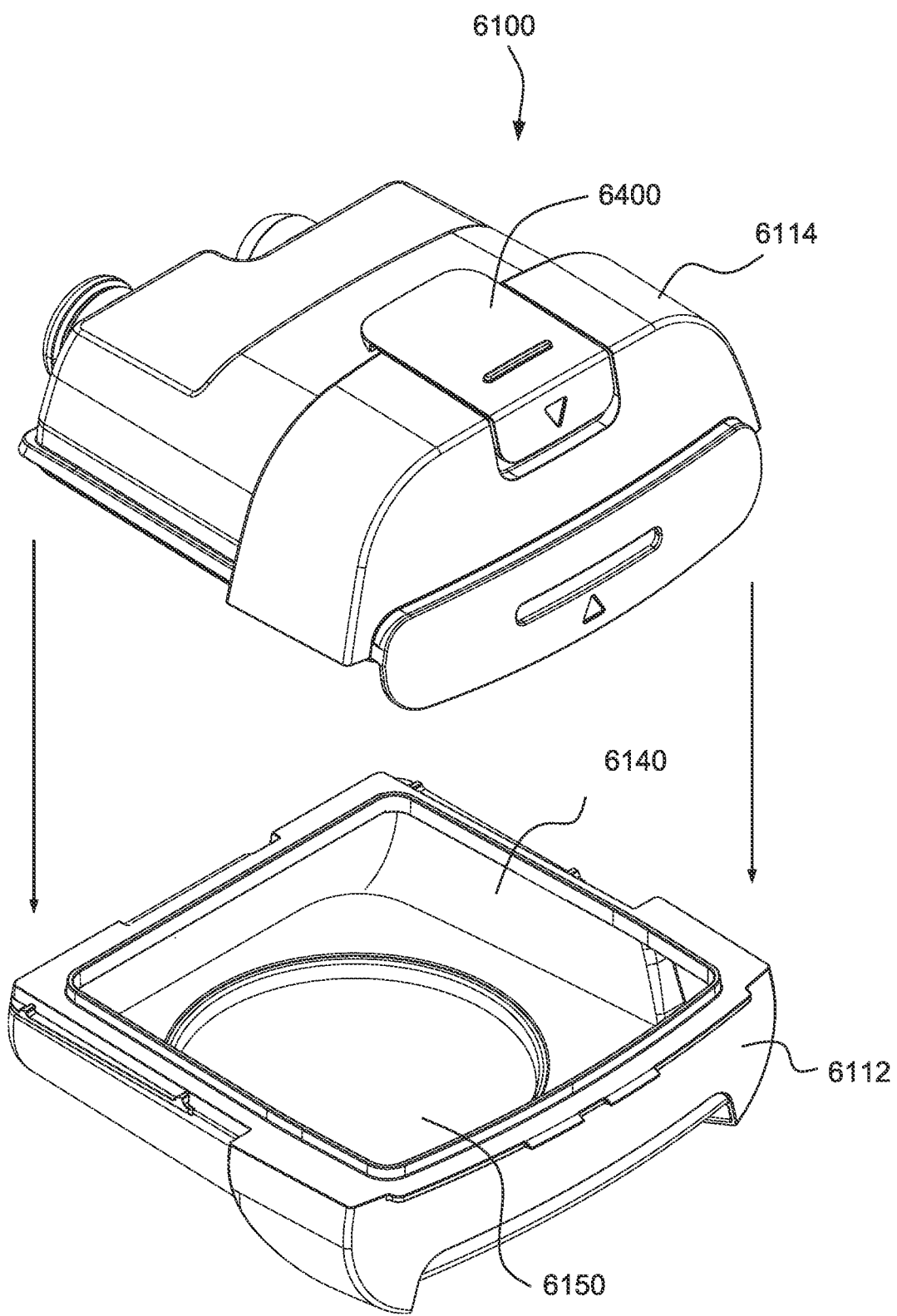

FIG. 9 is an exploded view of a water reservoir including a circular metal plate according to an example of the present technology.

Figure 10A:
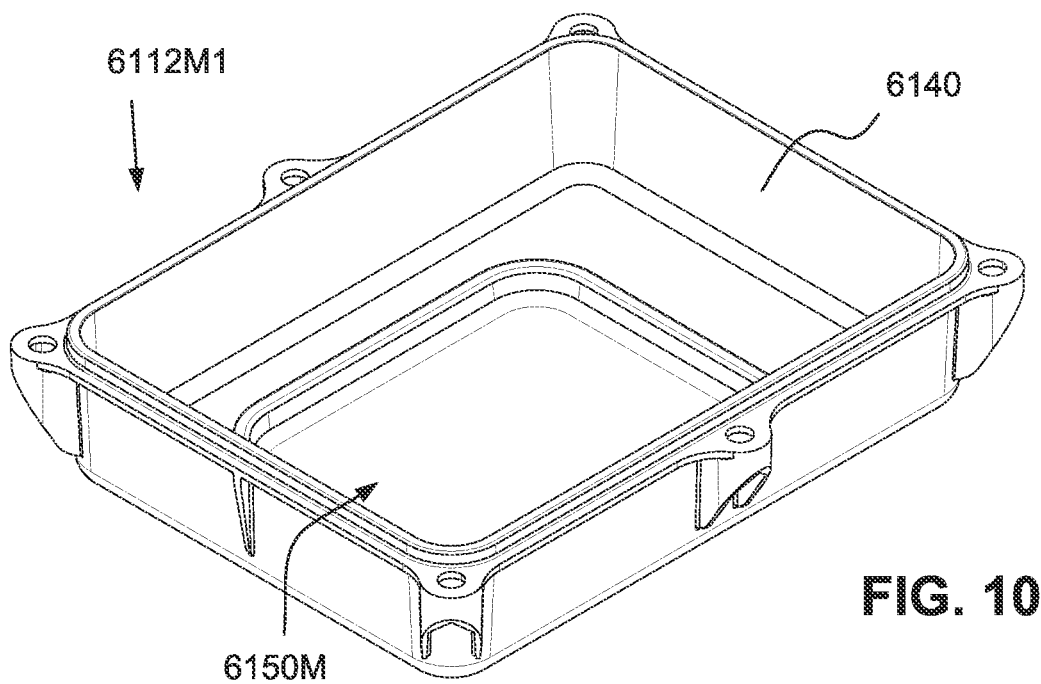

FIG. 10A is a top perspective view of a reservoir base of a humidifier reservoir including a rectangular metal plate according to an example of present technology.

Figure 10B:
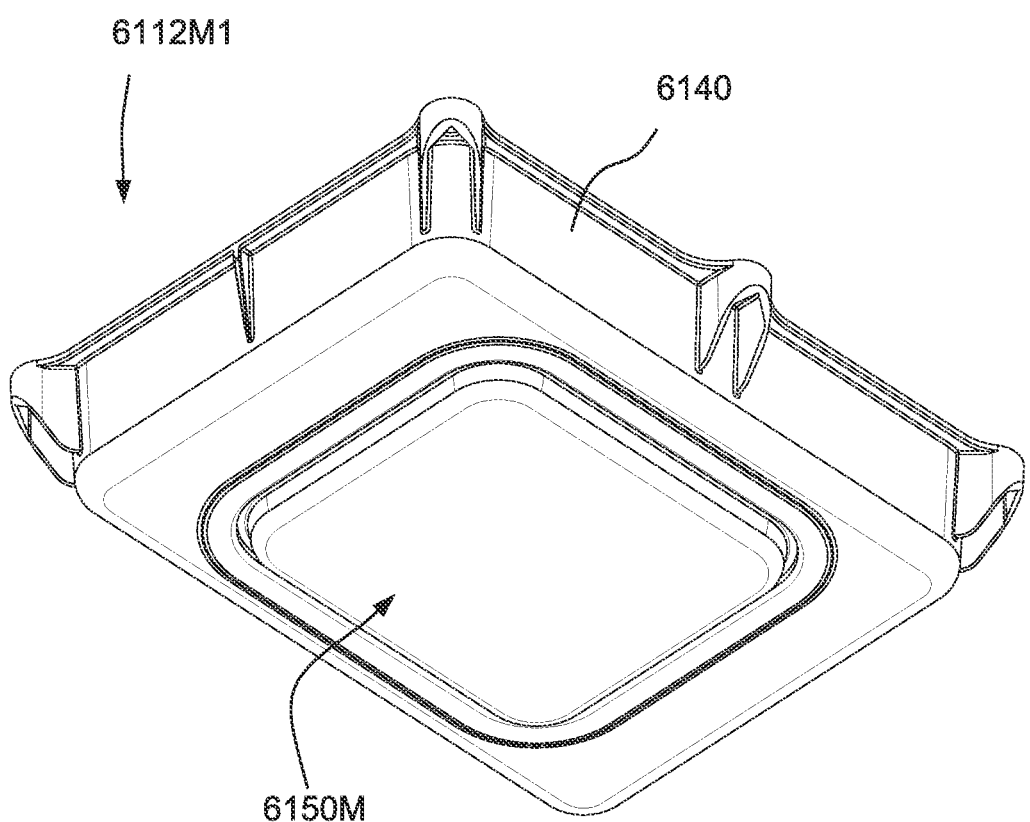

FIG. 10B is a bottom perspective view of the reservoir base of FIG. 10A.

Figure 10C:
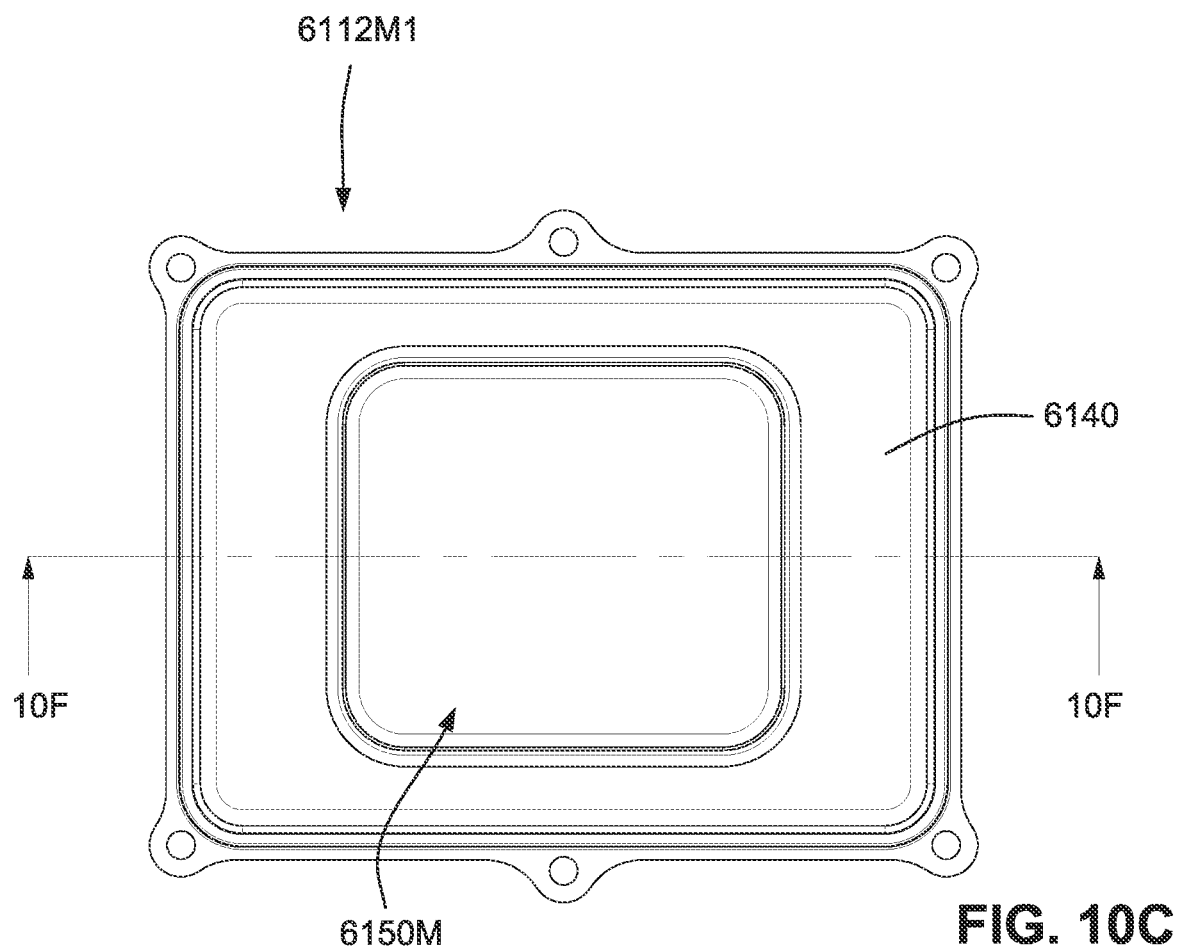

FIG. 10C is a top view of the reservoir base of FIG. 10A.

Figure 10D:
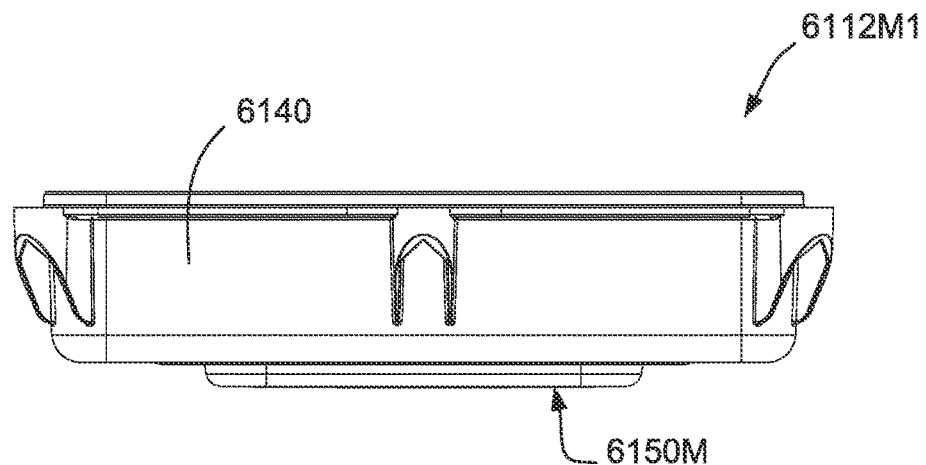

FIG. 10D is a side view of the reservoir base of FIG. 10A.

Figure 10E:
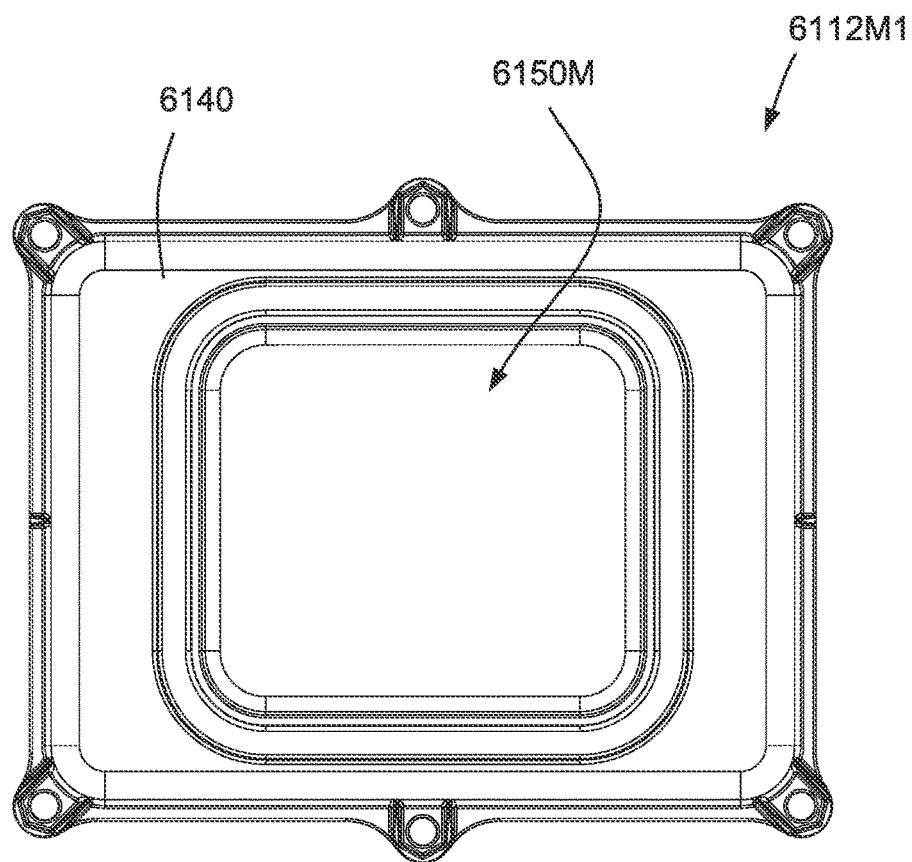

FIG. 10E is a bottom view of the reservoir base of FIG. 10A.

Figure 10F:
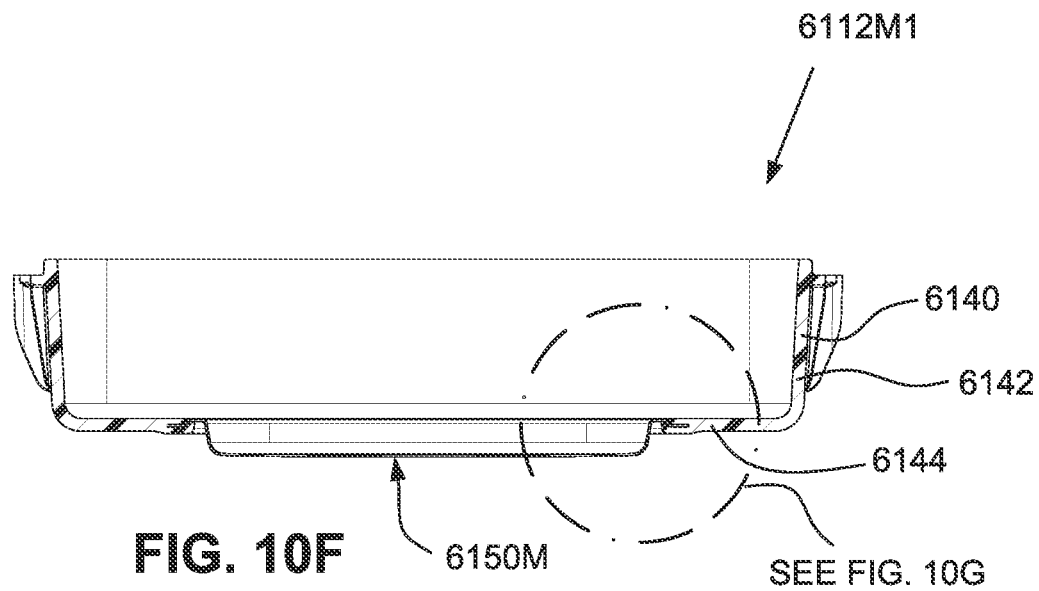

FIG. 10F is a cross-sectional view of the reservoir base taken along line 10F-10F of FIG. 10C according to an example of present technology.

Figure 10G:
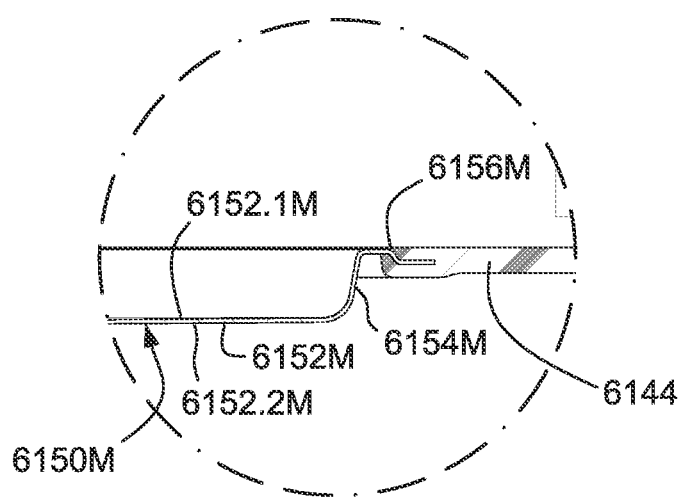

FIG. 10G is an enlarged view of a portion of the reservoir base of FIG. 10F.

Figure 11A:
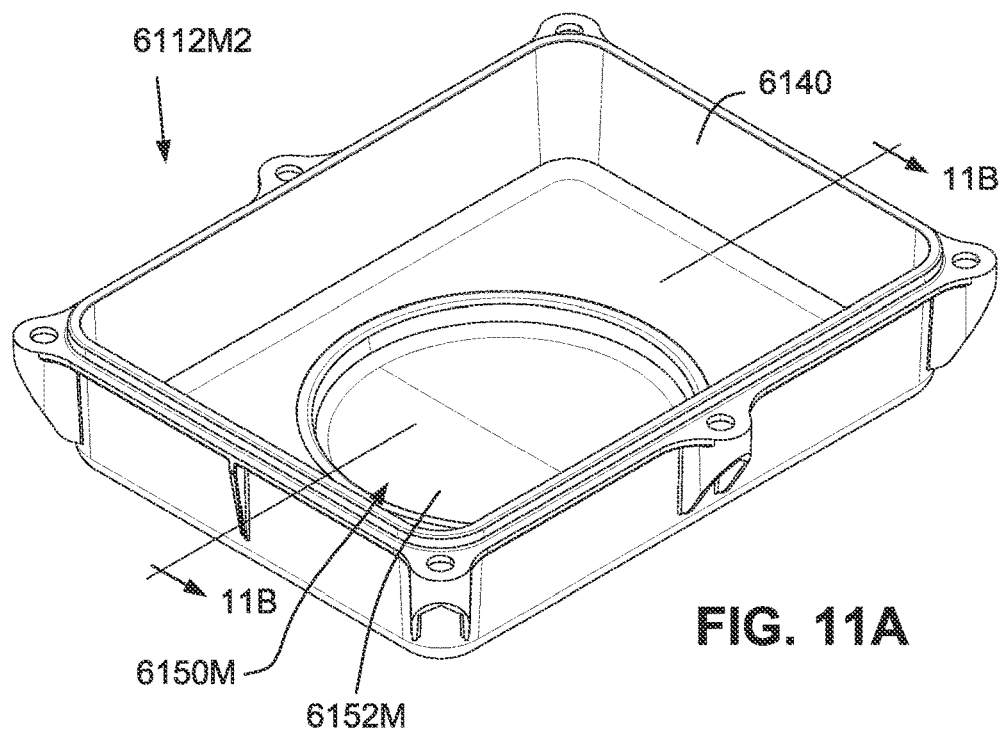

FIG. 11A is a top perspective view of a reservoir base of a humidifier reservoir including a circular metal plate according to an example of present technology.

Figure 11B:
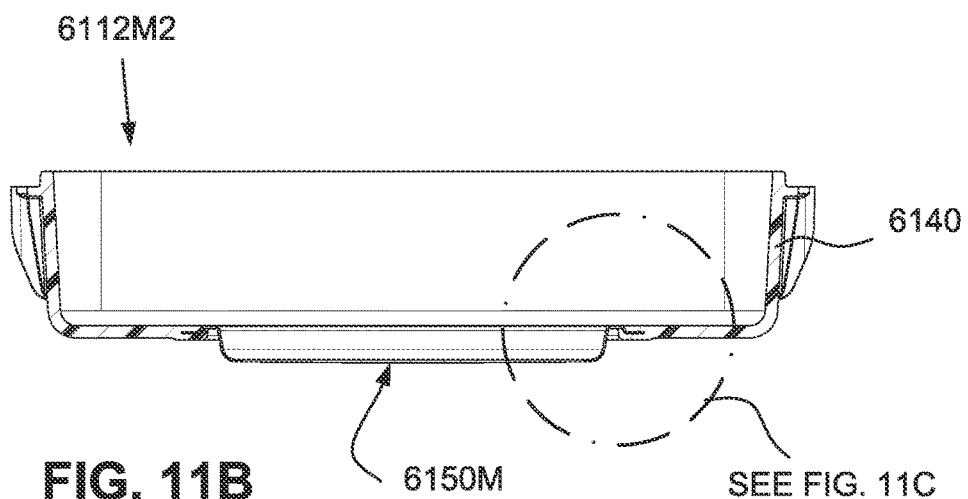

FIG. 11B is a cross-sectional view of the reservoir base taken along ling 11B-11B of FIG. 11A according to an example of present technology.

Figure 11C:
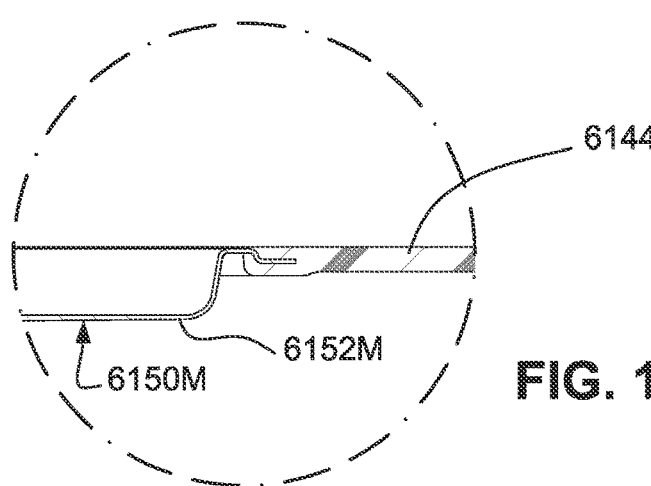

FIG. 11C is an enlarged view of a portion of the reservoir base of FIG. 11B.

Figure 12A:
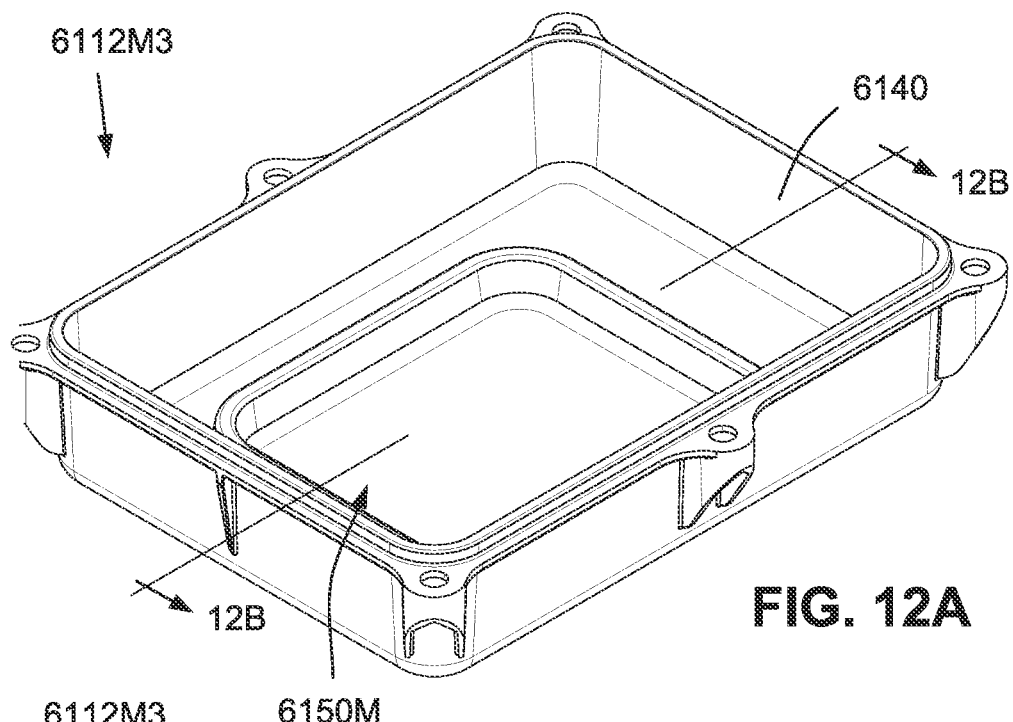

FIG. 12A is a top perspective view of a reservoir base of a humidifier reservoir including a deeper drawn rectangular metal plate according to an example of present technology.

Figure 12B:
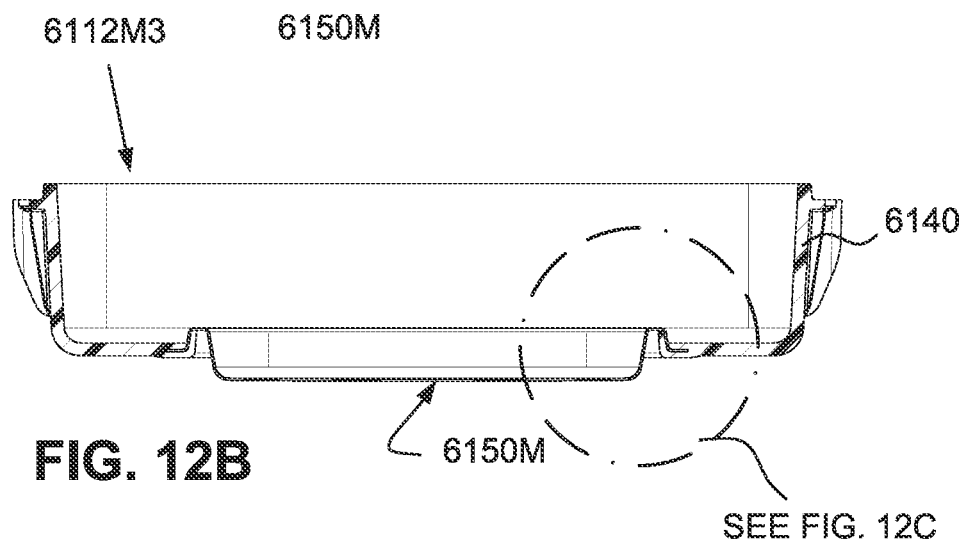

FIG. 12B is a cross-sectional view of the reservoir base taken along line 12B-12B of FIG. 12A according to an example of present technology.

Figure 12C:
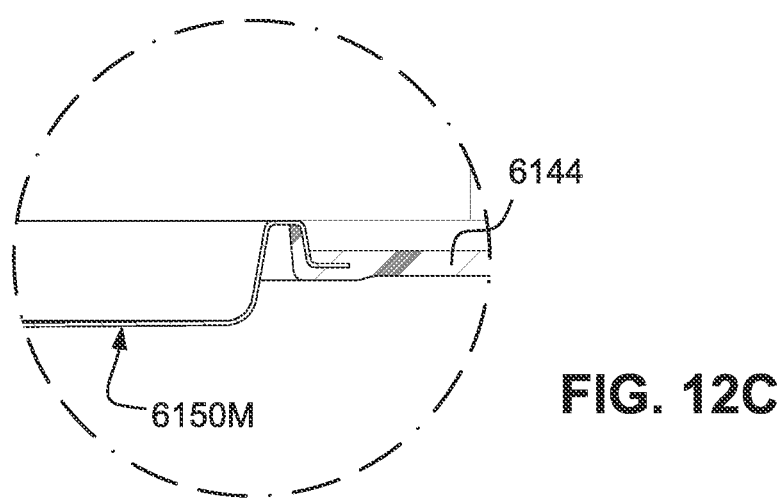

FIG. 12C is an enlarged view of a portion of the reservoir base of FIG. 12B.

Figure 13A:
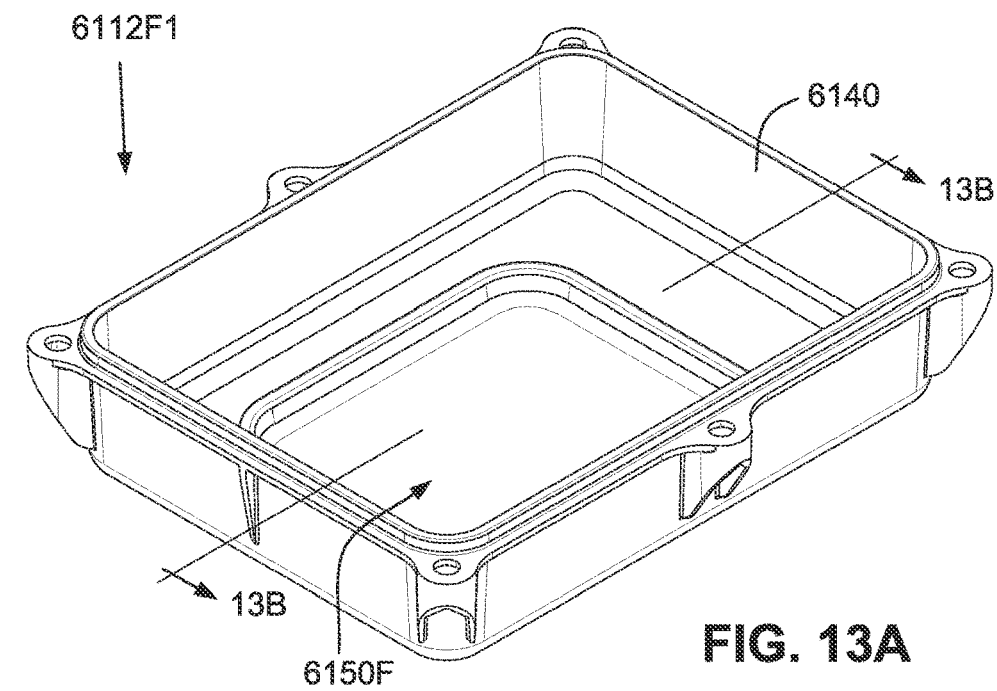

FIG. 13A is a top perspective view of a reservoir base of a humidifier reservoir including a rectangular, thin nonmetallic film according to an example of present technology.

Figure 13B:
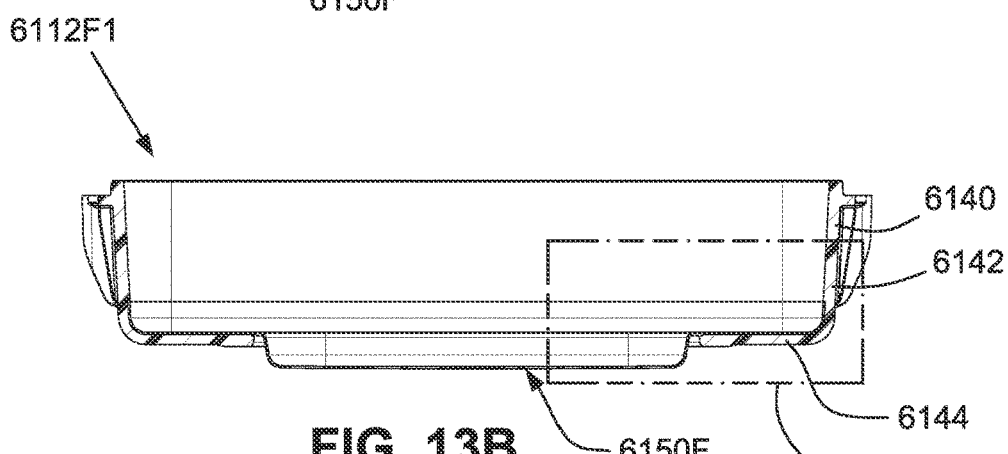

FIG. 13B is a cross-sectional view of the reservoir base taken along line 13B-13B of FIG. 13A according to an example of present technology.

Figure 13C:
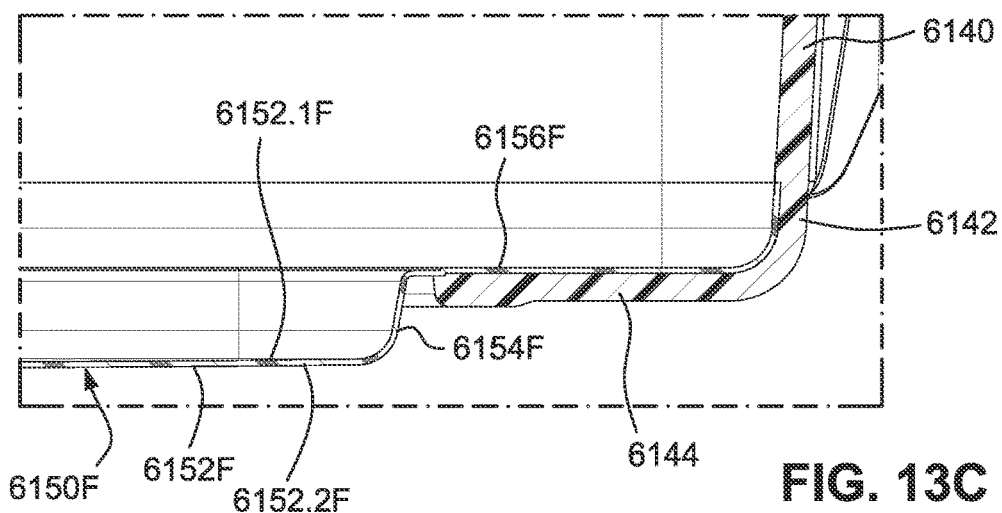

FIG. 13C is an enlarged view of a portion of the reservoir base of FIG. 13B.

Figure 14A:
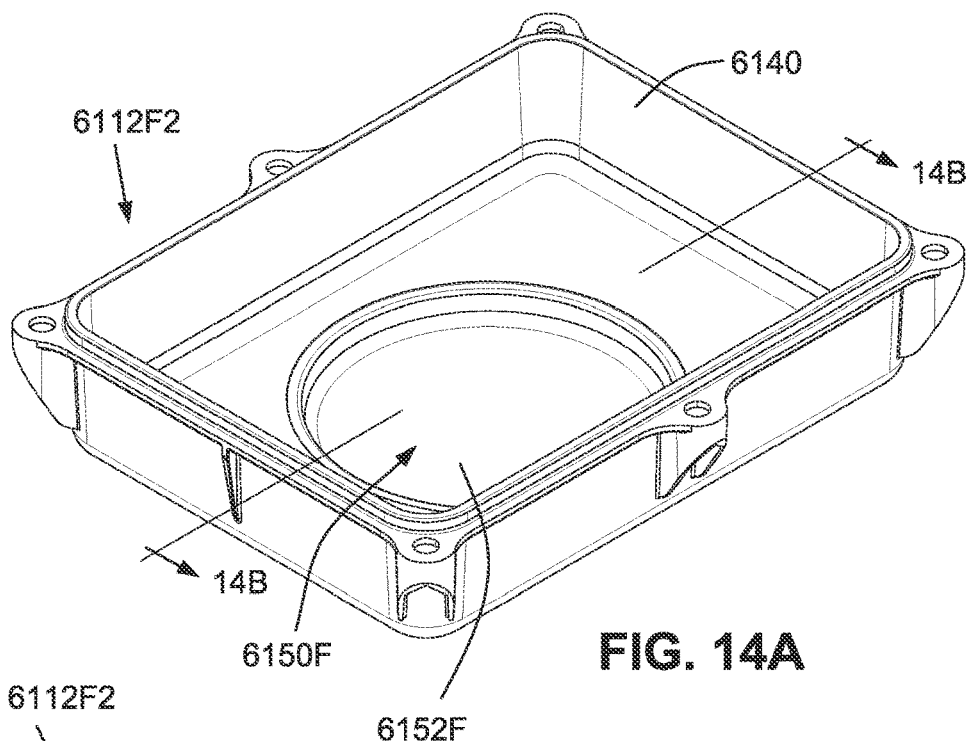

FIG. 14A is a top perspective view of a reservoir base of a humidifier reservoir including a circular, thin non-metallic film according to an example of present technology.

Figure 14B:
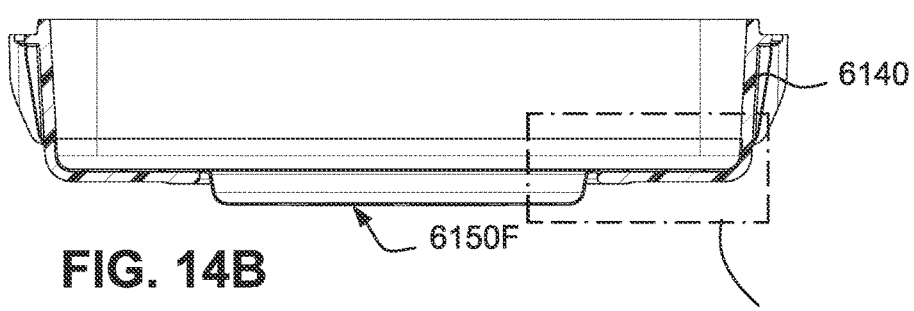

FIG. 14B is a cross-sectional view of the reservoir base taken along line 14B-14B of FIG. 14A according to an example of present technology.

Figure 14C:
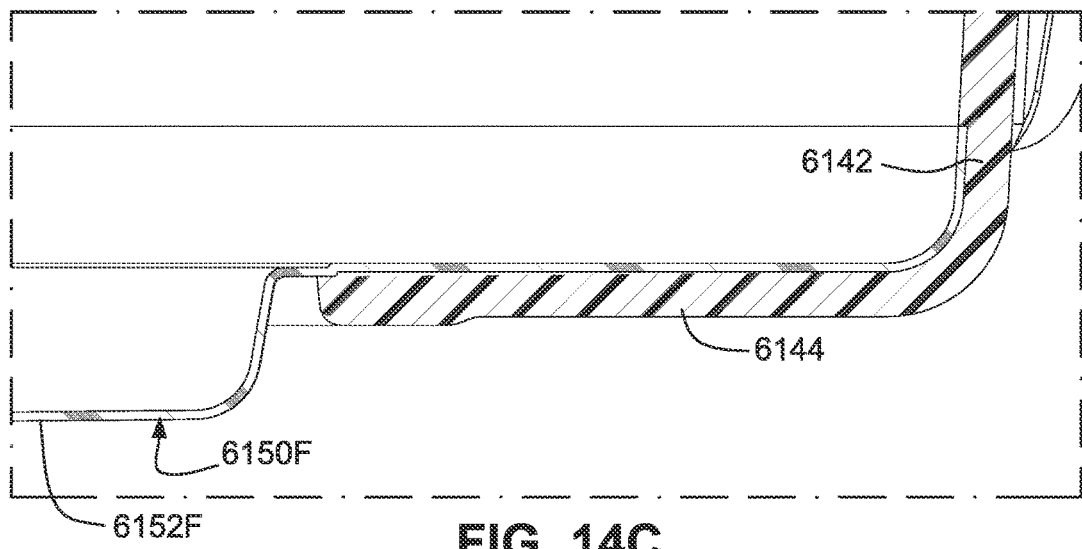

FIG. 14C is an enlarged view of a portion of the reservoir base of FIG. 14B.

Figure 15A:
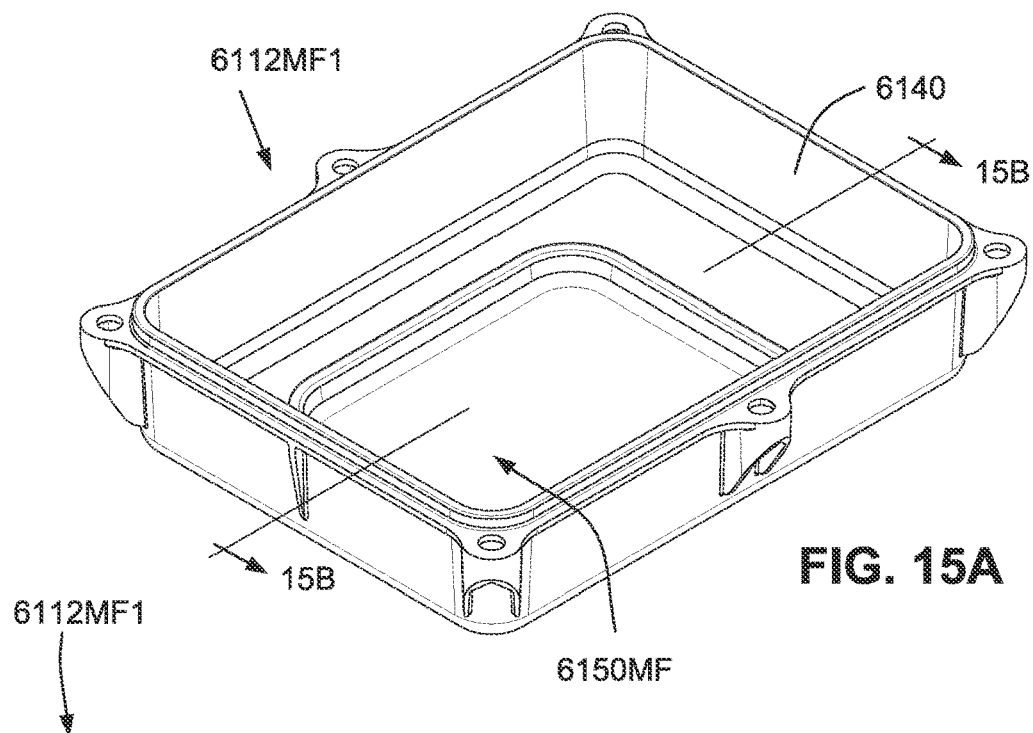

FIG. 15A is a top perspective view of a reservoir base of a humidifier reservoir including a combined layered arrangement of a rectangular, metal plate and thin non-metallic film according to an example of present technology.

Figure 15B:
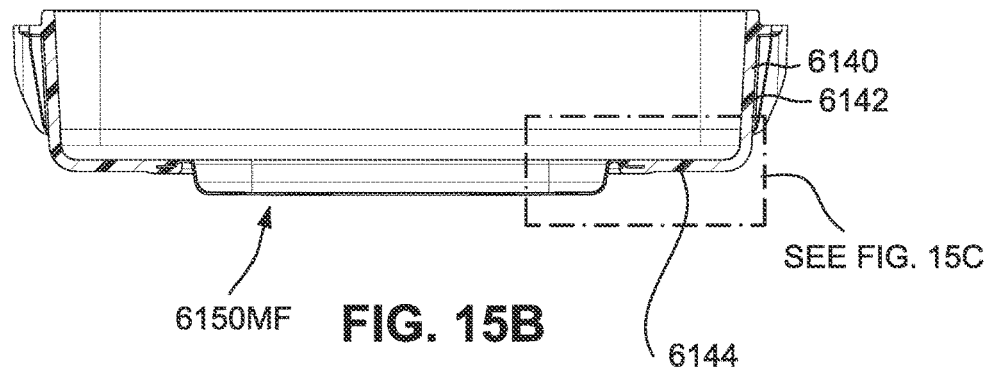

FIG. 15B is a cross-sectional view of the reservoir base taken along line 15B-15B of FIG. 15A according to an example of present technology.

Figure 15C:
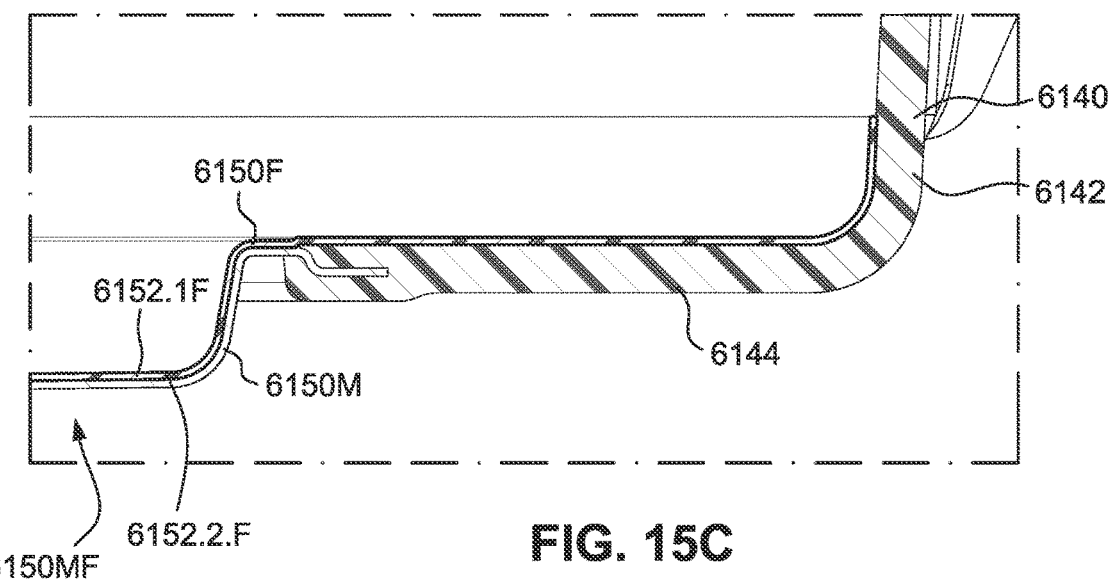

FIG. 15C is an enlarged view of a portion of the reservoir base of FIG. 15B.

Figure 16A:
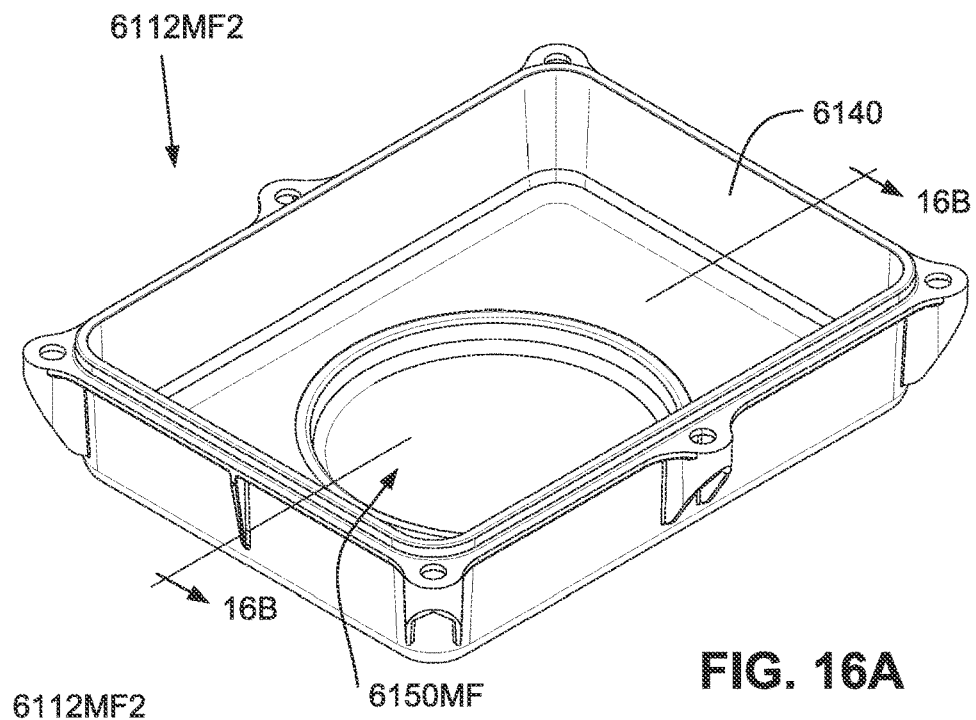

FIG. 16A is a top perspective view of a reservoir base of a humidifier reservoir including a combined layered arrangement of a circular, metal plate and thin non-metallic film according to an example of present technology.

Figure 16B:
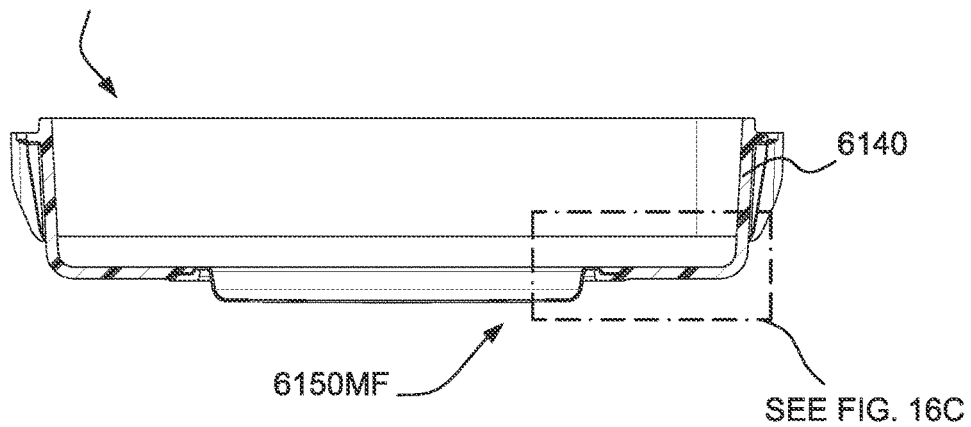

FIG. 16B is a cross-sectional view of the reservoir base taken along line 16B-16B of FIG. 16A according to an example of present technology.

Figure 16C:
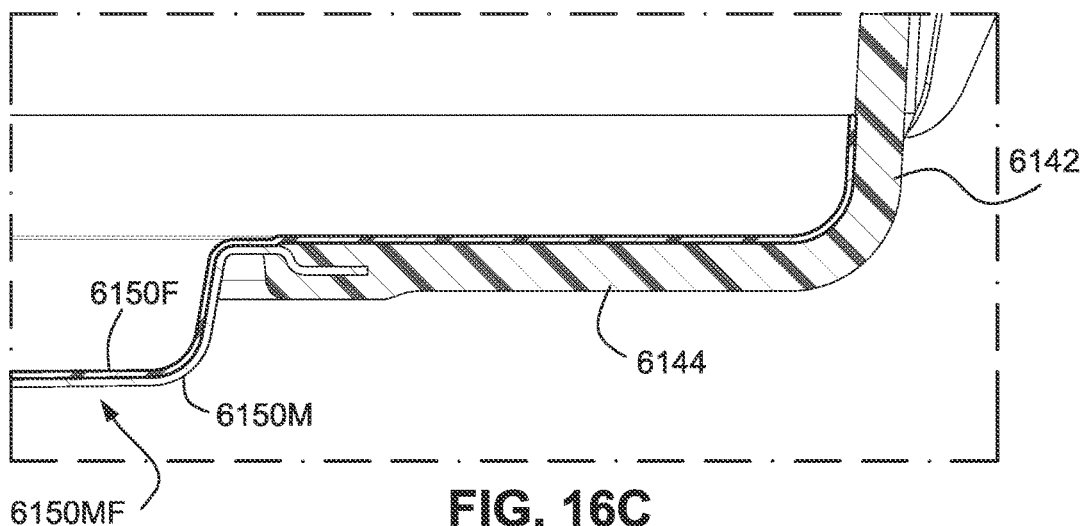

FIG. 16C is an enlarged view of a portion of the reservoir base of FIG. 16B.

Figure 17A:
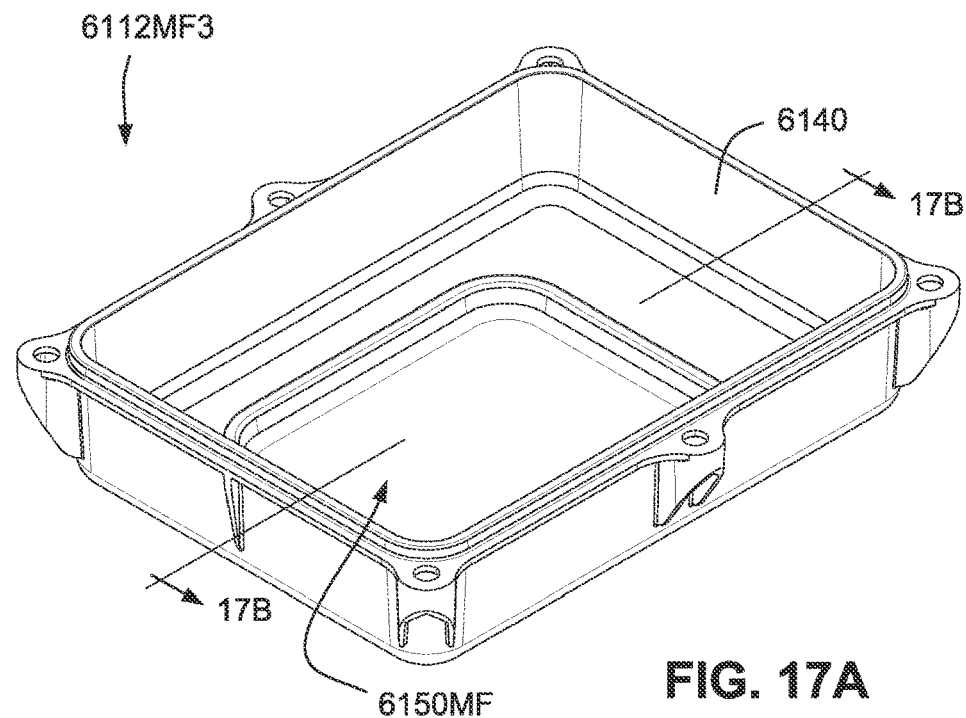

FIG. 17A is a top perspective view of a reservoir base of a humidifier reservoir including a combined layered arrangement of a deeper drawn rectangular, metal plate and thin non-metallic film according to an example of present technology.

Figure 17B:
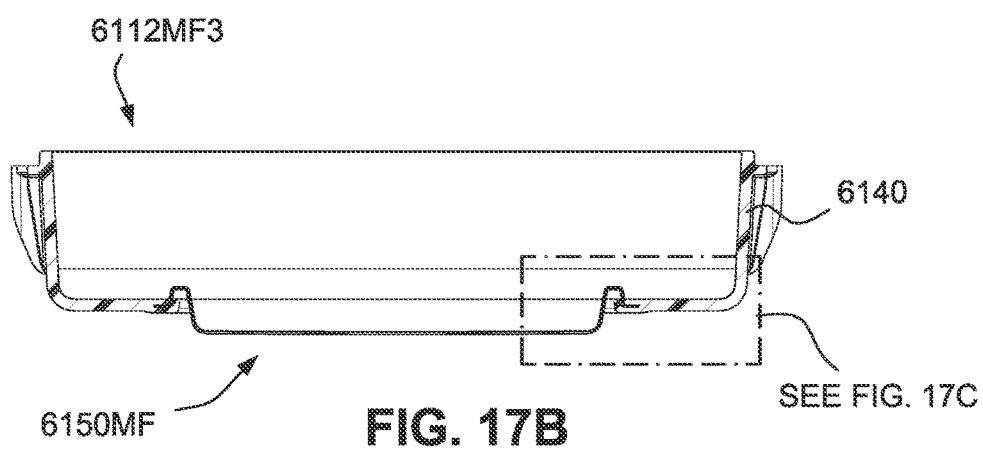

FIG. 17B is a cross-sectional view of the reservoir base taken along line 17B-17B of FIG. 17A according to an example of present technology.

Figure 17C:
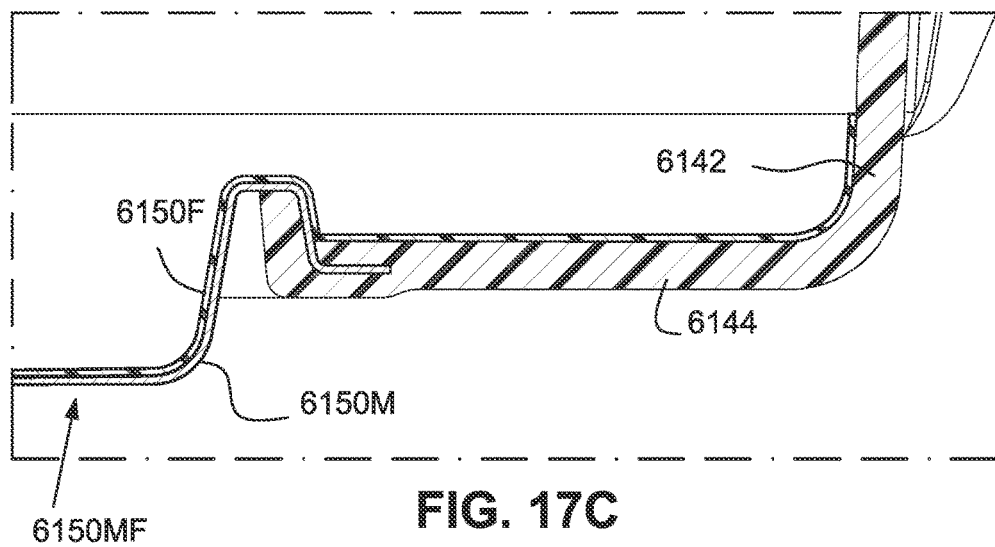

FIG. 17C is an enlarged view of a portion of the reservoir base of FIG. 17B.

Figure 18A:
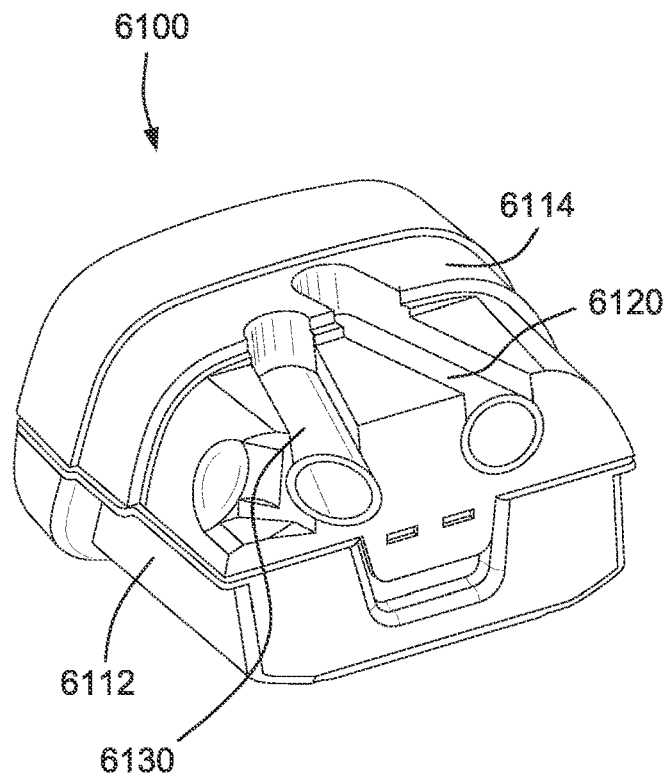

FIG. 18A is a perspective view of a water reservoir according to an example of the present technology.

Figure 18B:
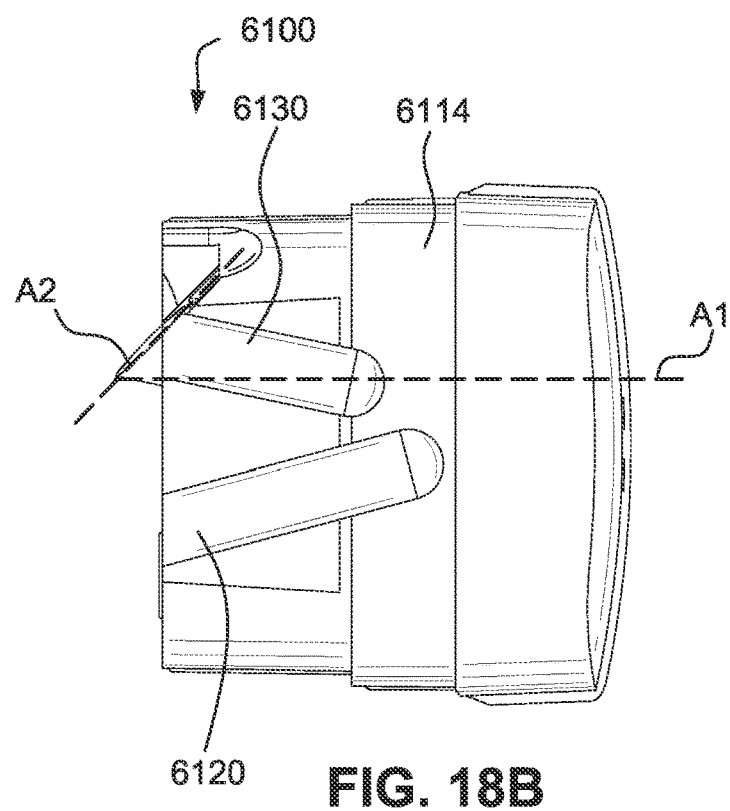

FIG. 18B is a top view of the water reservoir of FIG. 18A.

Figure 19A:
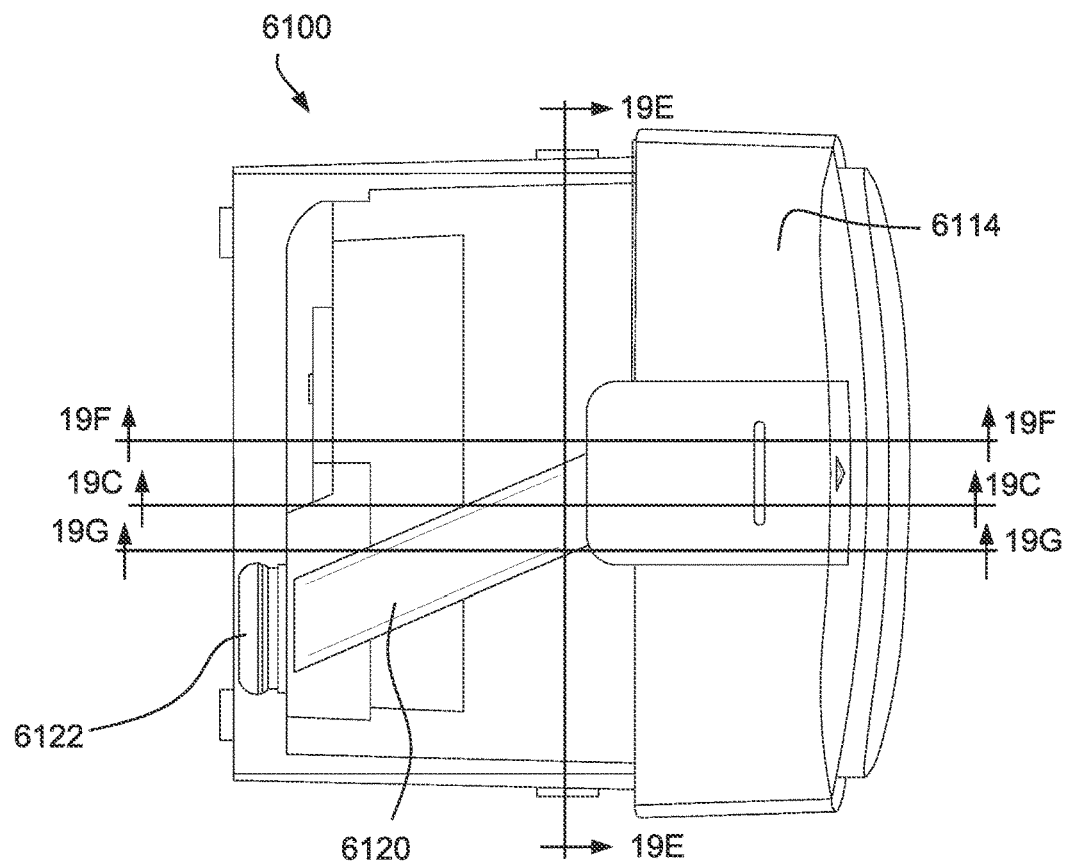

FIG. 19A is a top view of a water reservoir according to an example of the present technology.

Figure 19B:
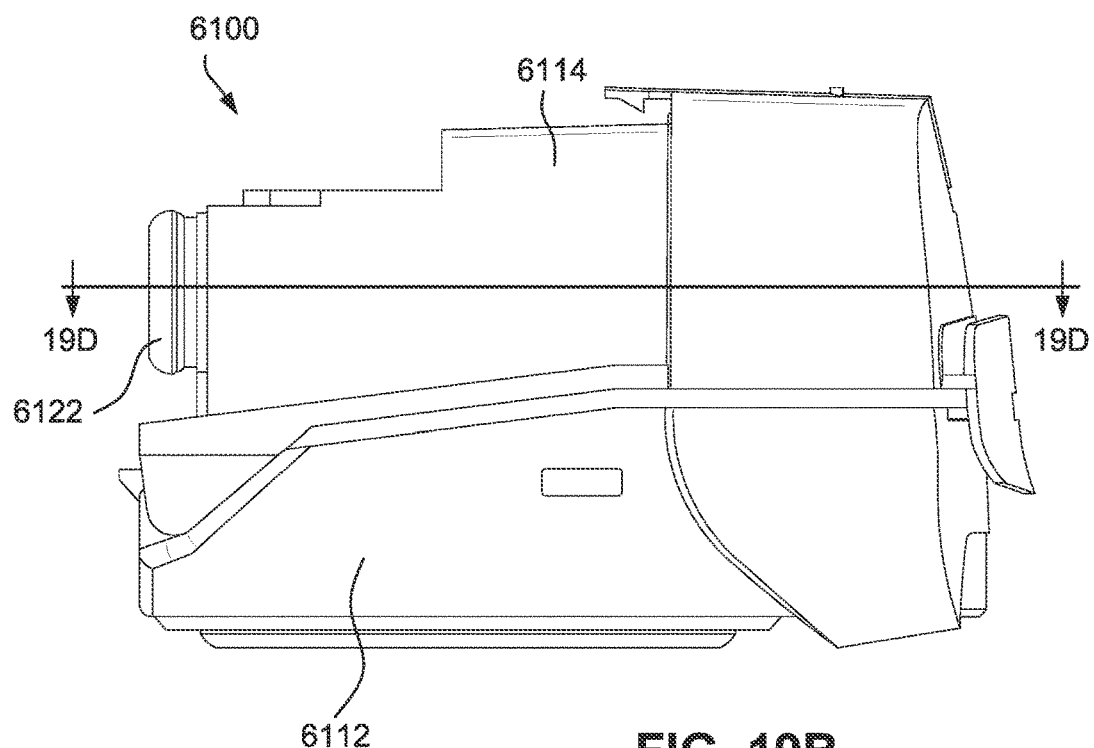

FIG. 19B is a side view of the water reservoir of FIG. 19A.

Figure 19C:
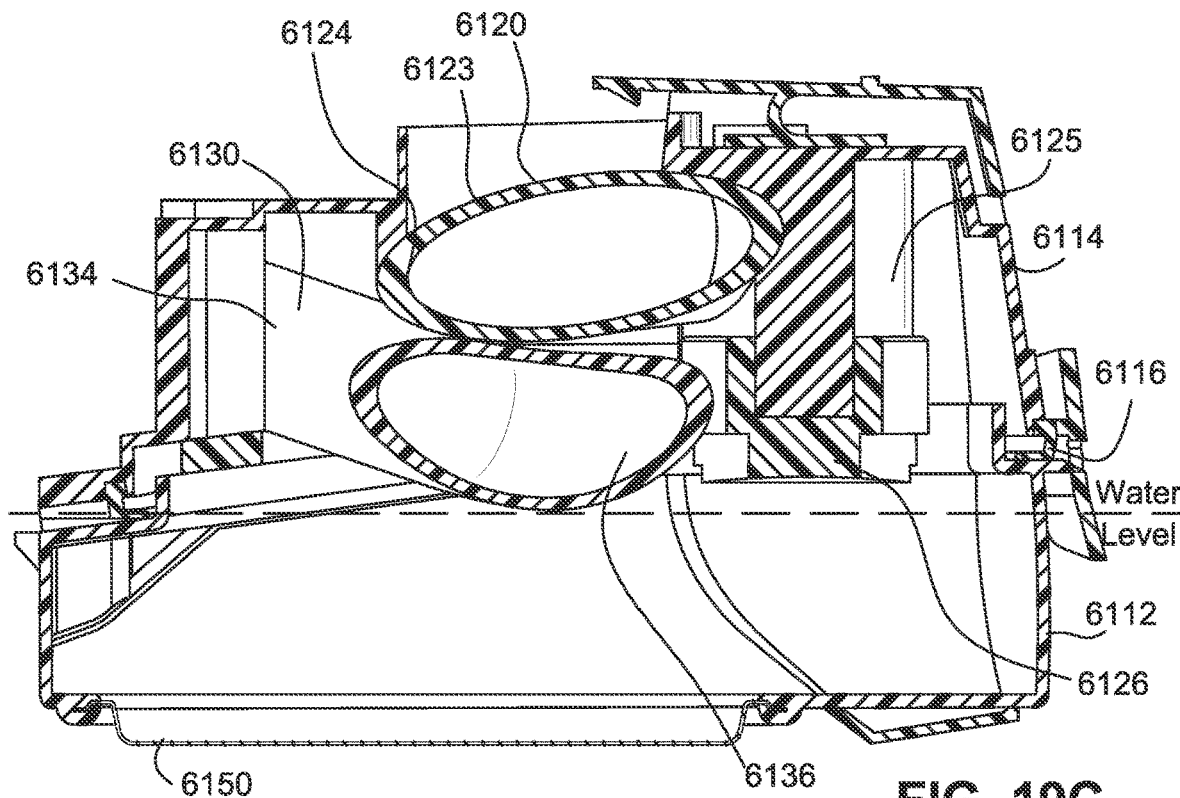

FIG. 19C is a cross-sectional view of the water reservoir taken along line 19C-19C of FIG. 19A showing an inlet tube and outlet tube arrangement according to an example of the present technology.

Figure 19D:
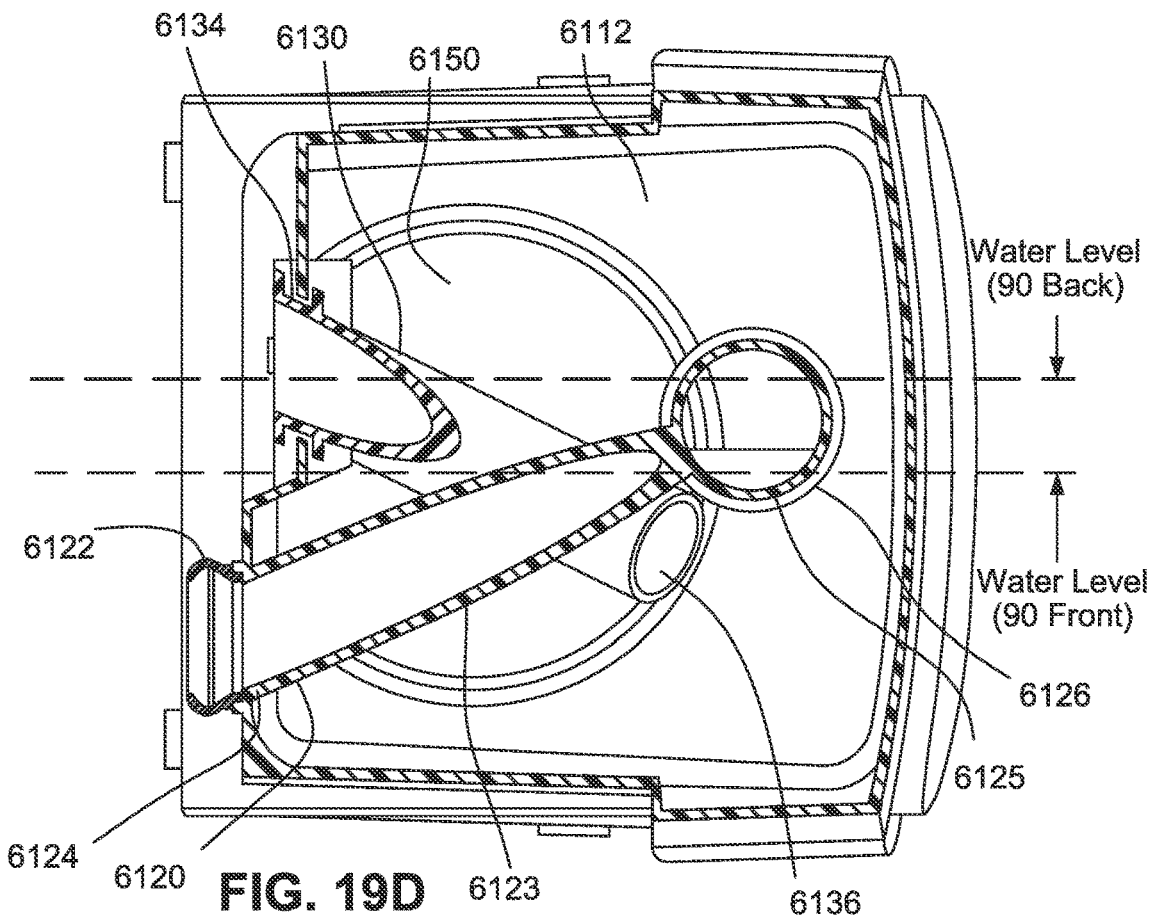

FIG. 19D is a cross-sectional view of the water reservoir taken along line 19D-19D of FIG. 19B showing the inlet tube and outlet tube arrangement according to an example of the present technology.

Figure 19E:
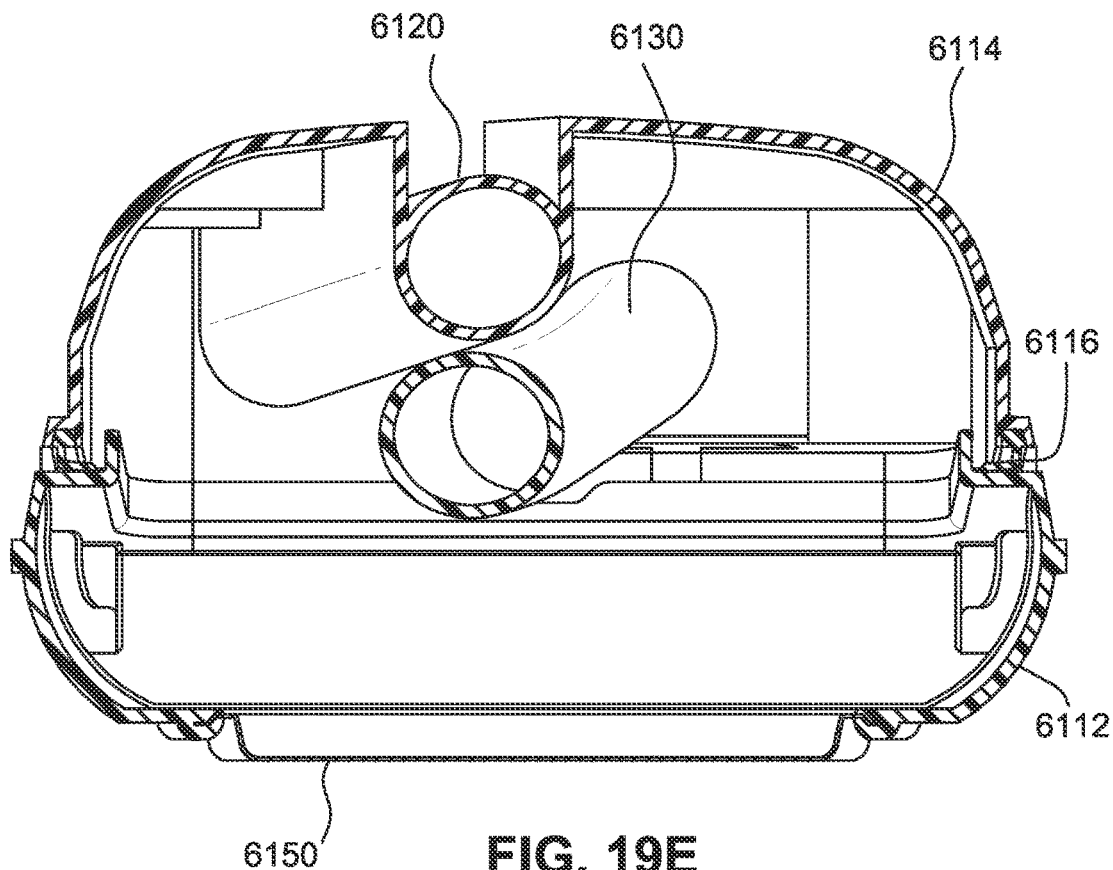

FIG. 19E is a cross-sectional view of the water reservoir taken along line 19E-19E of FIG. 19A showing the inlet tube and outlet tube arrangement according to an example of the present technology.

Figure 19F:
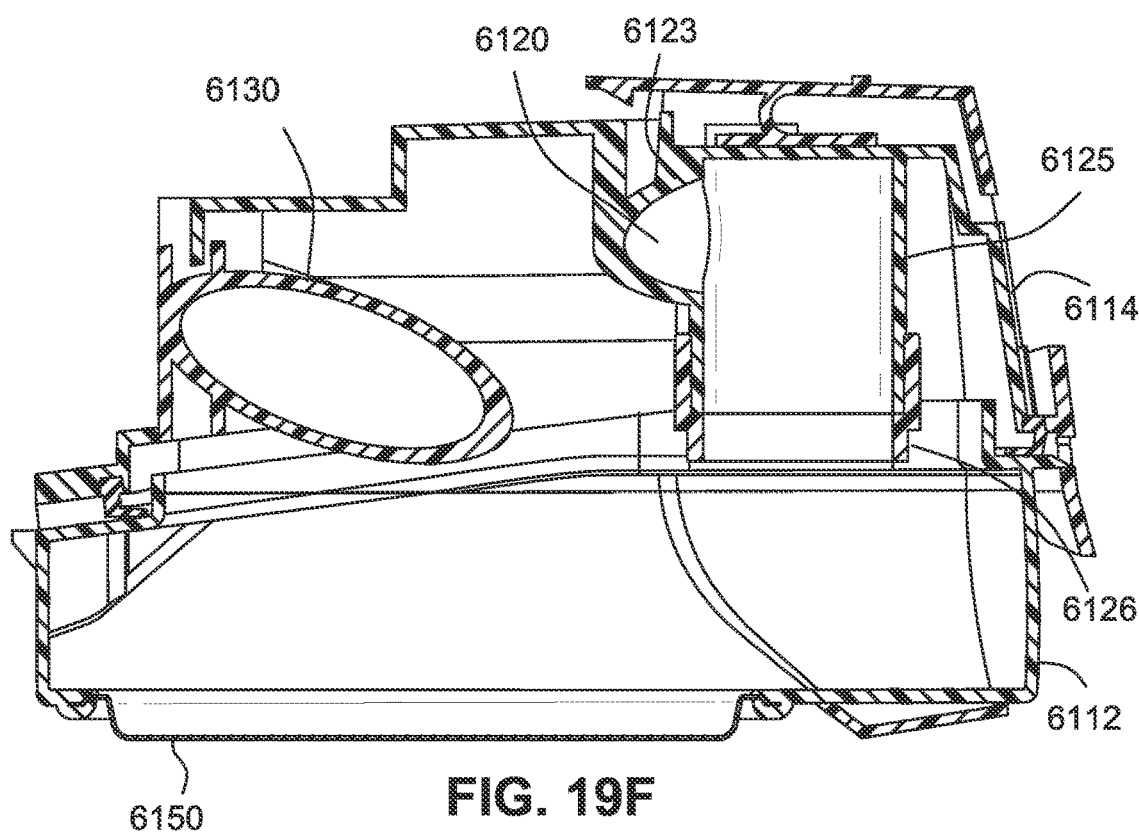

FIG. 19F is a cross-sectional view of the water reservoir taken along line 19F-19F of FIG. 19A showing the inlet tube and outlet tube arrangement according to an example of the present technology.

Figure 19G:
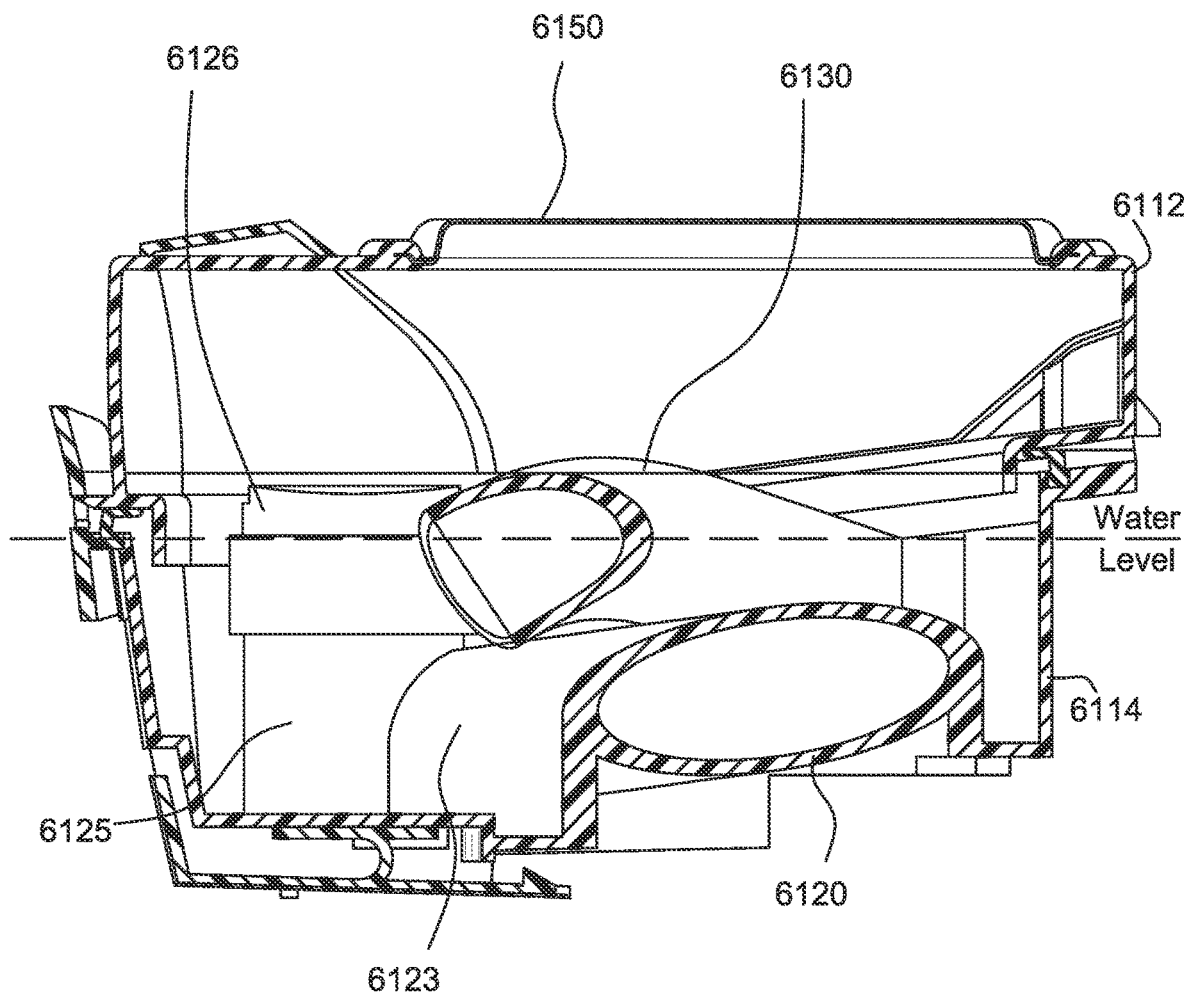

FIG. 19G is a cross-sectional view of the water reservoir taken along line 19G-19G of FIG. 19A showing the inlet tube and outlet tube arrangement according to an example of the present technology, the water reservoir rotated by 180 degrees to show spillback protection provided by the inlet tube and outlet tube arrangement.

Figures 1, 19H:
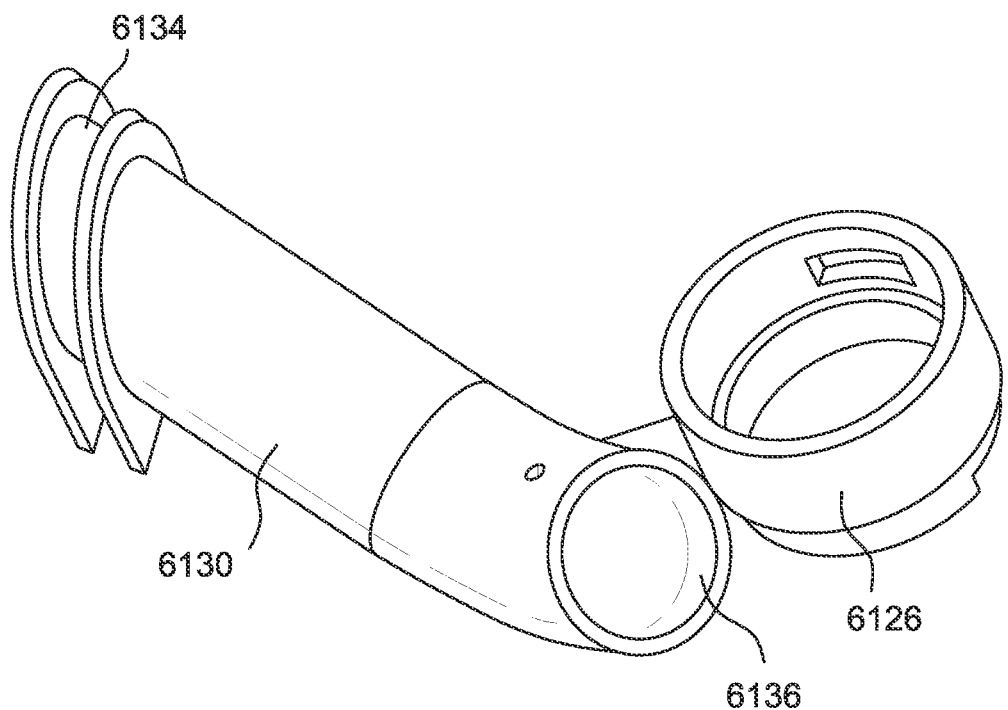

FIG. 19H-1 is a top perspective view of a removable outlet tube arrangement for a water reservoir according to an example of the present technology.

Figures 2, 19H:
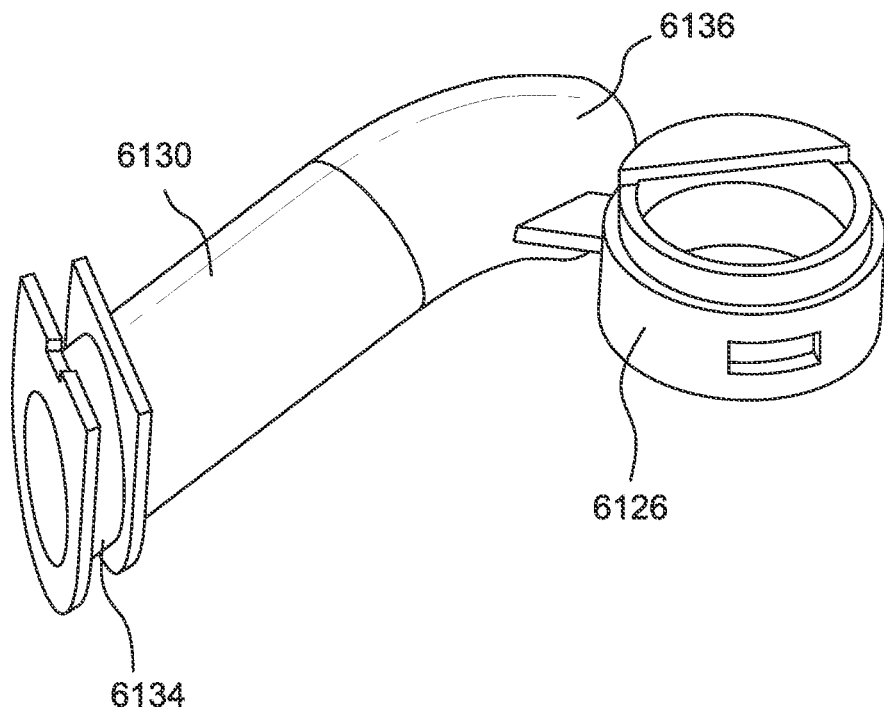

FIG. 19H-2 is a bottom perspective view of the removable outlet tube arrangement of FIG. 19G-1.

Figure 19I:
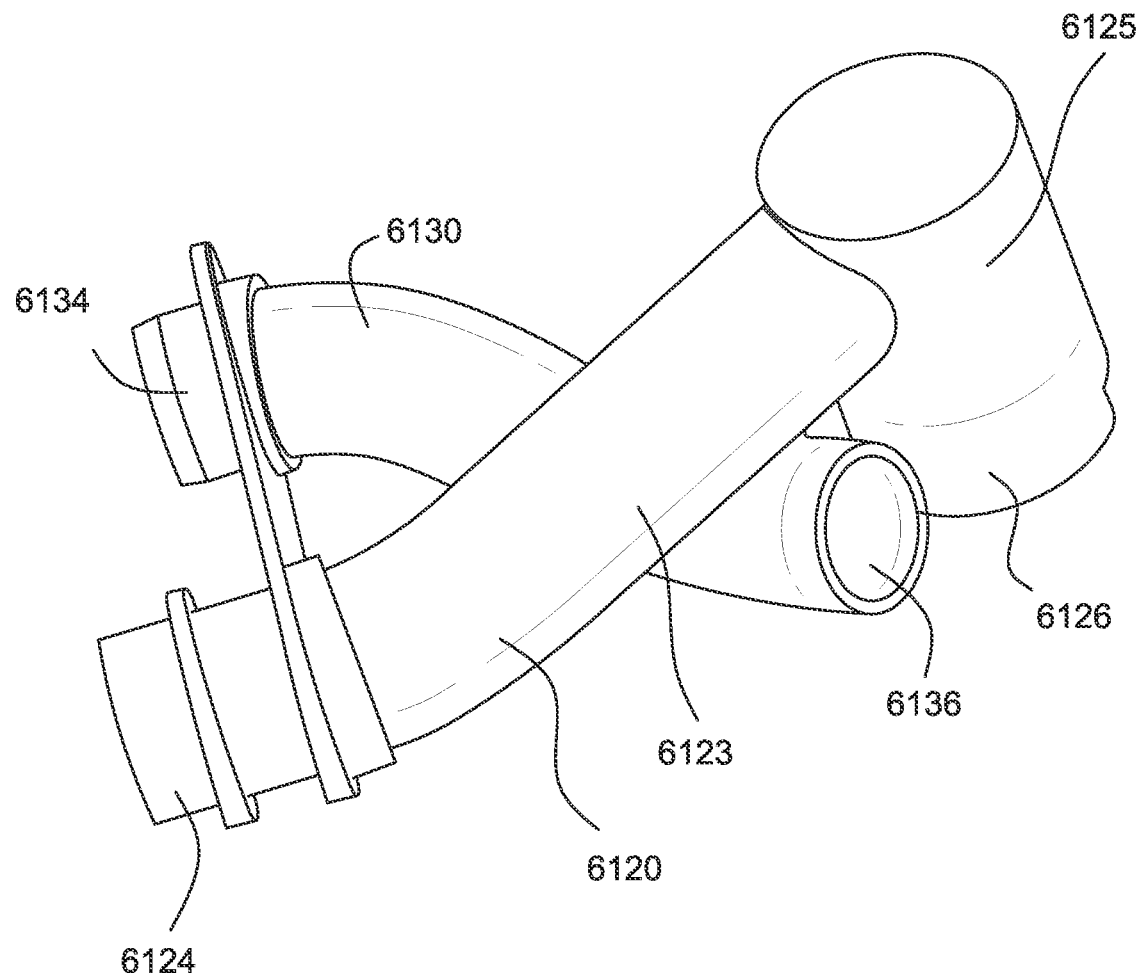

FIG. 19I is a perspective view of a removable inlet tube and outlet tube arrangement for a water reservoir according to an example of the present technology.

Figure 20A:
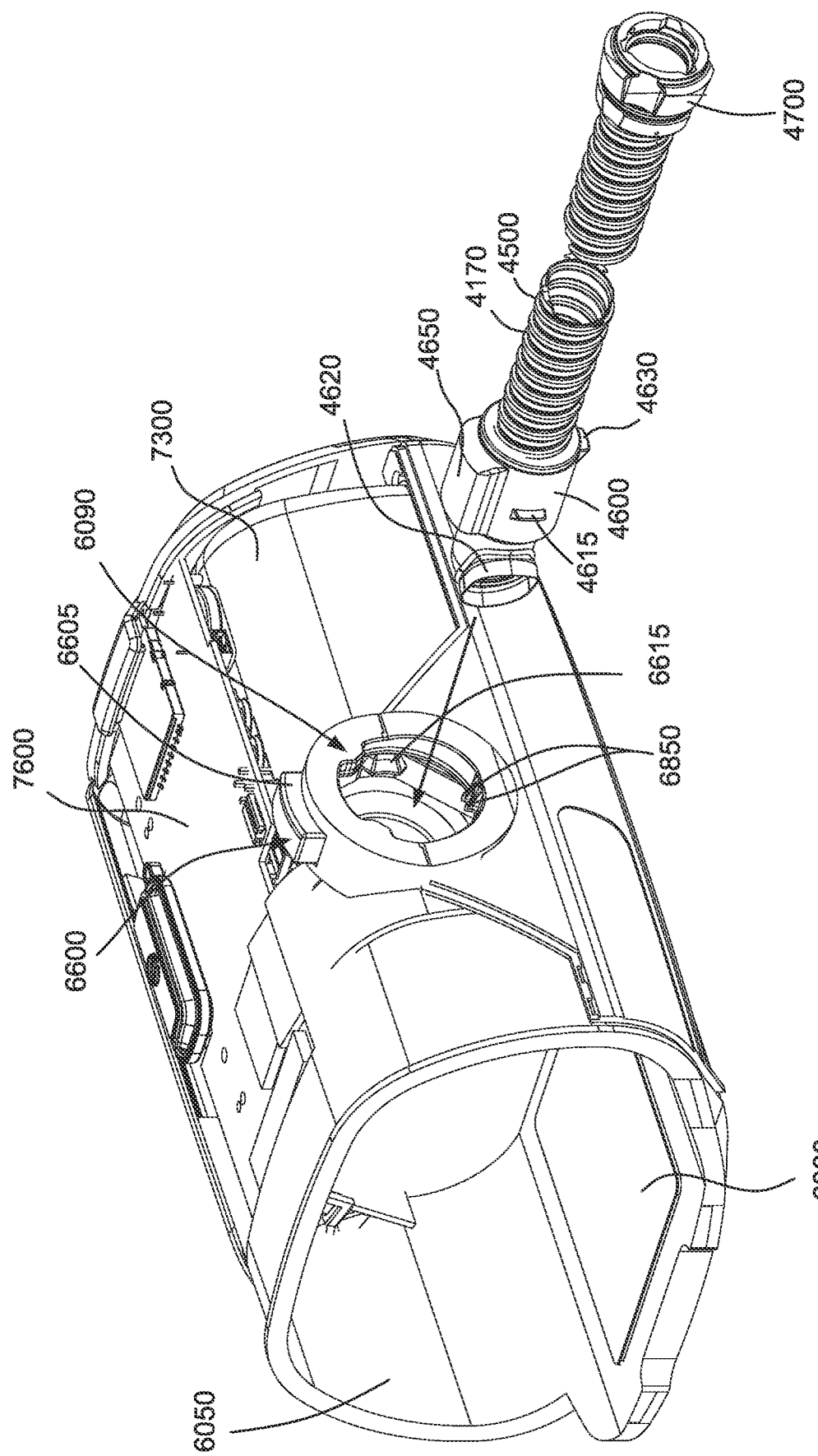

FIG. 20A is a perspective view showing a reservoir dock and an air delivery tube according to an example of the present technology.

Figure 20B:
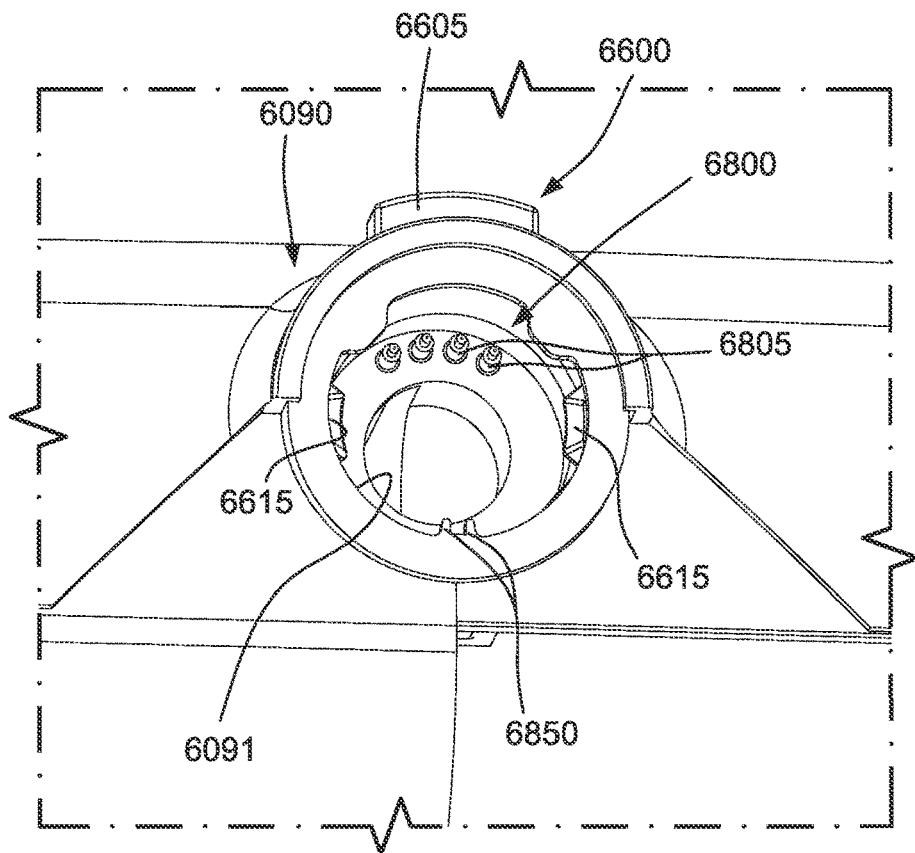

FIG. 20B is a cut-out perspective view showing a dock outlet of a reservoir dock according to an example of the present technology.

Figure 20C:
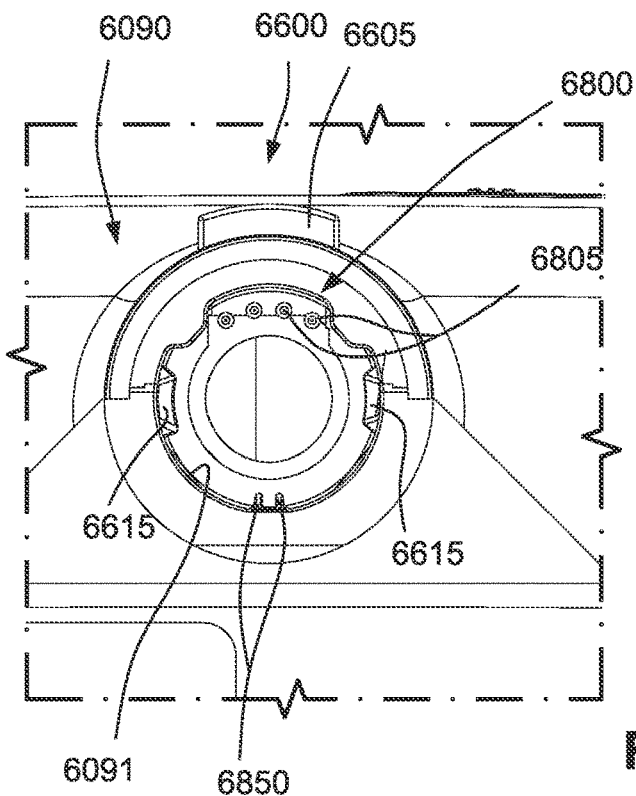

FIG. 20C is a cut-out front view showing a dock outlet of a reservoir dock according to an example of the present technology.

Figure 20D:
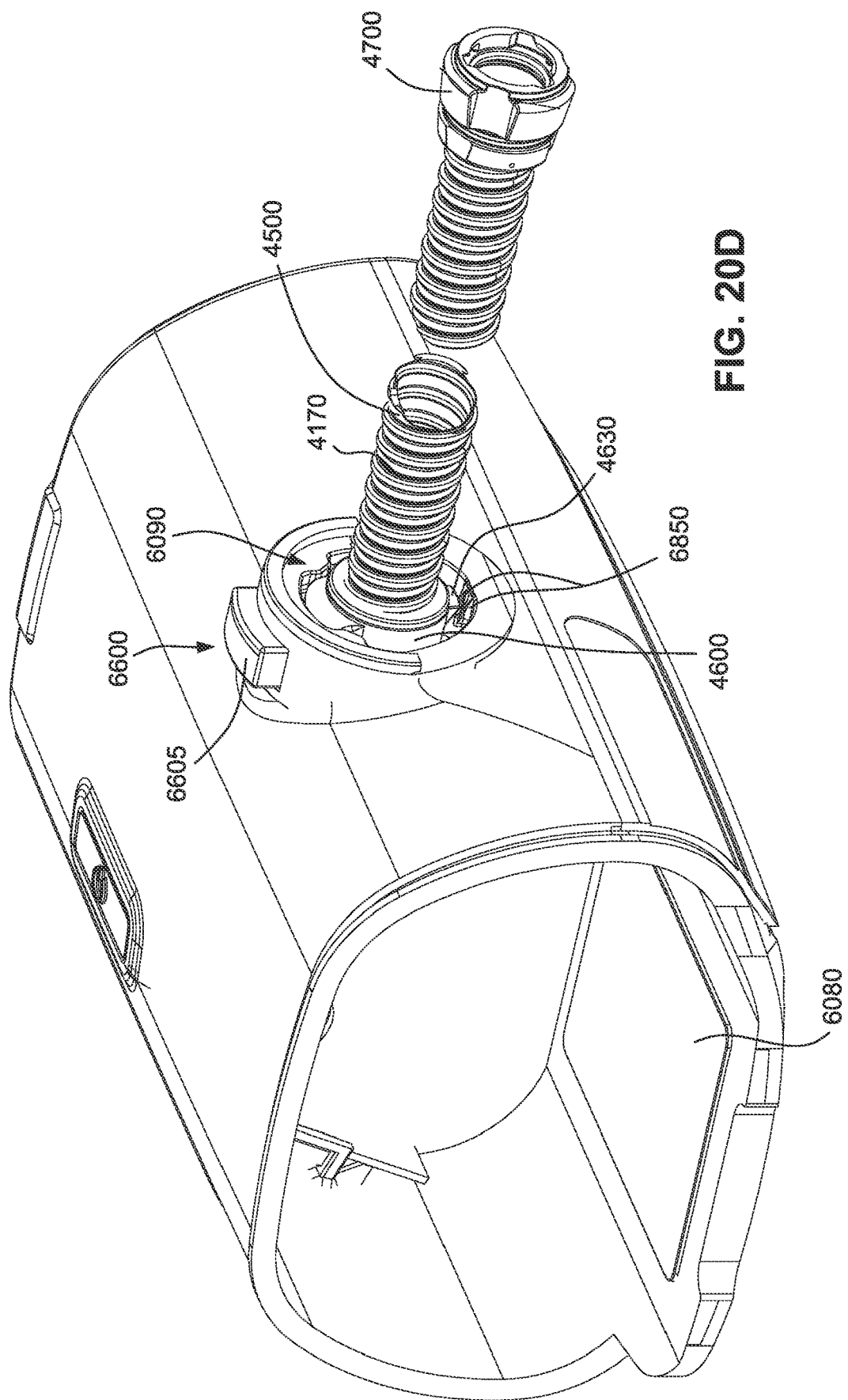

FIG. 20D is a perspective view showing a reservoir dock and an air delivery tube connected to the dock outlet of the reservoir dock according to an example of the present technology.

Figure 20E:
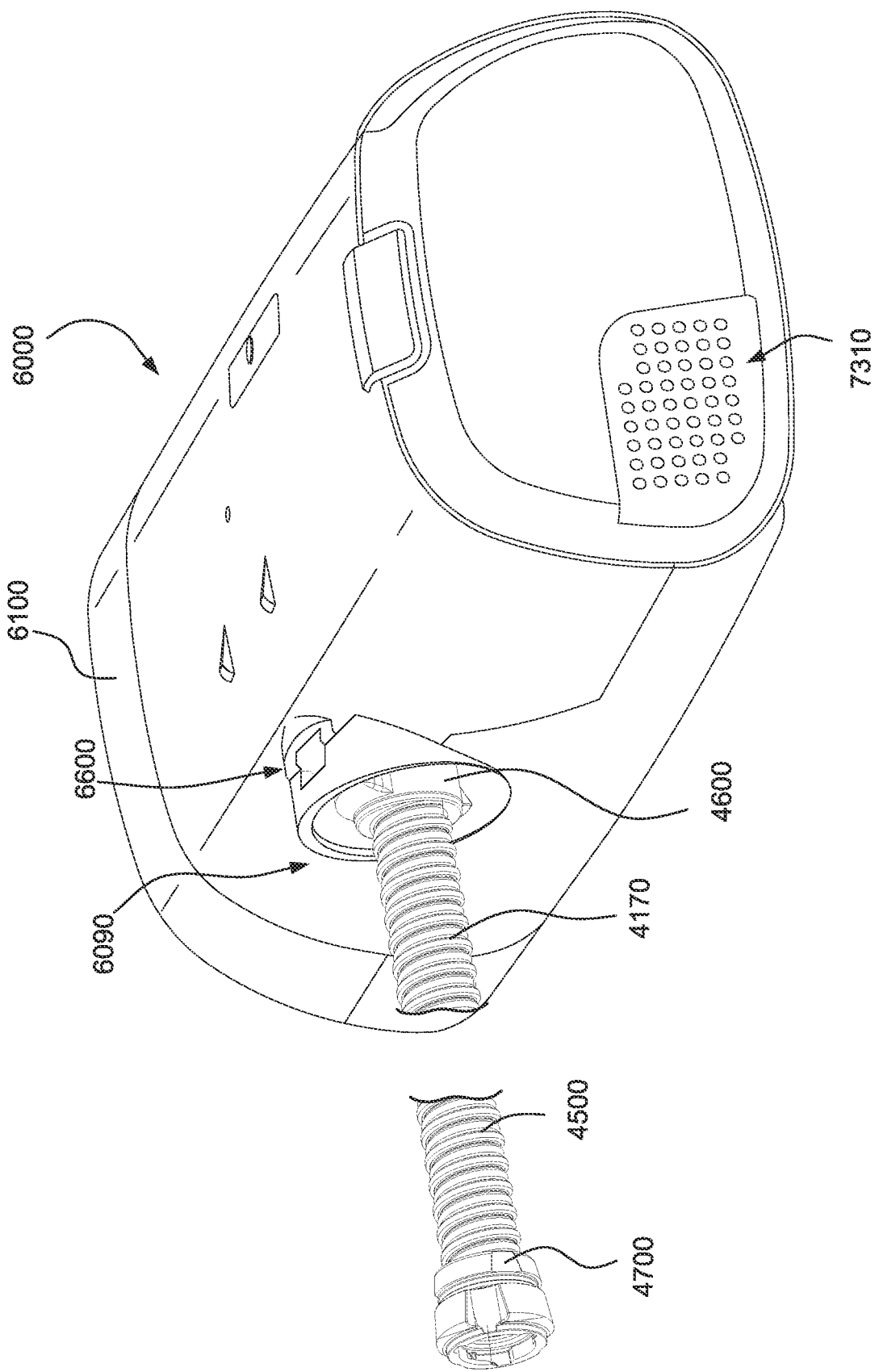

FIG. 20E is another perspective view showing a reservoir dock and an air delivery tube connected to the dock outlet of the reservoir dock according to an example of the present technology.

Figure 20F:
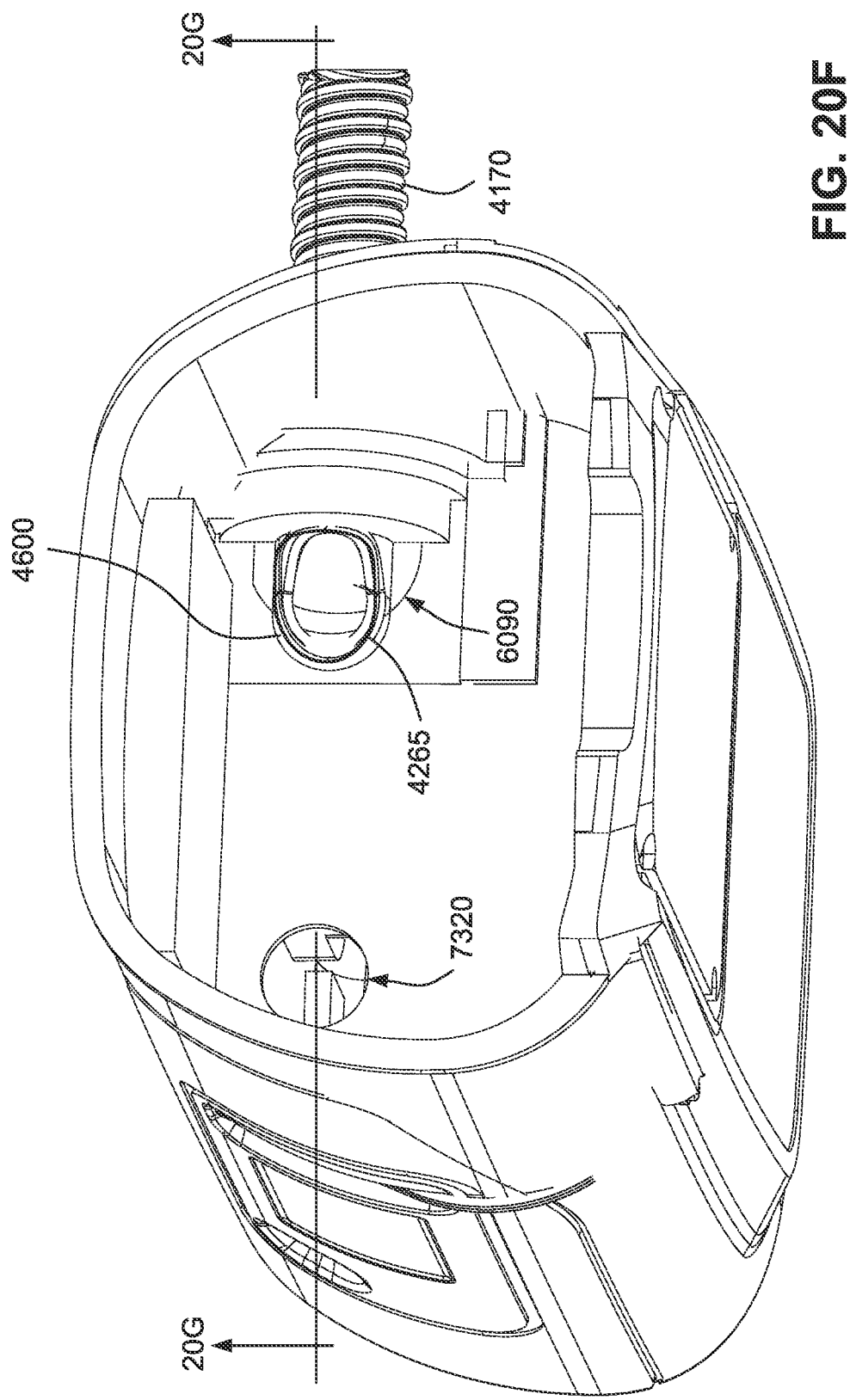

FIG. 20F is another perspective view showing a reservoir dock and an air delivery tube connected to the dock outlet of the reservoir dock according to an example of the present technology.

FIG. 20G is a cross-sectional view along line 20G-20G of FIG. 20F showing a reservoir dock and an air delivery tube connected to the dock outlet of the reservoir dock according to an example of the present technology.

Figure 20H:
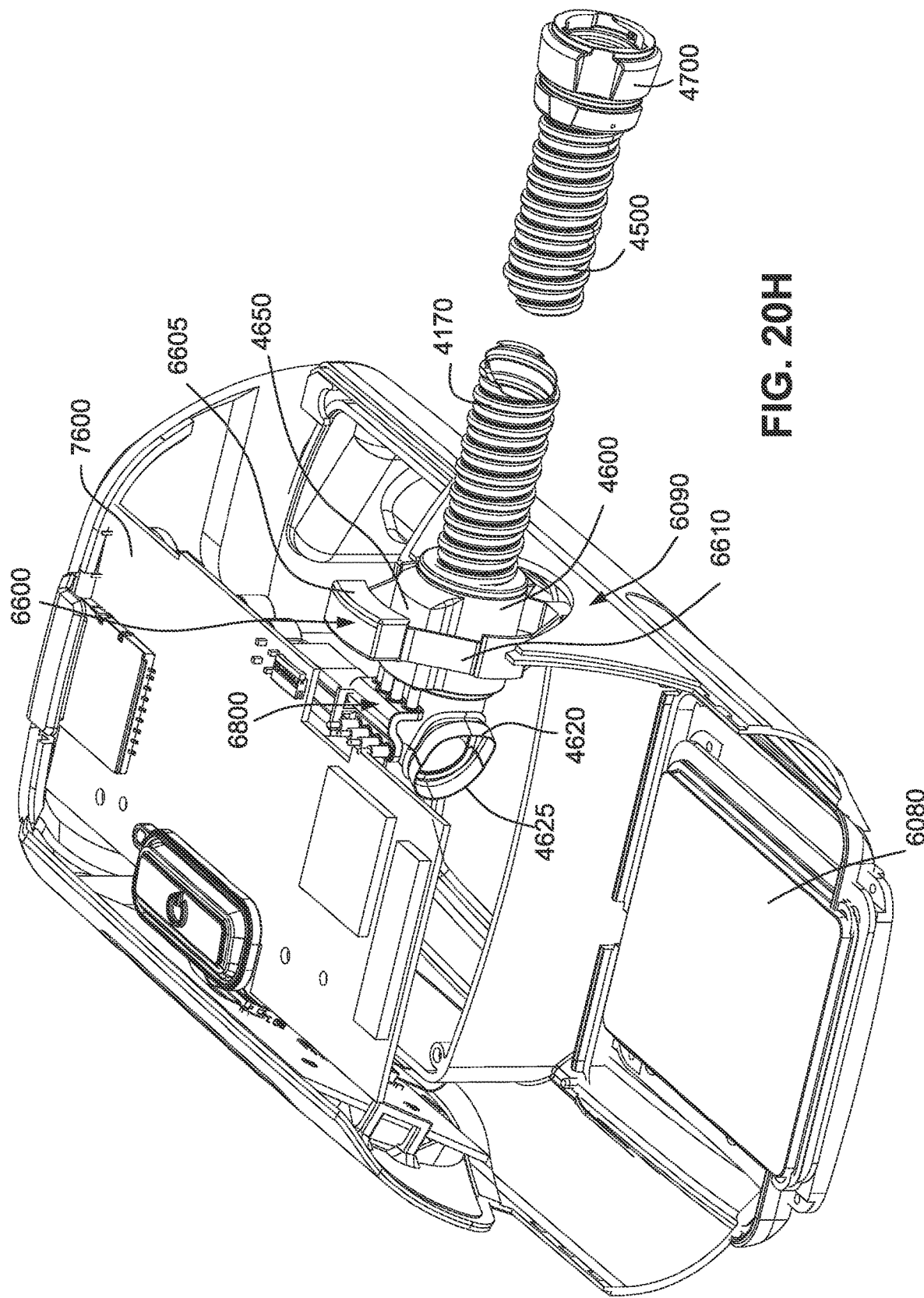

FIG. 20H is another perspective view showing a reservoir dock and an air delivery tube connected to the dock outlet of the reservoir dock according to an example of the present technology.

Figure 20I:
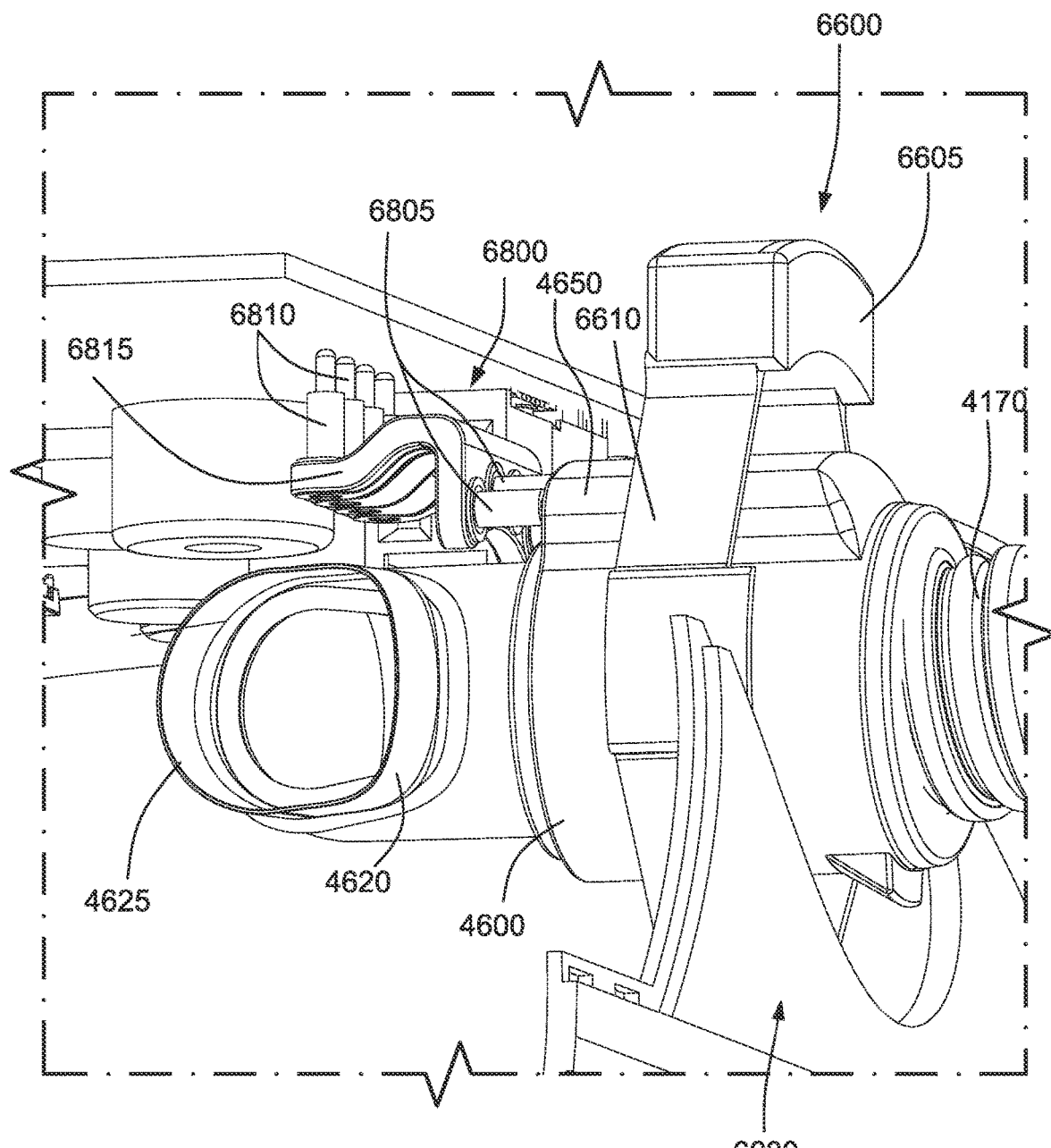

FIG. 20I is an enlarged perspective view showing a reservoir dock and an air delivery tube connected to the dock outlet of the reservoir dock according to an example of the present technology.

Figure 20J:
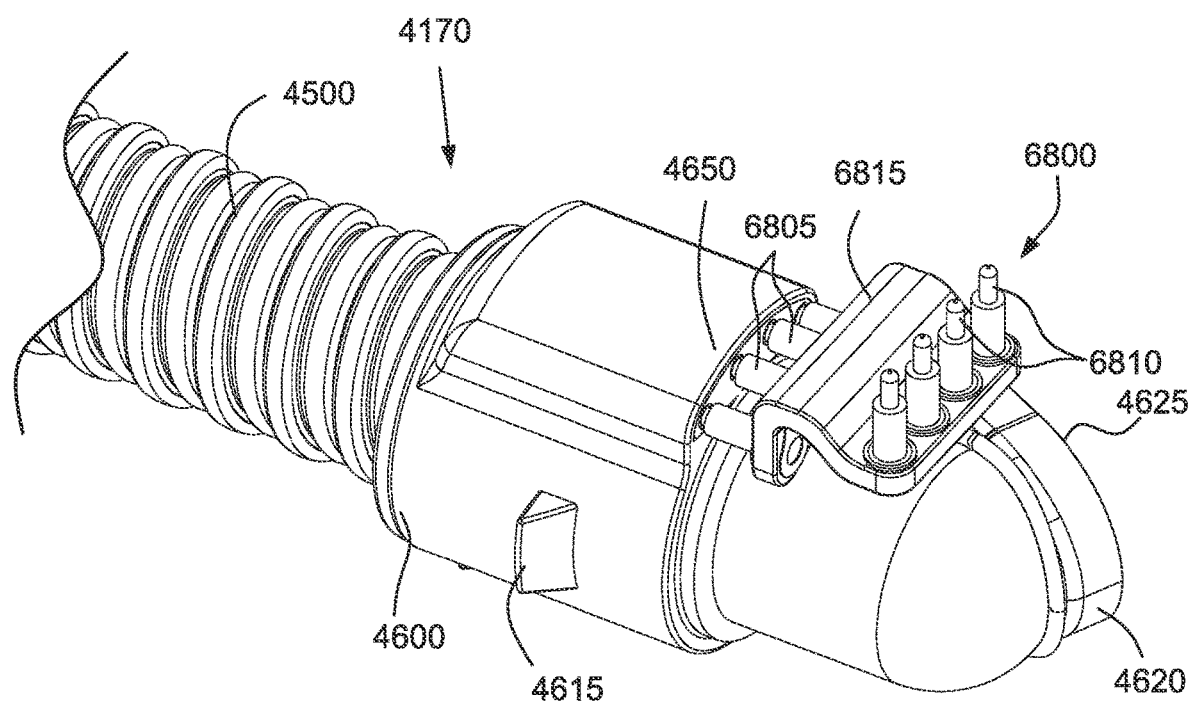

FIG. 20J is a perspective view showing an air delivery tube and its electrical connections to a contact assembly of the dock outlet of the reservoir dock according to an example of the present technology.

Figure 20K:
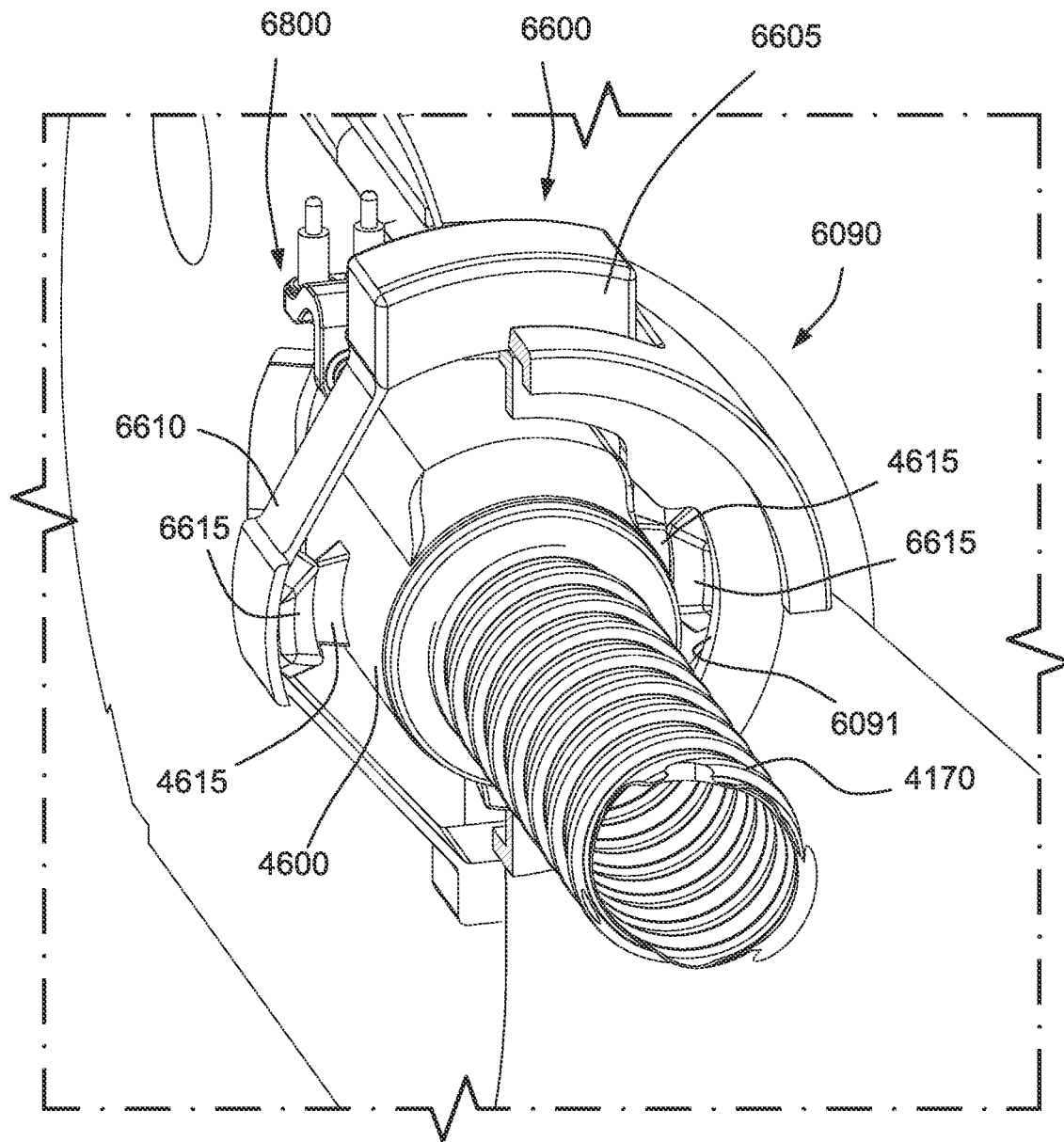

FIG. 20K is an enlarged cut-out perspective view showing a reservoir dock and an air delivery tube connected to the dock outlet of the reservoir dock according to an example of the present technology.

Figure 20L:
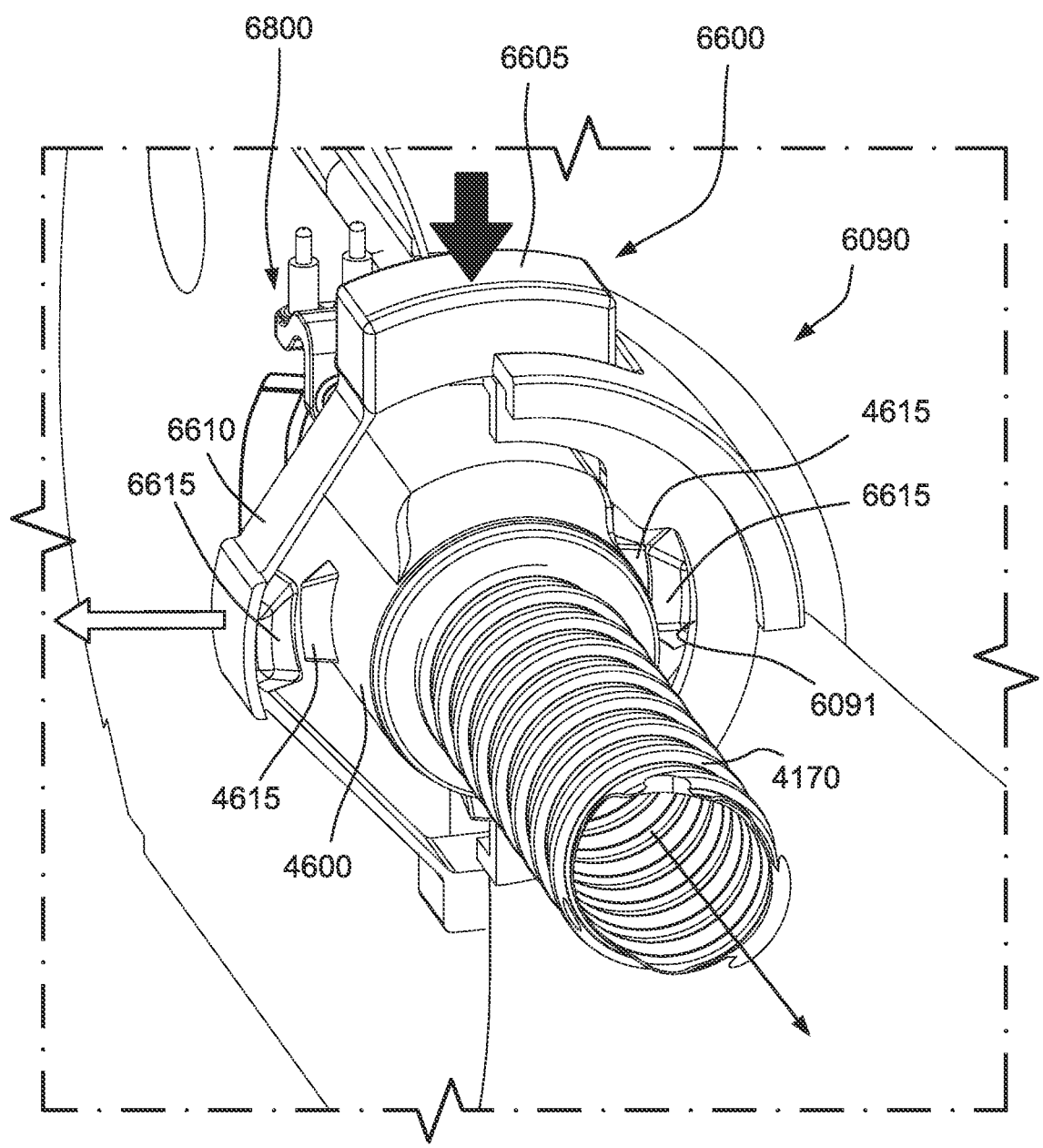

FIG. 20L is an enlarged cut-out perspective view showing a reservoir dock and an air delivery tube being disconnected from the dock outlet of the reservoir dock according to an example of the present technology.

FIG. 20M is a cross-sectional view showing a reservoir dock and an air delivery tube connected to the dock outlet of the reservoir dock according to an example of the present technology.

Figure 20N:
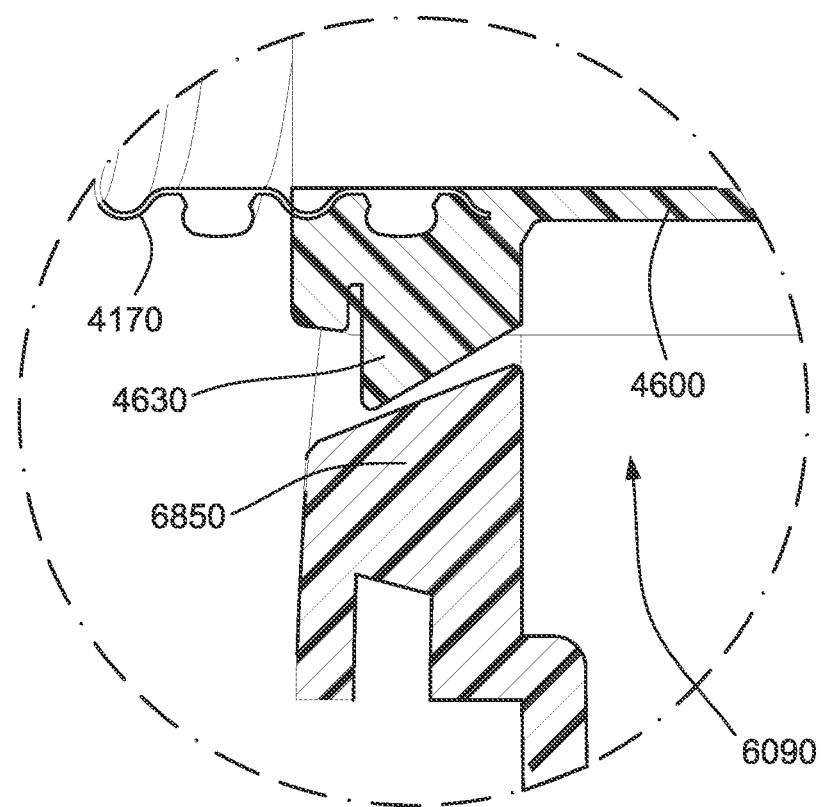

FIG. 20N is an enlarged view of a portion of the reservoir dock and air delivery tube of FIG. 20M.

Figure 21:
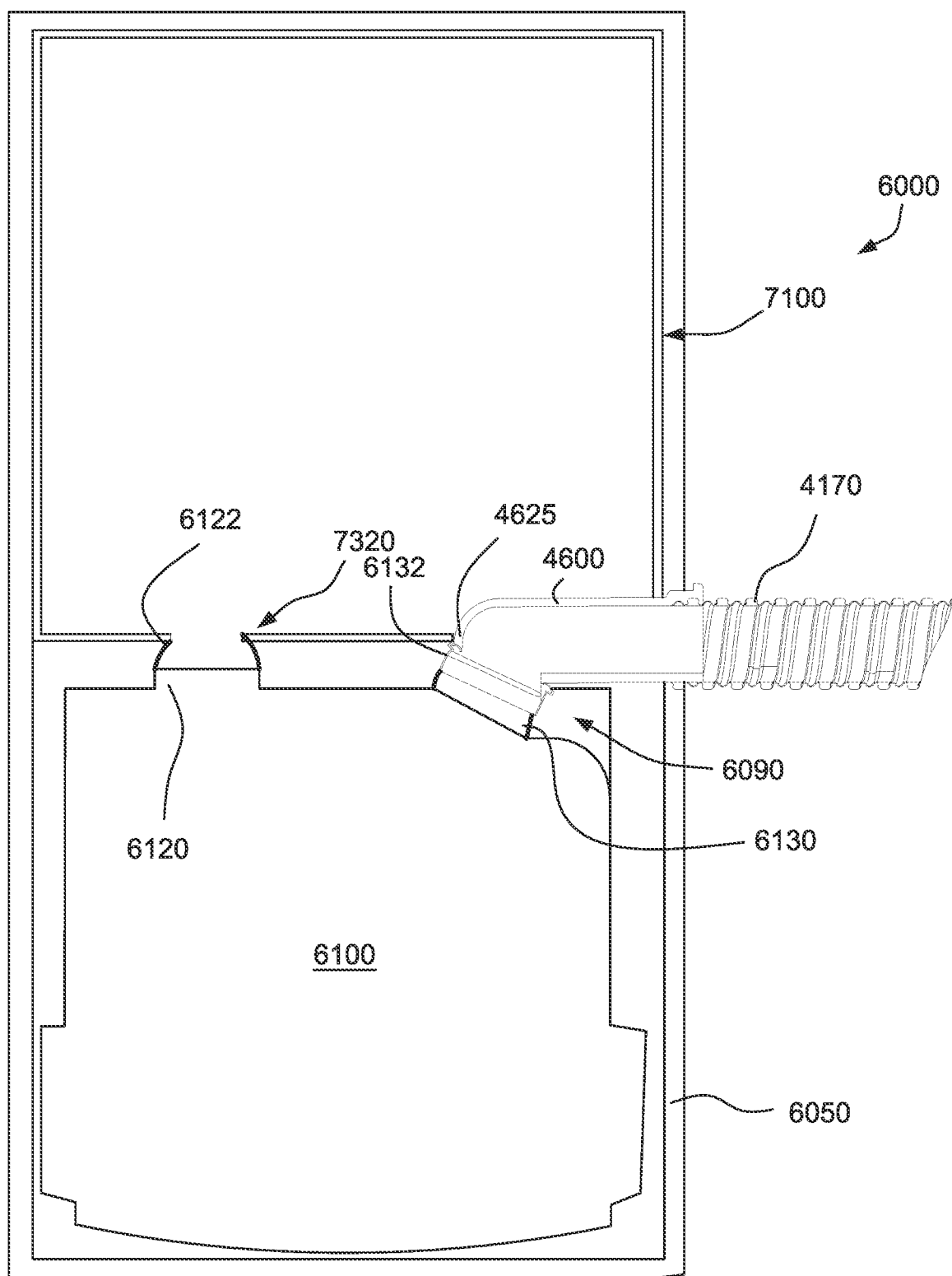

FIG. 21 is a schematic view showing a reservoir dock with an air delivery tube and a water reservoir connected to the reservoir dock according to an example of the present technology.

Figure 22A:
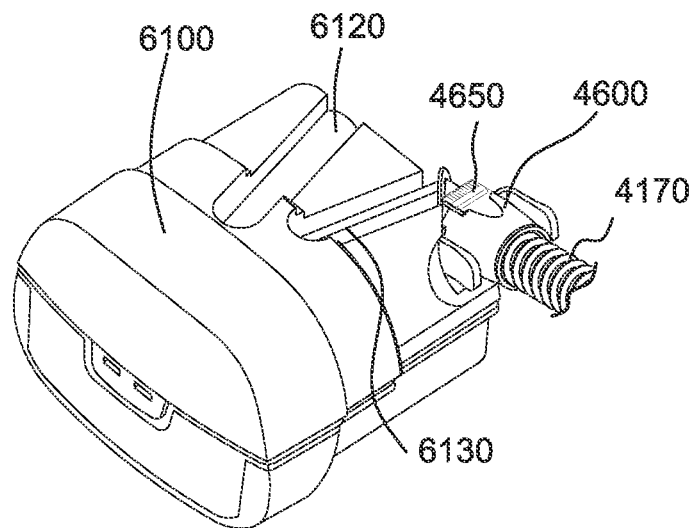

FIG. 22A is a perspective view showing an air delivery tube engaged with a water reservoir according to an example of the present technology.

Figure 22B:
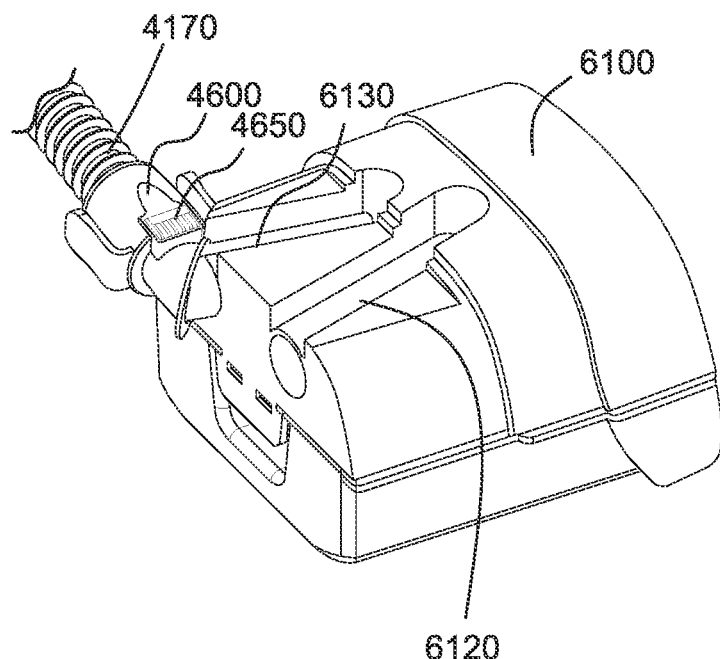

FIG. 22B is another perspective view of the air delivery tube and water reservoir of FIG. 22A.

Figure 22C:
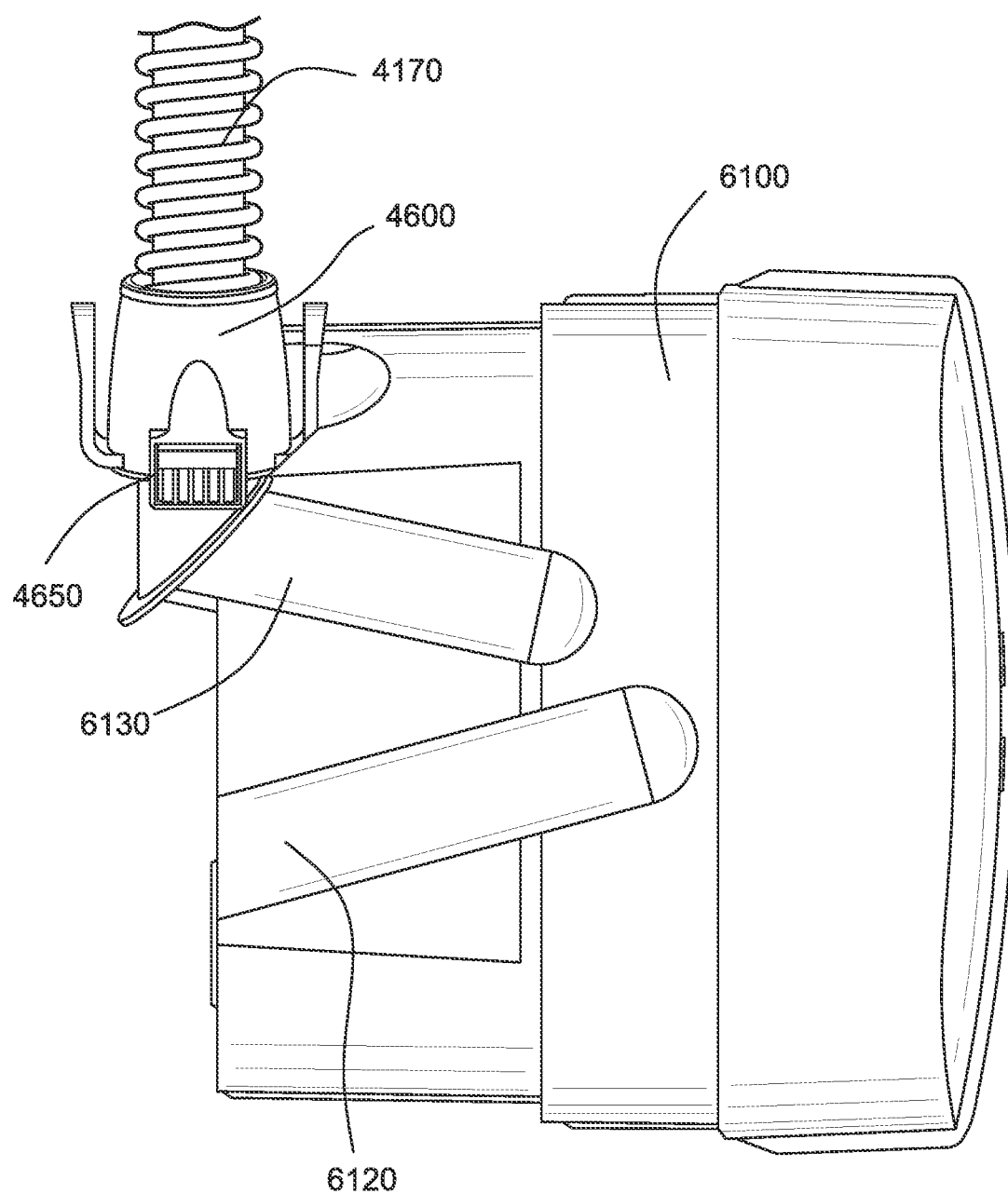

FIG. 22C is a top view of the air delivery tube and water reservoir of FIG. 22A.

Figure 23B:
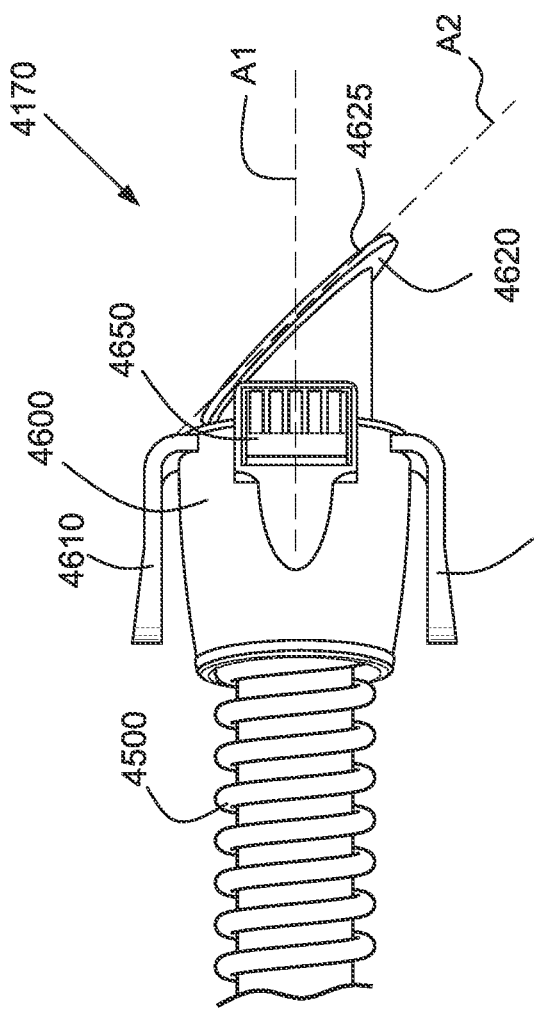
Figure 23A:
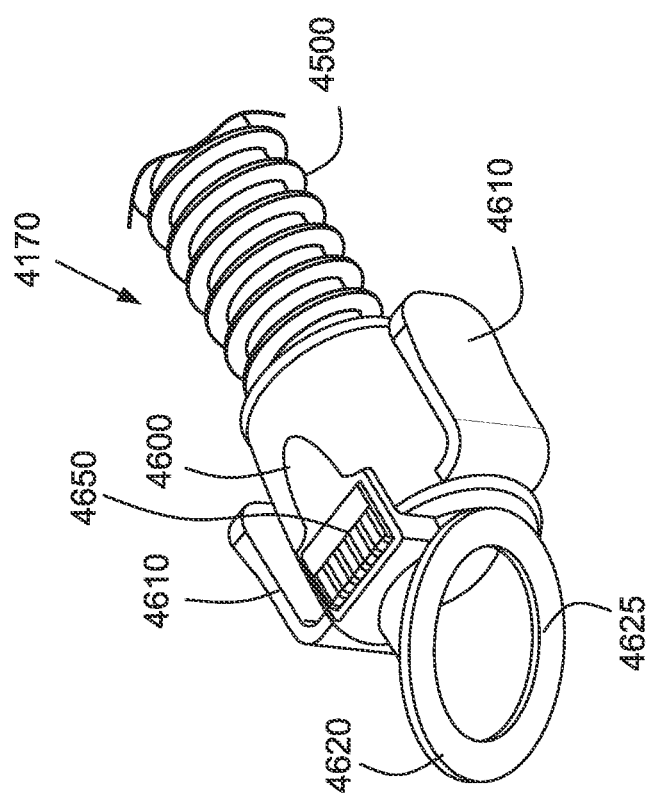

FIG. 23A is a perspective view showing a dock connector of an air delivery tube according to an example of the present technology.

FIG. 23B is a top view of the air delivery tube of FIG. 23A.

Figure 24A:
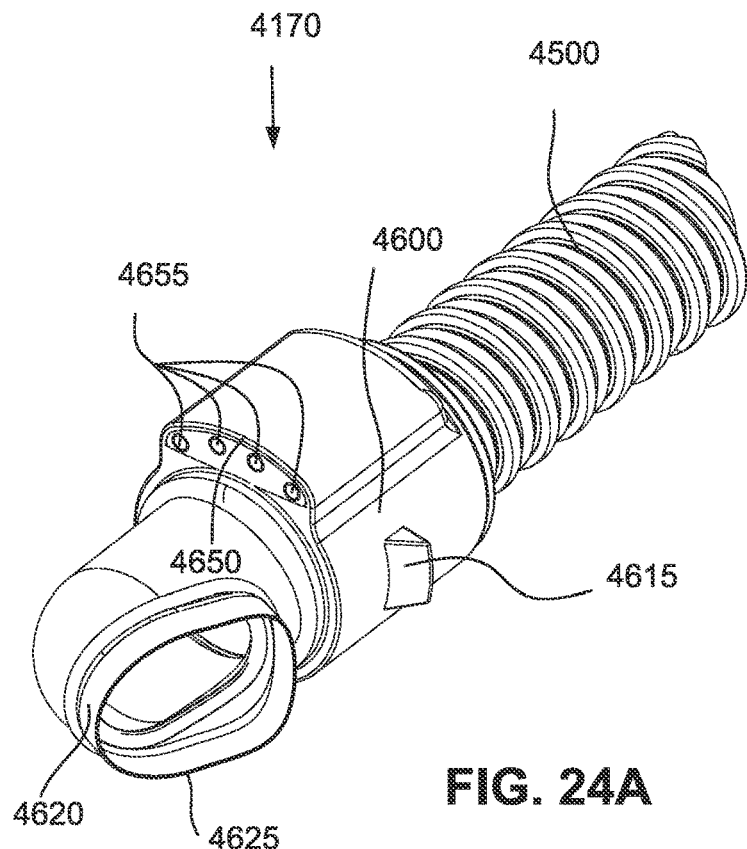

FIG. 24A is a perspective view showing a dock connector of an air delivery tube according to another example of the present technology.

Figure 24B:
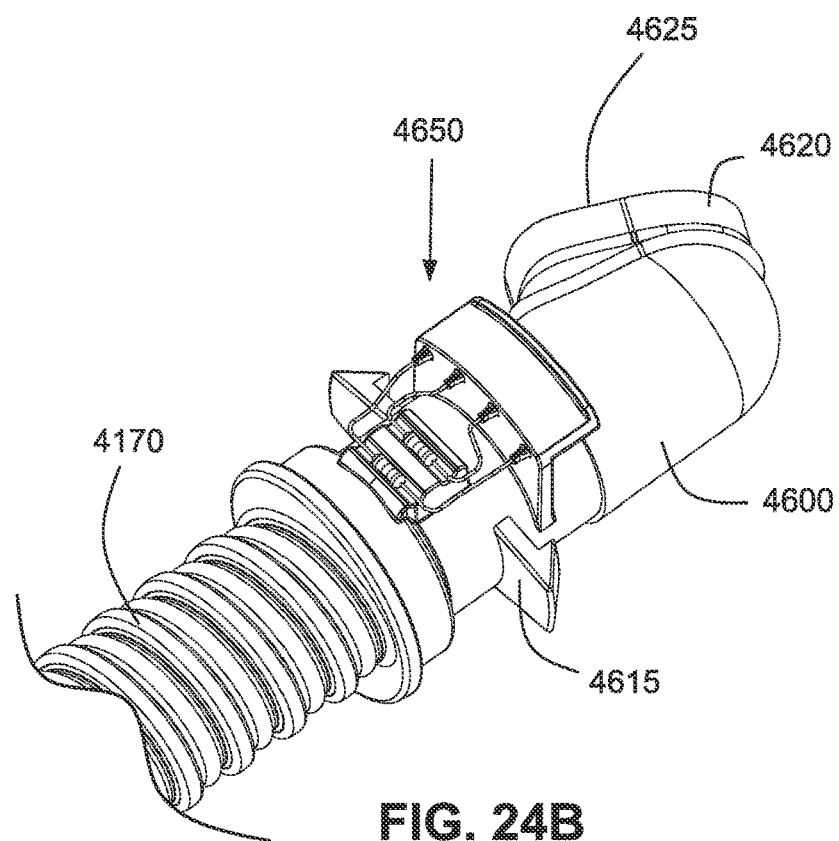

FIG. 24B is another perspective view of the air delivery tube of FIG. 24A without the overmolded grip.

FIG. 25A is a perspective view of a reservoir dock (in a cut-away representation) and a water reservoir including guiding structures according to an example of the present technology.

Figure 25B:
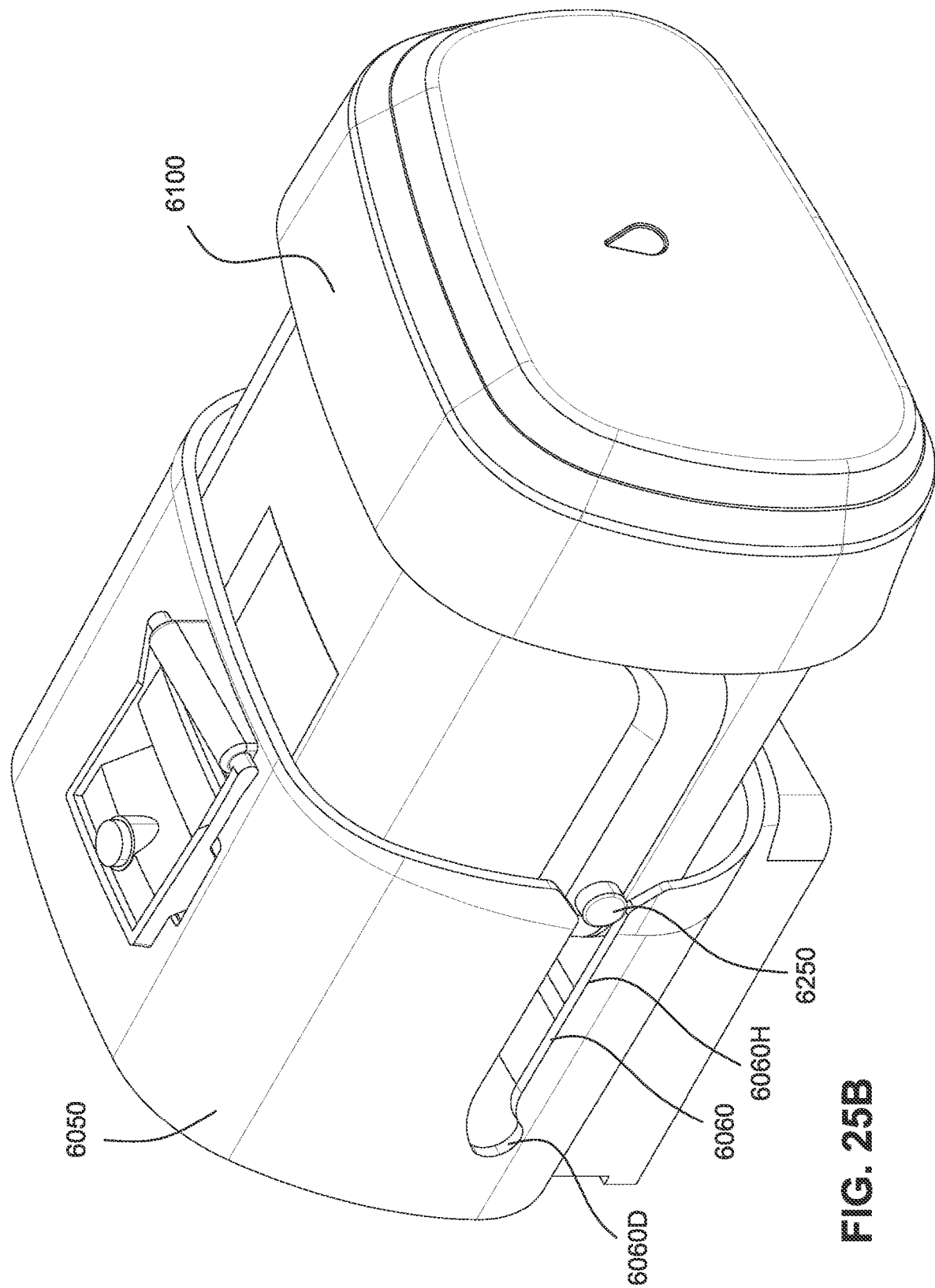

FIG. 25B is a perspective view of the reservoir dock and water reservoir of FIG. 25A showing the water reservoir being inserted into the reservoir dock.

Figure 26A:
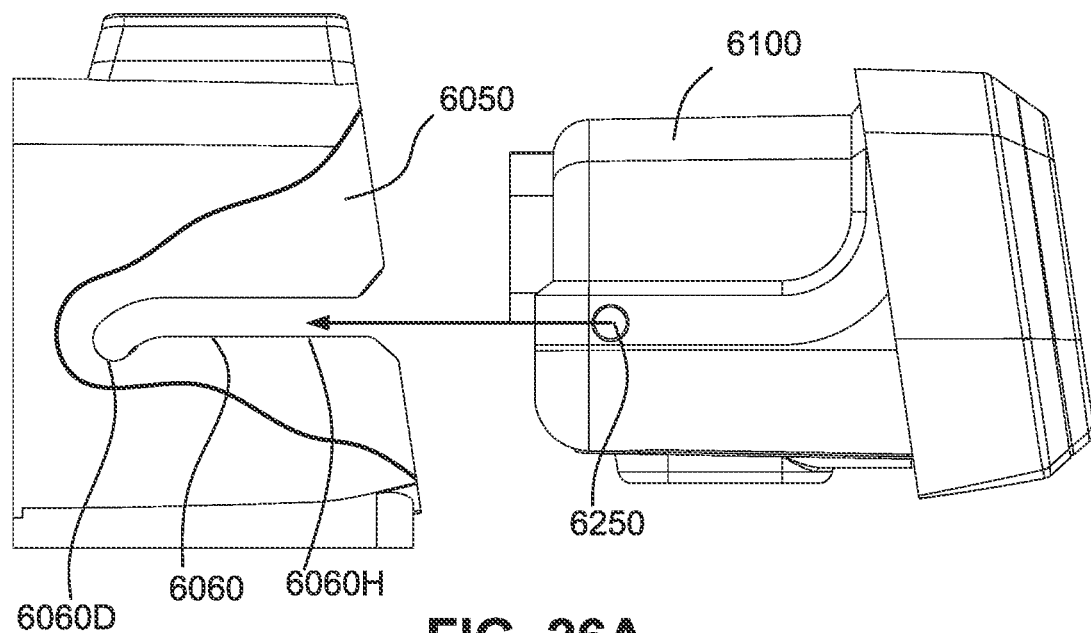

FIG. 26A is side view of the reservoir dock and water reservoir of FIG. 25A showing the water reservoir being inserted into the reservoir dock.

Figure 26B:
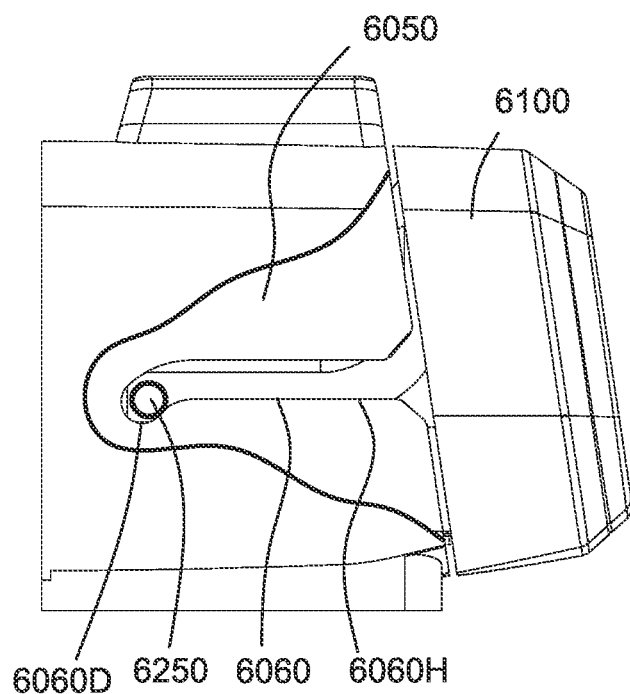

FIG. 26B is side view of the reservoir dock and water reservoir of FIG. 25A showing the water reservoir inserted into the reservoir dock.

Figure 27A:
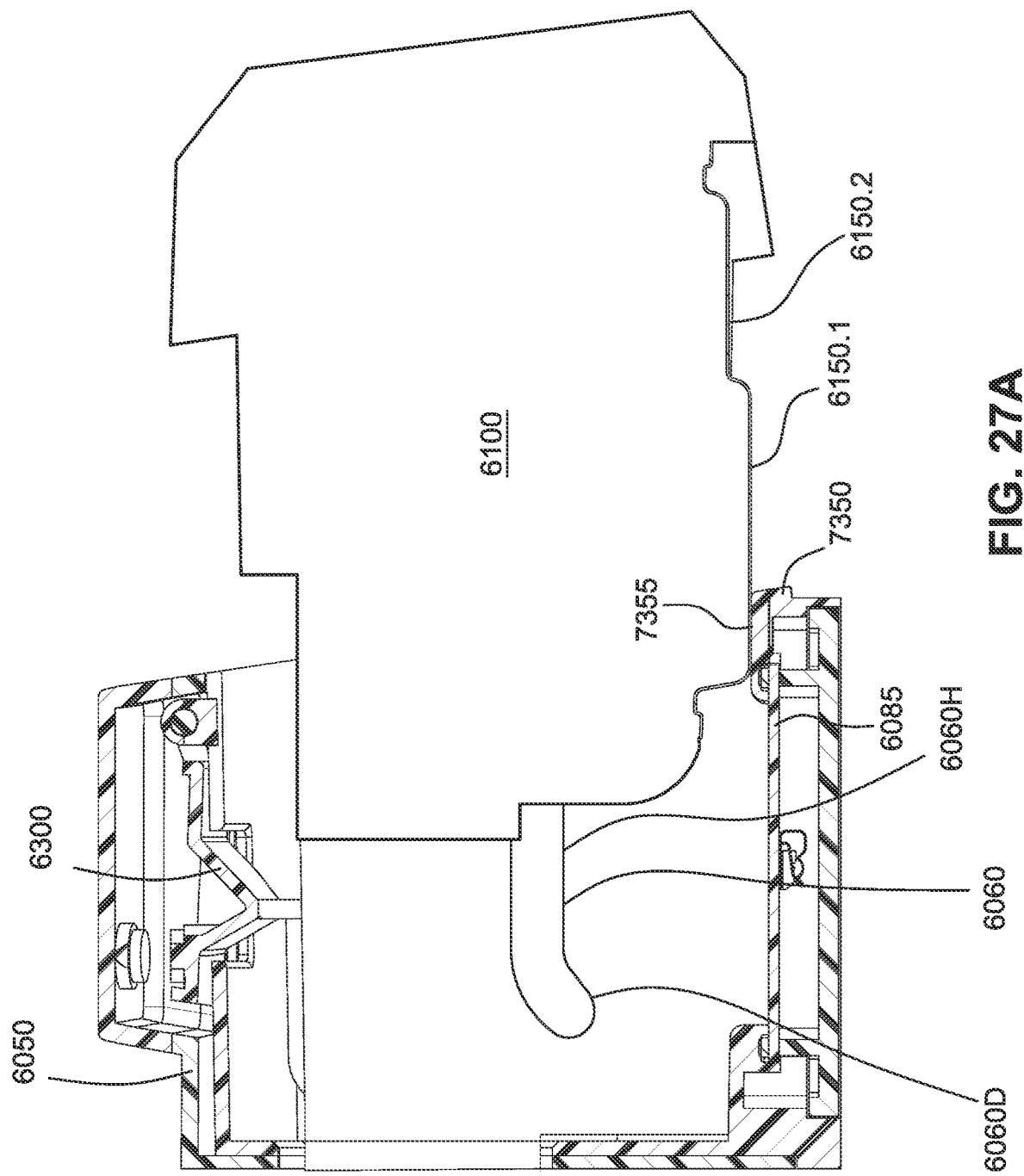

FIG. 27A is a cross-sectional view of the reservoir dock and water reservoir of FIG. 25A showing the water reservoir being inserted into the reservoir dock.

Figure 27B:
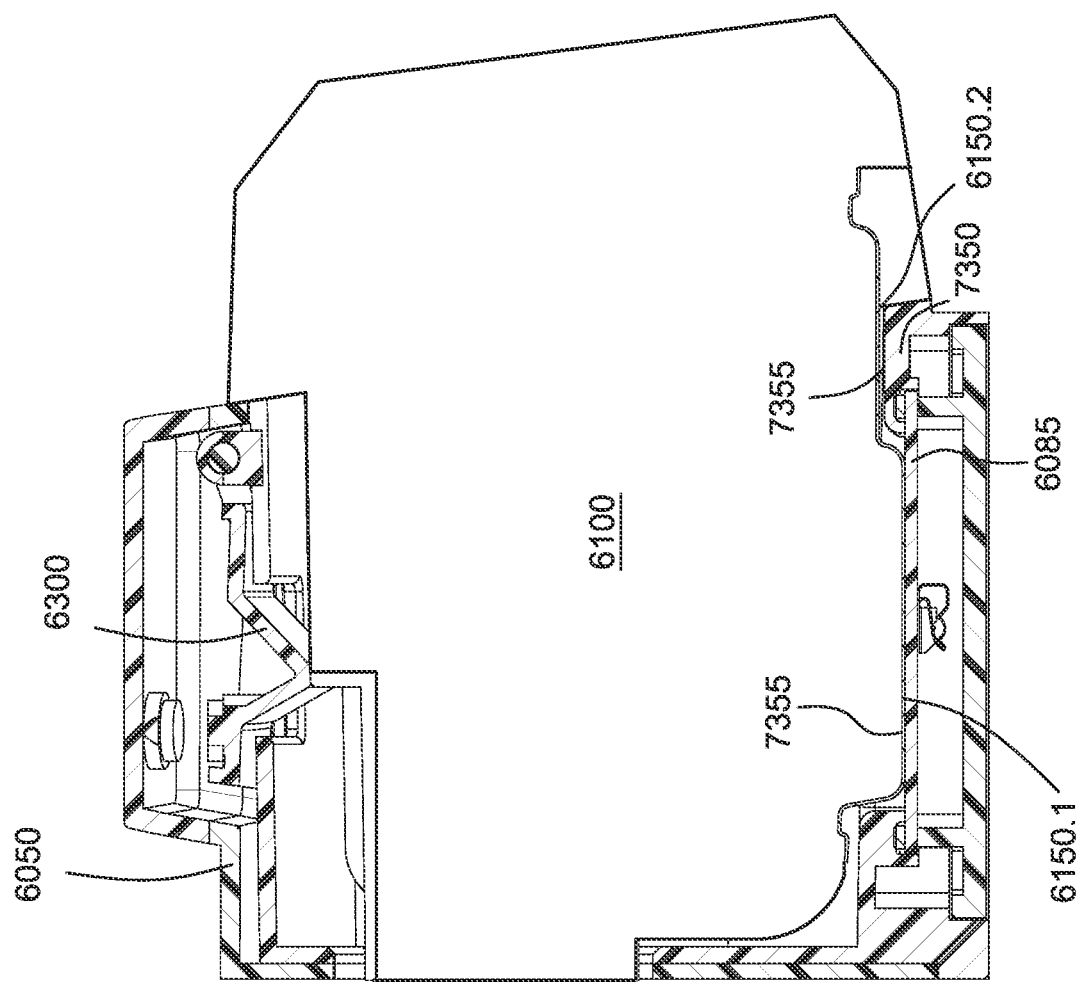

FIG. 27B is a cross-sectional view of the reservoir dock and water reservoir of FIG. 25A showing the water reservoir inserted into the reservoir dock.

FIG. 28A is a perspective view showing a reservoir dock including a recessed heating element according to an example of the present technology.

FIG. 28B is a perspective view showing a heating element of the reservoir dock of FIG. 28A according to an example of the present technology.

FIG. 28C is an enlarged cross-sectional view showing the reservoir dock and recessed heating element of FIG. 28A.

Figure 29:
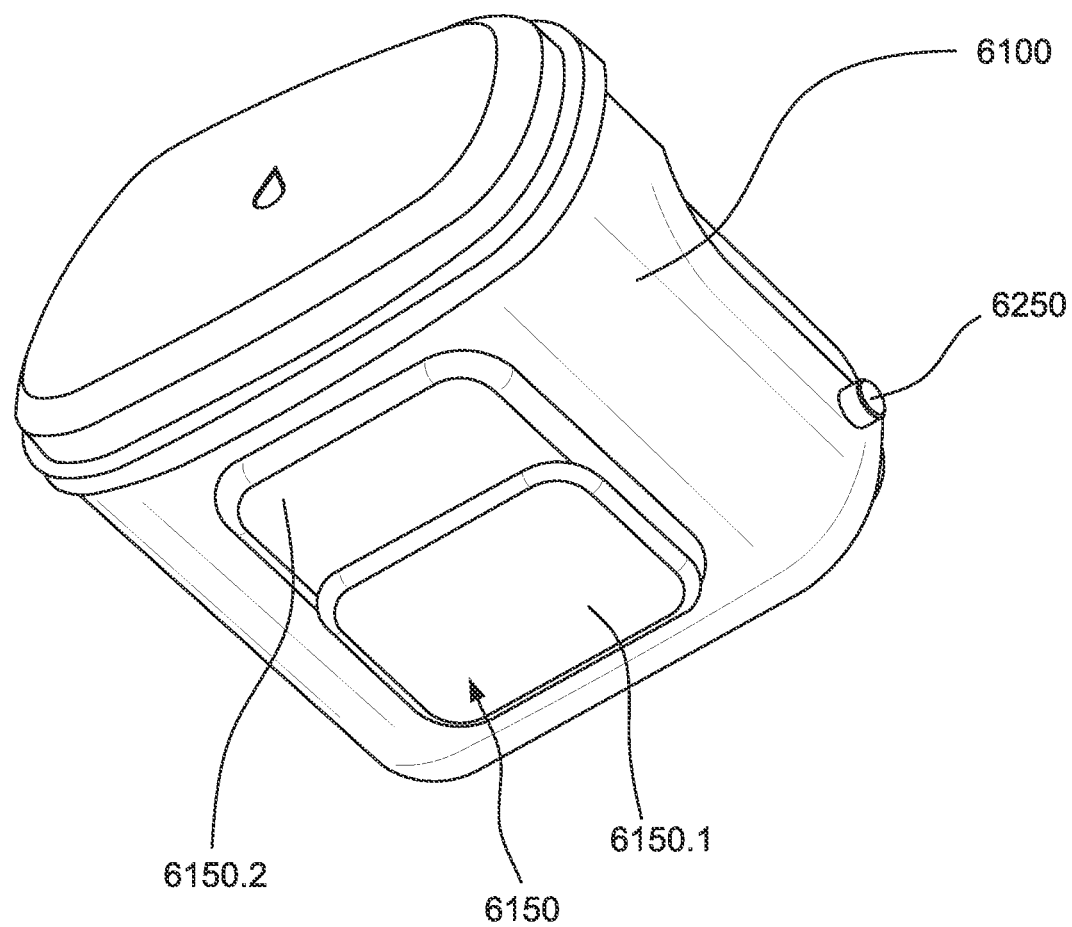

FIG. 29 is a bottom perspective view of a water reservoir according to an example of the present technology.

Figure 30:
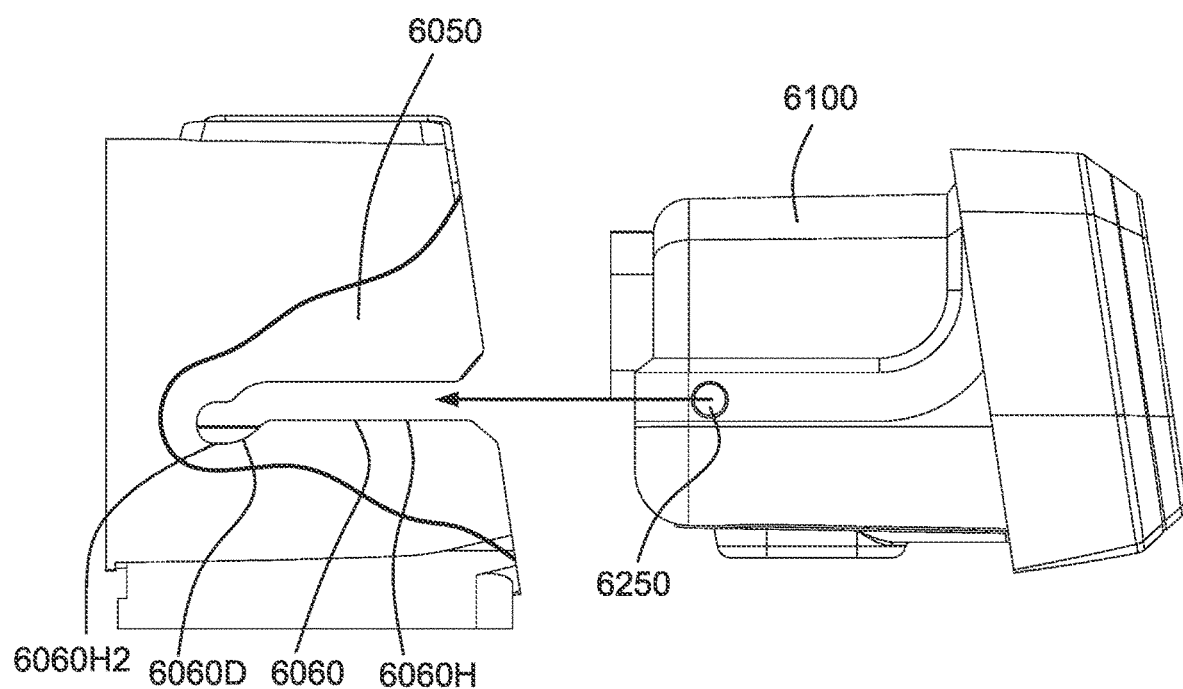

FIG. 30 is side view of a reservoir dock and a water reservoir including guiding structures according to another example of the present technology, and showing the water reservoir being inserted into the reservoir dock.

Figure 31:
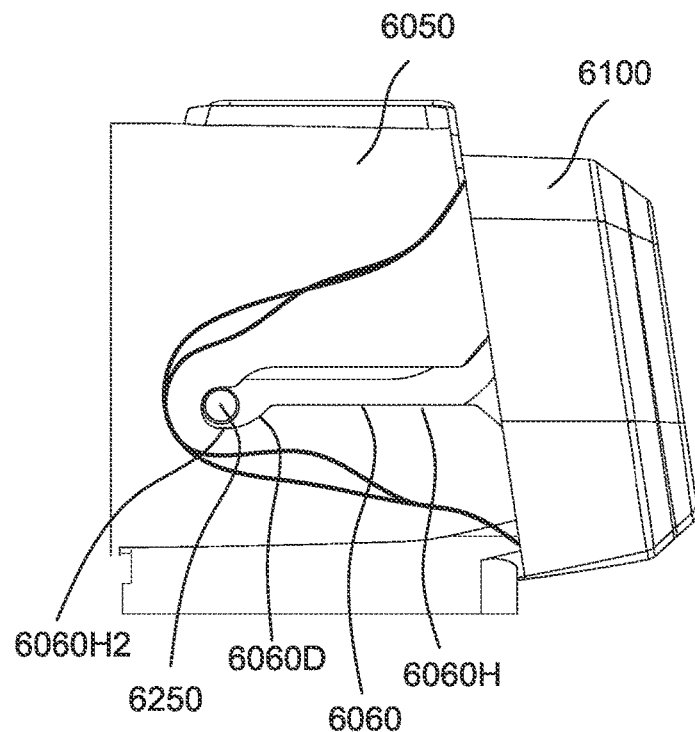

FIG. 31 is side view of the reservoir dock and water reservoir of FIG. 30A showing the water reservoir inserted into the reservoir dock.

Figure 32A:
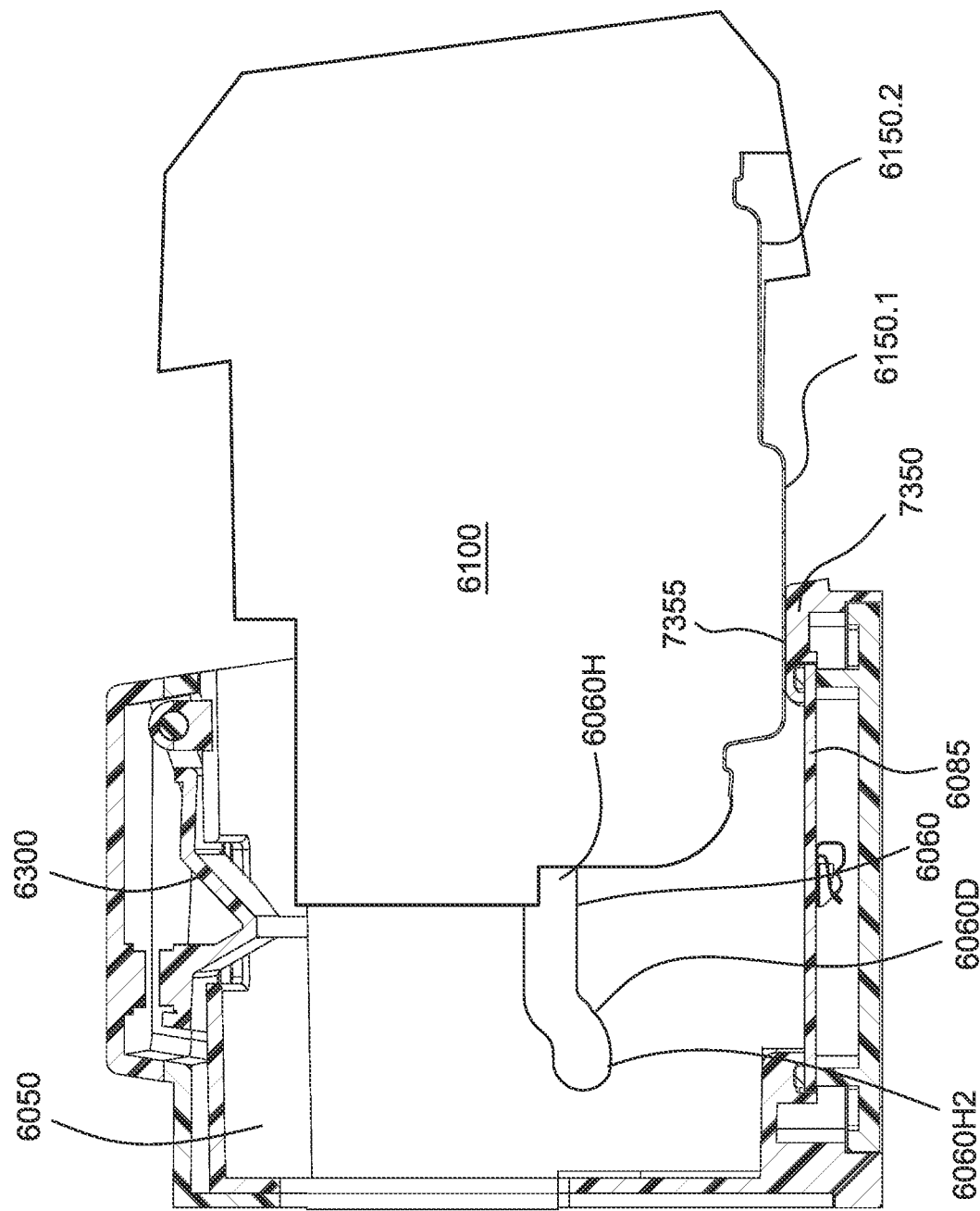

FIG. 32A is a cross-sectional view of the reservoir dock and water reservoir of FIG. 30 showing the water reservoir being inserted into the reservoir dock.

Figure 32B:
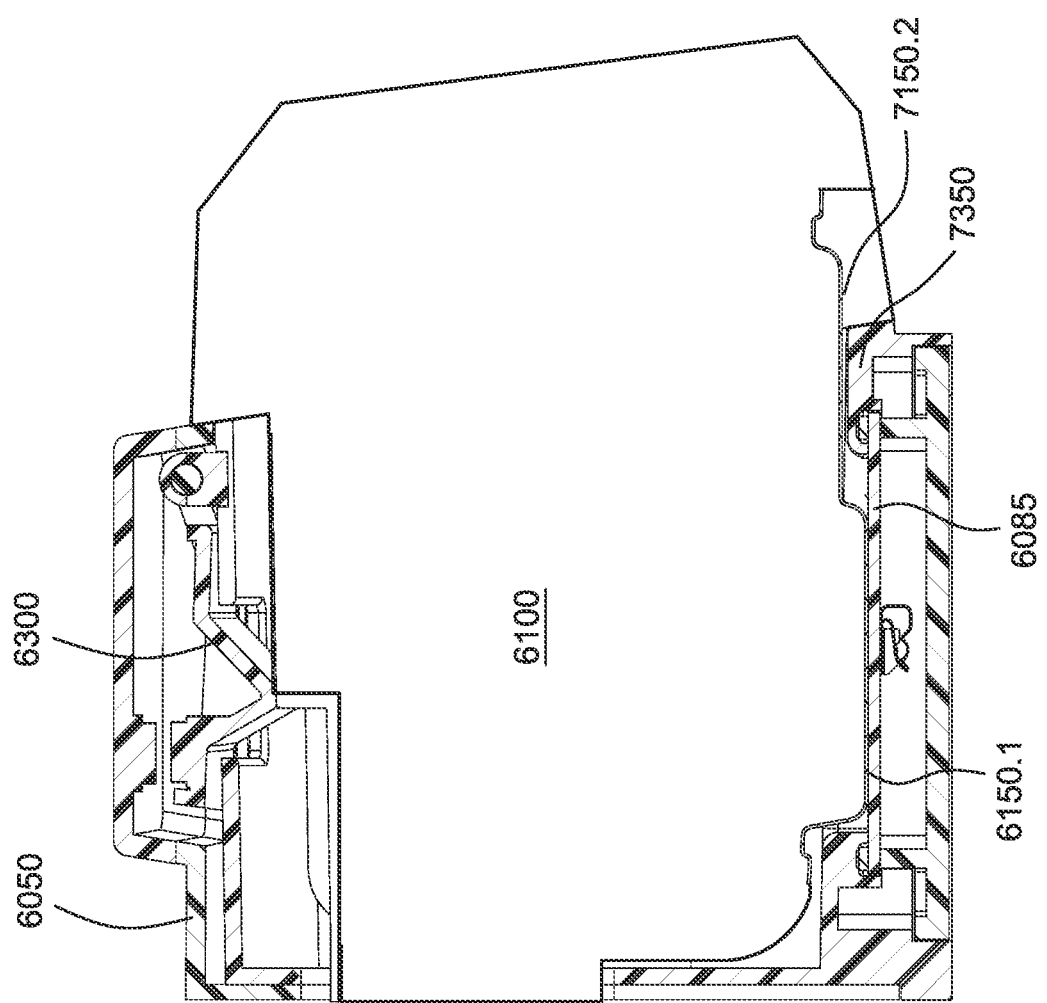

FIG. 32B is a cross-sectional view of the reservoir dock and water reservoir of FIG. 30 showing the water reservoir inserted into the reservoir dock.

Figure 33A:
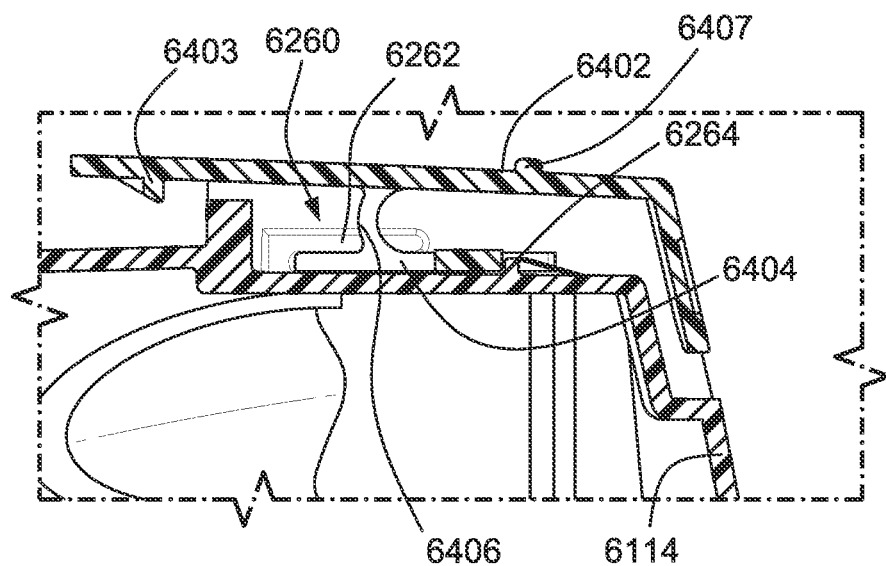

FIG. 33A is a cross-sectional view showing a latch for a water reservoir according to an example of the present technology.

Figure 33B:
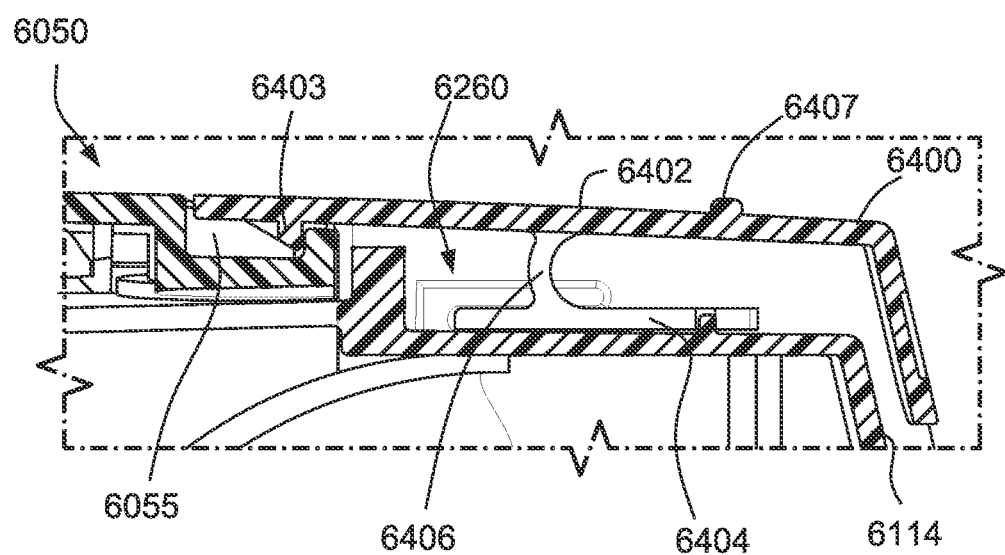

FIG. 33B is a cross-sectional view showing the latch of FIG. 33A engaged with a reservoir dock according to an example of the present technology.

Figure 33C:
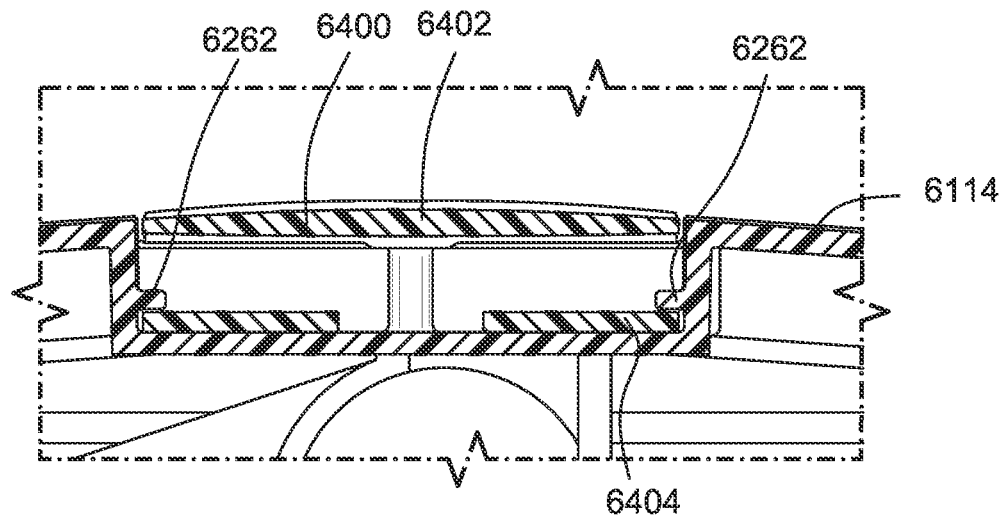

FIG. 33C is another cross-sectional view showing the latch of FIG. 33A.

Figure 33D:
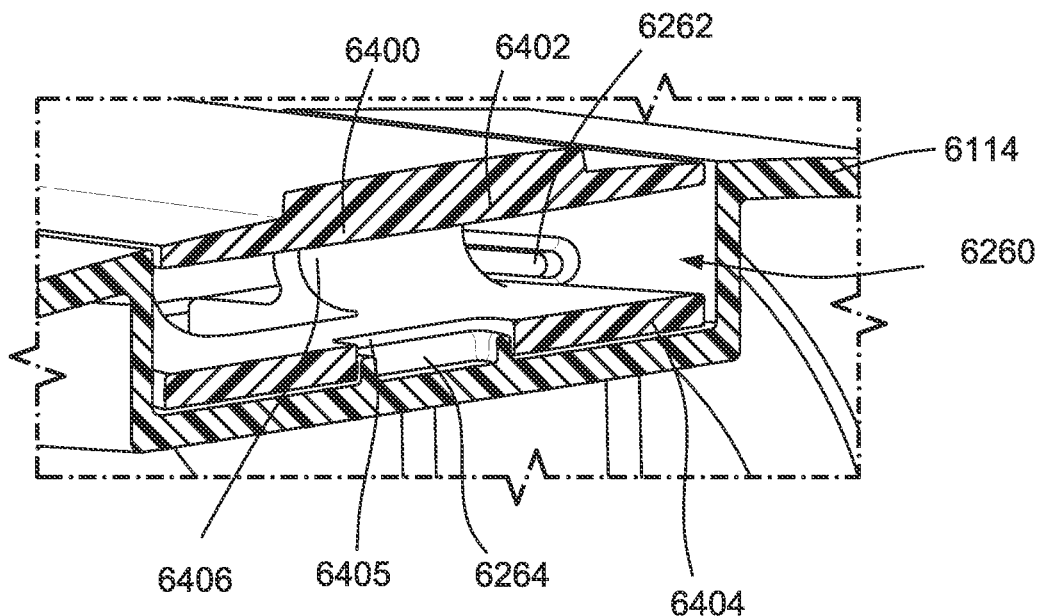

FIG. 33D is another cross-sectional view showing the latch of FIG. 33A.

Figure 33E:
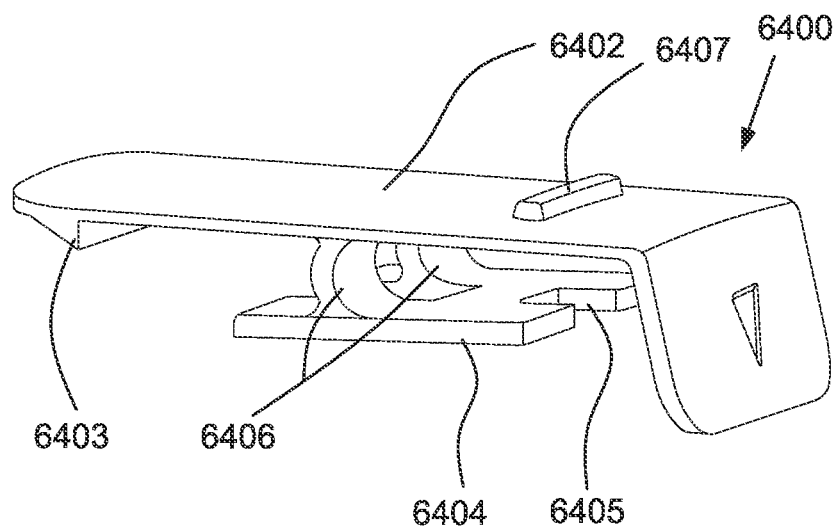

FIG. 33E is a perspective view showing the latch of FIG. 33A.

Figure 33F:
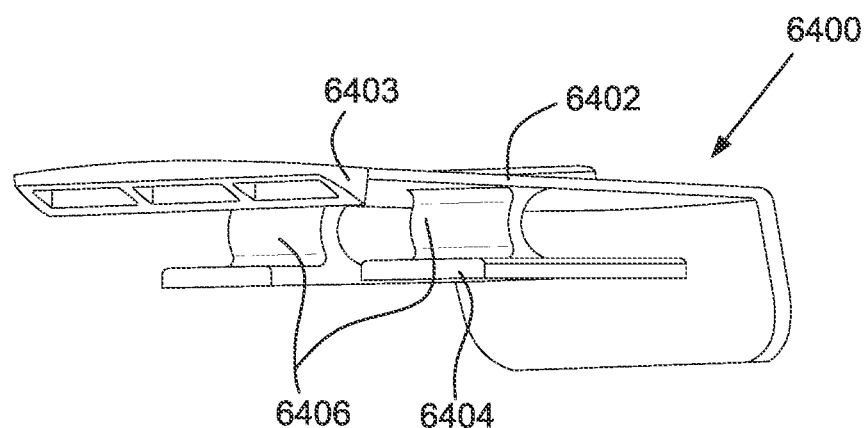

FIG. 33F is another perspective view showing the latch of FIG. 33A.

Figure 33G:
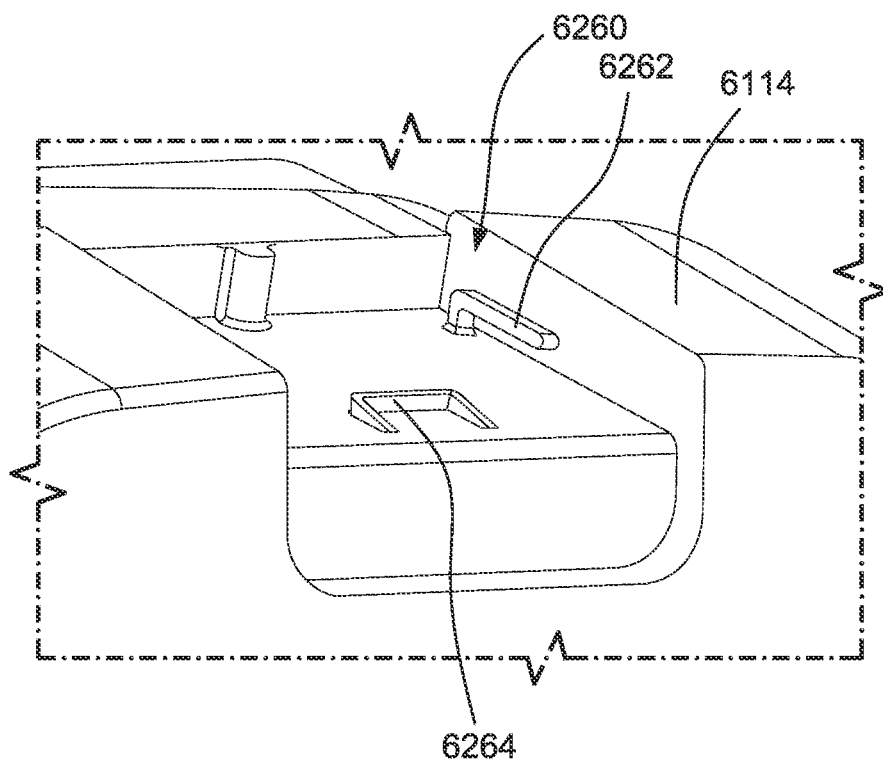

FIG. 33G is a perspective view showing a recess in a water reservoir for receiving a latch according to an example of the present technology.

Figure 34A:
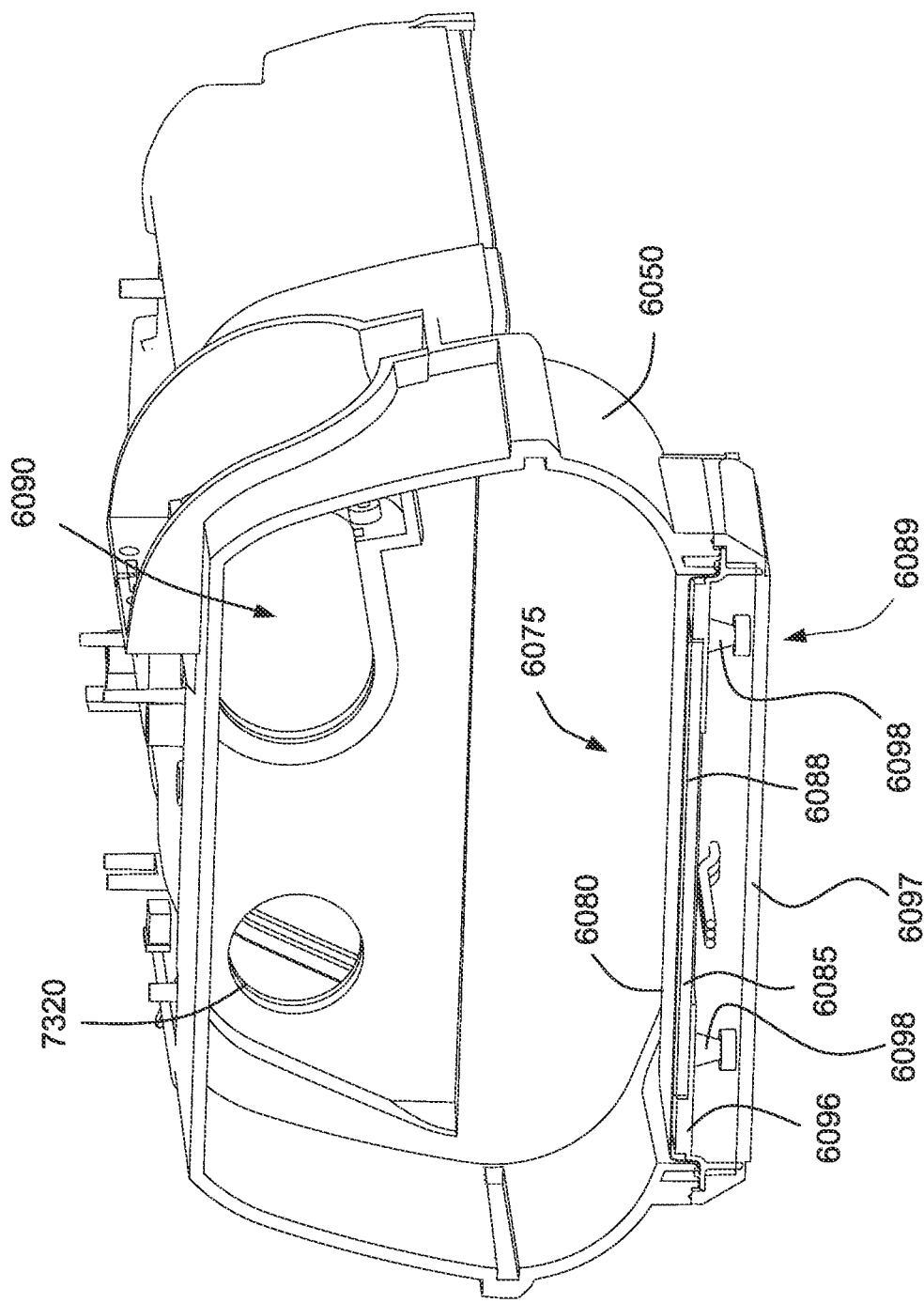

FIG. 34A is a cross-sectional view showing a heating assembly for a reservoir dock according to an example of the present technology.

Figure 34B:
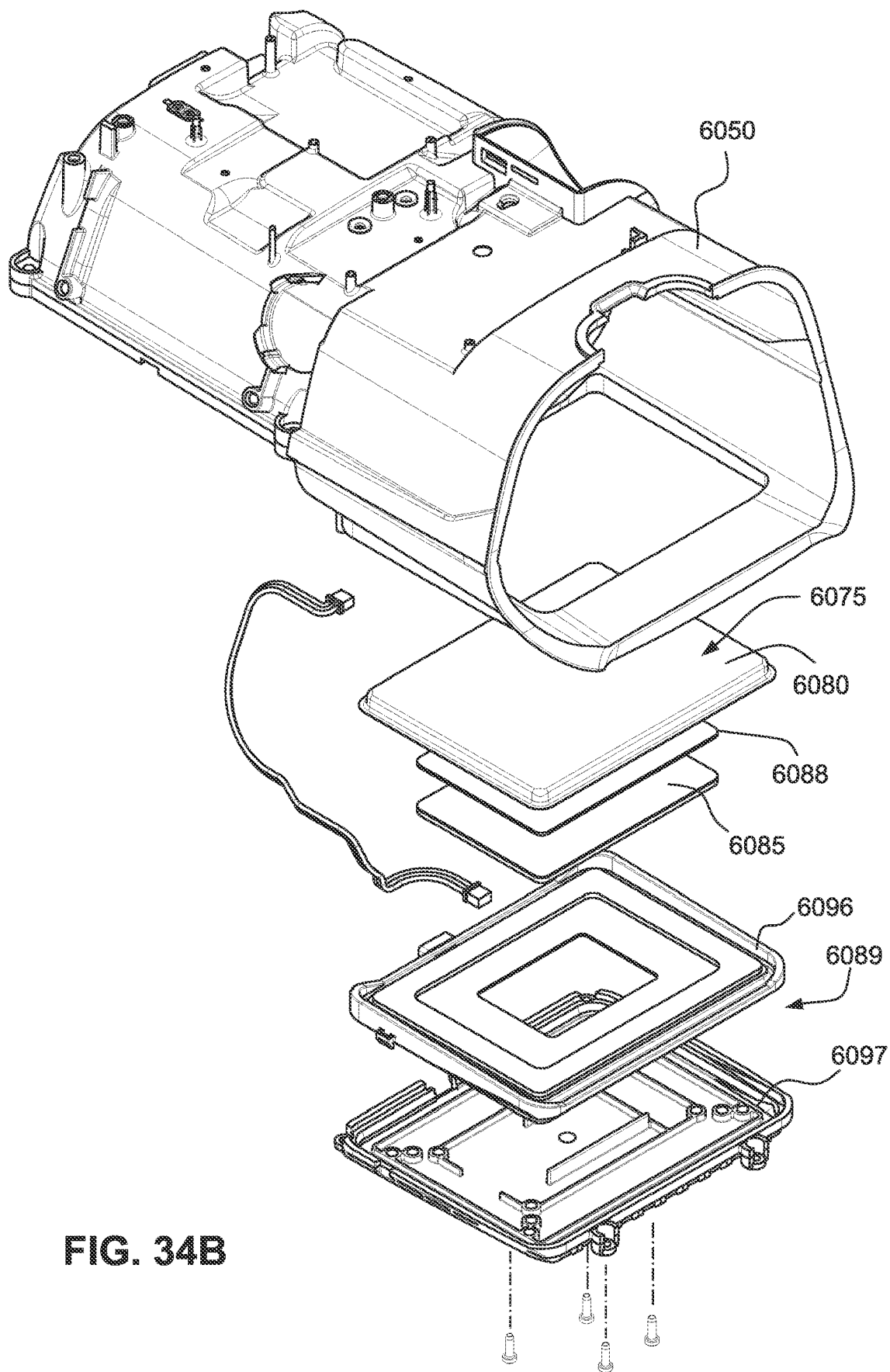

FIG. 34B is an exploded view of the heating assembly of FIG. 34A.

Figure 34C:
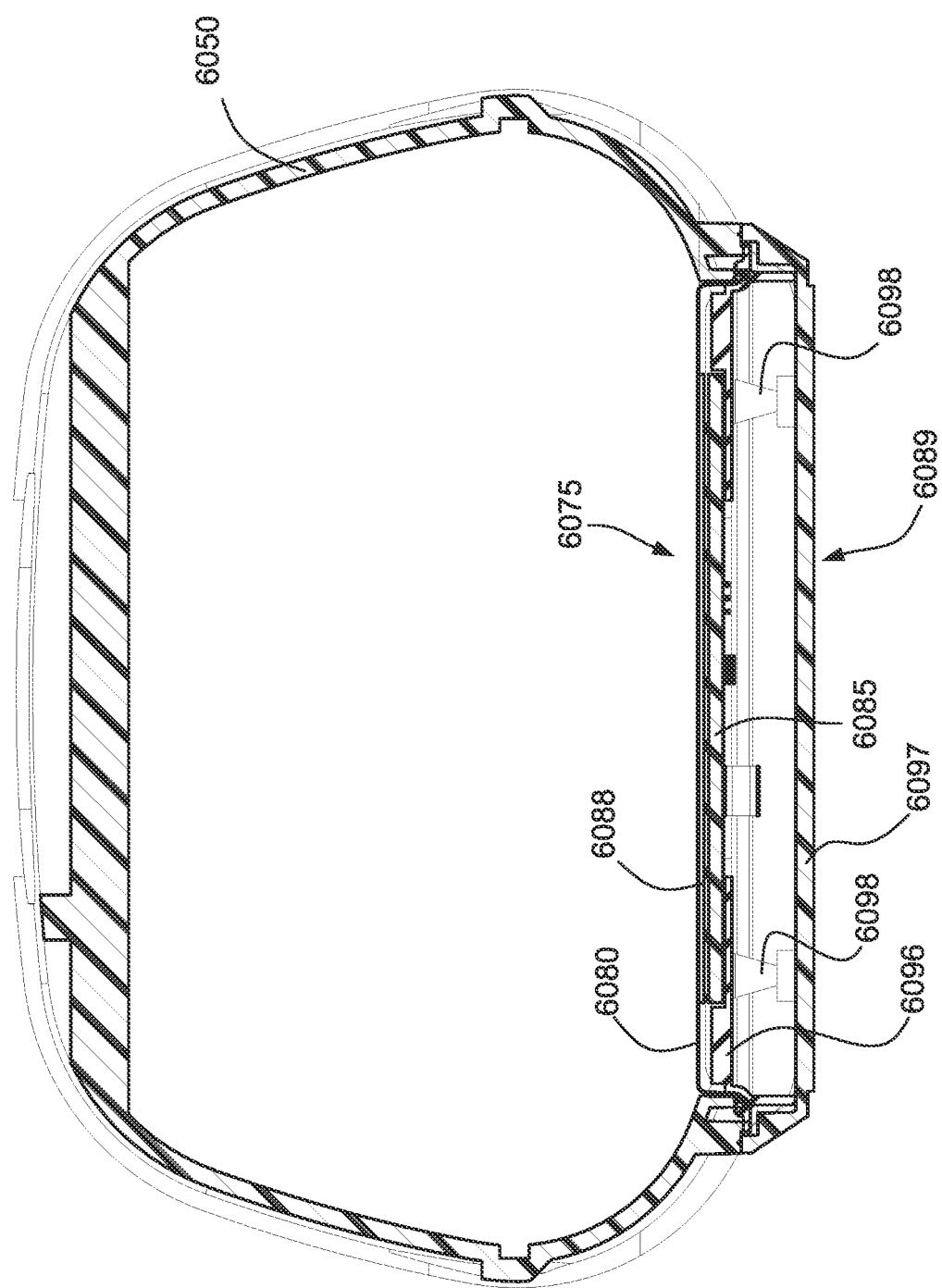

FIG. 34C is another cross-sectional view of the heating assembly of FIG. 34A.

Figure 35A:
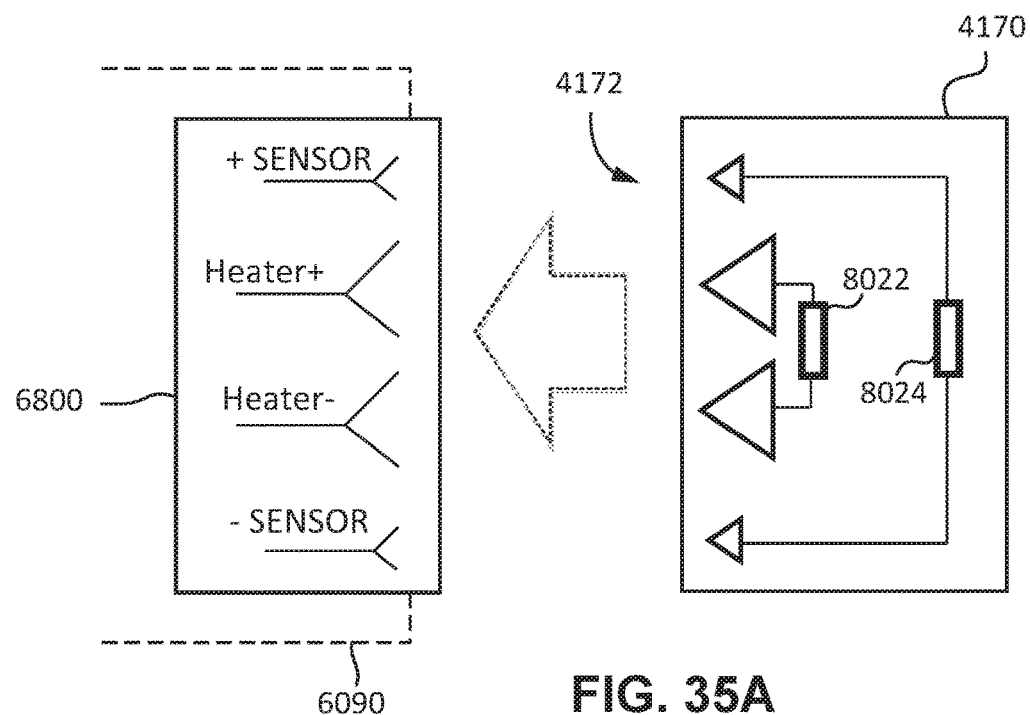

FIG. 35A shows a dock and a tube schematic connection in accordance with one form of the present technology.

Figure 35B:
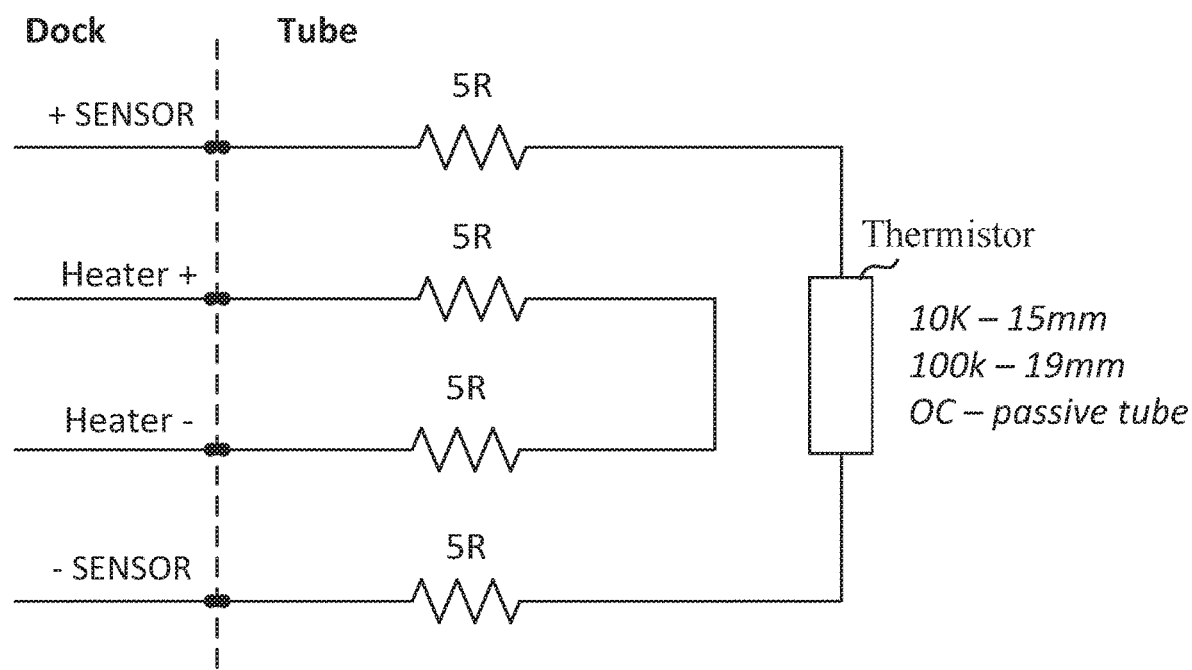

FIG. 35B shows a circuit diagram of the dock and tube connection in accordance with one form of the present technology.

Figure 36:
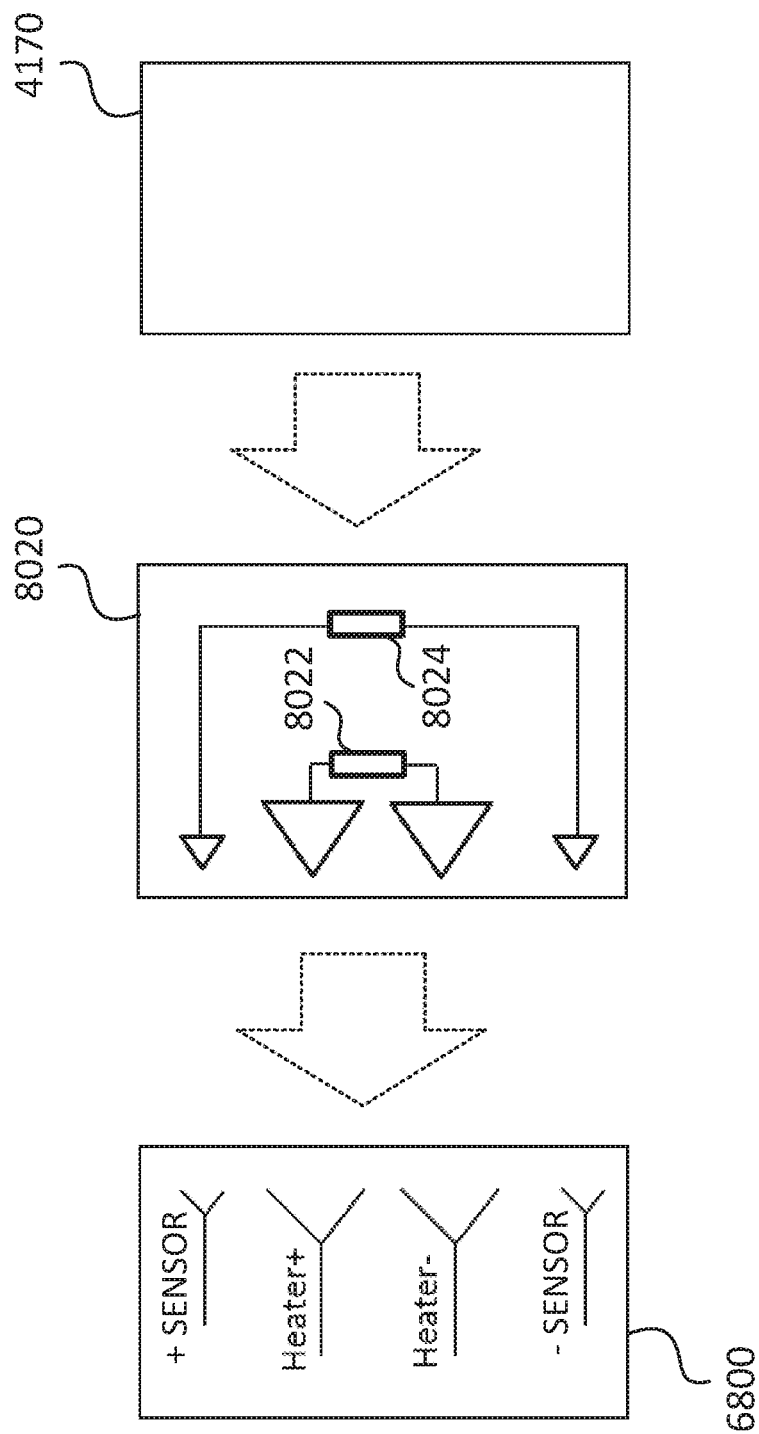

FIG. 36 shows a dock and a tube schematic connection in accordance with one form of the present technology.

Figure 37:
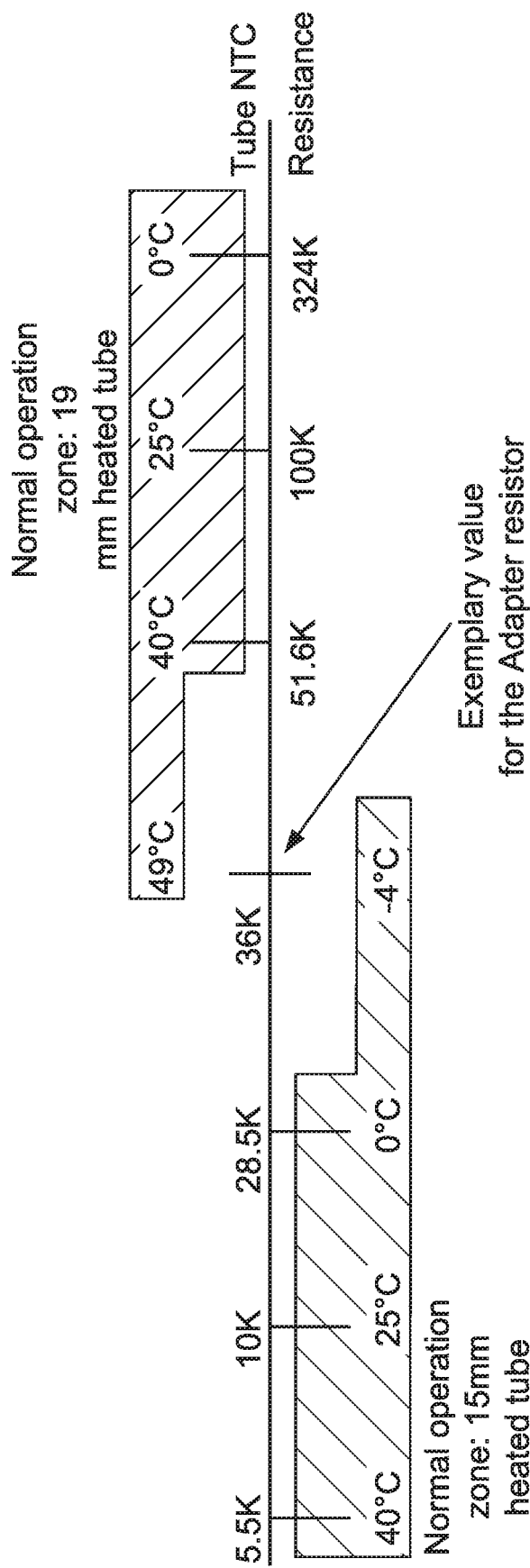

FIG. 37 shows exemplary tube NTC sensor resistance variations over different temperatures for a 100 k thermistor and a 10 k thermistor.

Figure 38:
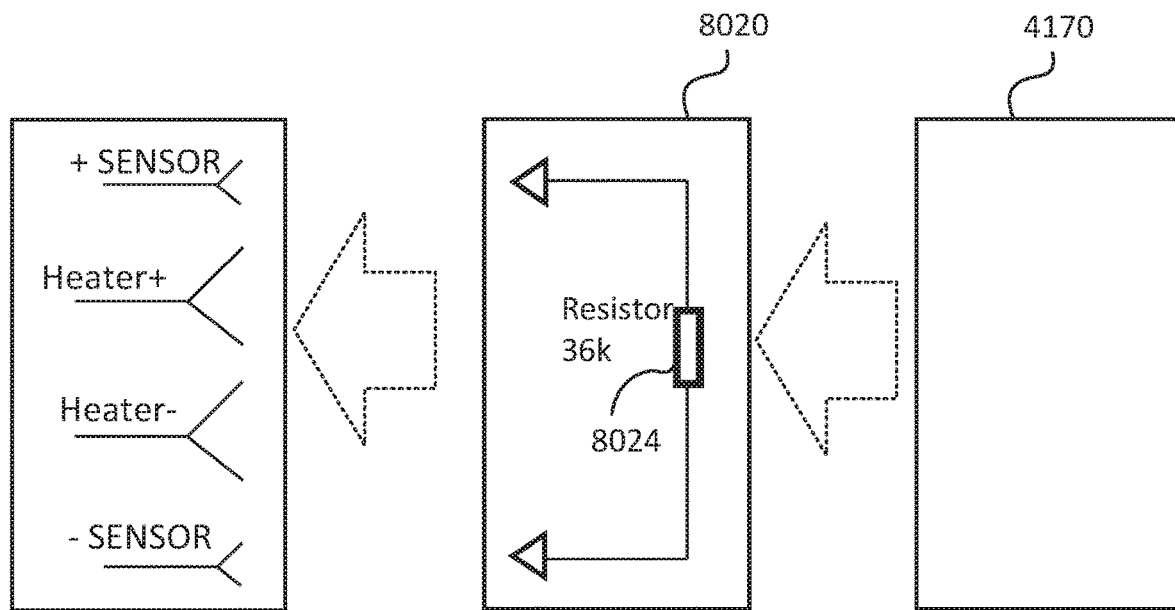

FIG. 38 shows a dock and a tube schematic connection in accordance with another form of the present technology.

Figure 39:
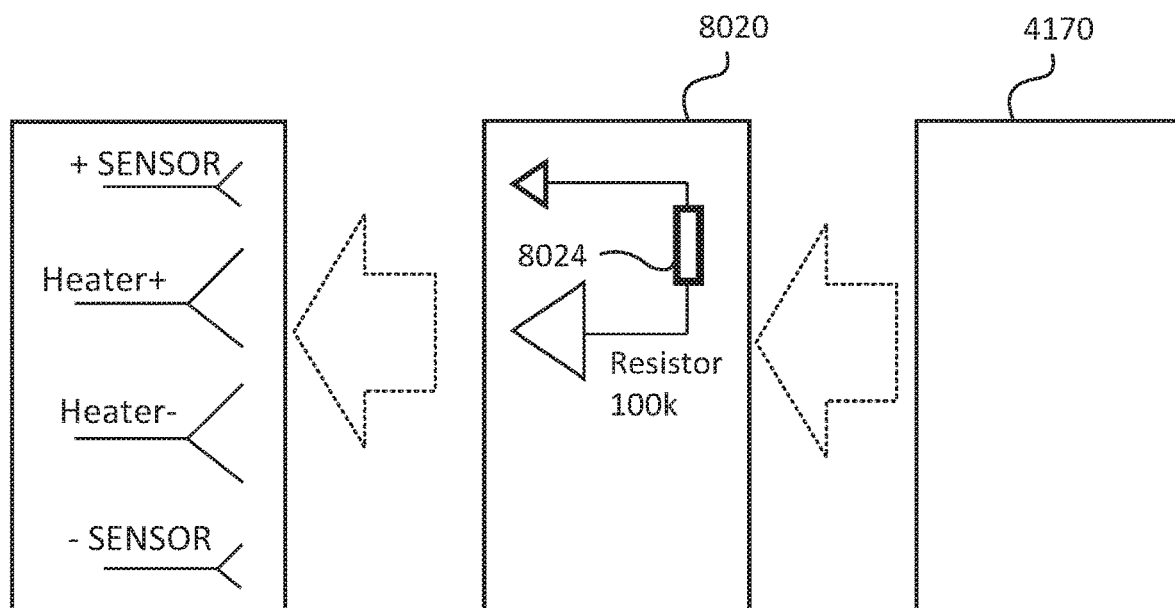

FIG. 39 shows a dock and a tube schematic connection in accordance with another form of the present technology.

Figure 40:
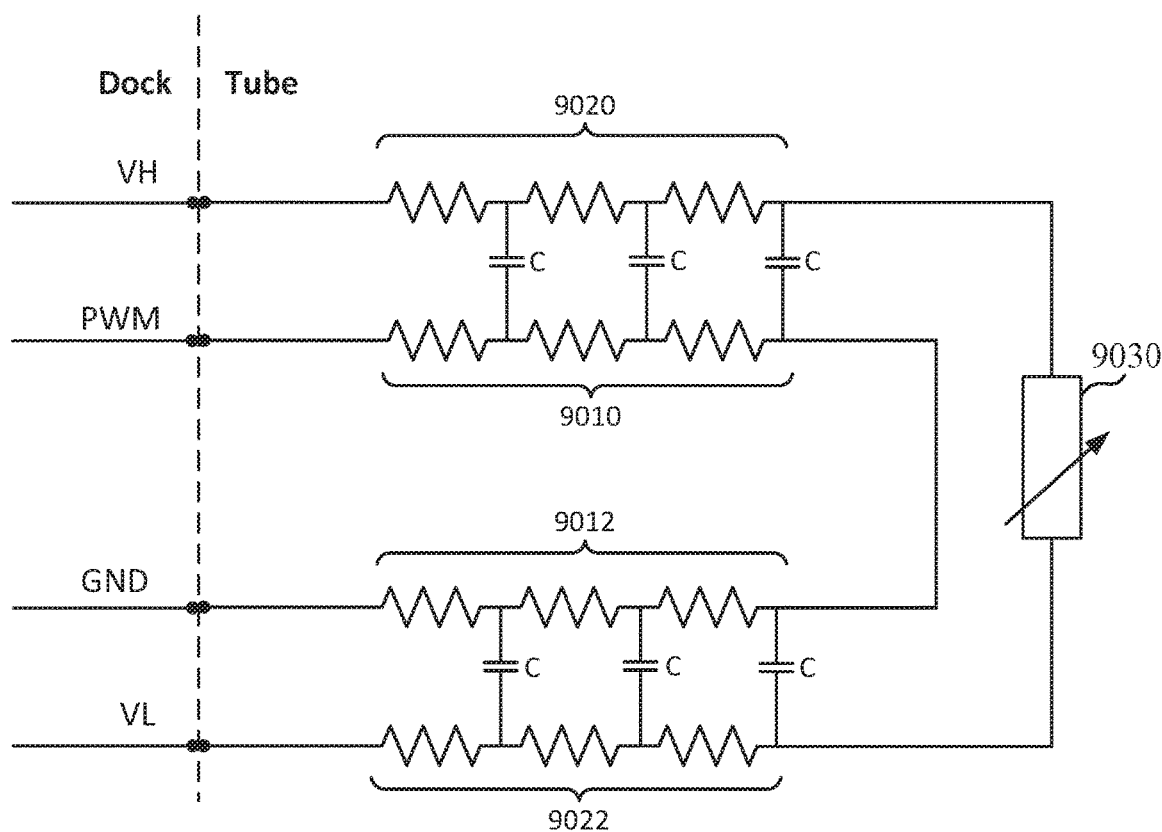

FIG. 40 shows a tube with a four wire circuit coupled to a dock in accordance with one form of the present technology.

Figure 41:
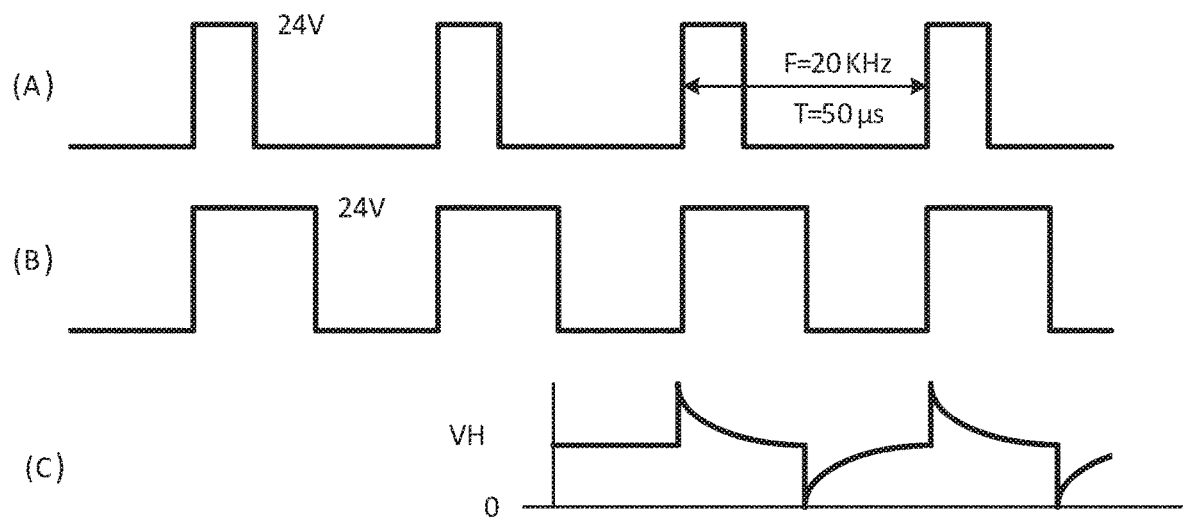

FIG. 41 shows an exemplary signal diagram of a PWM signal that may be applied to the heating elements and portions of PWM induced signal that may be observed in the sensing circuit.

Figure 42:
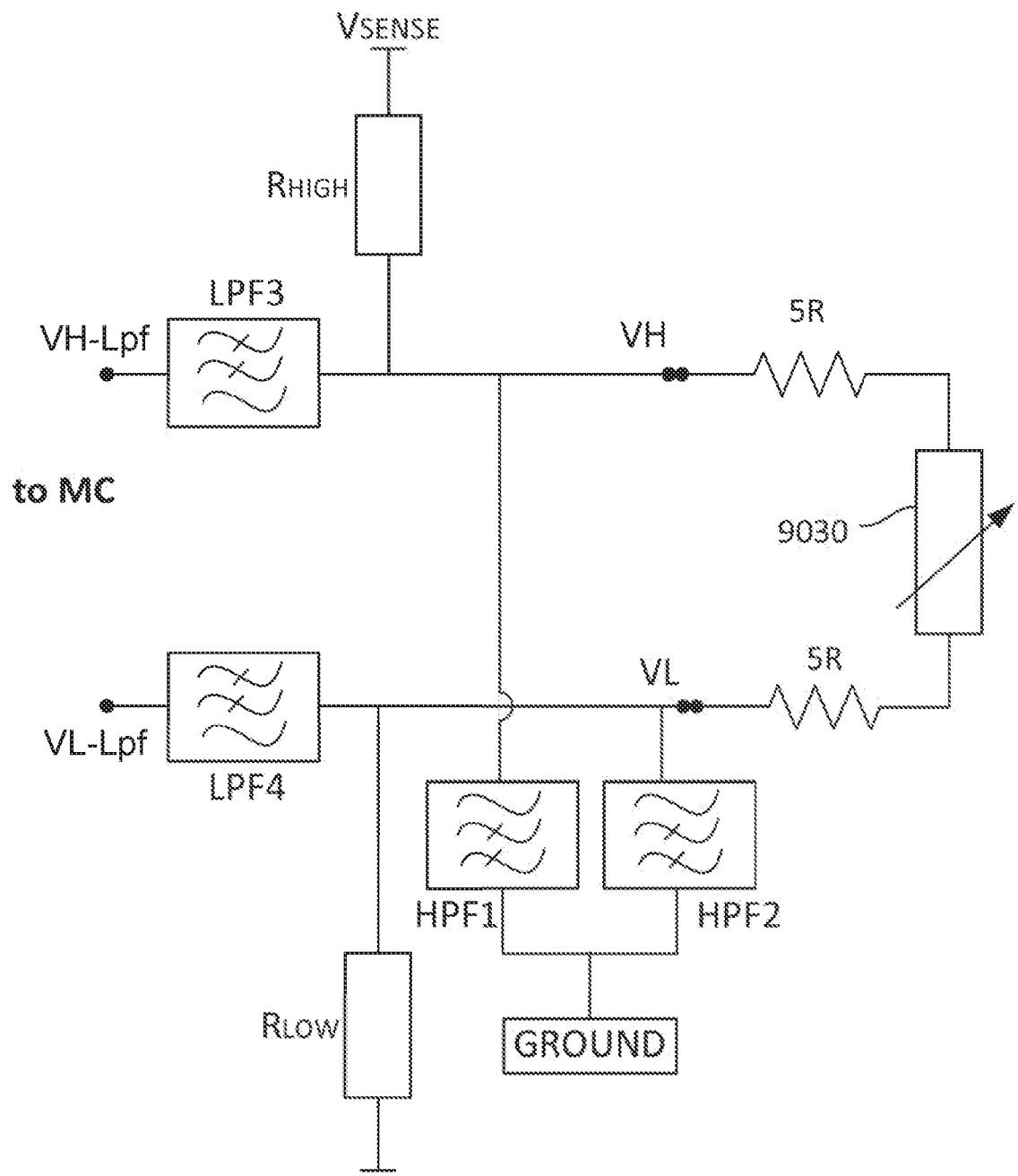

FIG. 42 shows an exemplary divider network including low pass filters in accordance with one form of the present technology.

Figure 43:
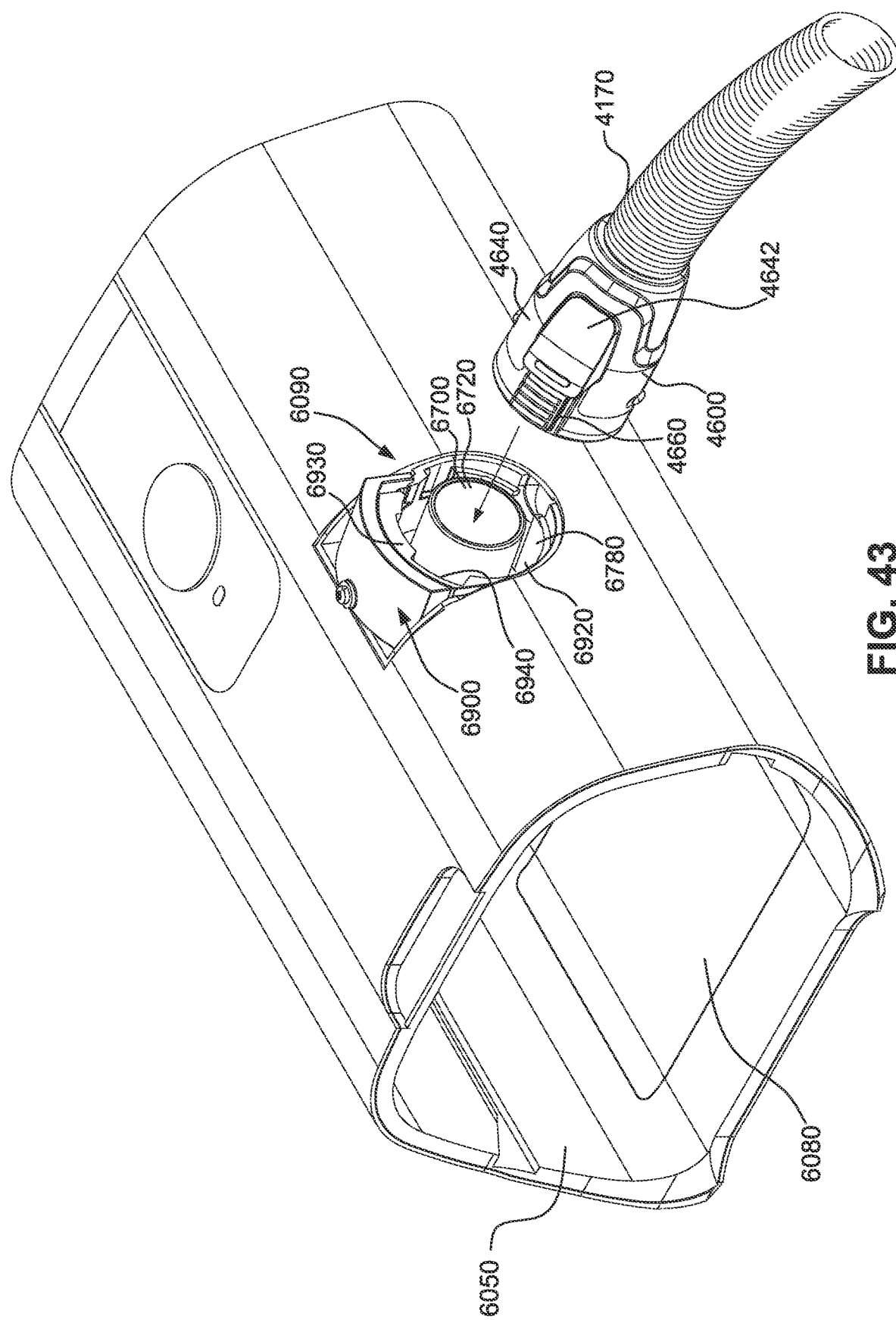

FIG. 43 is a perspective view showing a reservoir dock, an intermediate component, and an air delivery tube according to an example of the present technology, the air delivery tube oriented for engagement with the intermediate component and a locking and contact assembly provided to the reservoir dock.

Figure 44:
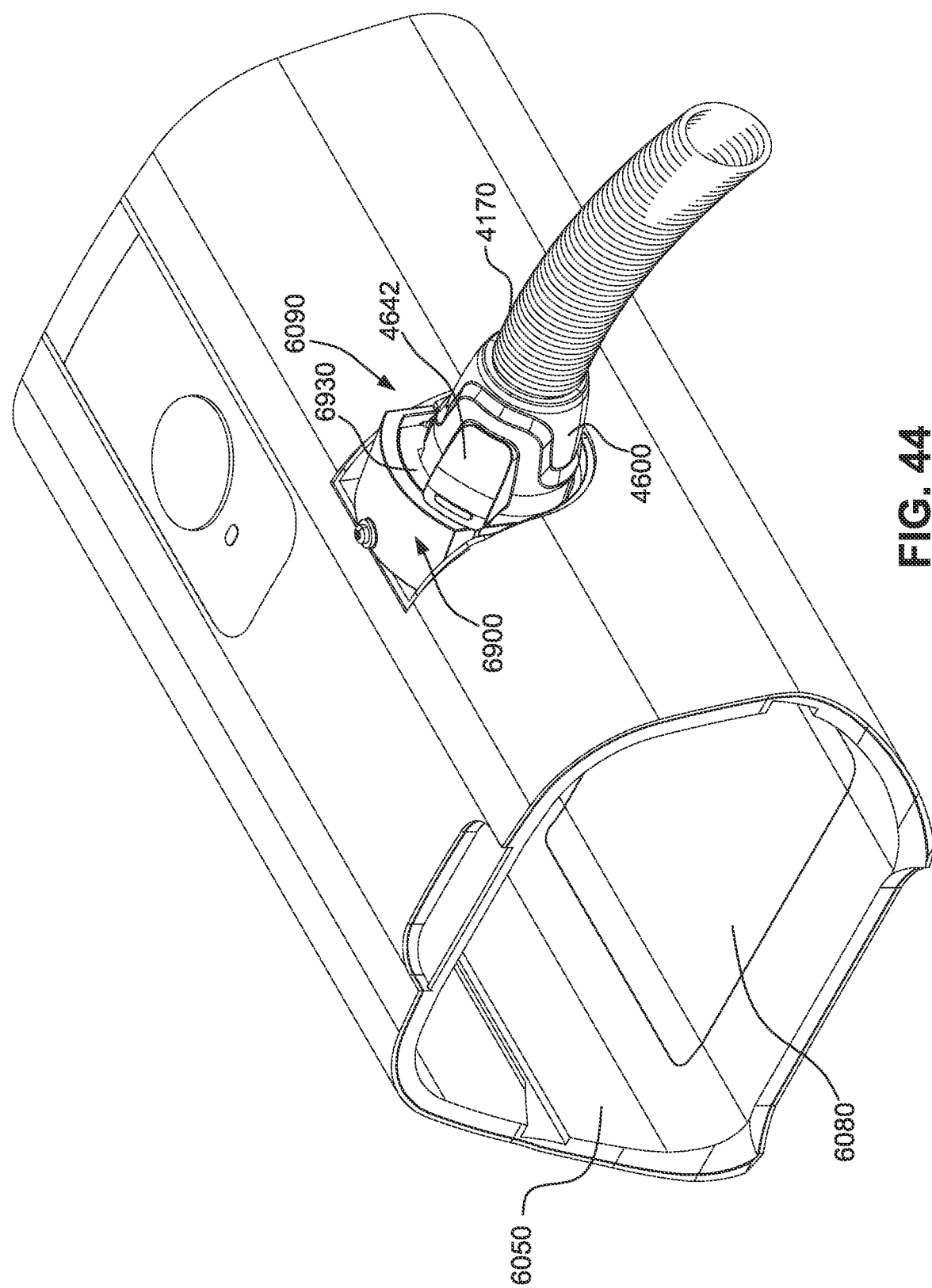

FIG. 44 is a perspective view showing the reservoir dock and the air delivery tube of FIG. 43, the air delivery tube engaged with the locking and contact assembly provided to the reservoir dock in an unlocked, engaged position.

Figure 45:
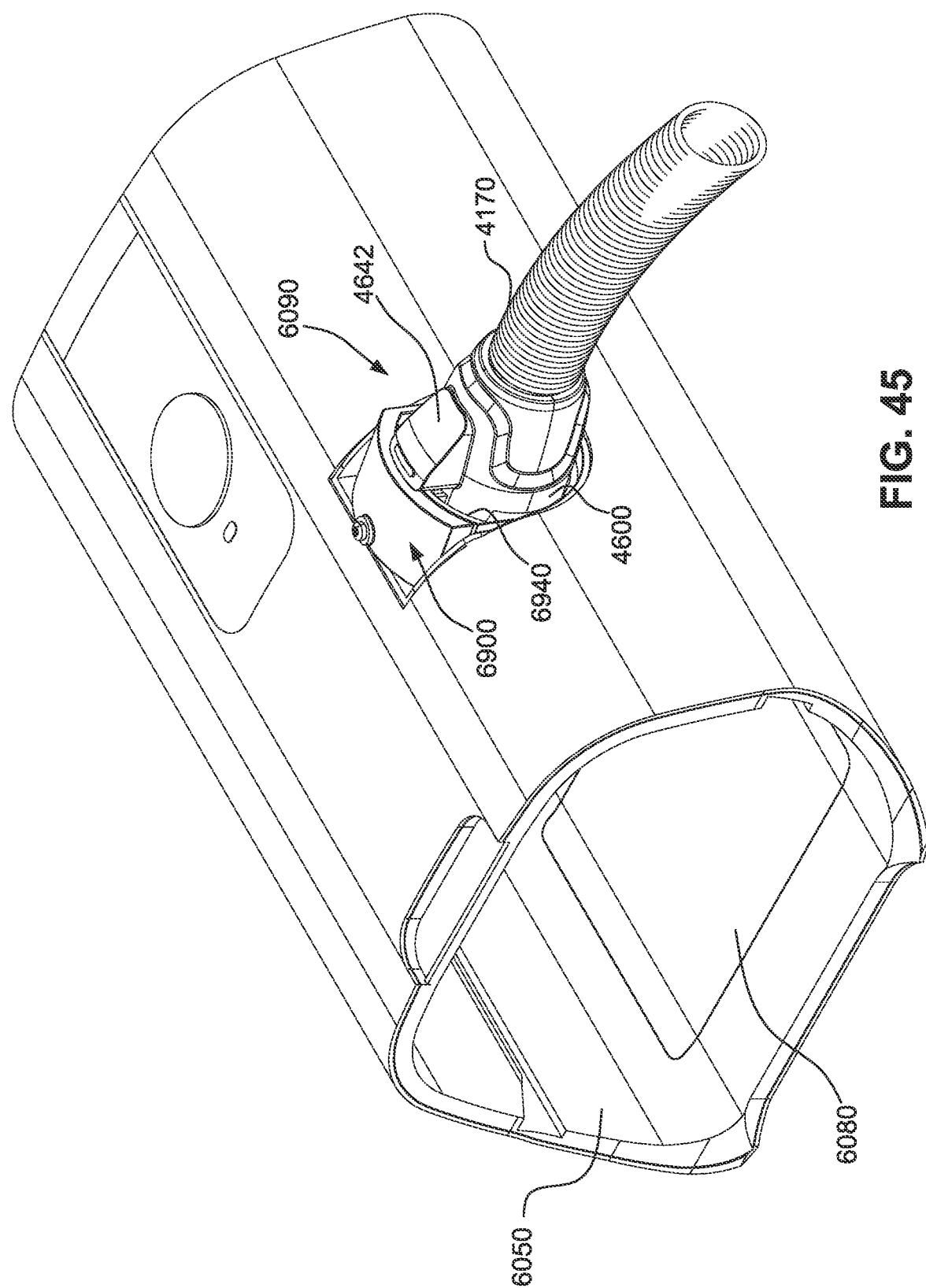

FIG. 45 is a perspective view showing the reservoir dock and the air delivery tube of FIG. 43, the air delivery tube engaged with the locking and contact assembly provided to the reservoir dock in a locked position.

Figure 46:
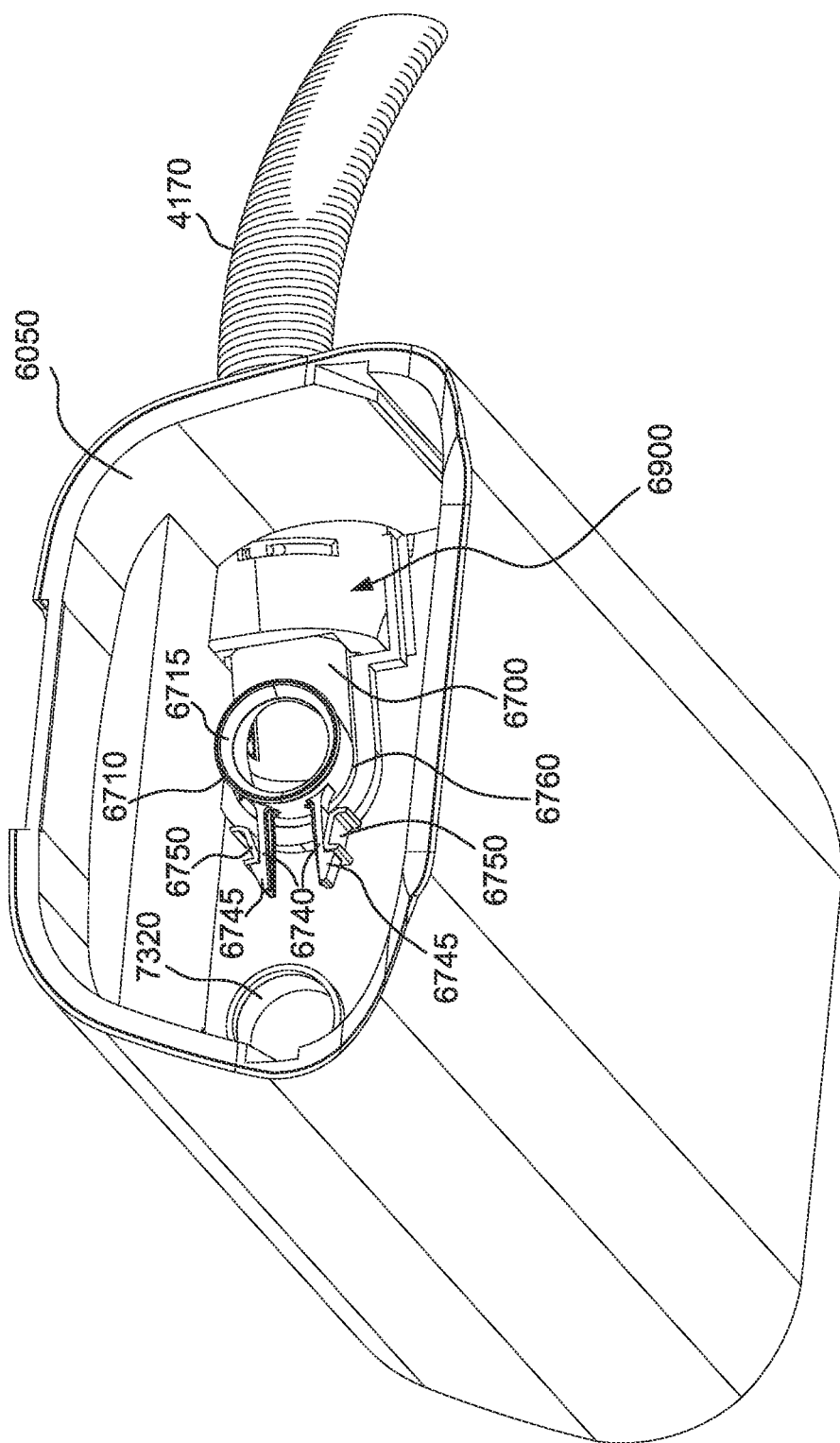

FIG. 46 is a perspective view showing the reservoir dock, the intermediate component, and the air delivery tube of FIG. 43.

Figure 47:
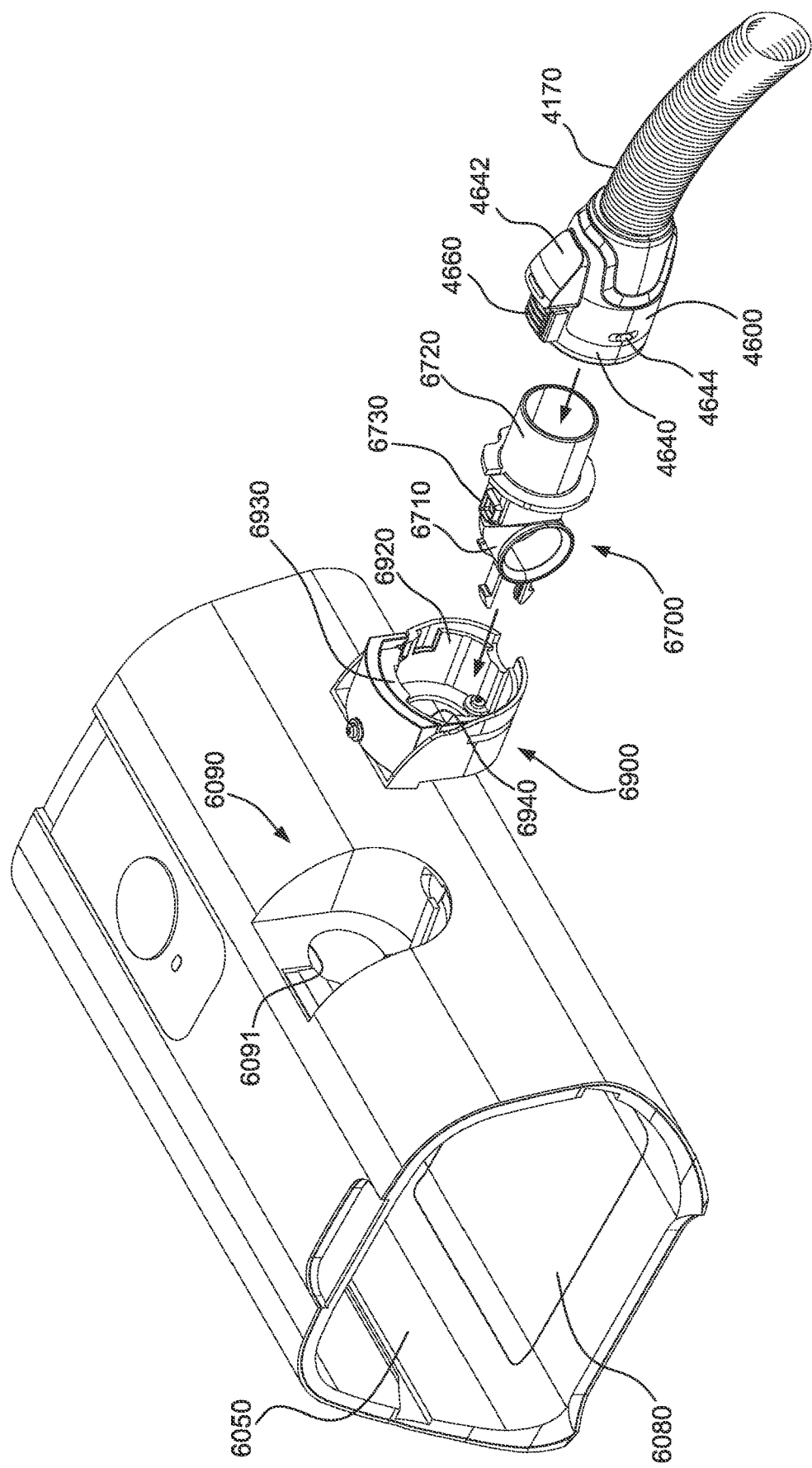

FIG. 47 is an exploded view showing the reservoir dock, the intermediate component, the air delivery tube, and the locking and contact assembly of the reservoir dock of FIG. 43.

Figure 48:
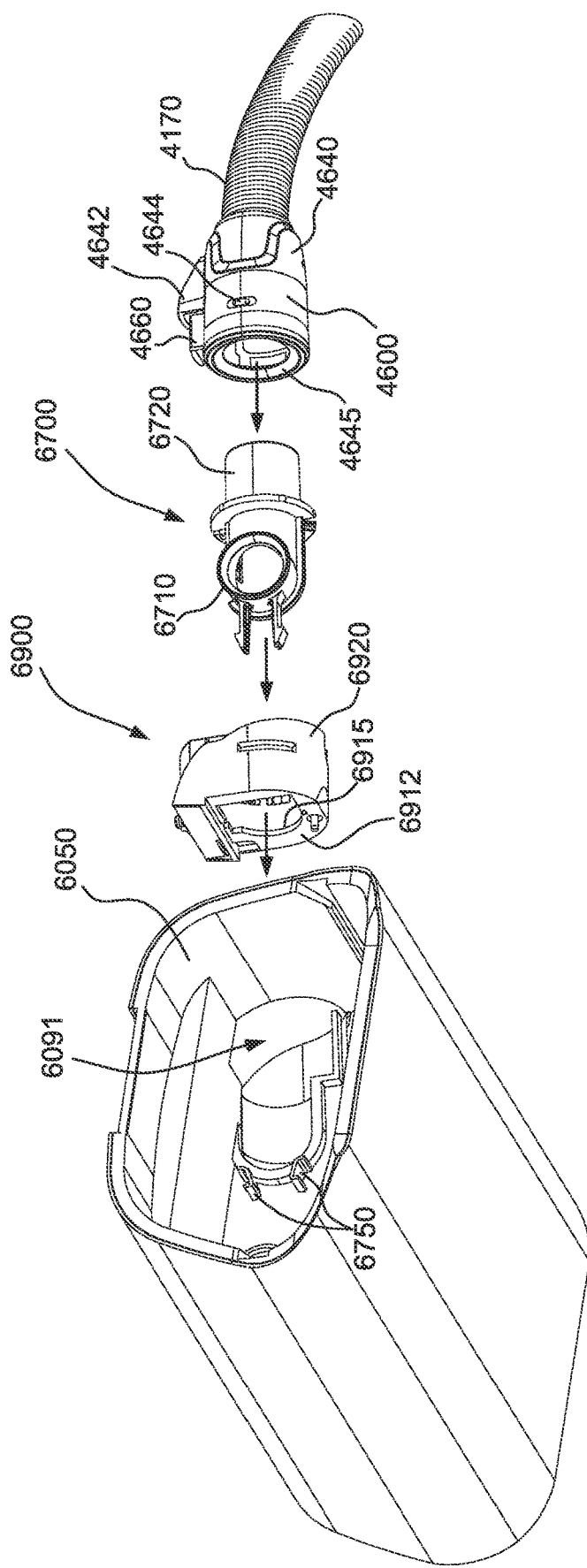

FIG. 48 is another exploded view showing the reservoir dock, the intermediate component, the air delivery tube, and the locking and contact assembly of the reservoir dock of FIG. 43.

Figure 49:
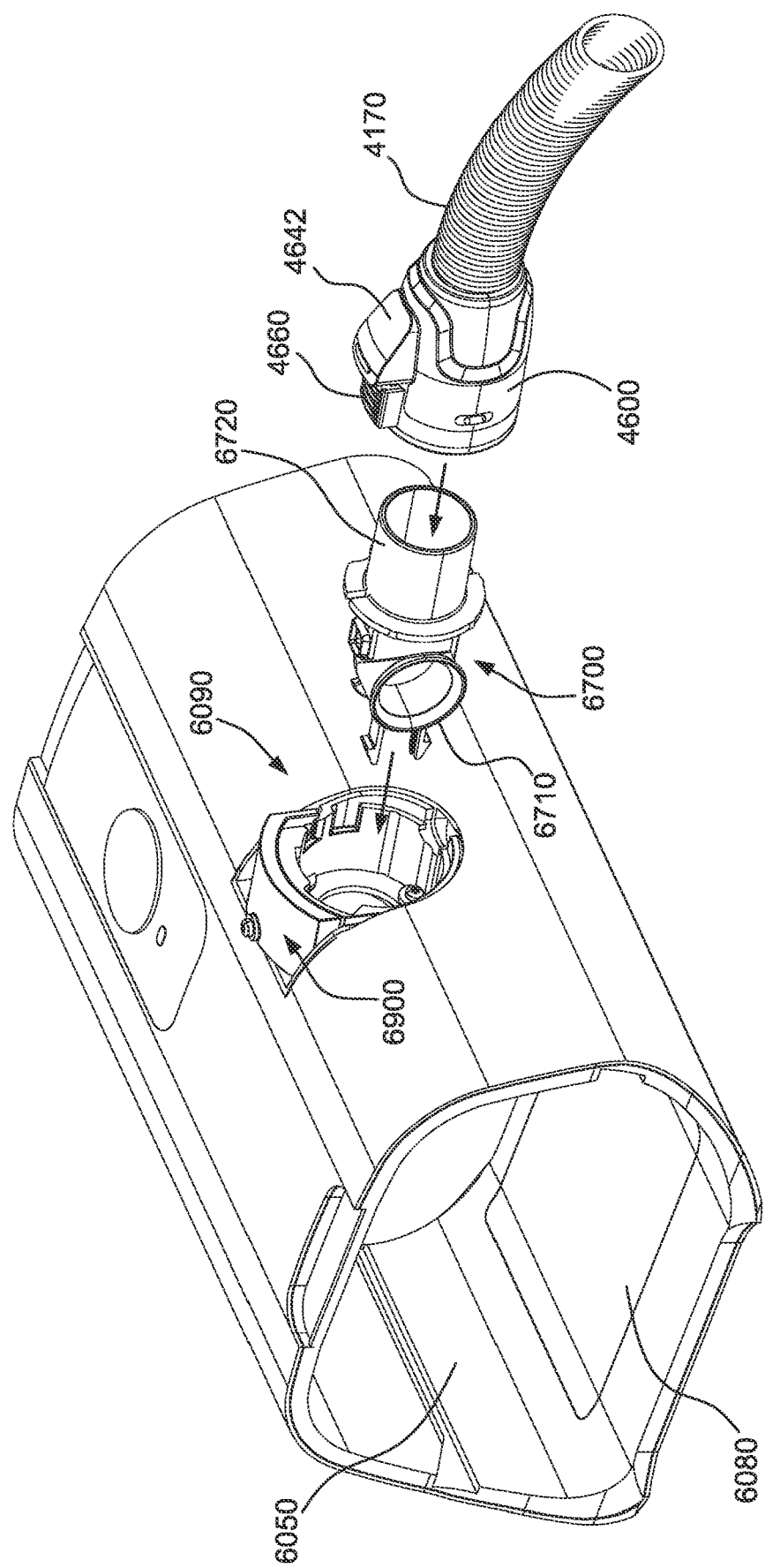

FIG. 49 is an exploded view showing the reservoir dock and the locking and contact assembly thereof, the intermediate component, and the air delivery tube of FIG. 43.

Figure 50:
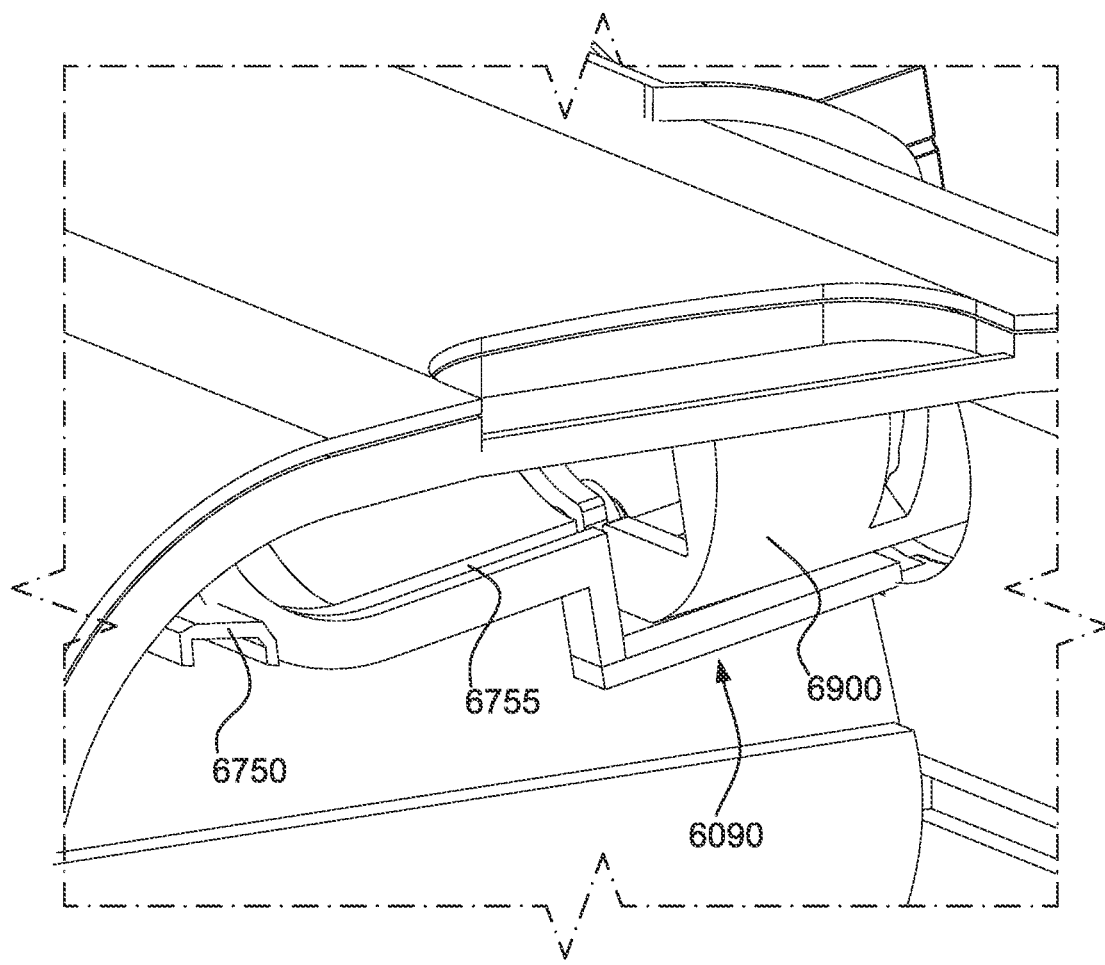

FIG. 50 is an enlarged elevated front perspective view of the reservoir dock of FIG. 43.

Figure 51:
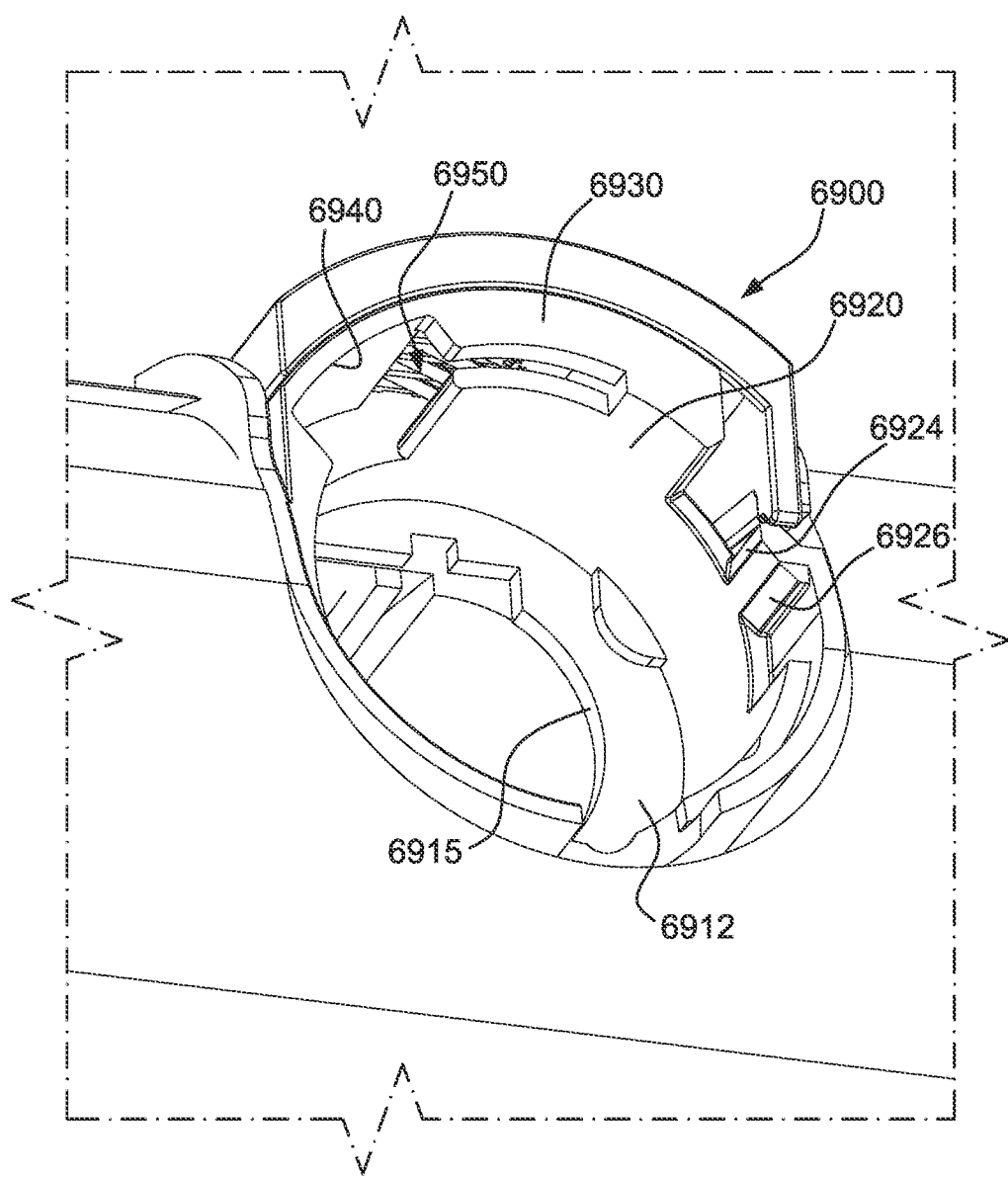

FIG. 51 is an enlarged perspective view showing the locking and contact assembly provided to the reservoir dock of FIG. 43.

Figure 52:
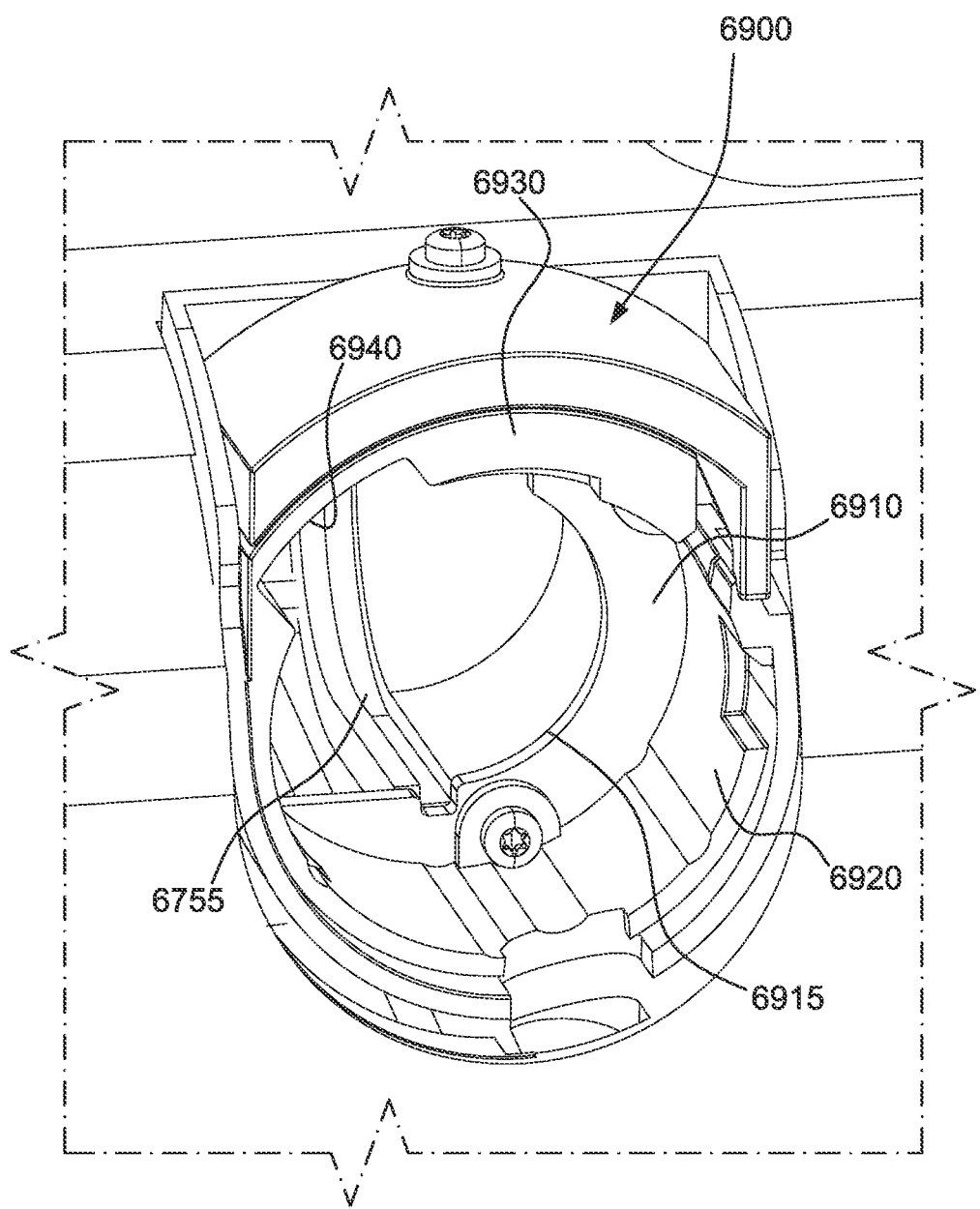

FIG. 52 is another enlarged perspective view showing the locking and contact assembly provided to the reservoir dock of FIG. 43.

Figure 53:
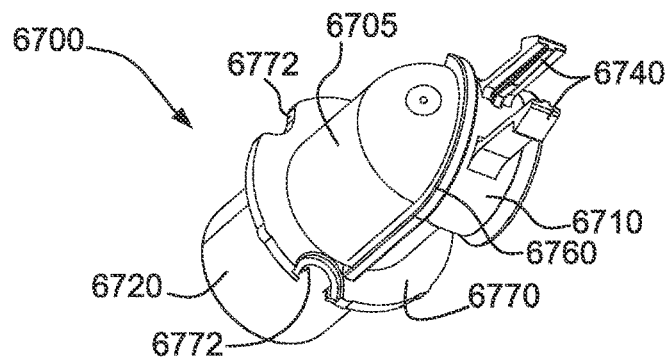

FIG. 53 is a rear perspective view showing an intermediate component according to an example of the present technology.

Figure 54:
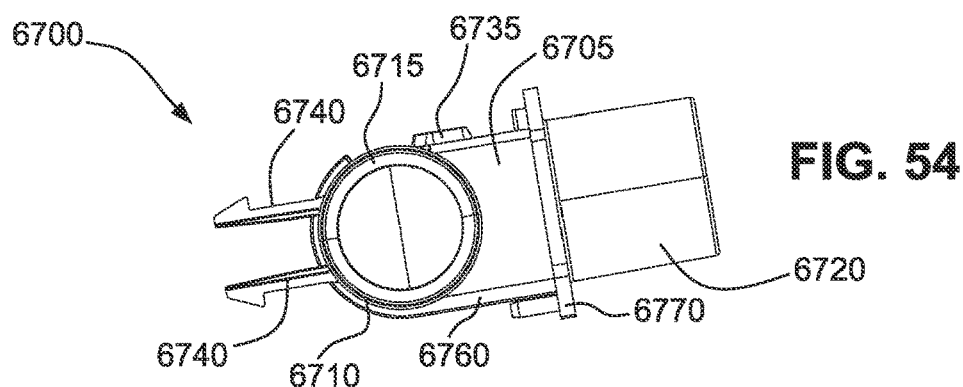

FIG. 54 is a front view of the intermediate component of FIG. 53.

Figure 55:
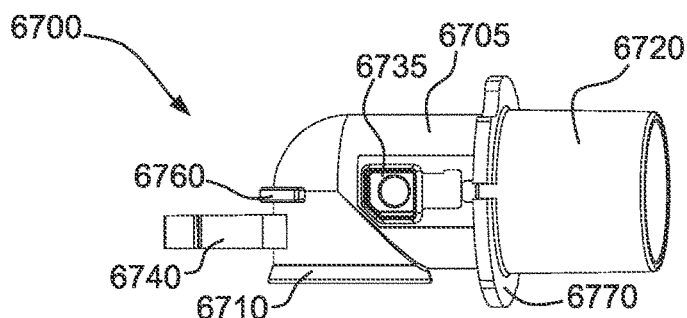

FIG. 55 is a top view of the intermediate component of FIG. 53.

Figure 56:
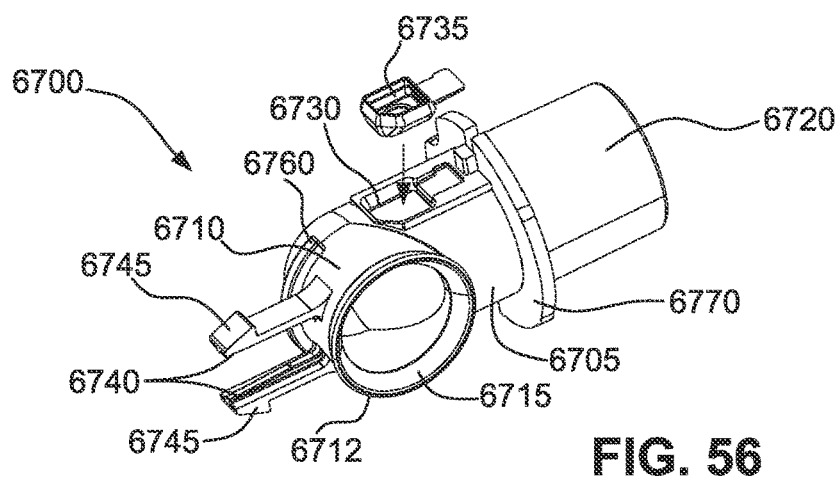

FIG. 56 is an exploded view of the intermediate component of FIG. 53.

Figure 57:
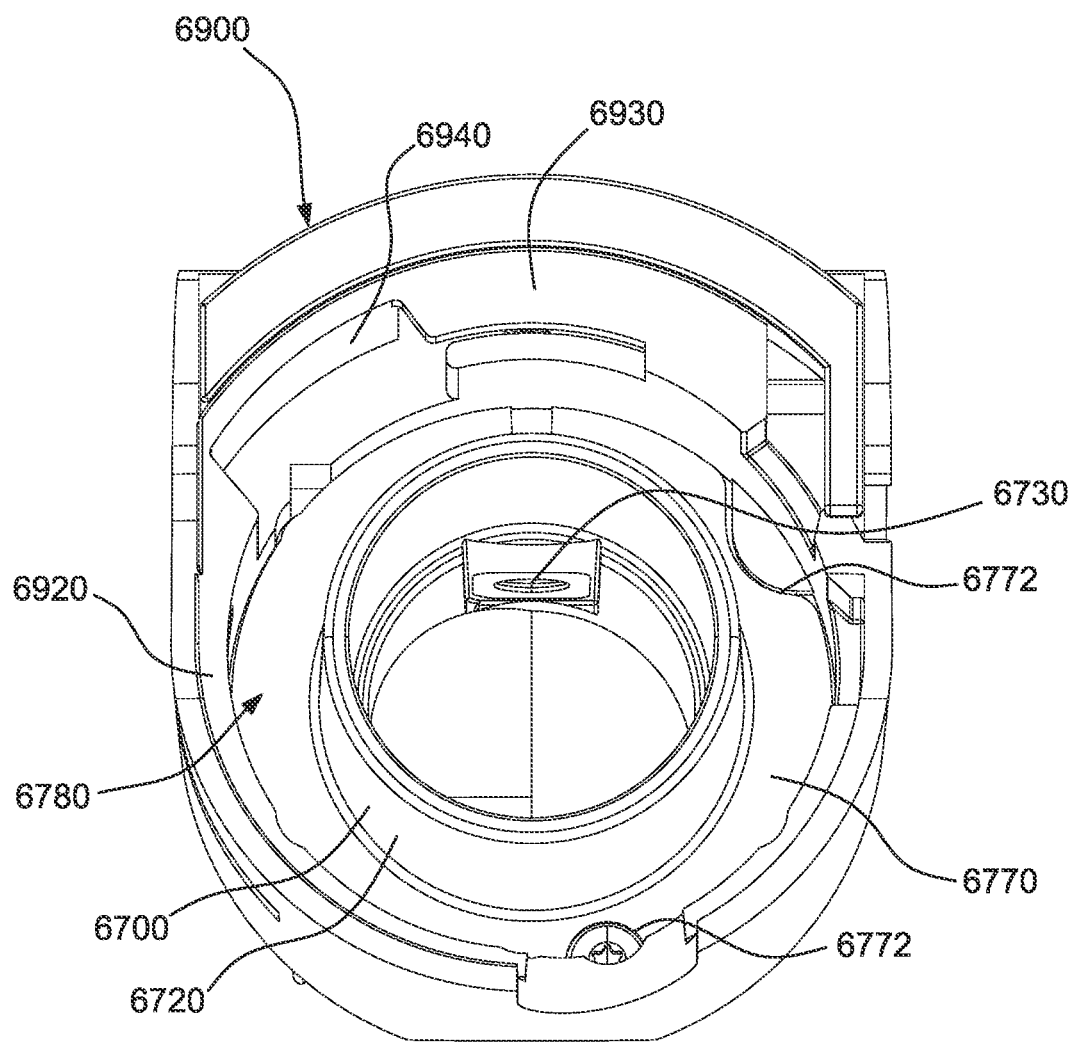

FIG. 57 is an enlarged front perspective view showing the locking and contact assembly and the intermediate component for the reservoir dock of FIG. 43.

Figure 58:
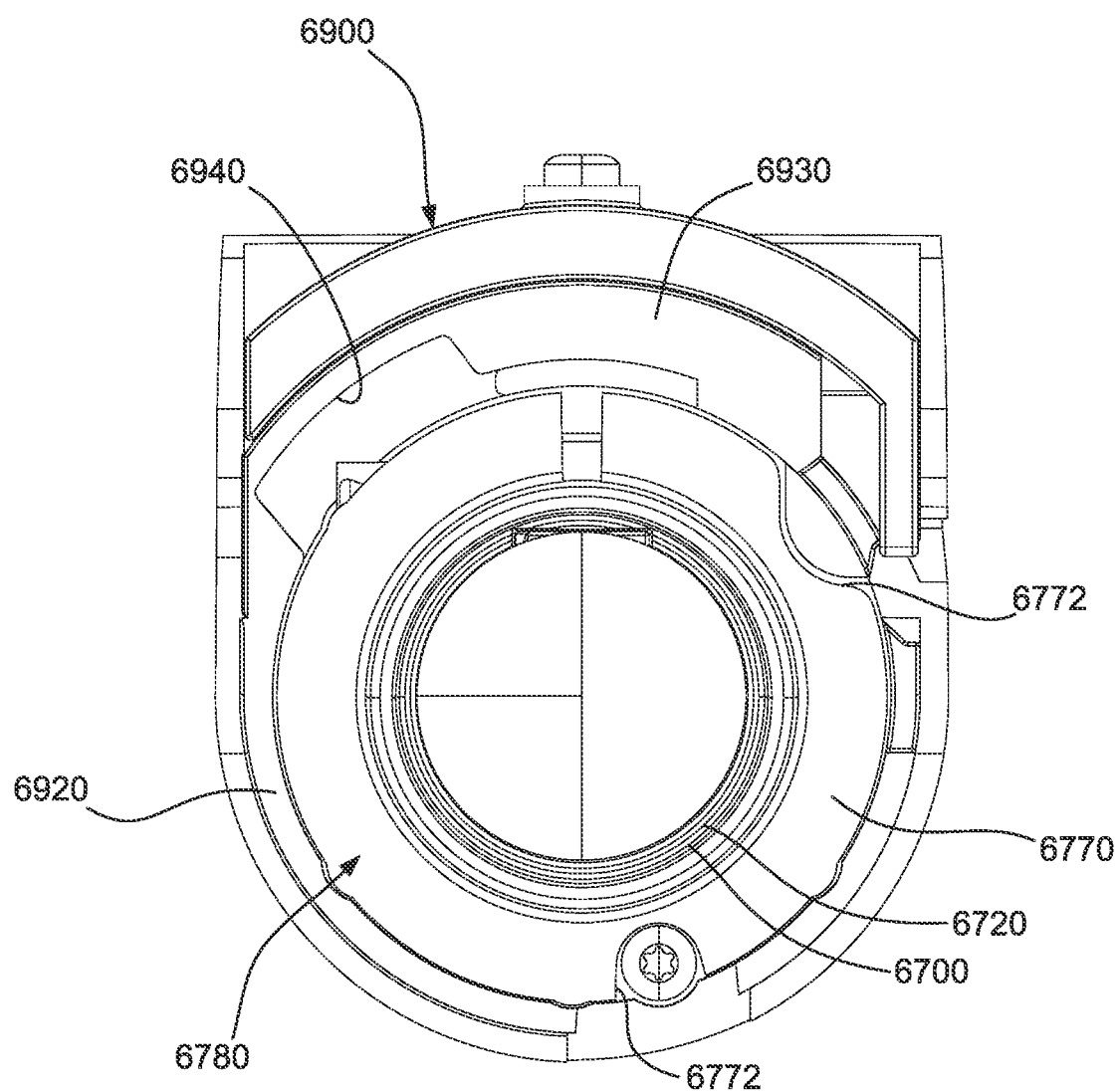

FIG. 58 is a front view of the locking and contact assembly and the intermediate component of FIG. 57.

Figure 59:
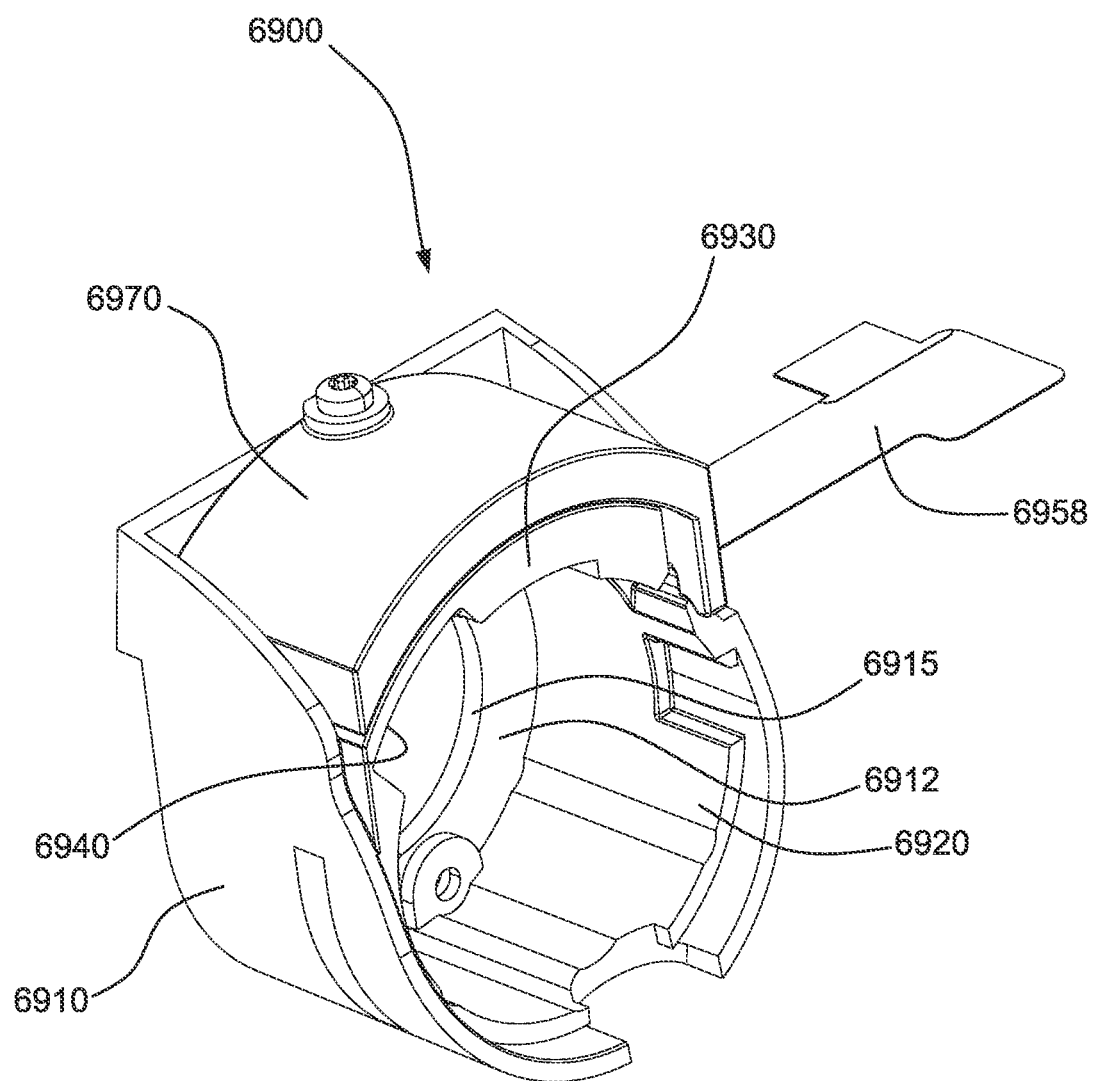

FIG. 59 is a perspective view showing a locking and contact assembly for a reservoir dock according to an example of the present technology.

Figure 60:
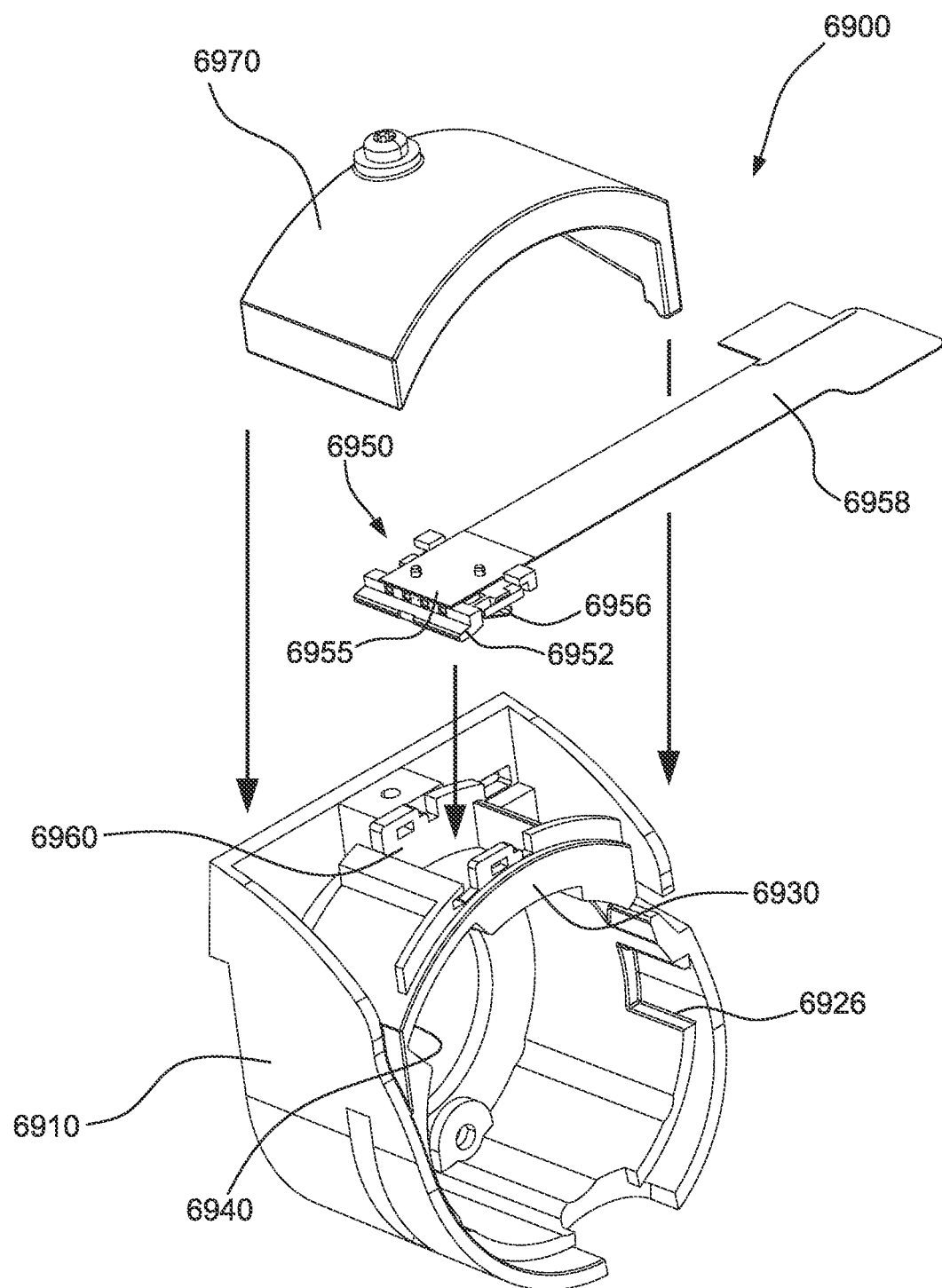

FIG. 60 is an exploded view of the locking and contact assembly of FIG. 59.

Figure 61:
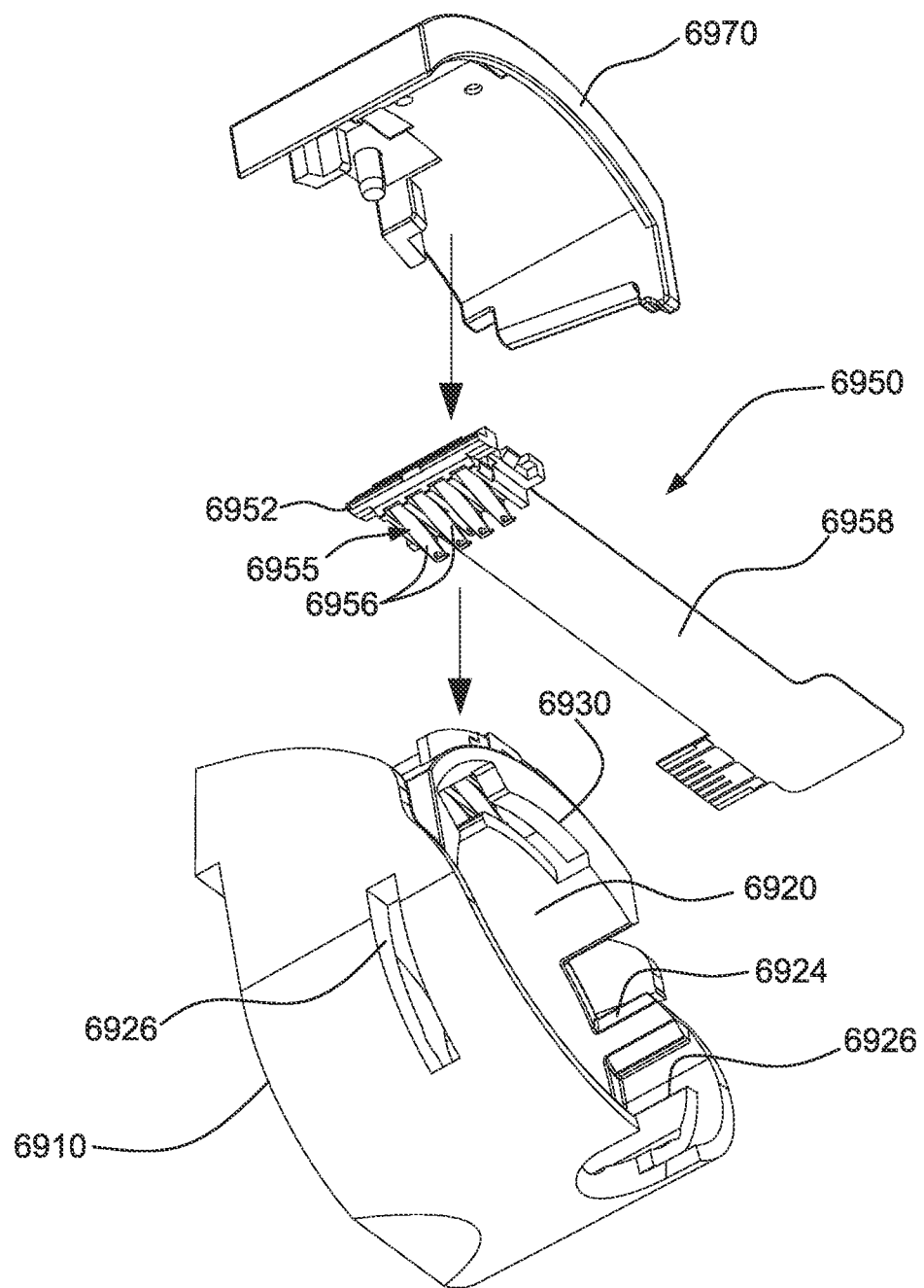

FIG. 61 is another exploded view of the locking and contact assembly of FIG. 59.

Figure 62:
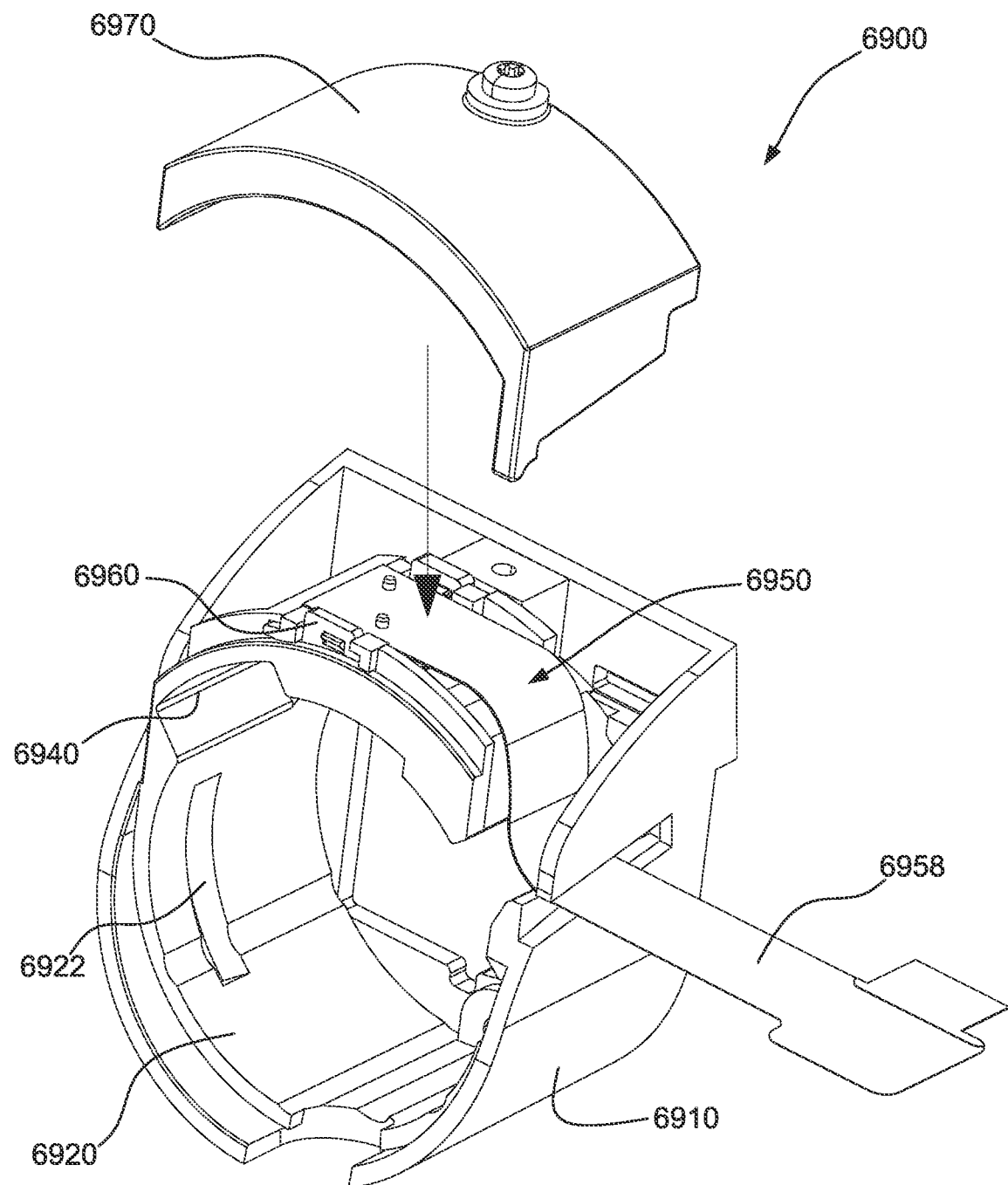

FIG. 62 is a perspective view of the locking and contact assembly of FIG. 59 with the cover removed.

Figure 63:
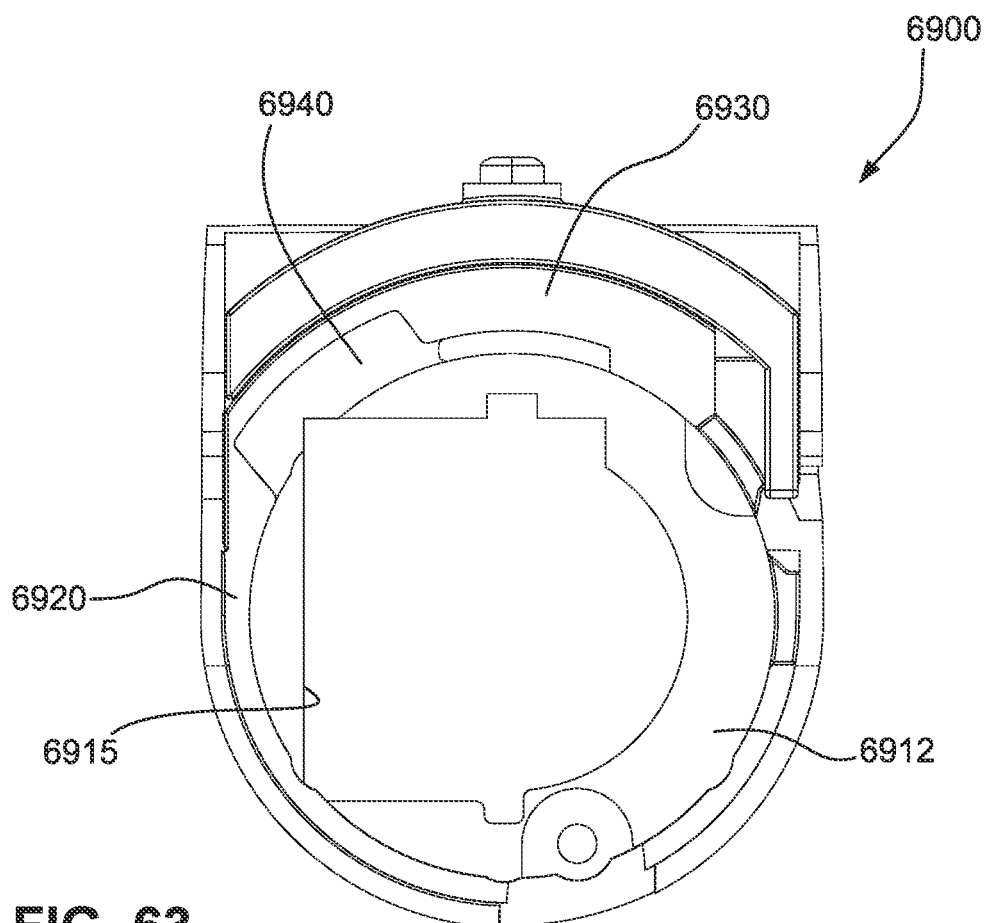

FIG. 63 is a front view of the locking and contact assembly of FIG. 59.

Figure 64:
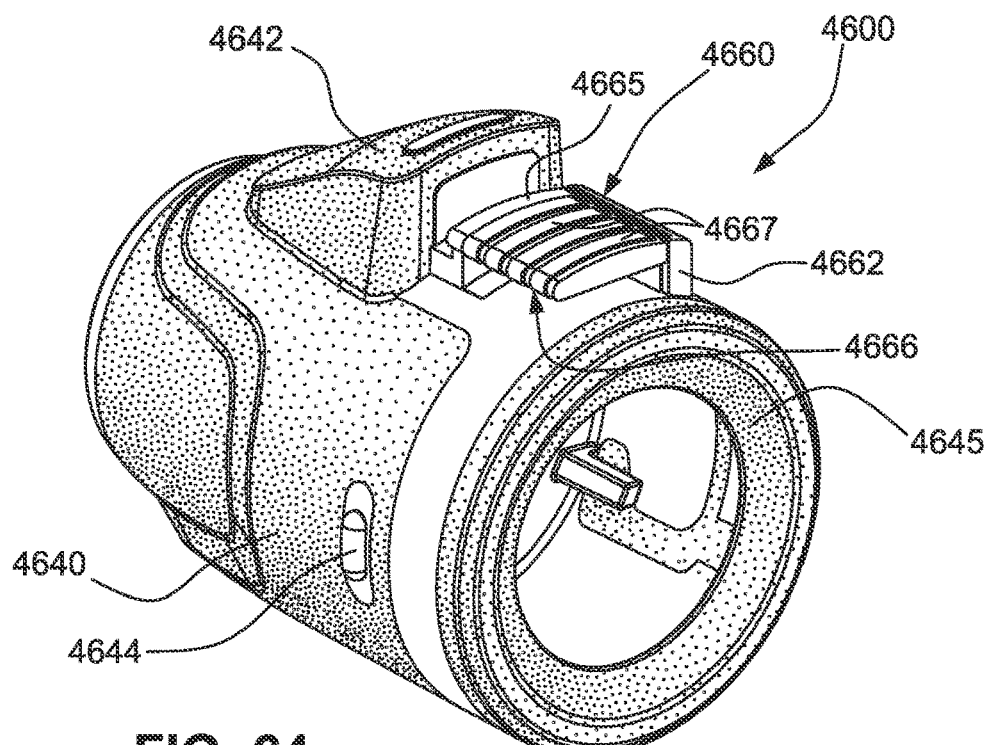

FIG. 64 is a perspective view of a dock connector for an air delivery tube according to an example of the present technology.

Figure 65:
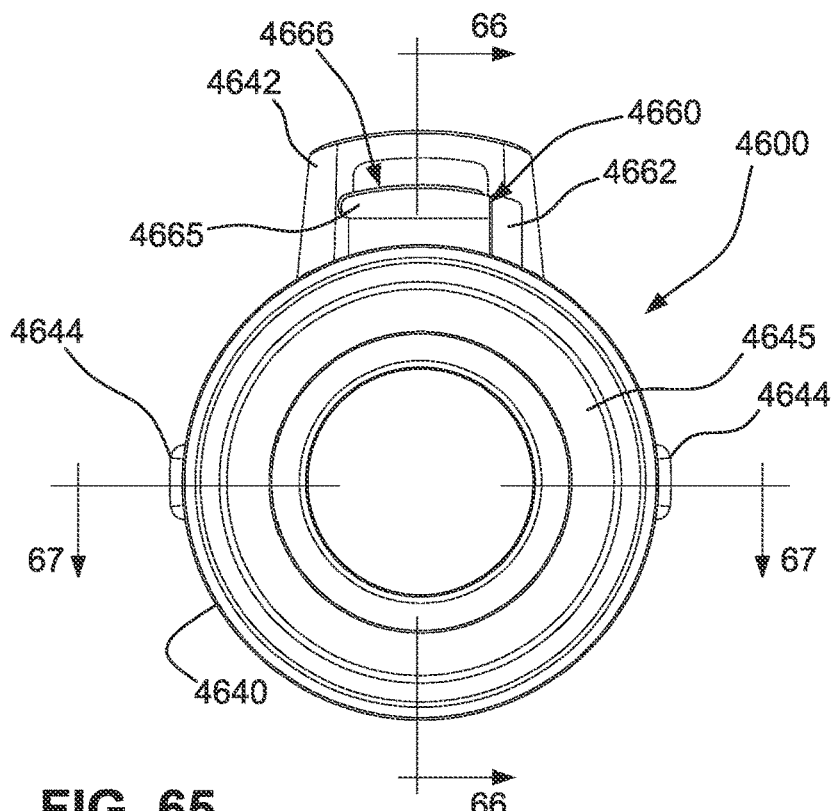

FIG. 65 is a front view of the dock connector of FIG. 64.

Figure 66:
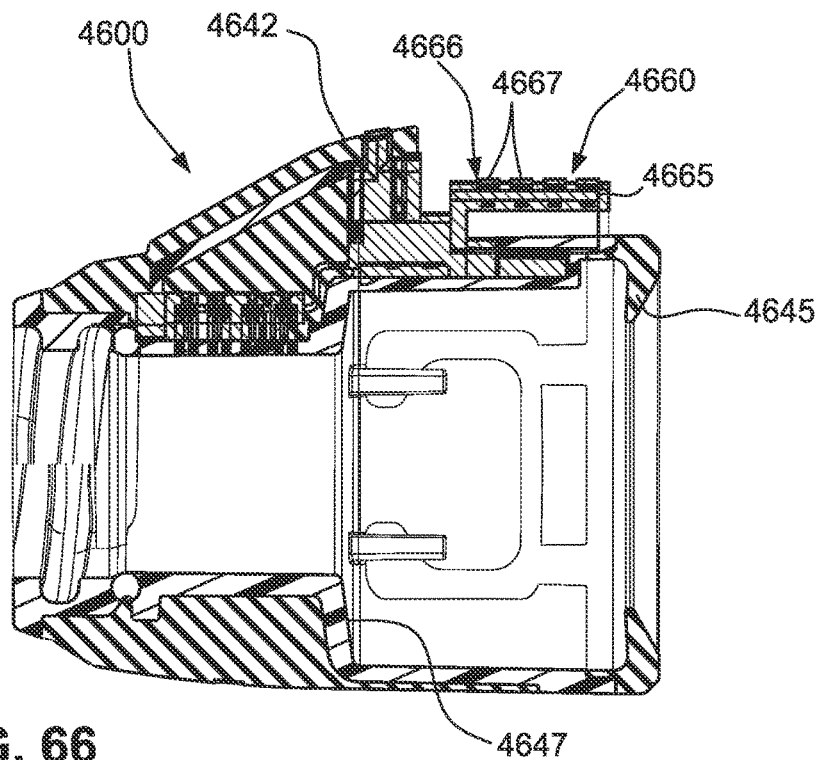

FIG. 66 is a cross-sectional view through line 66-66 of FIG. 65.

Figure 67:
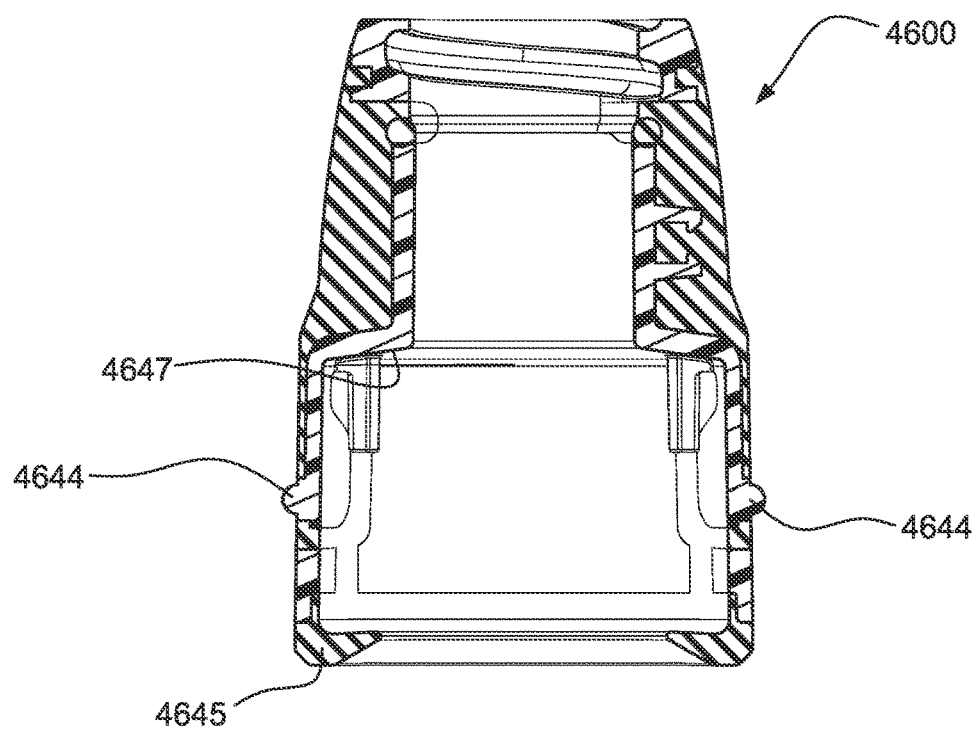

FIG. 67 is a cross-sectional view through line 67-67 of FIG. 65.

Figure 68:
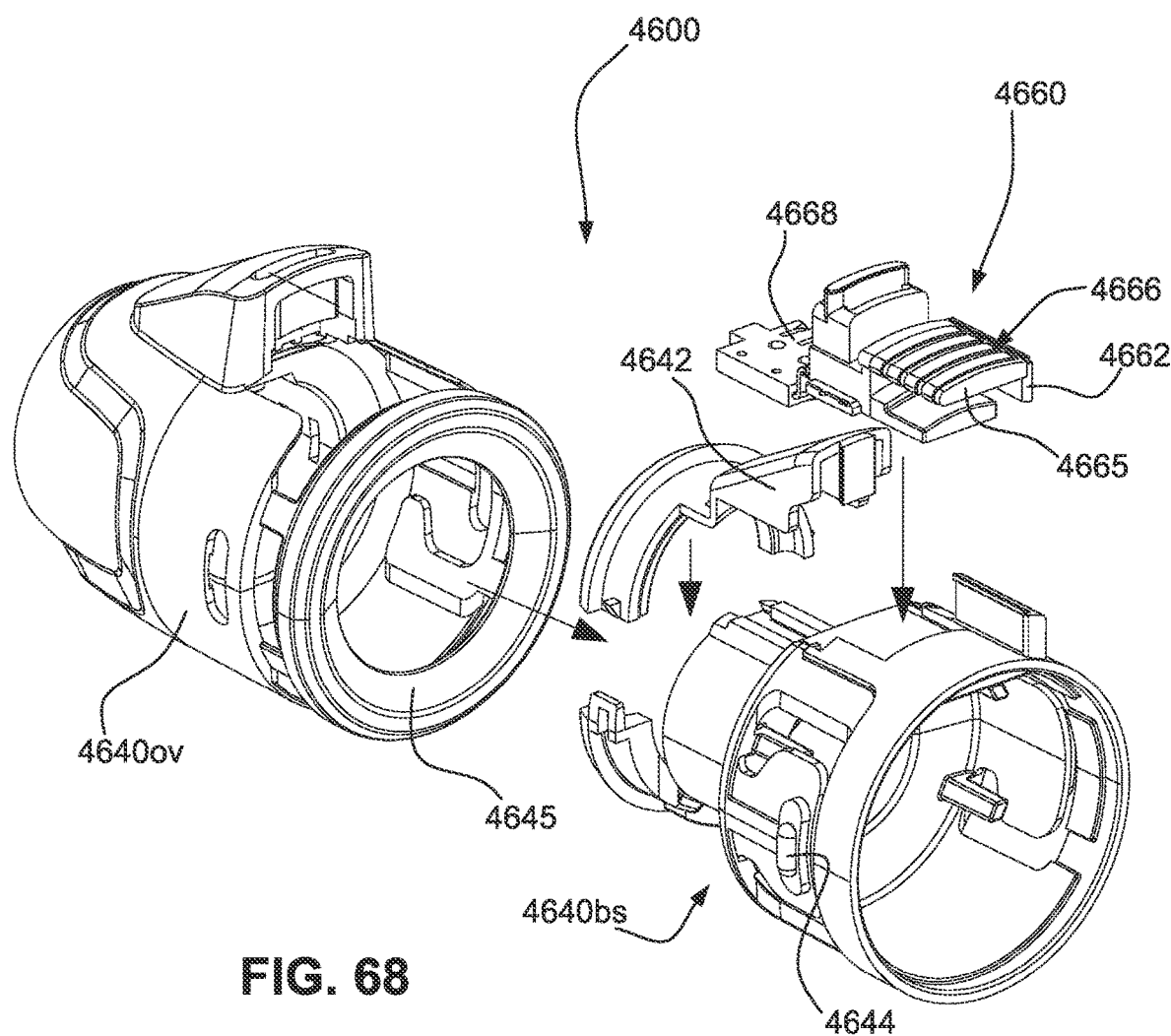

FIG. 68 is an exploded view of the dock connector of FIG. 64.

Figure 69:
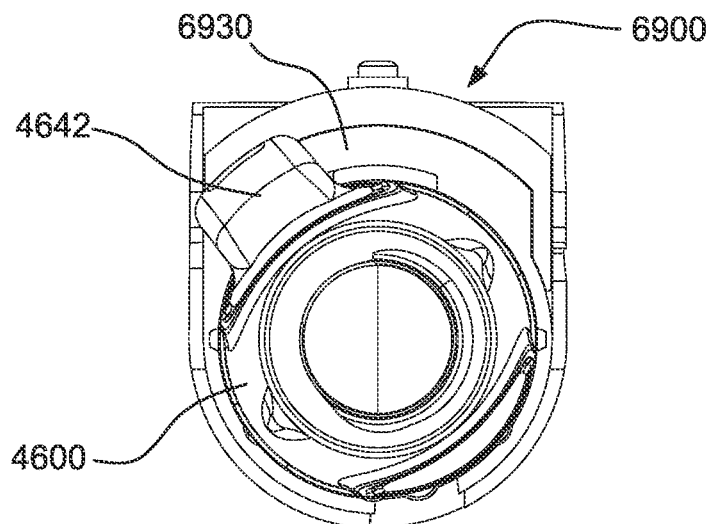

FIG. 69 is a front view showing engagement of the dock connector of the air delivery tube with the intermediate component and the locking and contact assembly provided to the reservoir dock according to an example of the present technology, the dock connector in an unlocked, engaged position.

Figure 70:
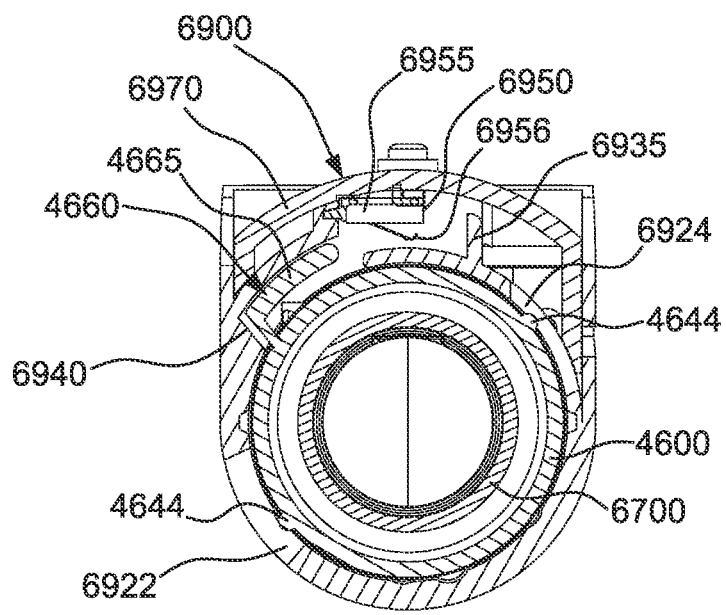

FIG. 70 is a cross-sectional view related to FIG. 69 showing the dock connector in an unlocked, engaged position.

Figure 71:
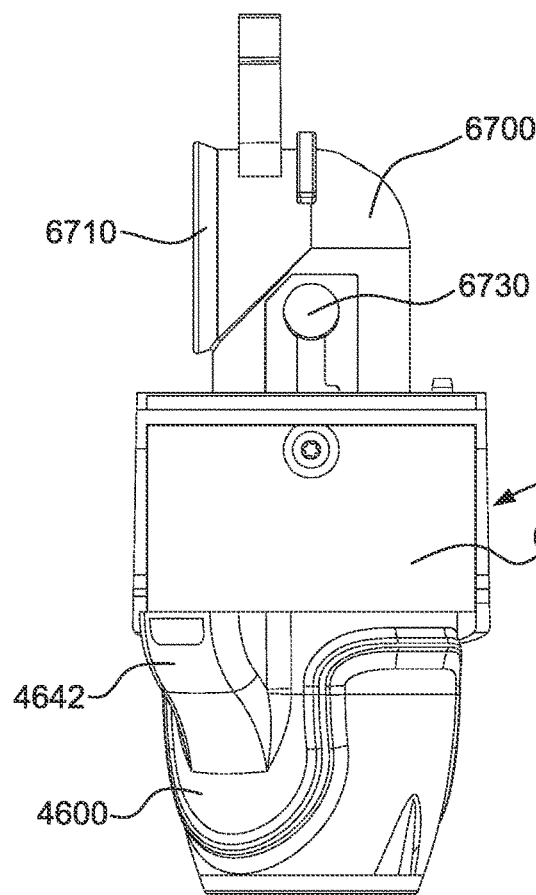

FIG. 71 is a top view related to FIG. 69 showing the dock connector in an unlocked, engaged position.

Figure 72:
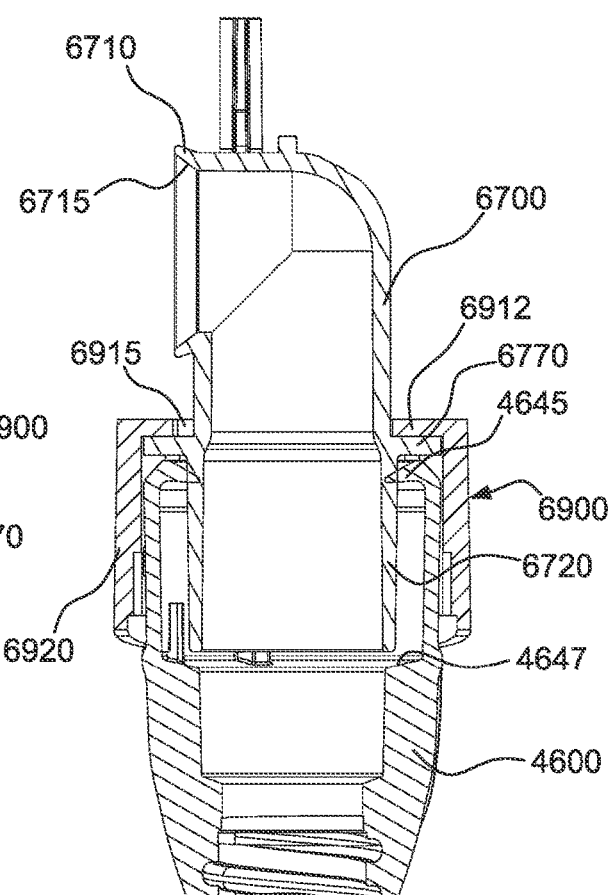

FIG. 72 is a cross-sectional view related to FIG. 69 showing the dock connector in an unlocked, engaged position.

Figure 73:
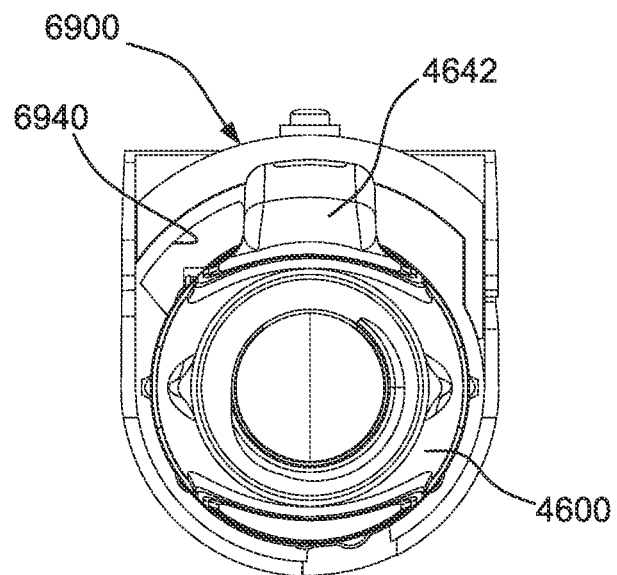

FIG. 73 is a front view showing engagement of the dock connector of the air delivery tube with the intermediate component and the locking and contact assembly provided to the reservoir dock according to an example of the present technology, the dock connector in a locked position.

Figure 74:
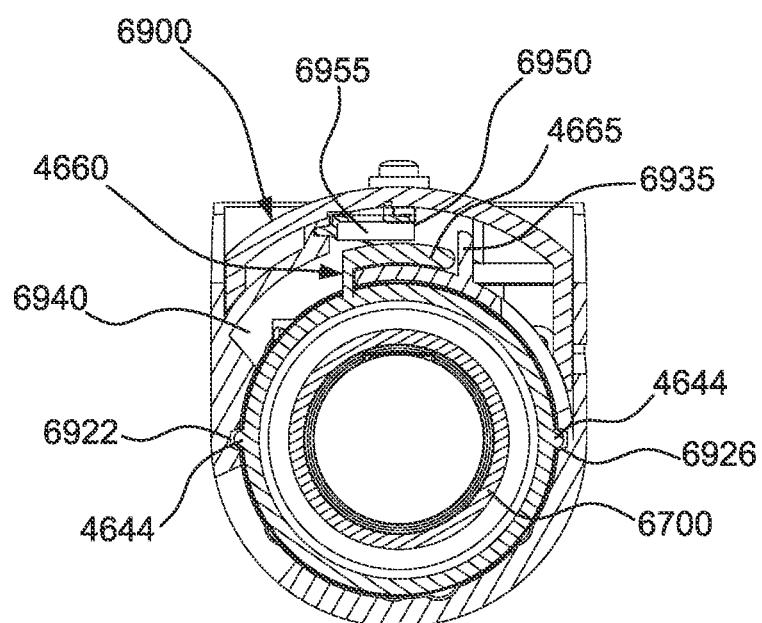

FIG. 74 is a cross-sectional view related to FIG. 73 showing the dock connector in a locked position.

Figure 75:
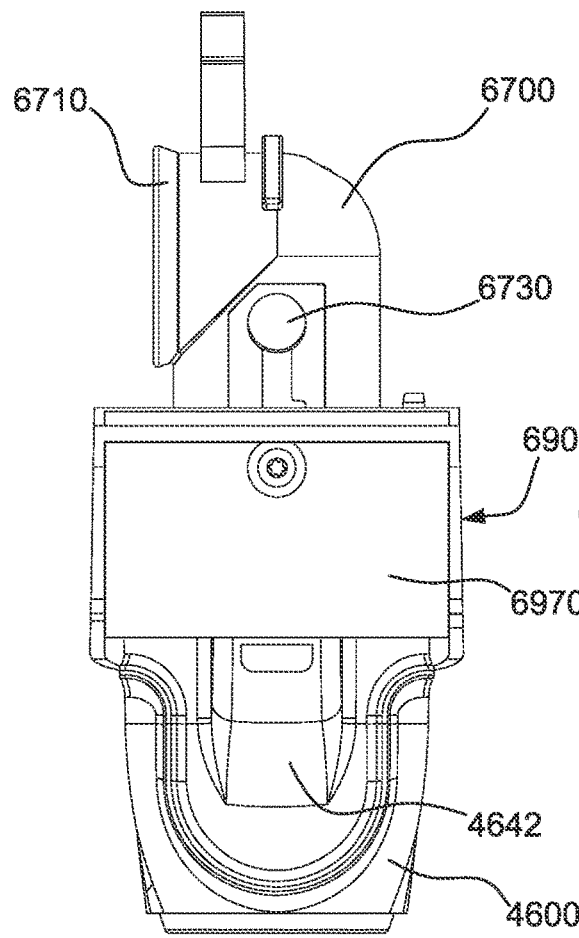

FIG. 75 is a top view related to FIG. 73 showing the dock connector in a locked position.

Figure 76:
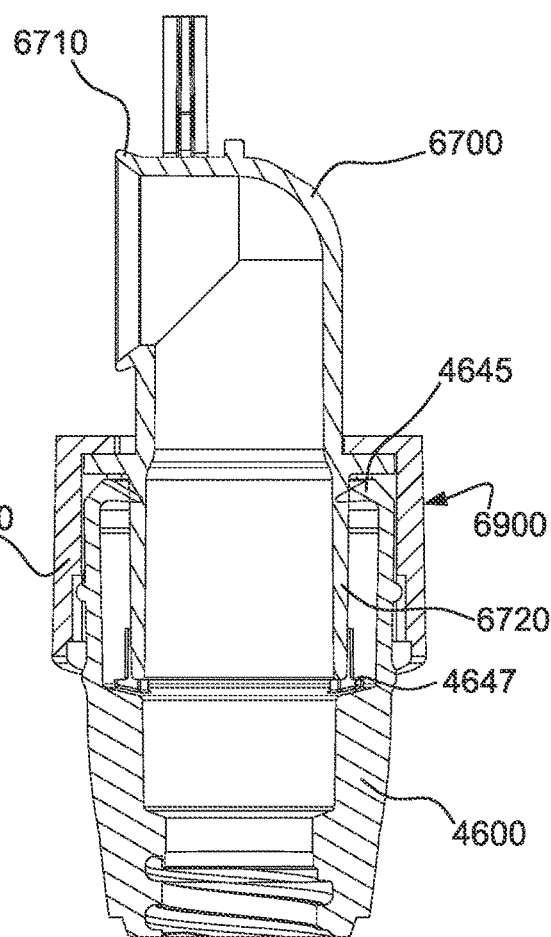

FIG. 76 is a cross-sectional view related to FIG. 73 showing the dock connector in a locked position.

Figure 77:
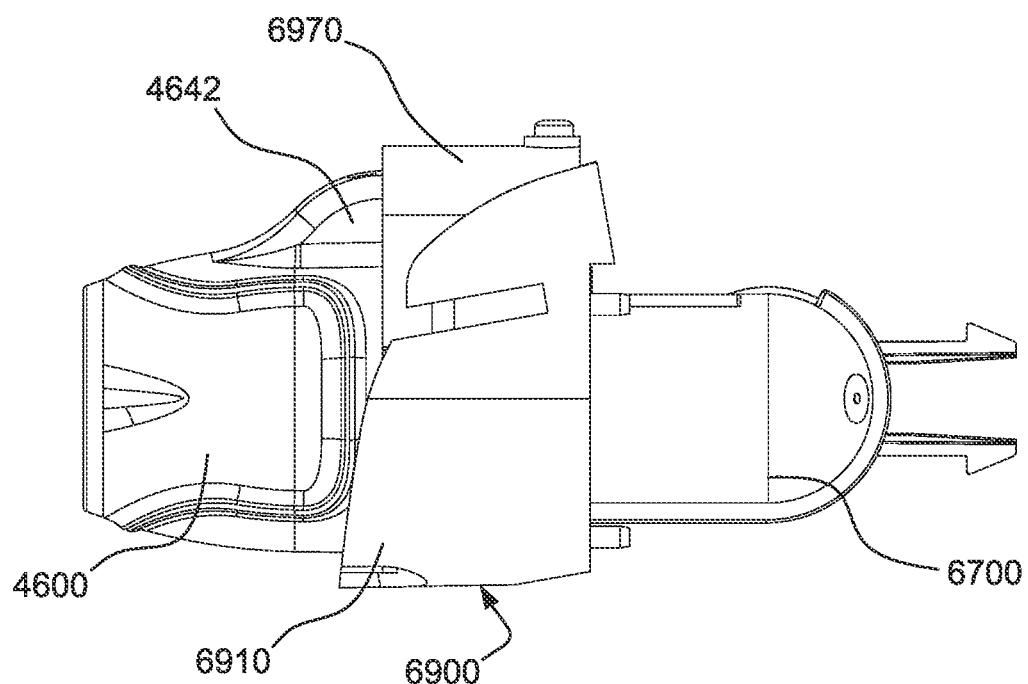

FIG. 77 is a side view related to FIG. 73 showing the dock connector in a locked position.

Figure 78:
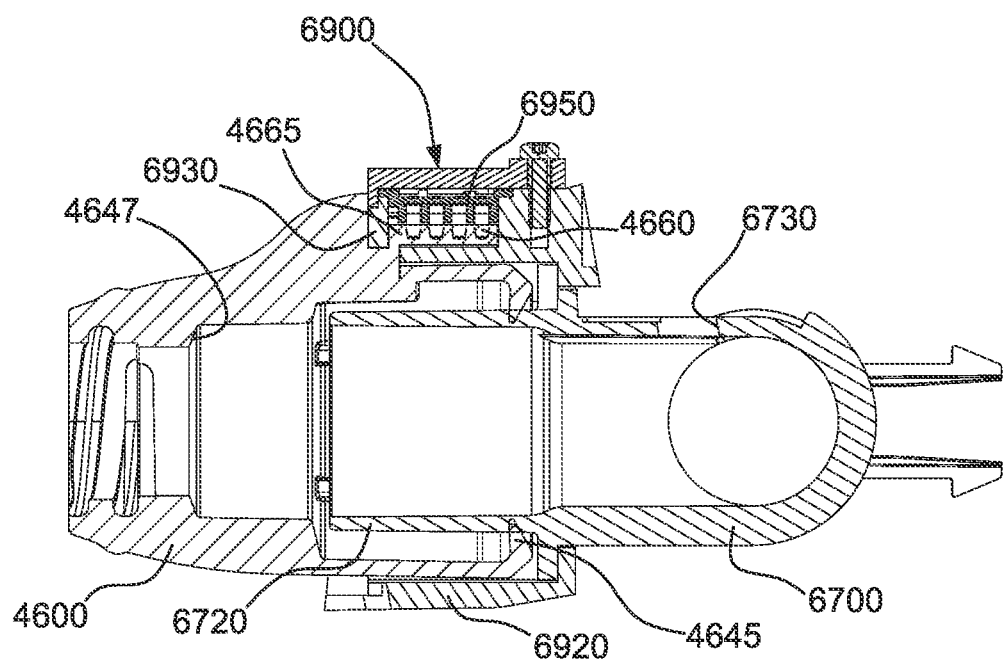

FIG. 78 is a cross-sectional view related to FIG. 73 showing the dock connector in a locked position.

Figure 79:
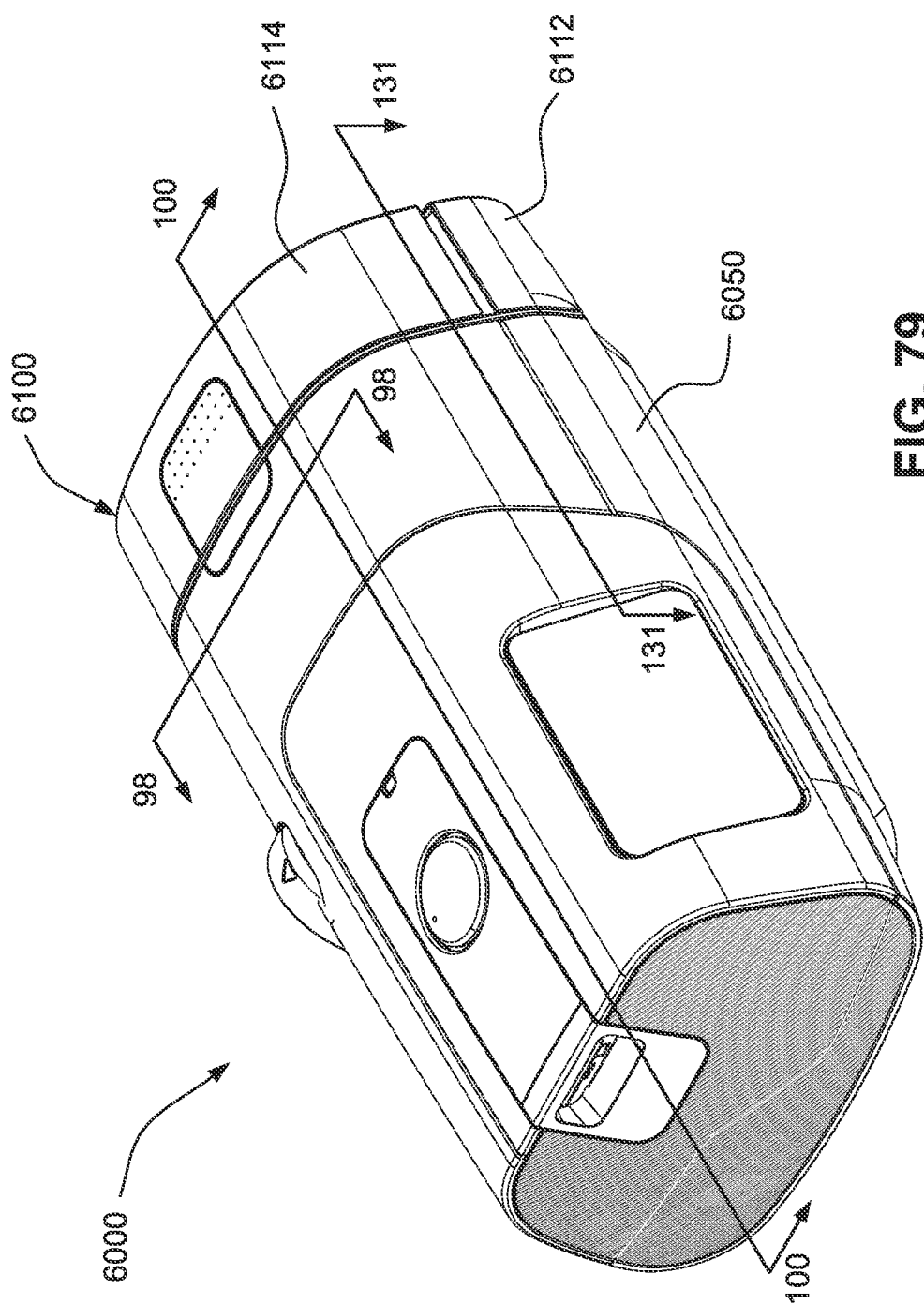

FIG. 79 is a perspective view of an integrated RPT device and humidifier with the water reservoir inserted into the reservoir dock according to an example of the present technology.

Figure 80:
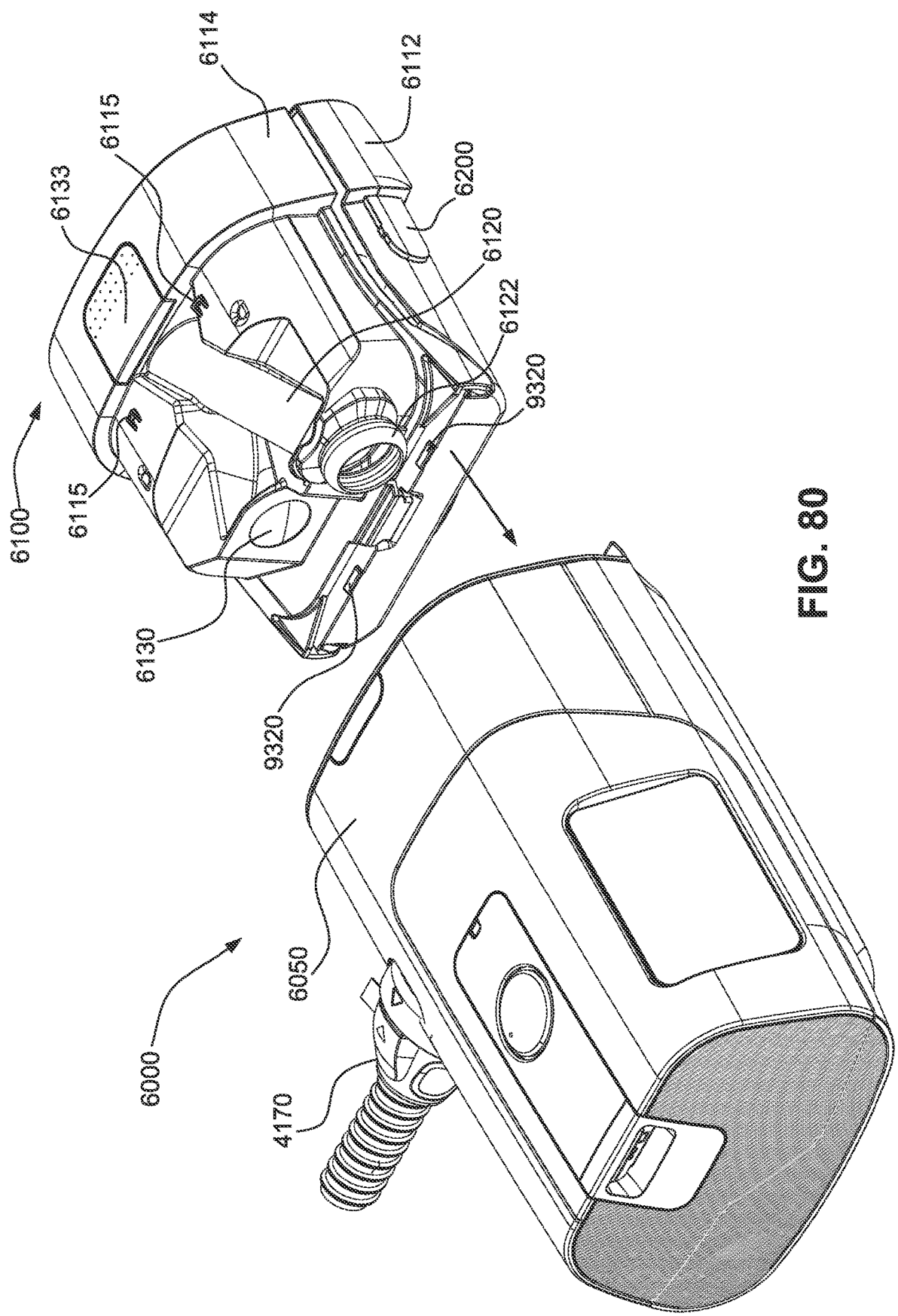

FIG. 80 is a perspective view of the integrated RPT device and humidifier of FIG. 79 with the water reservoir removed from the reservoir dock.

Figure 81:
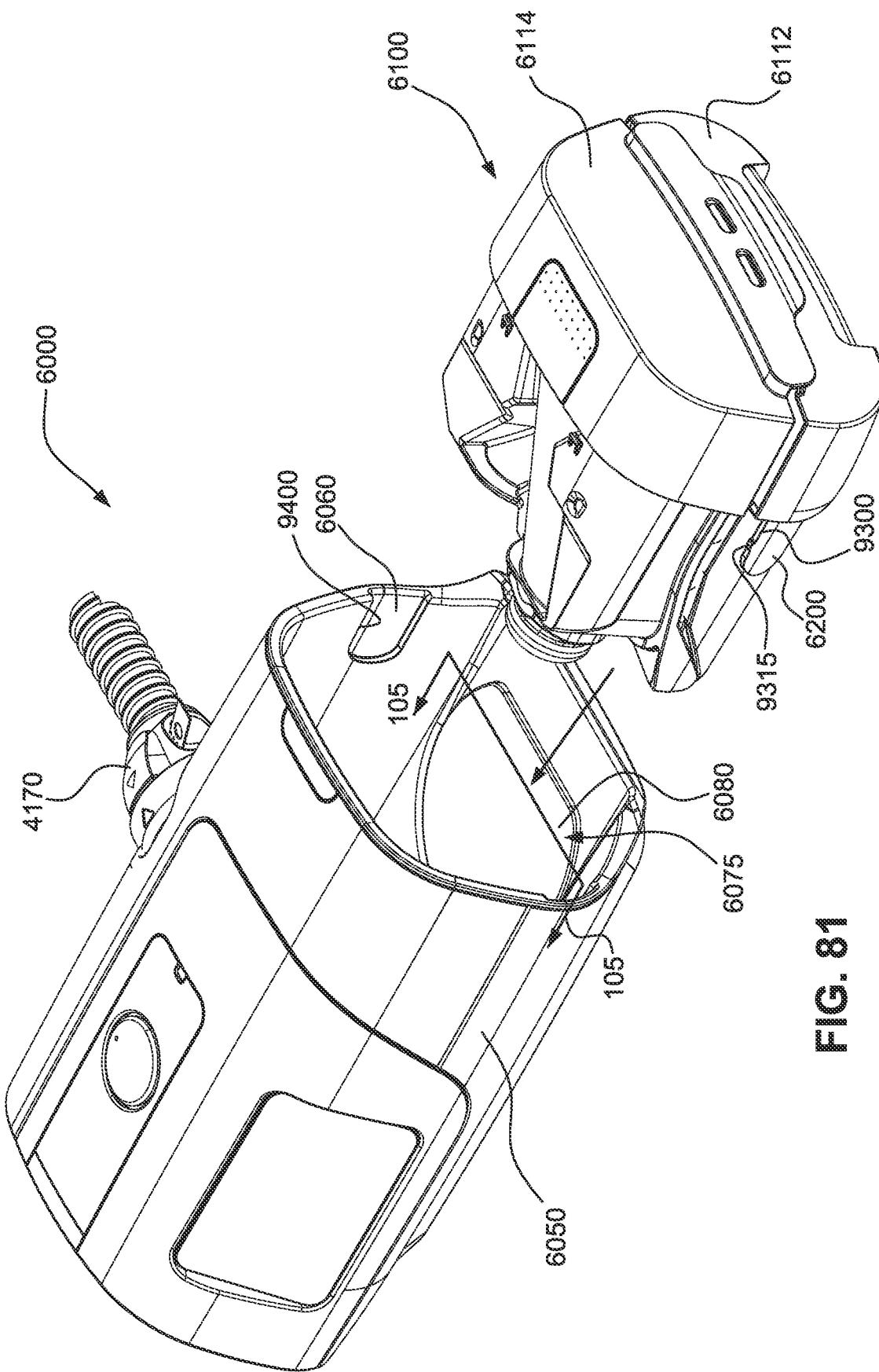

FIG. 81 is another perspective view of the integrated RPT device and humidifier of FIG. 79 with the water reservoir removed from the reservoir dock.

Figure 82:
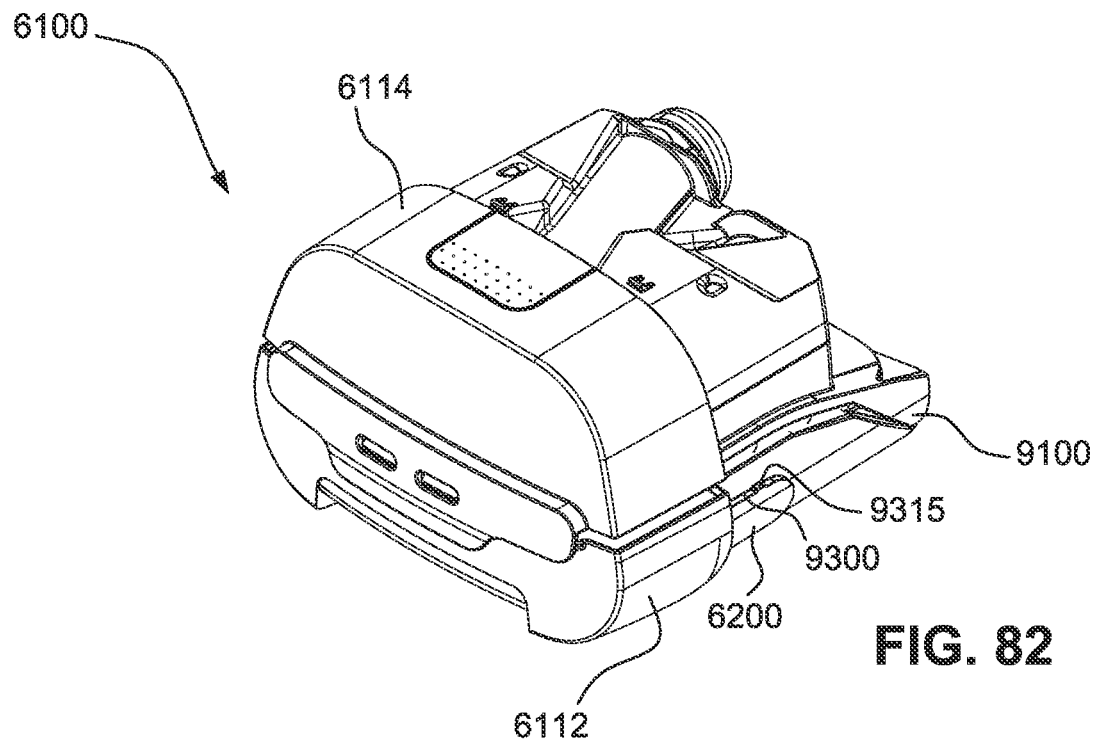

FIG. 82 is a top perspective view of a water reservoir according to an example of the present technology, the water reservoir in a closed position.

Figure 83:
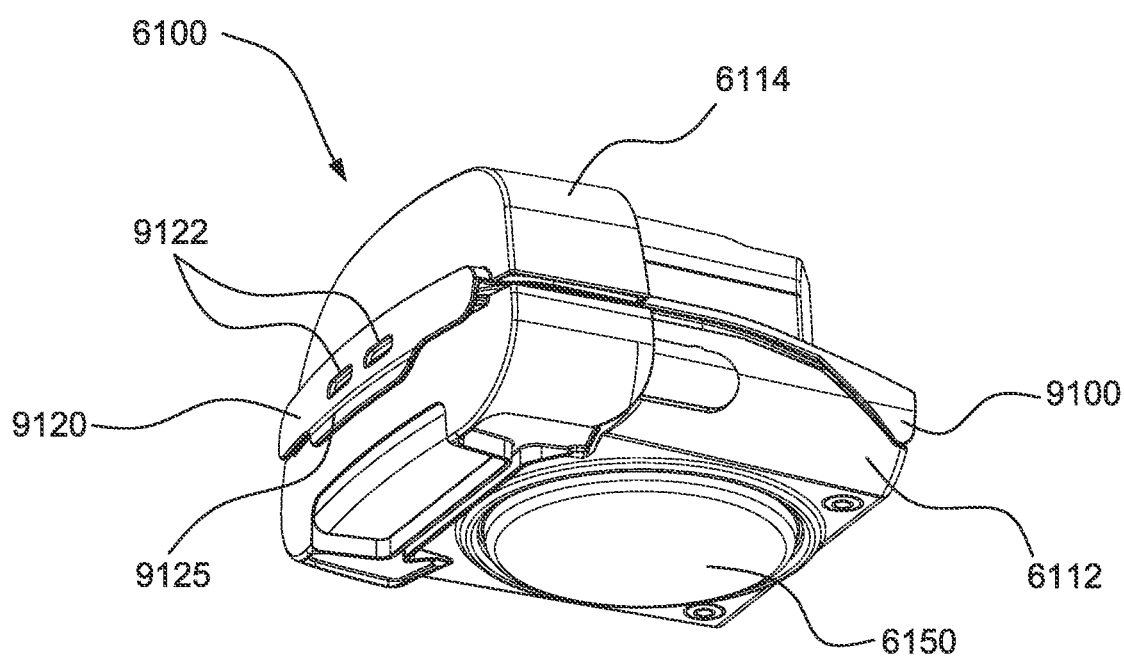

FIG. 83 is a bottom perspective view of the water reservoir of FIG. 82.

Figure 84:
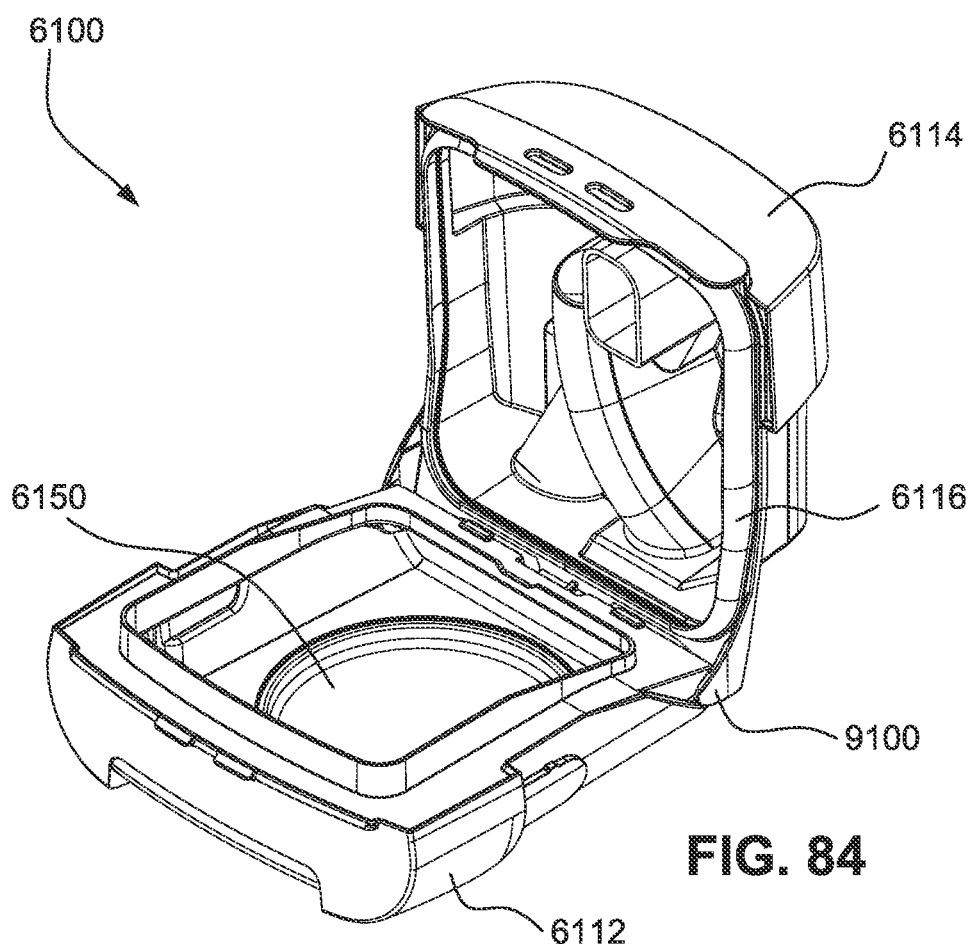

FIG. 84 is a top perspective view of the water reservoir of FIG. 82 in an open position.

Figure 85:
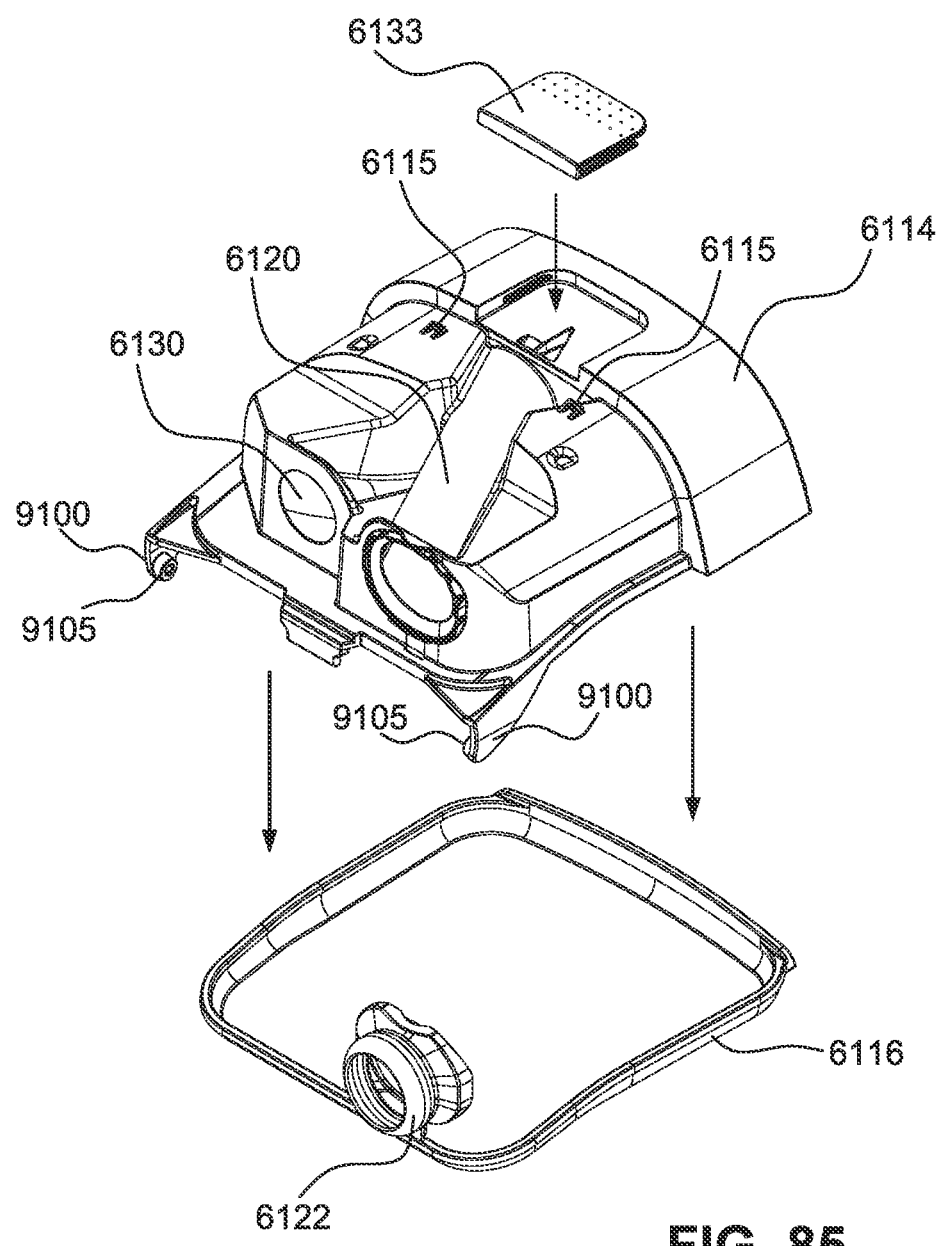

FIG. 85 is an exploded view of a lid of the water reservoir of FIG. 82.

FIG. 86 is an exploded view showing the lid and the base of the water reservoir of FIG. 82.

FIG. 87 is an enlarged view showing a portion of the lid of FIG. 86.

FIG. 88 is an enlarged view showing a portion of the base of FIG. 86.

FIG. 89 is a side view of the water reservoir of FIG. 82 in an open position.

FIG. 90 is a cross-sectional view showing a portion of the water reservoir of FIG. 89.

FIG. 91 is a side view of the water reservoir of FIG. 82 in a closed position.

FIG. 92 is a cross-sectional view showing a portion of the water reservoir of FIG. 91.

FIG. 93 is another cross-sectional view showing a portion of the water reservoir of FIG. 91.

Figure 94:
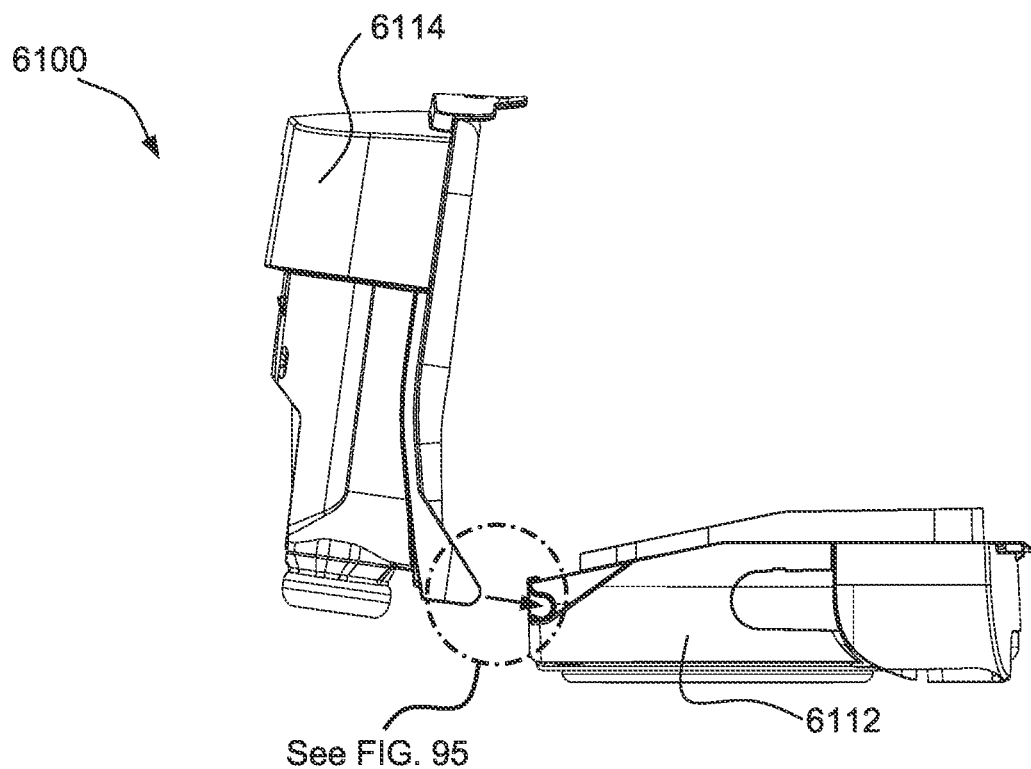

FIG. 94 is a side view of the water reservoir of FIG. 82 showing assembly of the lid to the base according to an example of the present technology.

Figure 95:
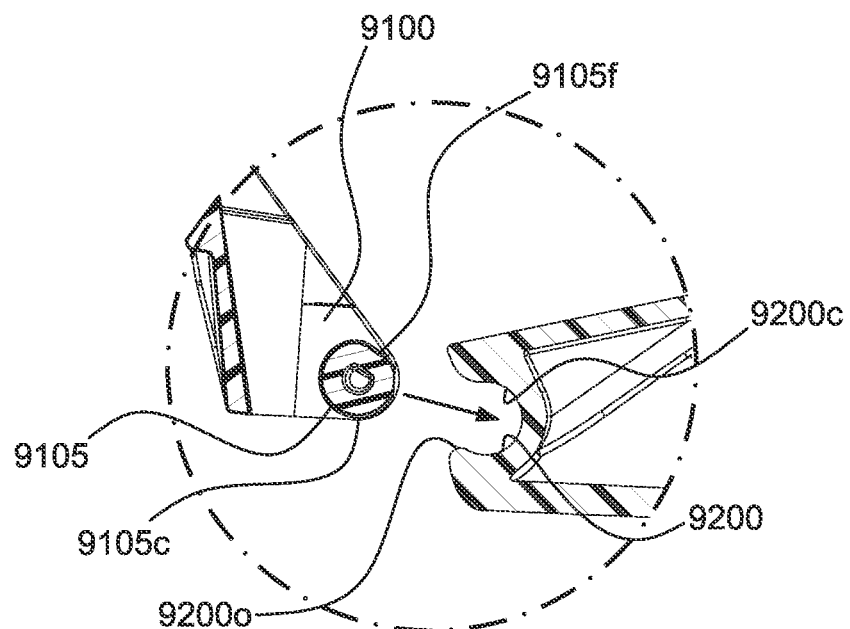

FIG. 95 is cross-sectional view showing a portion of the water reservoir of FIG. 94.

Figure 96:
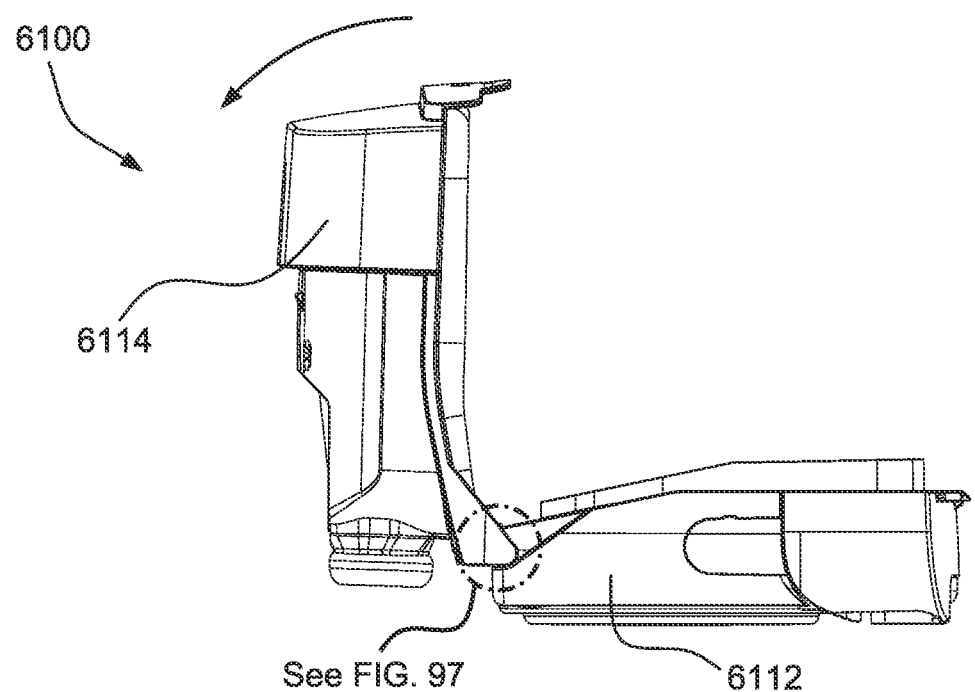

FIG. 96 is a side view of the water reservoir of FIG. 82 showing an initial stage of disassembling the lid from the base according to an example of the present technology.

Figure 97:
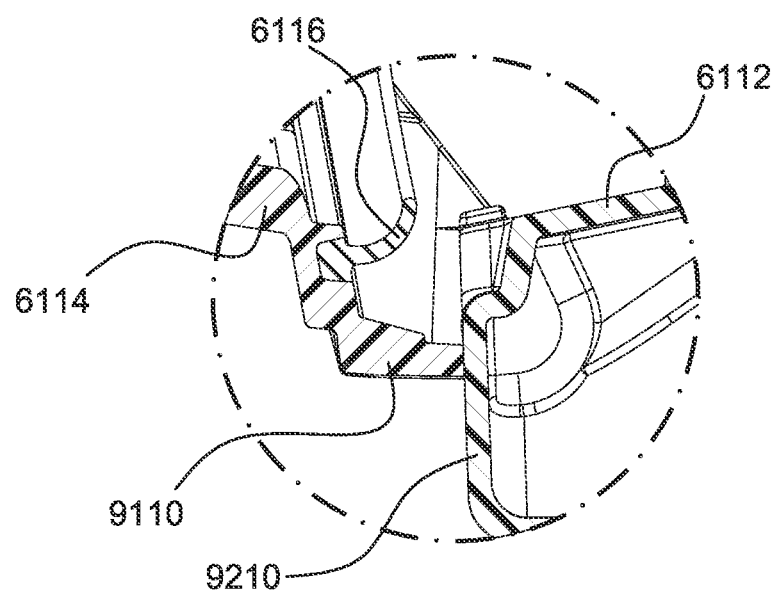

FIG. 97 is cross-sectional view showing a portion of the water reservoir of FIG. 96.

Figure 98:
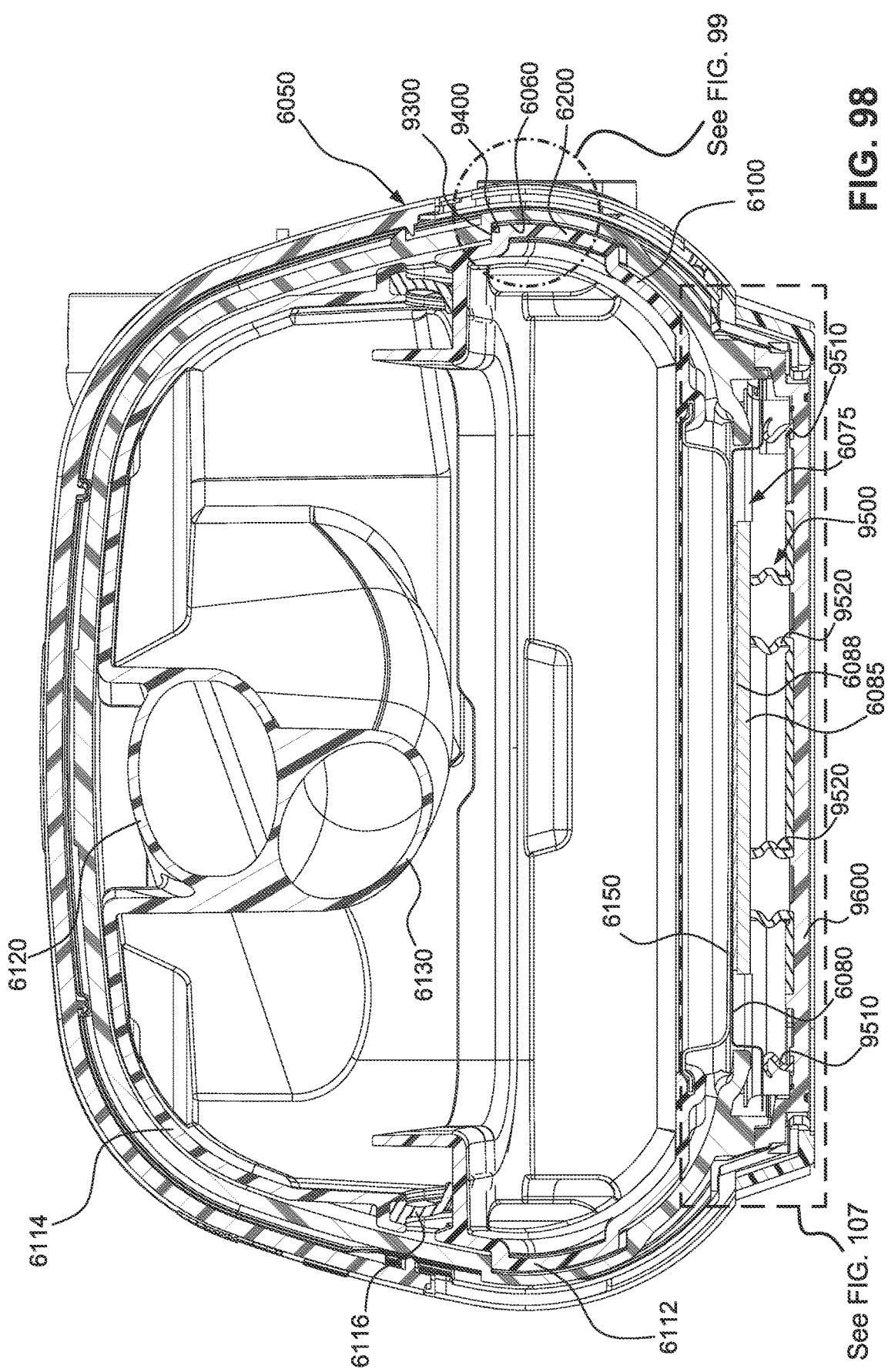

FIG. 98 is a cross-sectional view of the integrated RPT device and humidifier of FIG. 79, taken along line 98-98 of FIG. 79.

Figure 99:
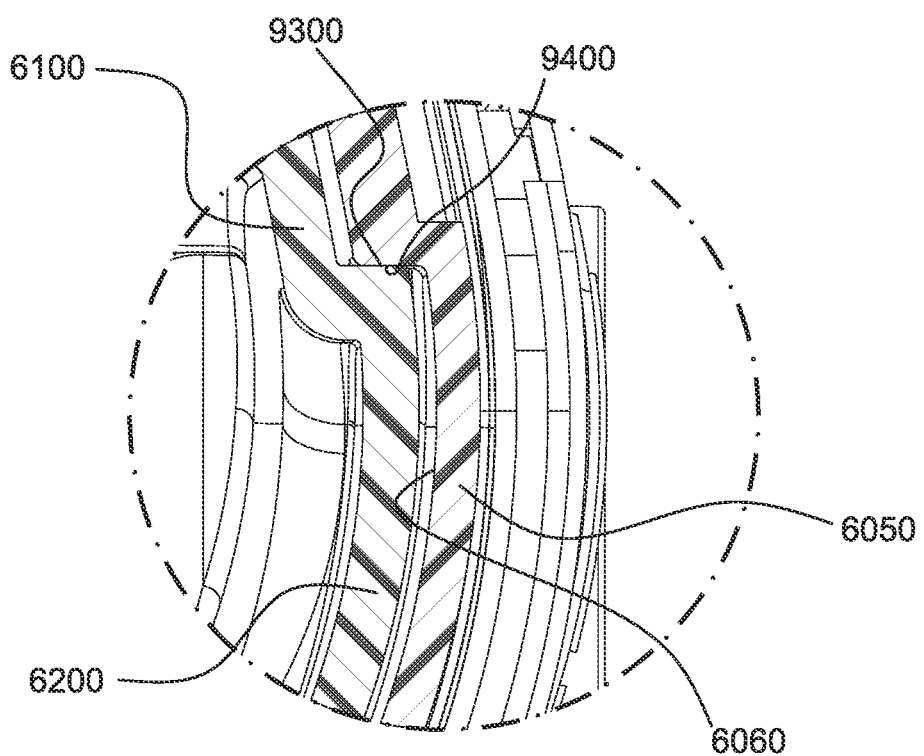

FIG. 99 is an enlarged cross-sectional view showing a portion of the integrated RPT device and humidifier of FIG. 98.

Figure 100:
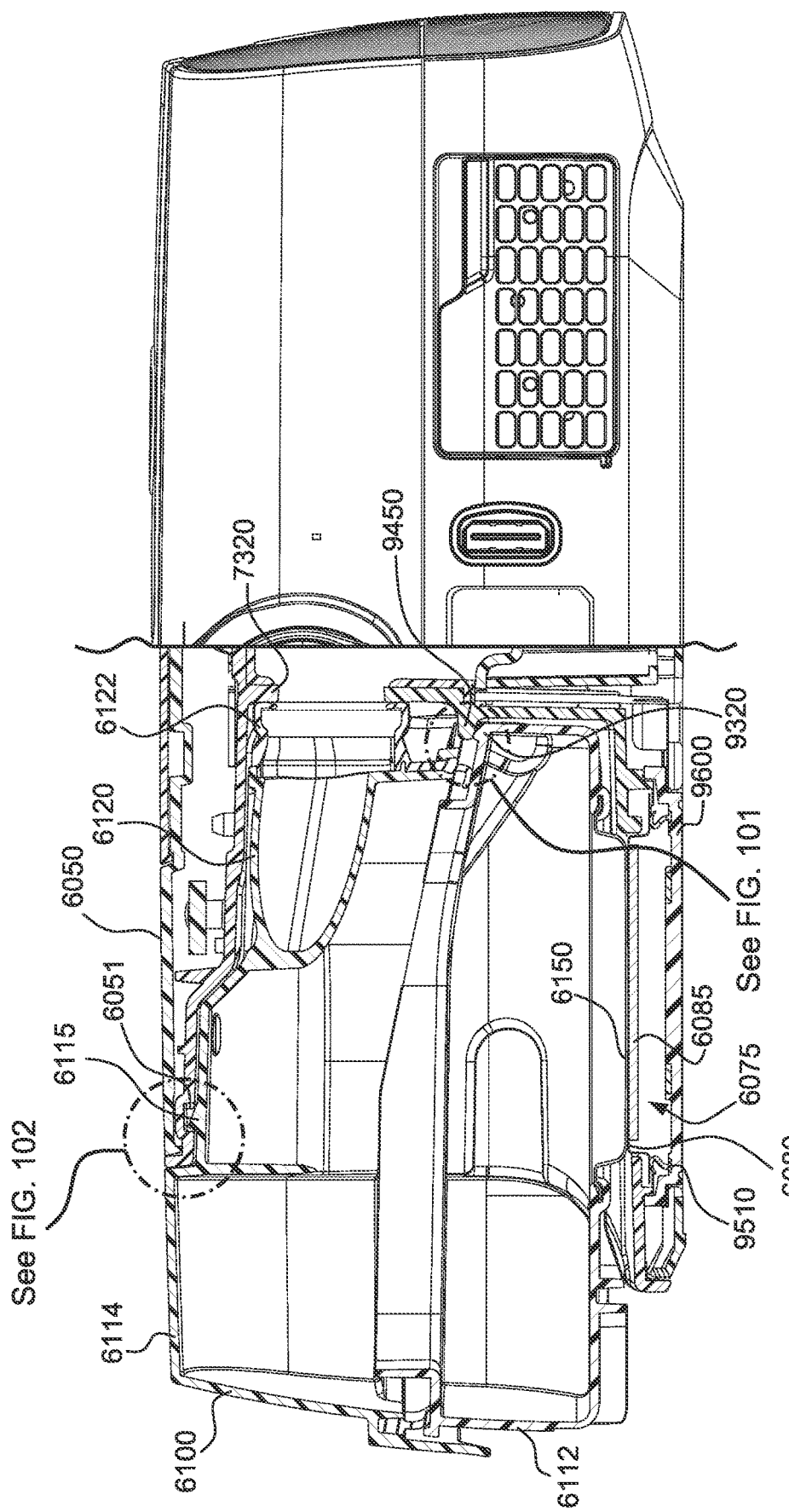

FIG. 100 is a cross-sectional view of the integrated RPT device and humidifier of FIG. 79, taken along line 100-100 of FIG. 79.

Figure 101:
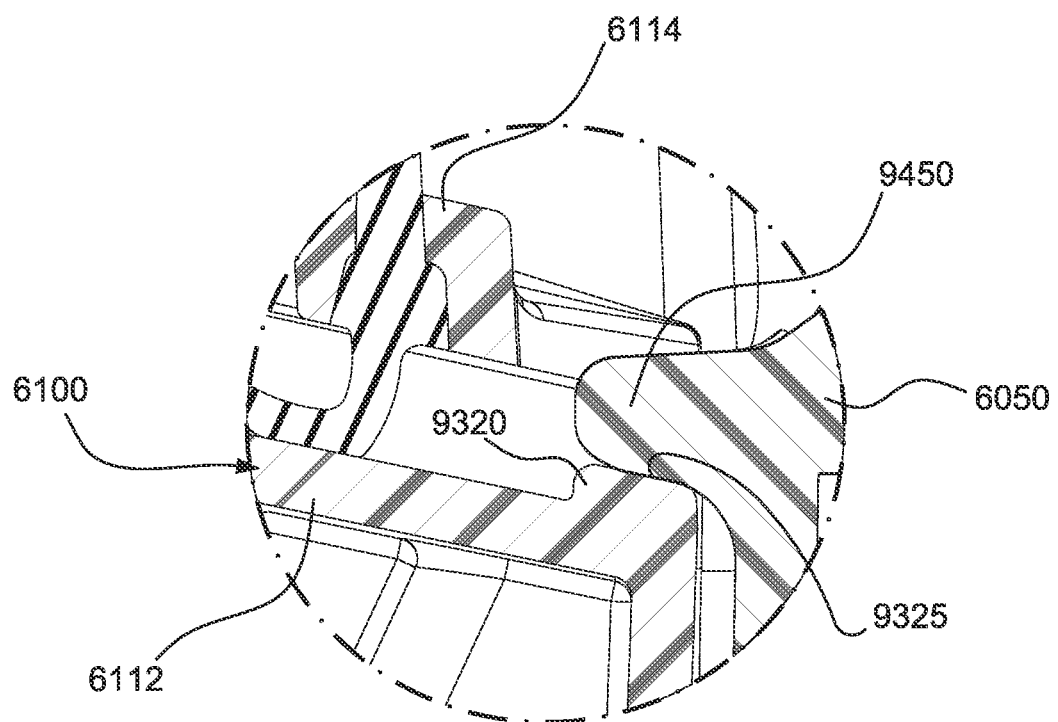

FIG. 101 is an enlarged view showing a portion of the integrated RPT device and humidifier of FIG. 100.

Figure 102:
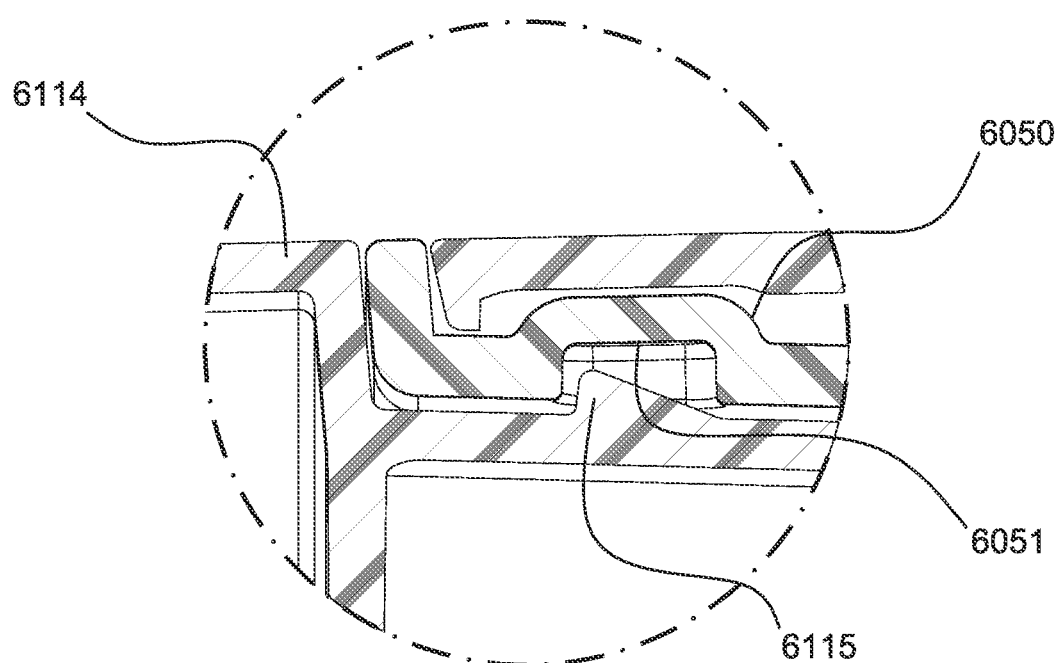

FIG. 102 is an enlarged view showing another portion of the integrated RPT device and humidifier of FIG. 100.

Figure 103:
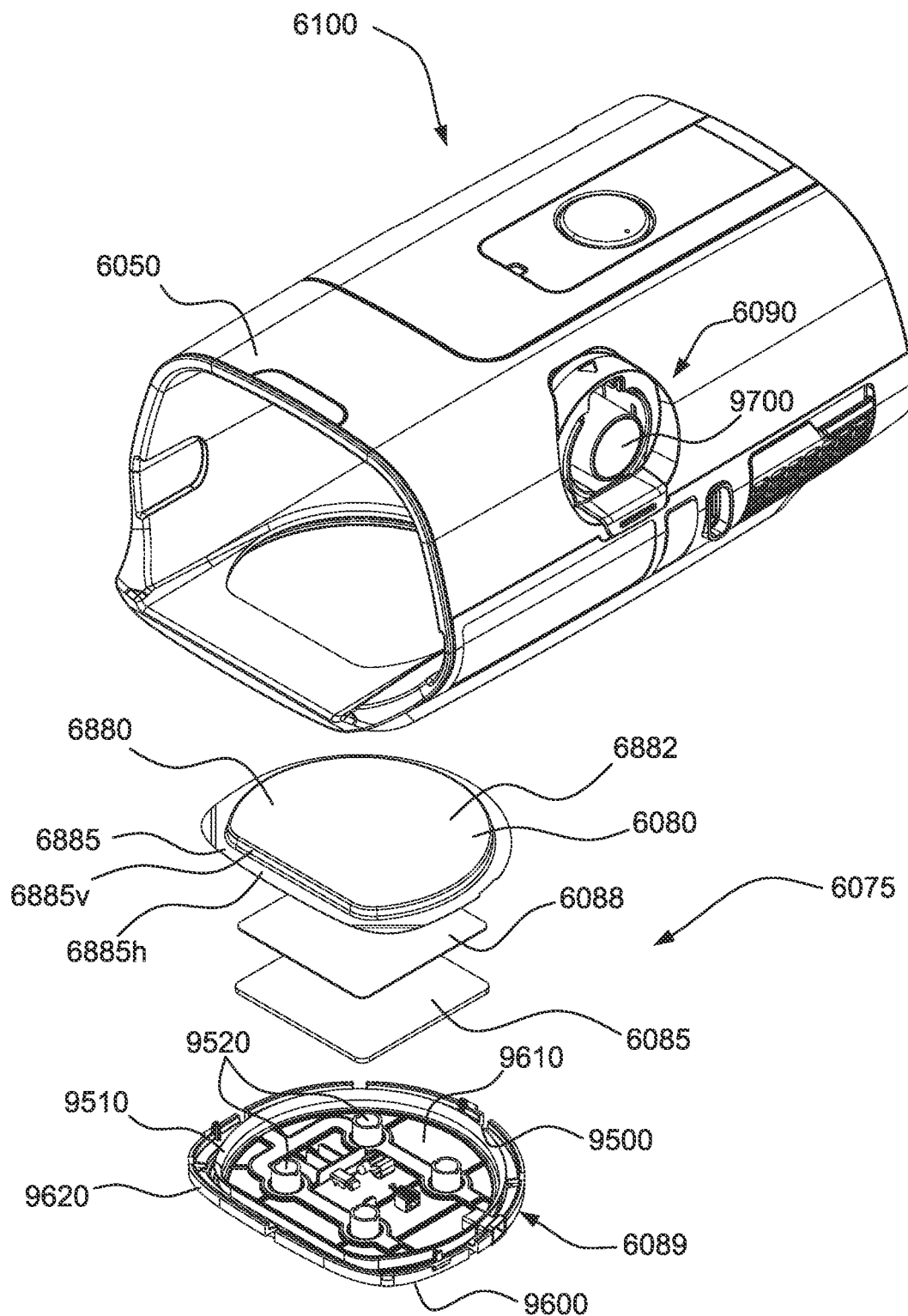

FIG. 103 is an exploded view showing a heating assembly of a reservoir dock according to an example of the present technology.

Figure 104:
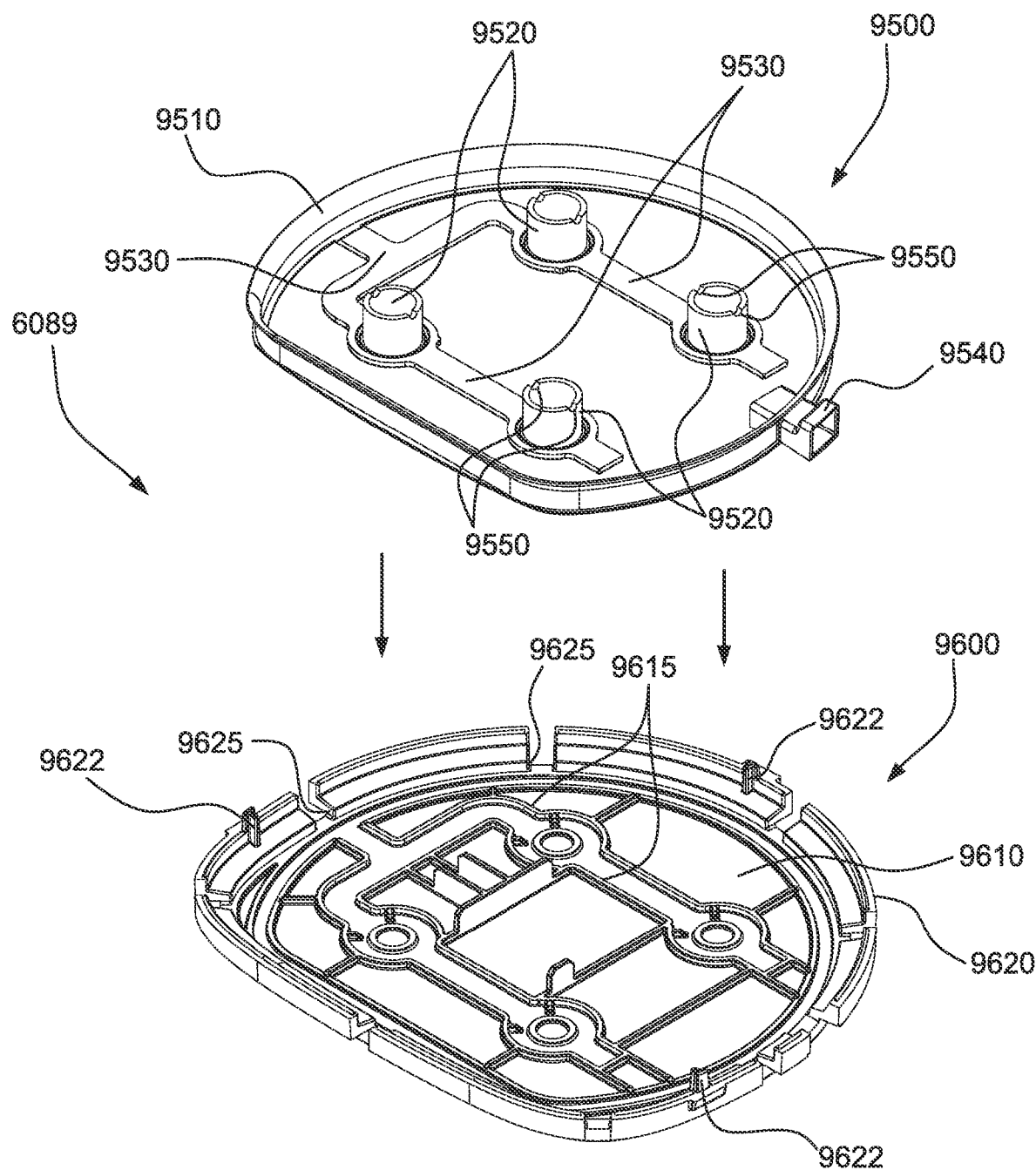

FIG. 104 is an exploded view showing the support structure for the heated plate in the heating assembly of FIG. 103.

Figure 105:
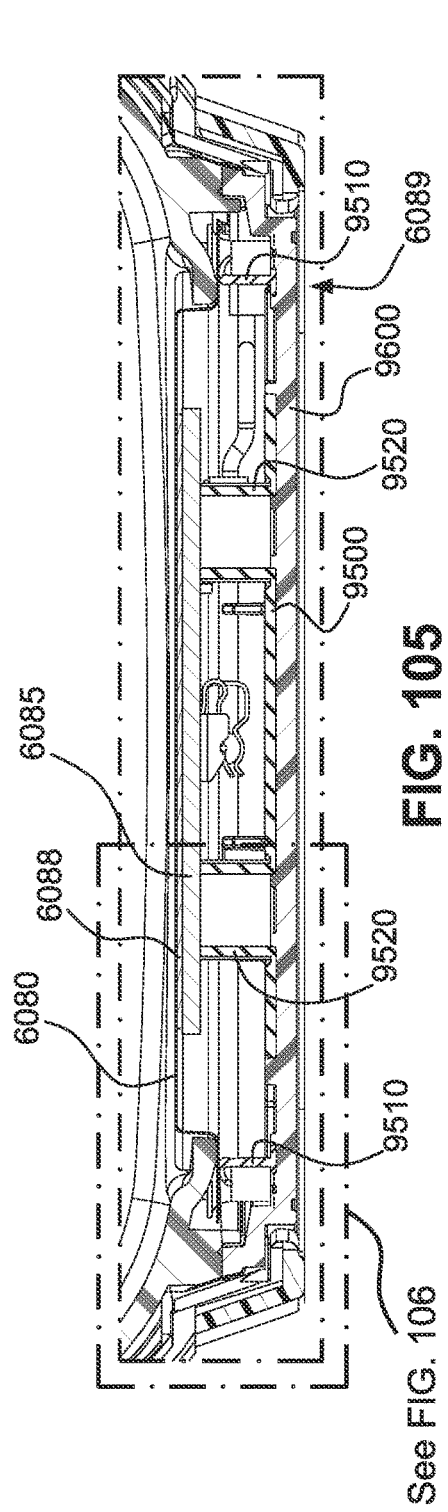

FIG. 105 is a cross-sectional view, taken along line 105-105 of FIG. 81, showing the heating assembly with the water reservoir removed from the reservoir dock according to an example of the present technology.

Figure 106:
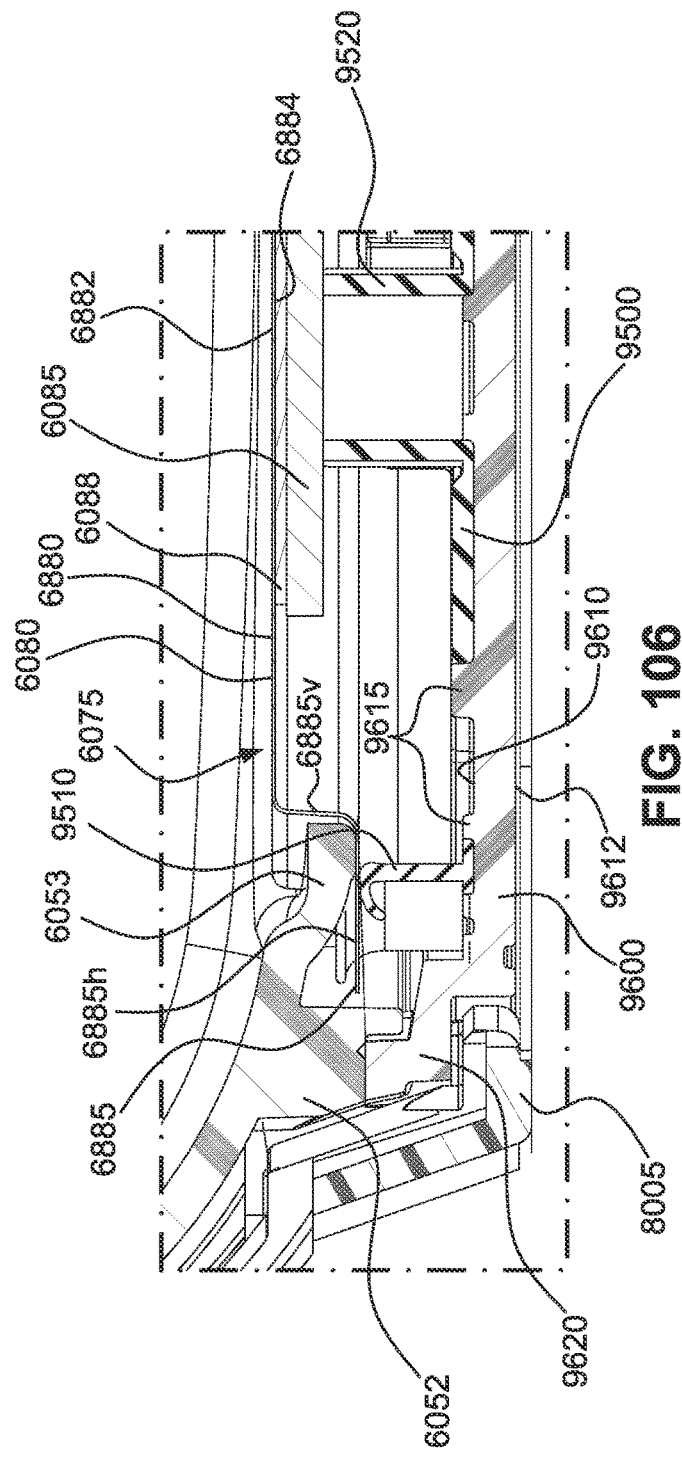

FIG. 106 is an enlarged cross-sectional view showing a portion of the heating assembly of FIG. 105.

Figure 107:
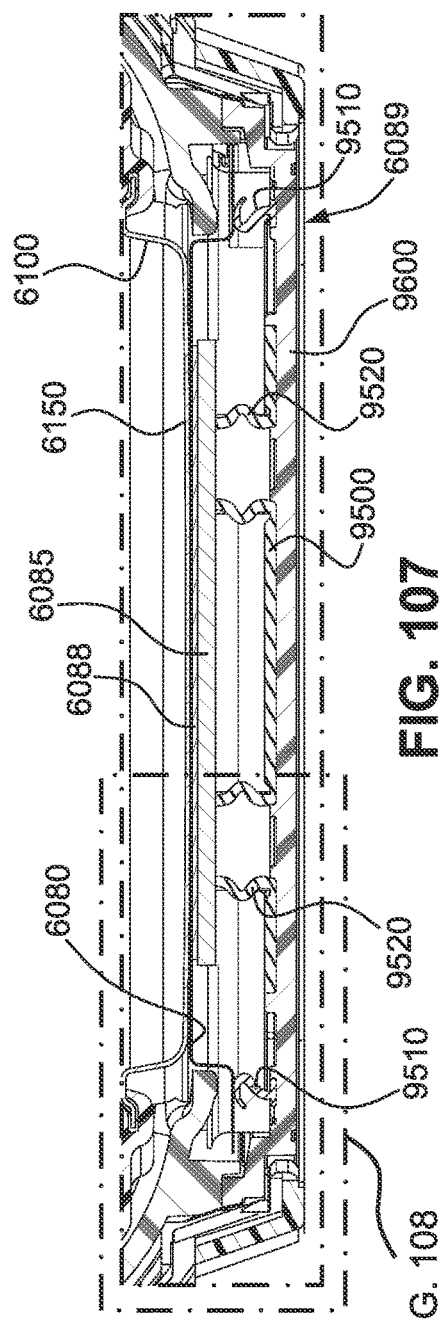

FIG. 107 is an enlarged cross-sectional view of a portion of FIG. 98 showing the heating assembly with the water reservoir inserted into the reservoir dock according to an example of the present technology.

Figure 108:
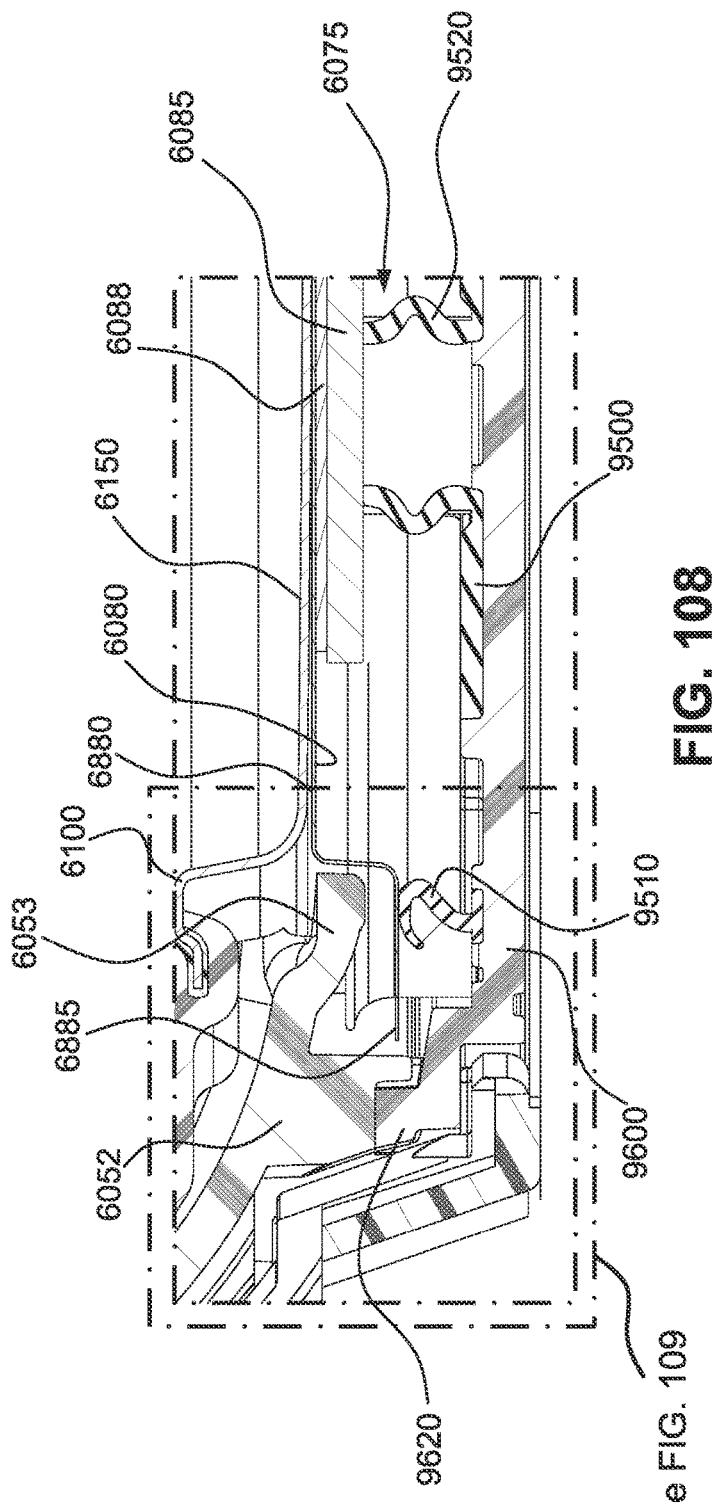

FIG. 108 is an enlarged cross-sectional view showing a portion of the heating assembly of FIG. 107.

Figure 109:
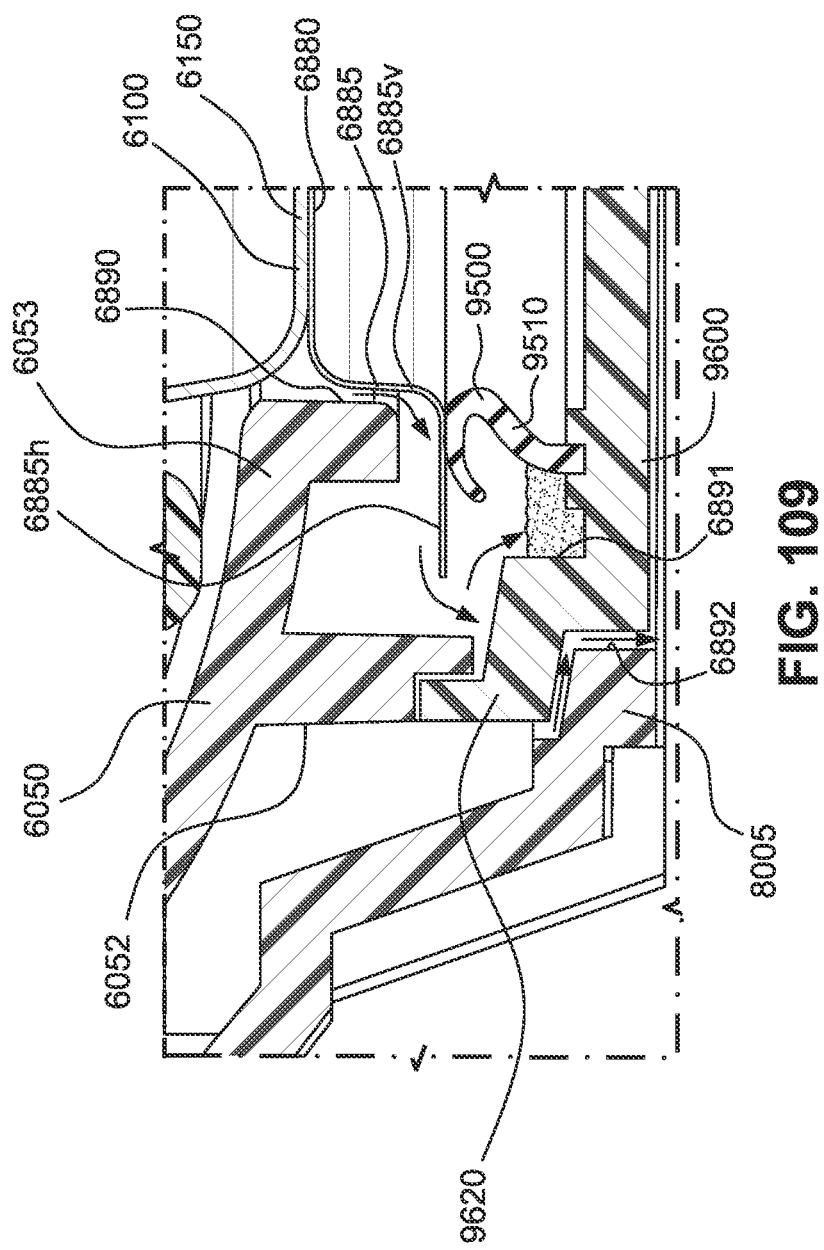

FIG. 109 is an enlarged cross-sectional view of a portion of FIG. 108 and showing water drainage provided by the heating assembly according to an example of the present technology.

Figure 110:
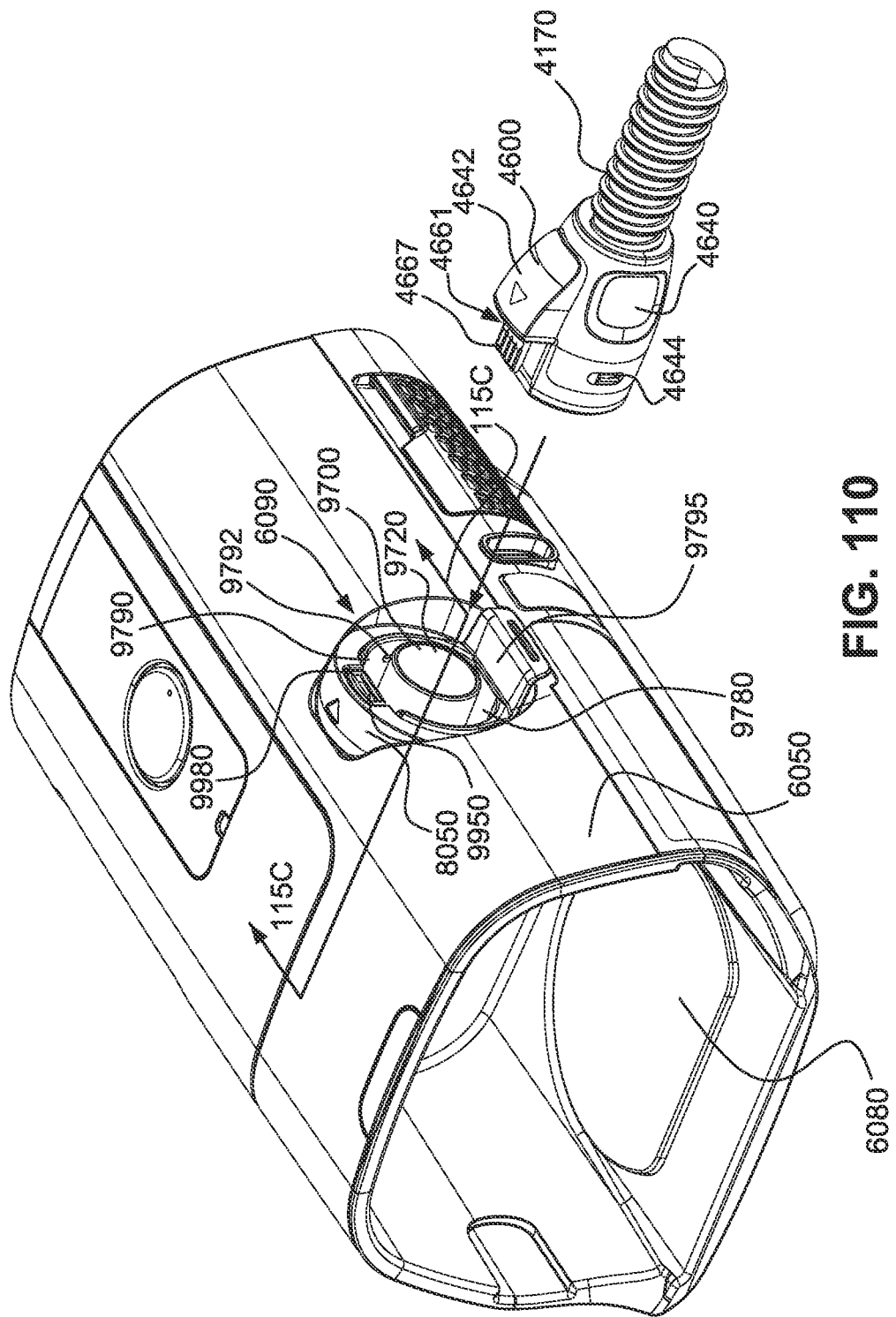

FIG. 110 is a perspective view showing a reservoir dock, an intermediate component, and an air delivery tube according to an example of the present technology, the air delivery tube oriented for engagement with the intermediate component and a contact assembly provided to the reservoir dock.

Figure 111:
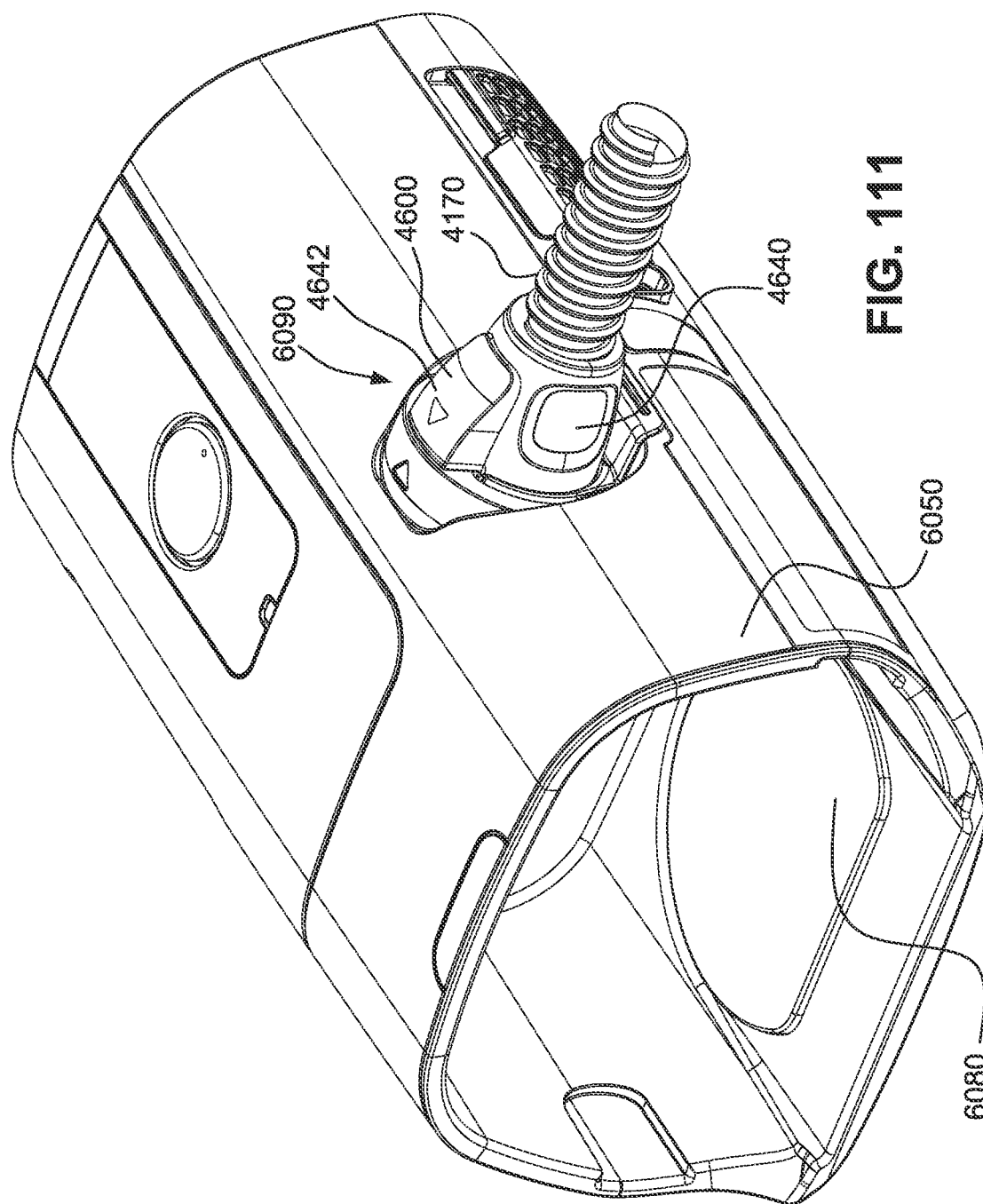

FIG. 111 is a perspective view showing the reservoir dock, the intermediate component and the air delivery tube of FIG. 110, the air delivery tube fully engaged with the intermediate component.

Figure 112:
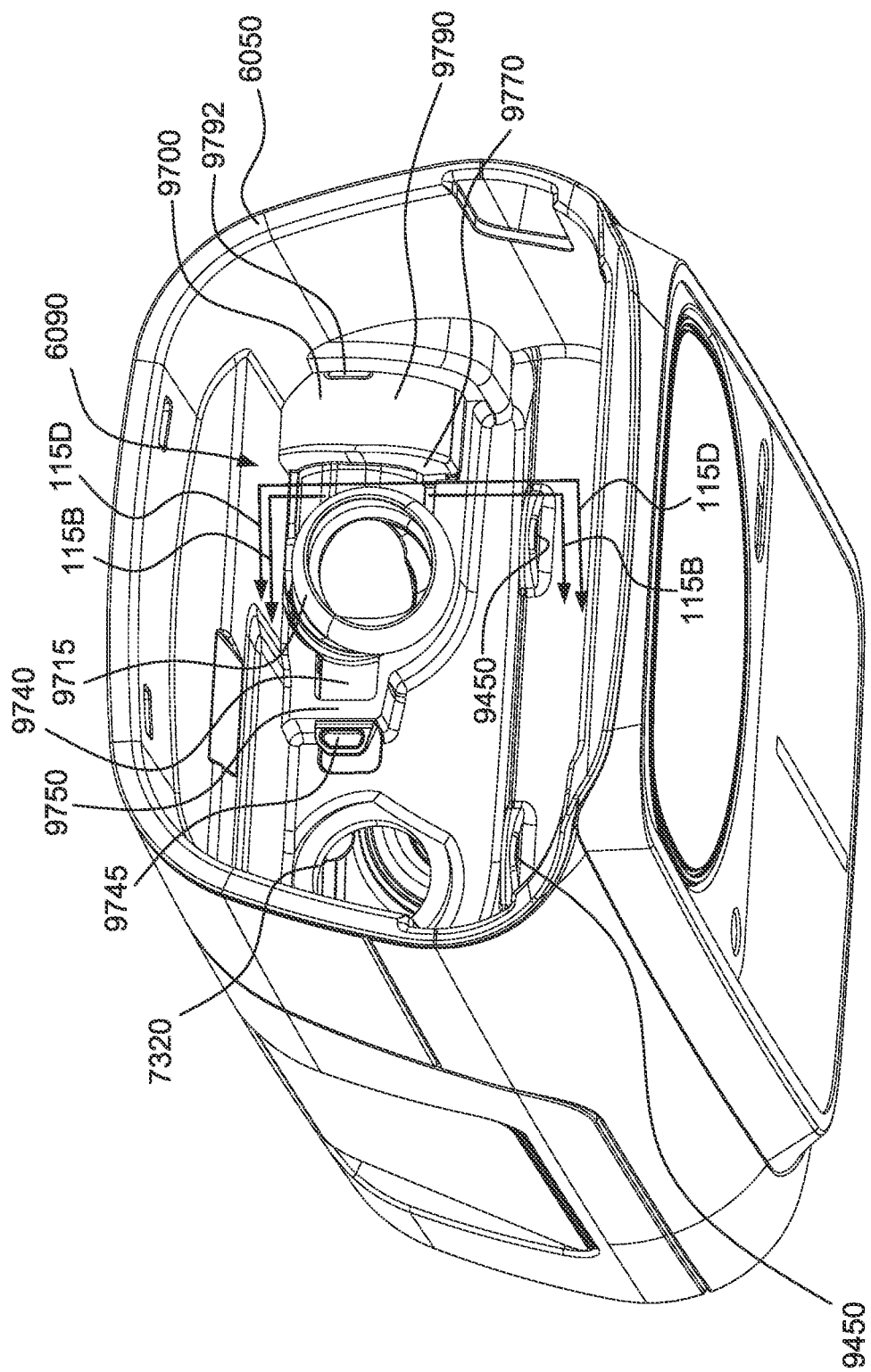

FIG. 112 is a perspective view showing the reservoir dock engaged with the intermediate component of FIG. 110.

Figure 113:
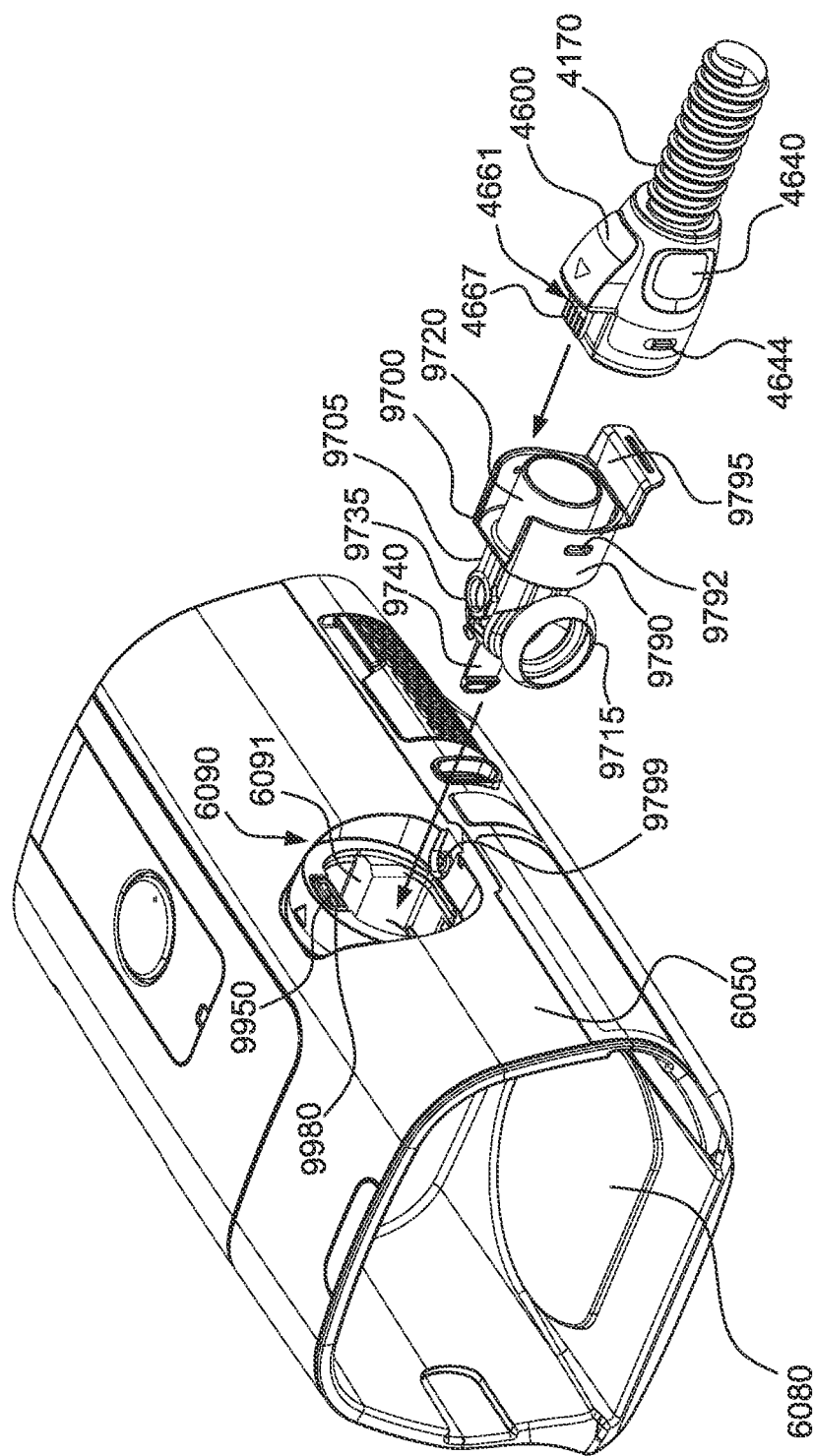

FIG. 113 is an exploded view showing the reservoir dock, the intermediate component, and the air delivery tube of FIG. 110.

Figure 114:
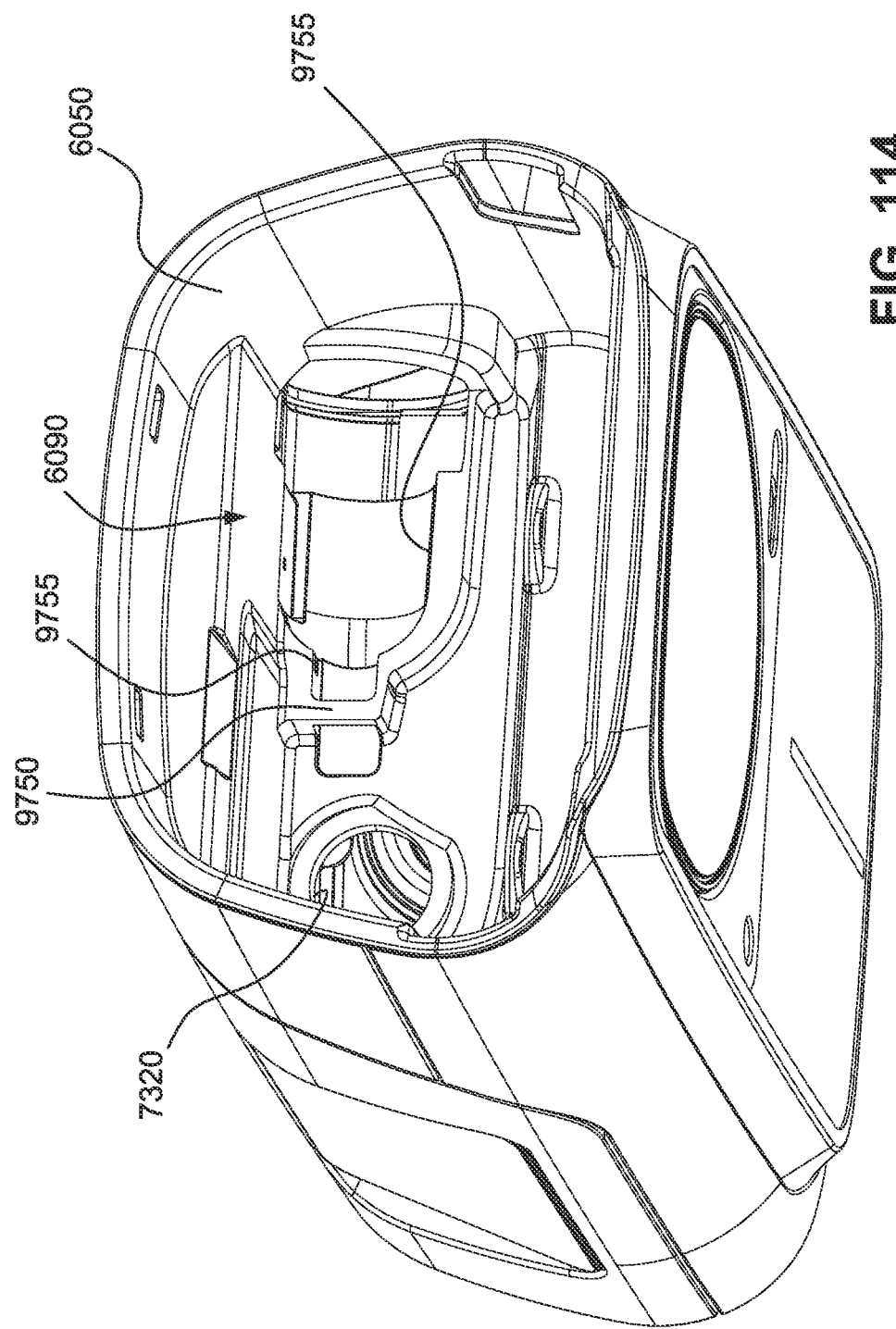

FIG. 114 is a perspective view showing the dock outlet of the reservoir dock of FIG. 110 with the intermediate component removed.

Figure 115A:
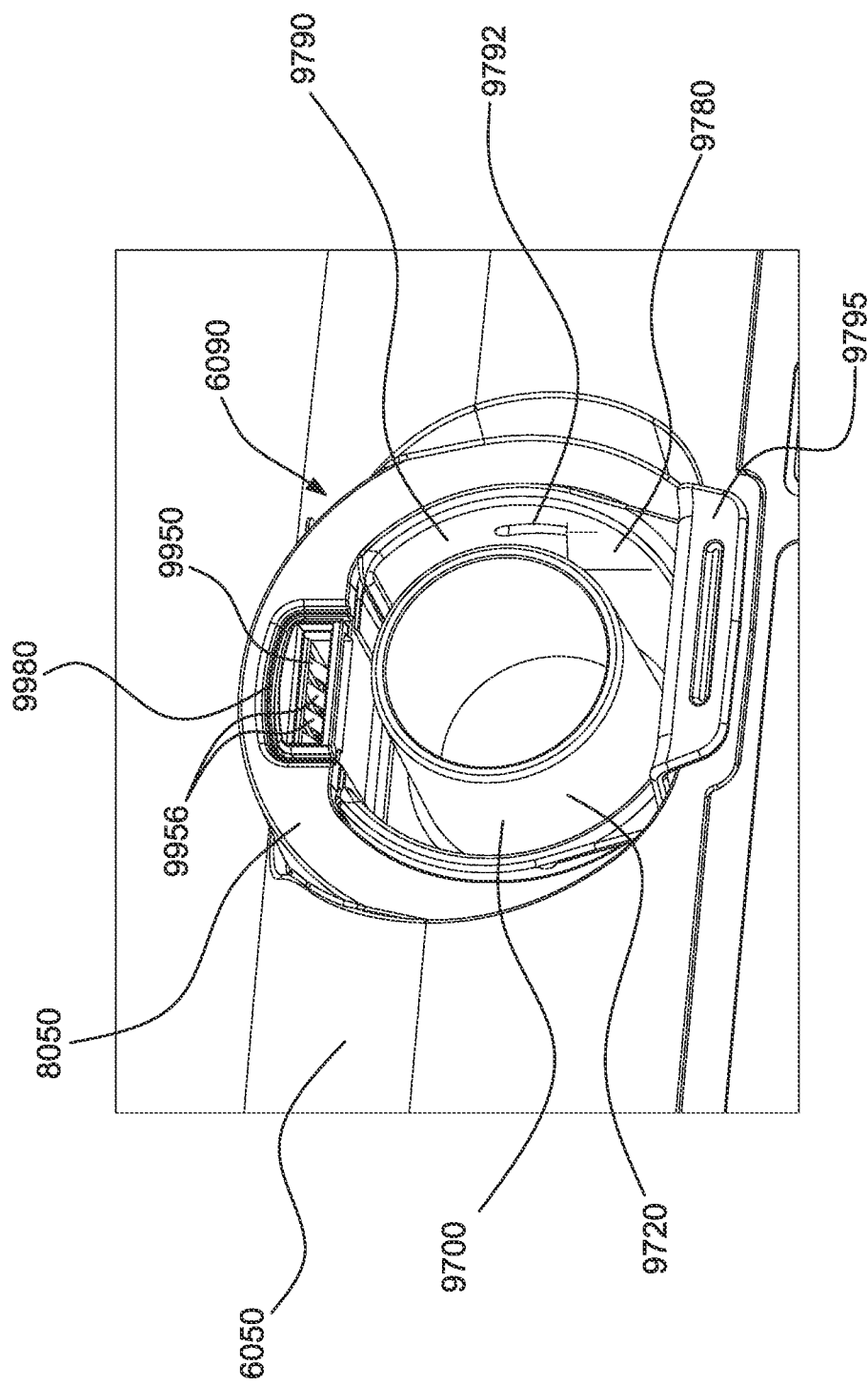

FIG. 115A is a perspective view showing the intermediate component and the contact assembly provided to the reservoir dock of FIG. 110.

FIG. 115B is a cross-sectional view, taken along line 115B-115B of FIG. 112, showing connection of the intermediate component to the reservoir dock according to an example of the present technology.

FIGS. 115C1, 115C2, and 115C3 are cross-sectional views, taken along line 115C-115C of FIG. 110, showing an assembly sequence of the intermediate component to the reservoir dock according to an example of the present technology.

Figure 115D:
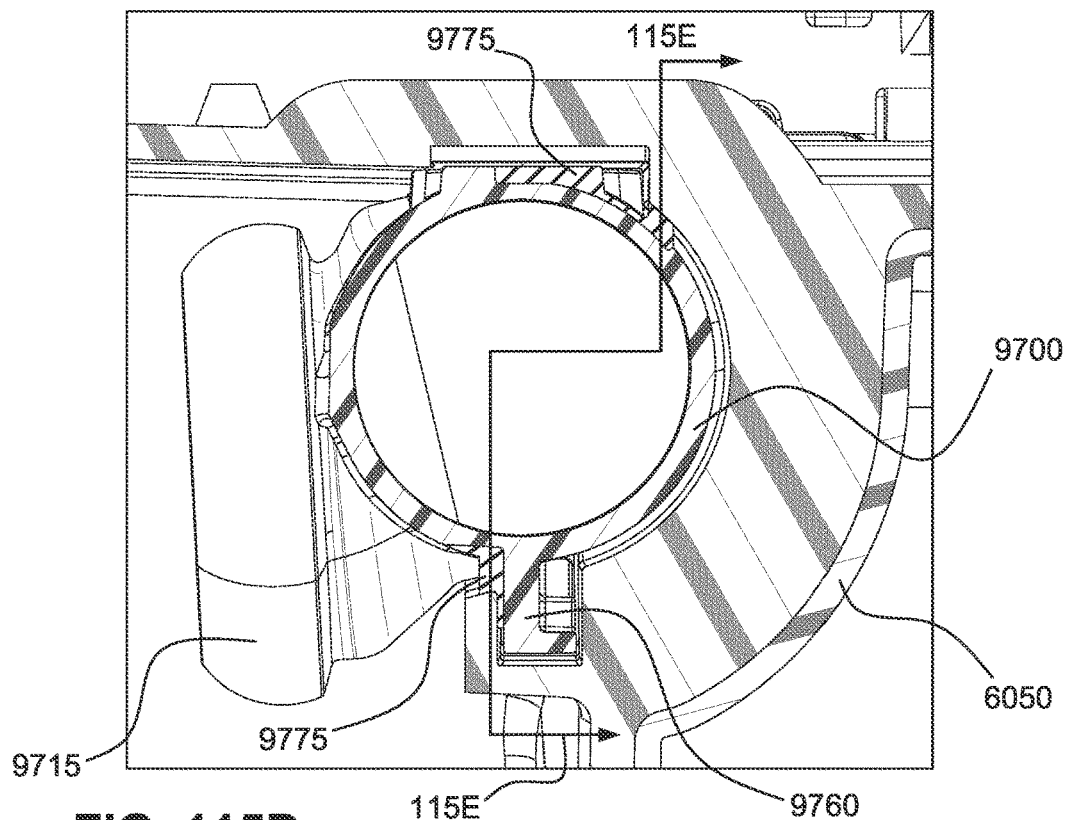

FIG. 115D is a cross-sectional view, taken along line 115D-115D of FIG. 112, showing connection of the intermediate component to the reservoir dock according to an example of the present technology.

Figure 115E:
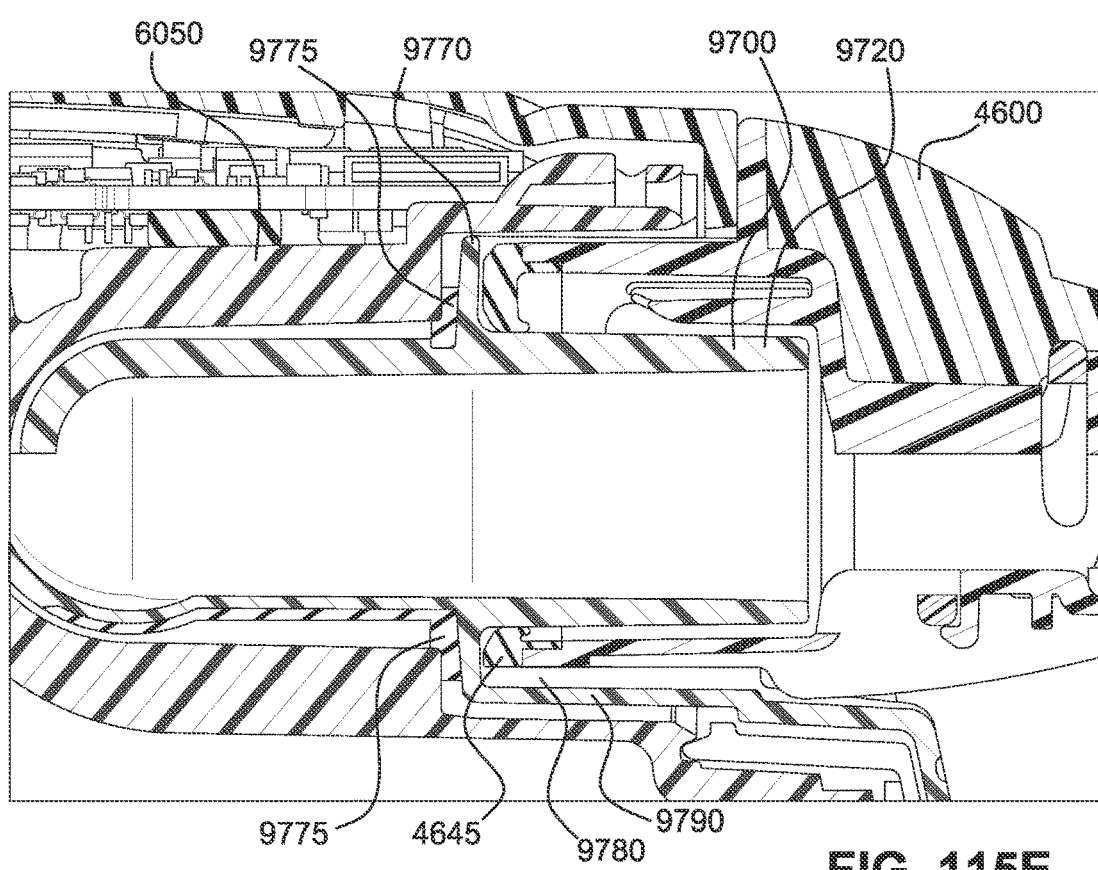

FIG. 115E is a cross-sectional view, taken along line 115E-115E of FIG. 115D, showing connection of the intermediate component to the reservoir dock according to an example of the present technology.

Figure 116:
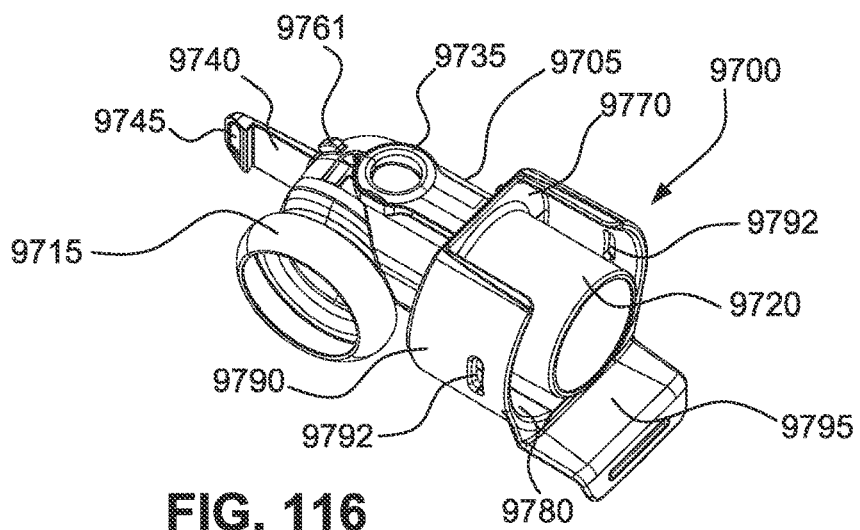

FIG. 116 is a top perspective view of an intermediate component according to an example of the present technology.

Figure 117:
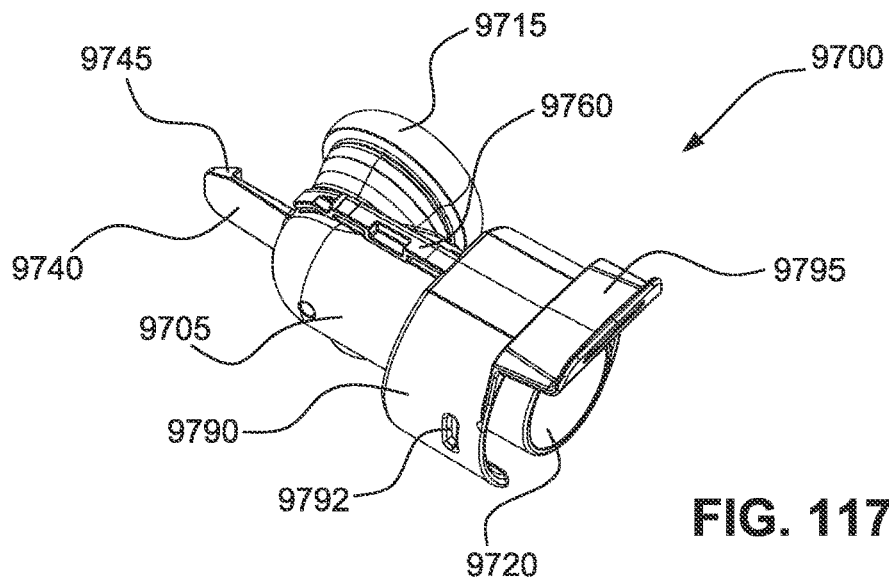

FIG. 117 is a bottom perspective view of the intermediate component of FIG. 116.

Figure 118:
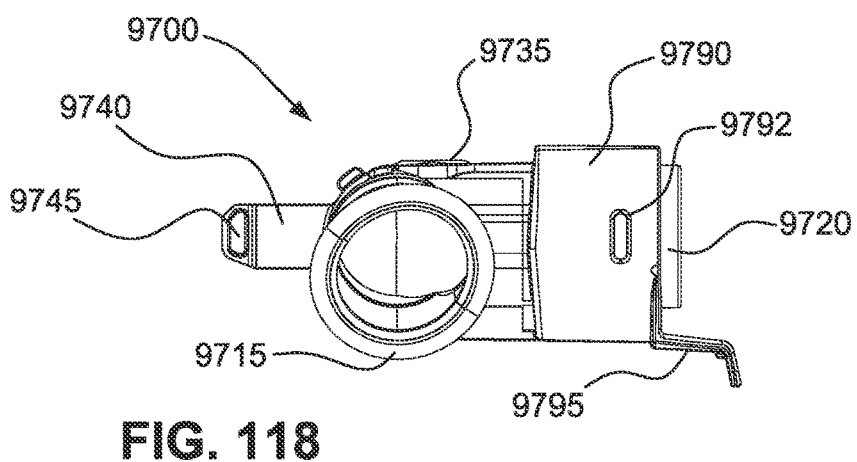

FIG. 118 is a front view of the intermediate component of FIG. 116.

Figure 119:
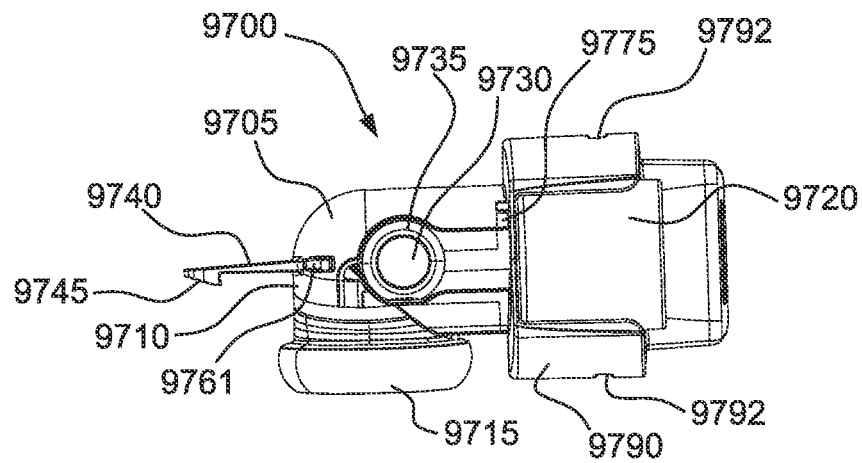

FIG. 119 is a top view of the intermediate component of FIG. 116.

Figure 120:
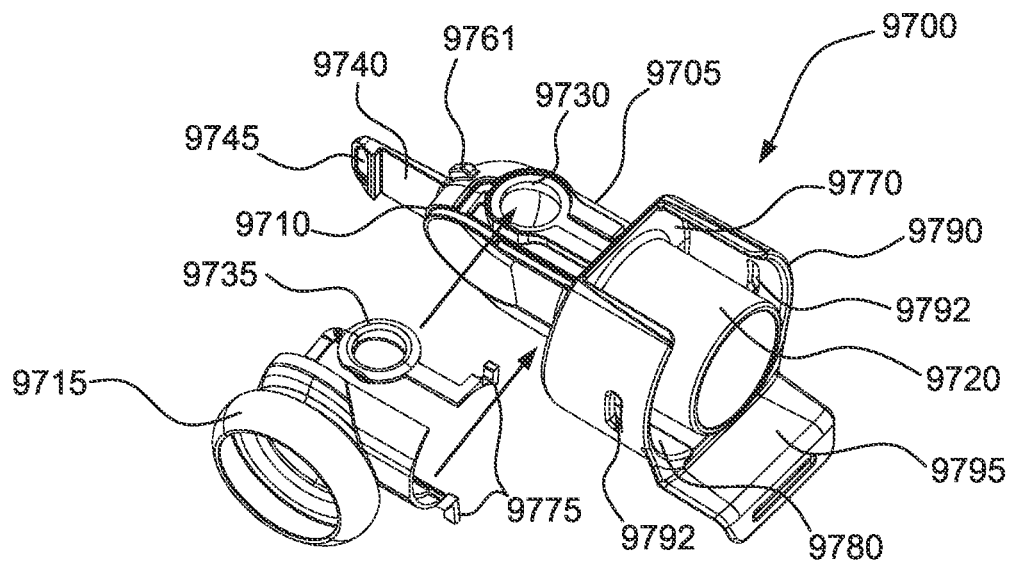

FIG. 120 is an exploded view of the intermediate component of FIG. 116.

Figure 121:
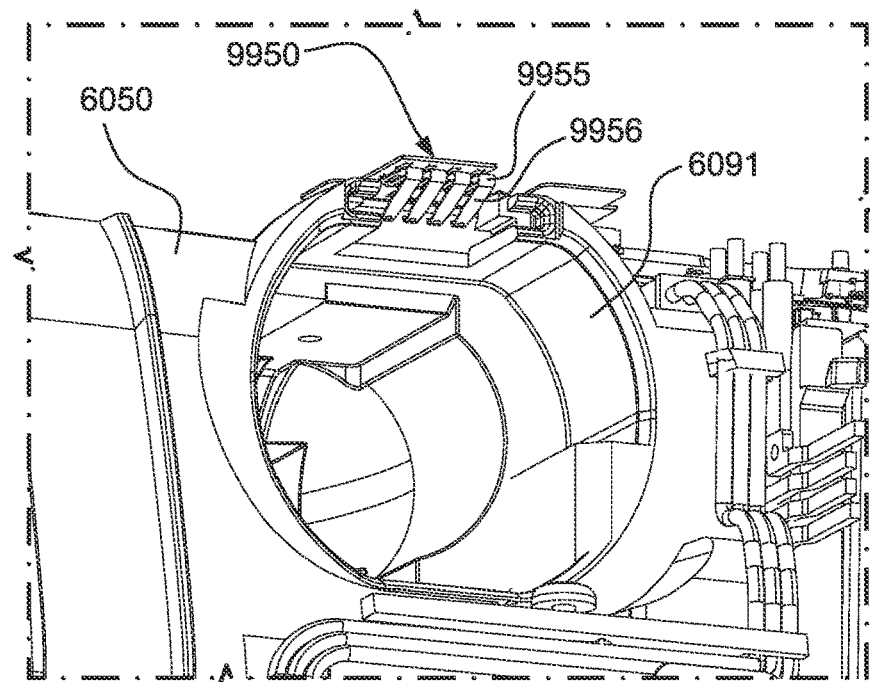

FIG. 121 is a perspective view showing the contact assembly provided to the reservoir dock of FIG. 110 with the intermediate component removed.

Figure 122:
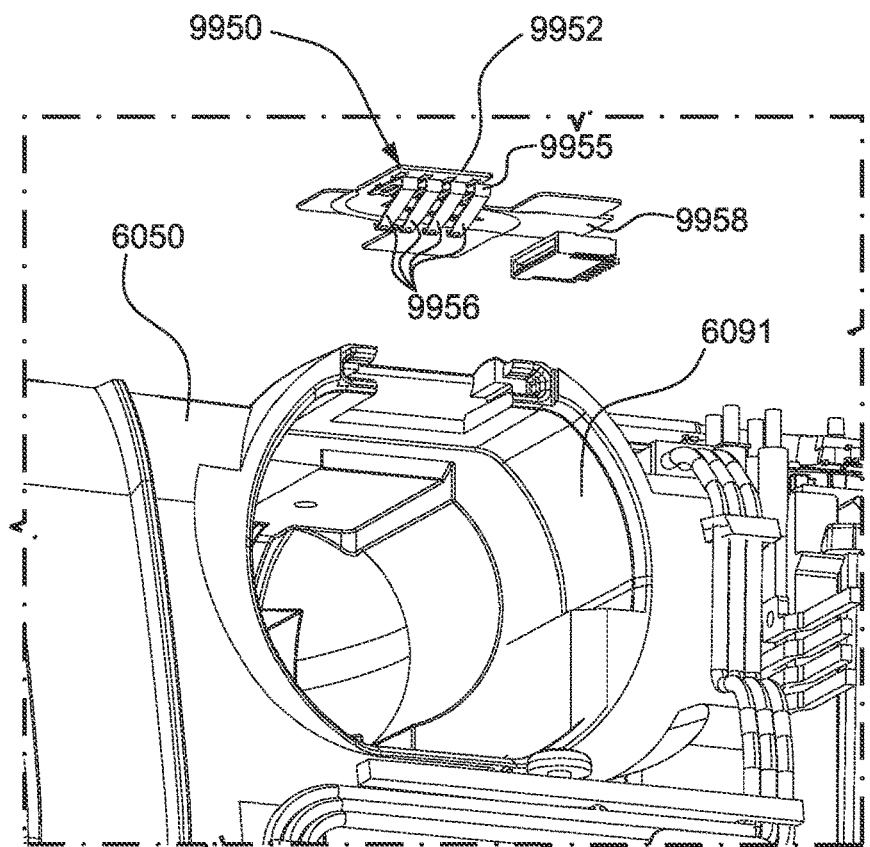

FIG. 122 is an exploded view of the contact assembly of FIG. 121.

Figure 123:
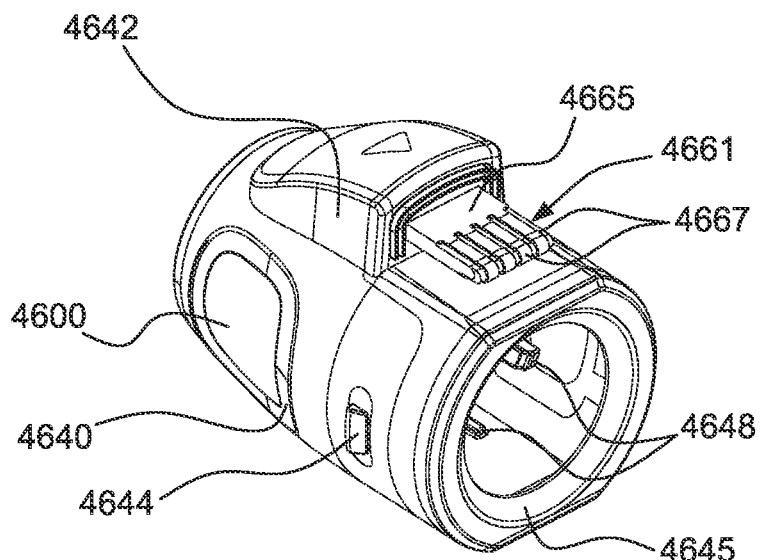

FIG. 123 is a perspective view of a dock connector for an air delivery tube according to an example of the present technology.

Figure 124:
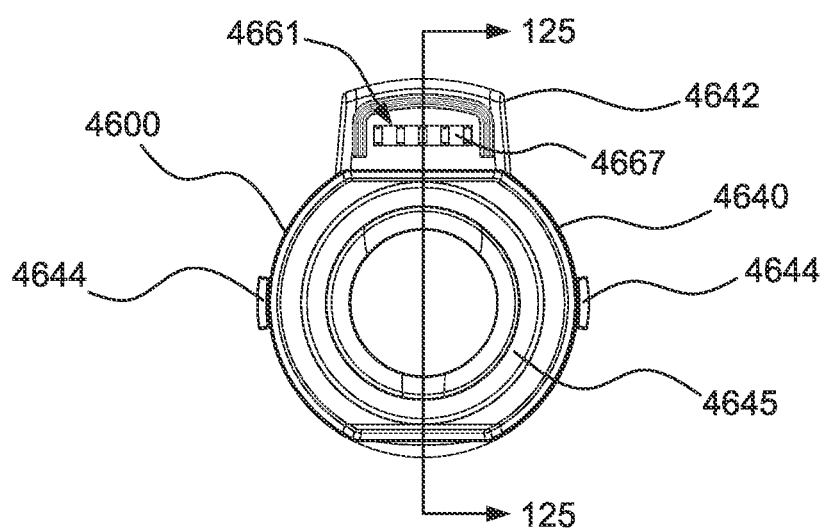

FIG. 124 is a front view of the dock connector of FIG. 123.

Figure 125:
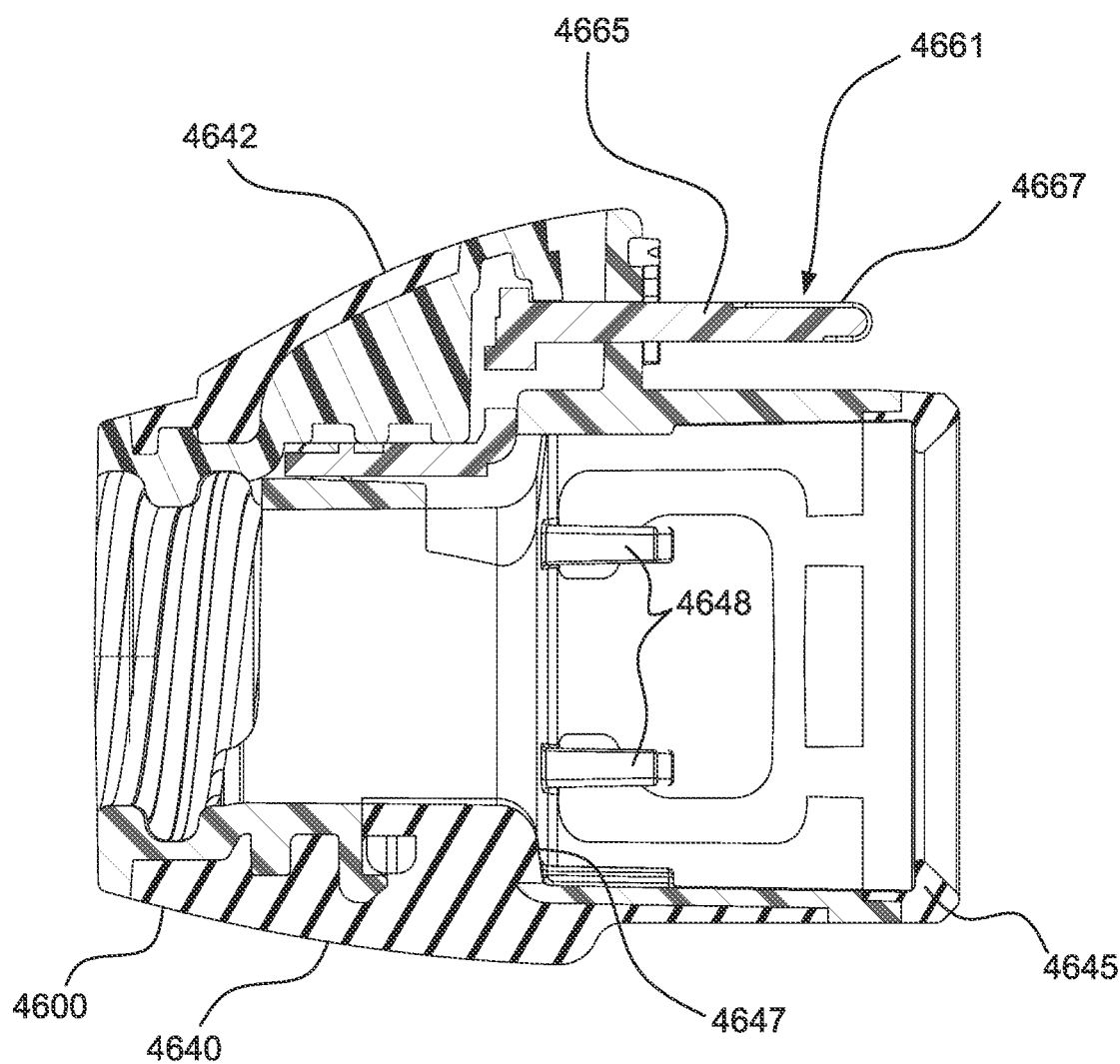

FIG. 125 is a cross-sectional view through line 125-125 of FIG. 124.

Figure 126:
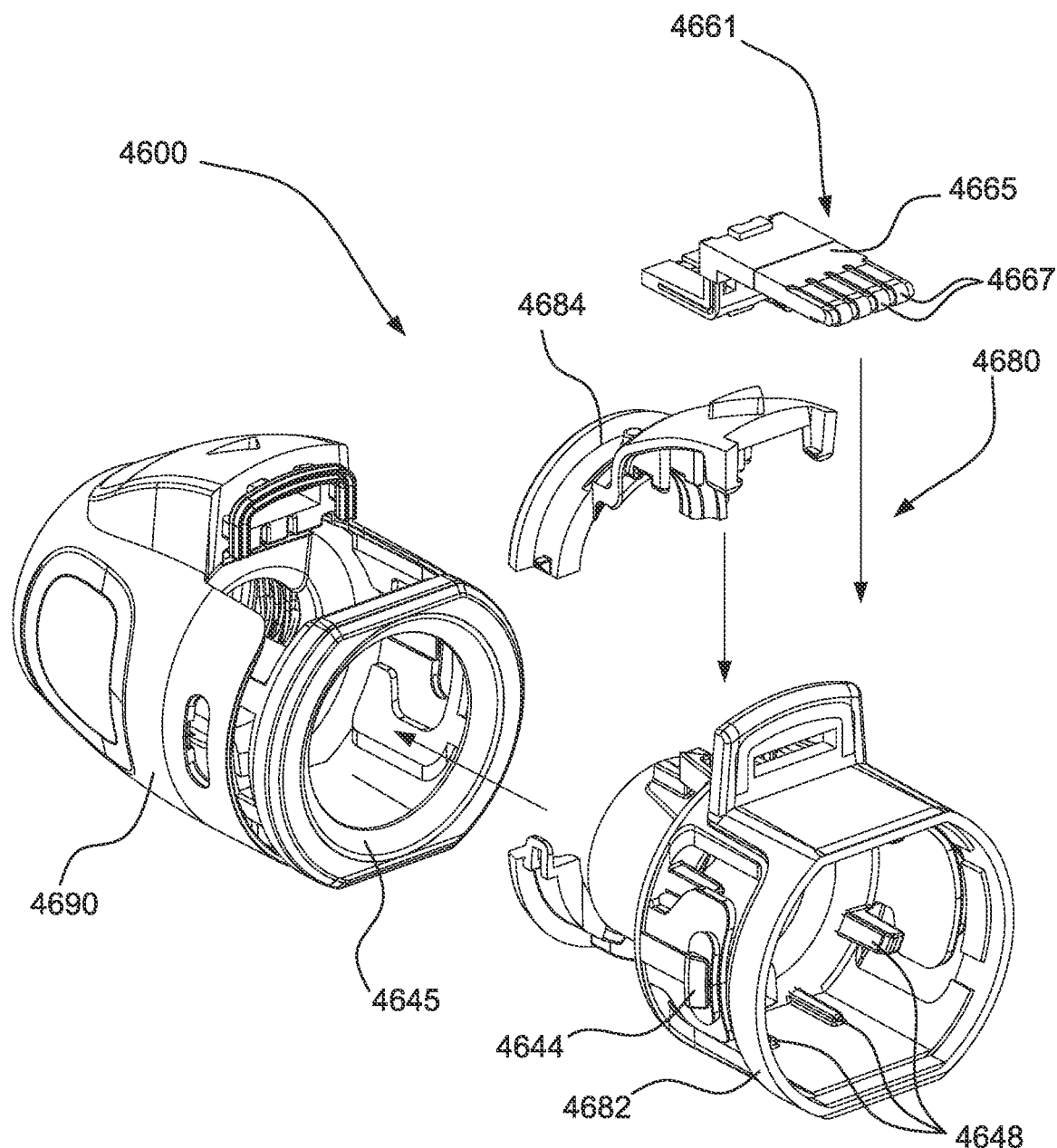

FIG. 126 is an exploded view of the dock connector of FIG. 123.

Figure 127:
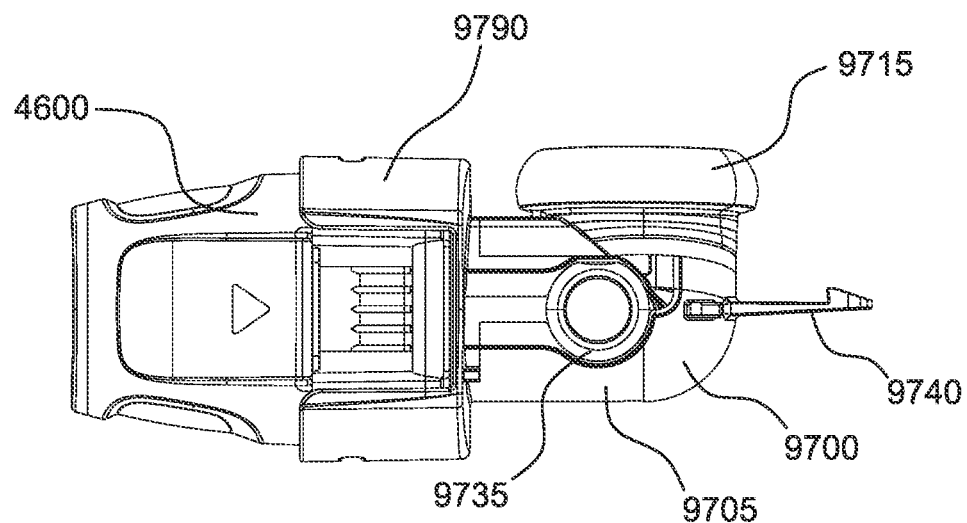

FIG. 127 is a top view showing engagement of the dock connector of the air delivery tube with the intermediate component according to an example of the present technology, the dock connector in a locked position.

Figure 128:
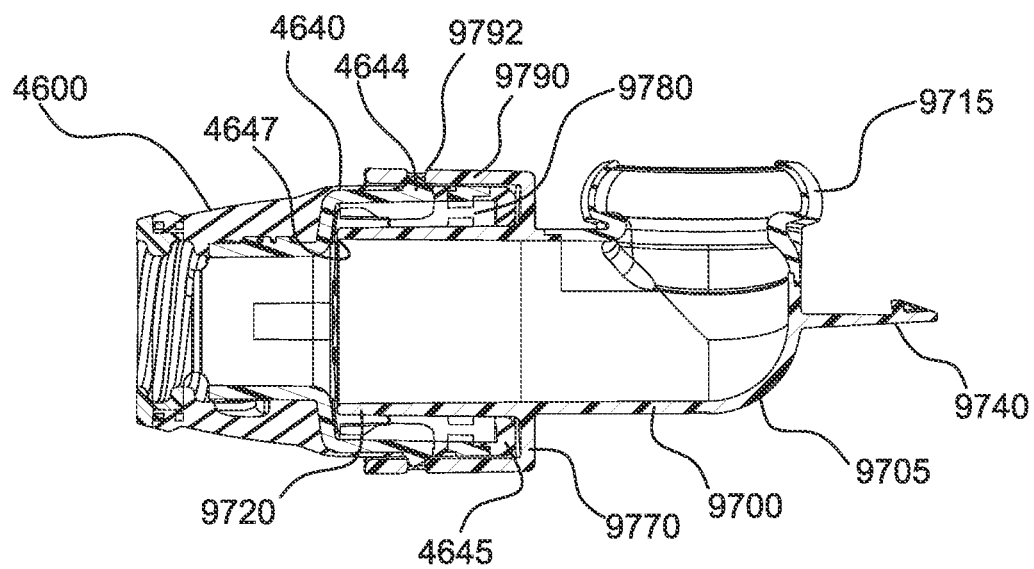

FIG. 128 is a cross-sectional view related to FIG. 127 showing the dock connector in a locked position.

Figure 129:
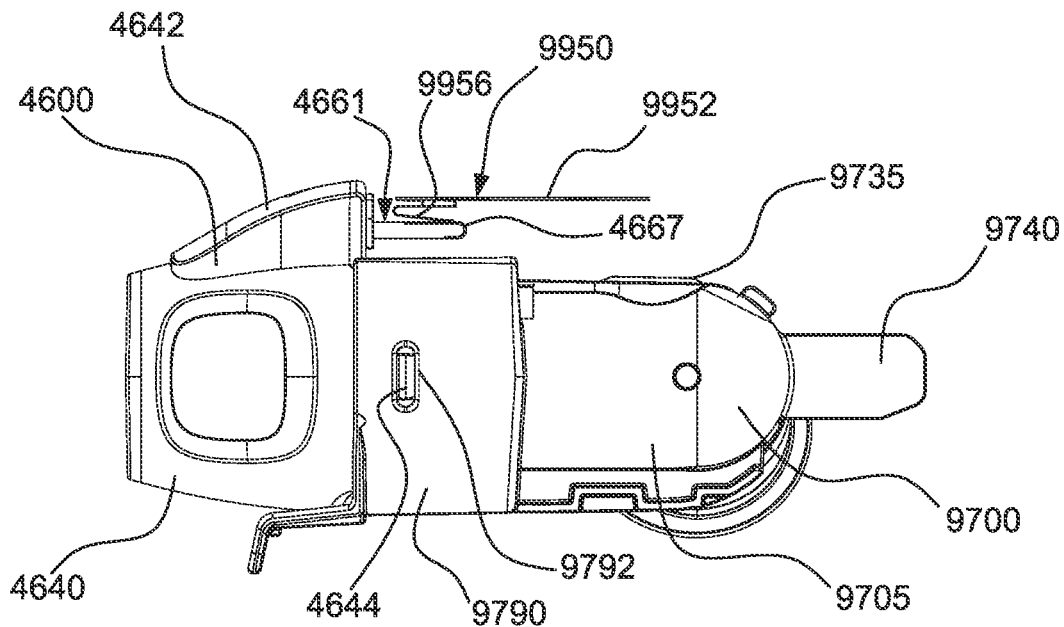

FIG. 129 is a side view showing engagement of the dock connector of the air delivery tube with the intermediate component and the contact assembly provided to the reservoir dock according to an example of the present technology, the dock connector in a locked position.

Figure 130:
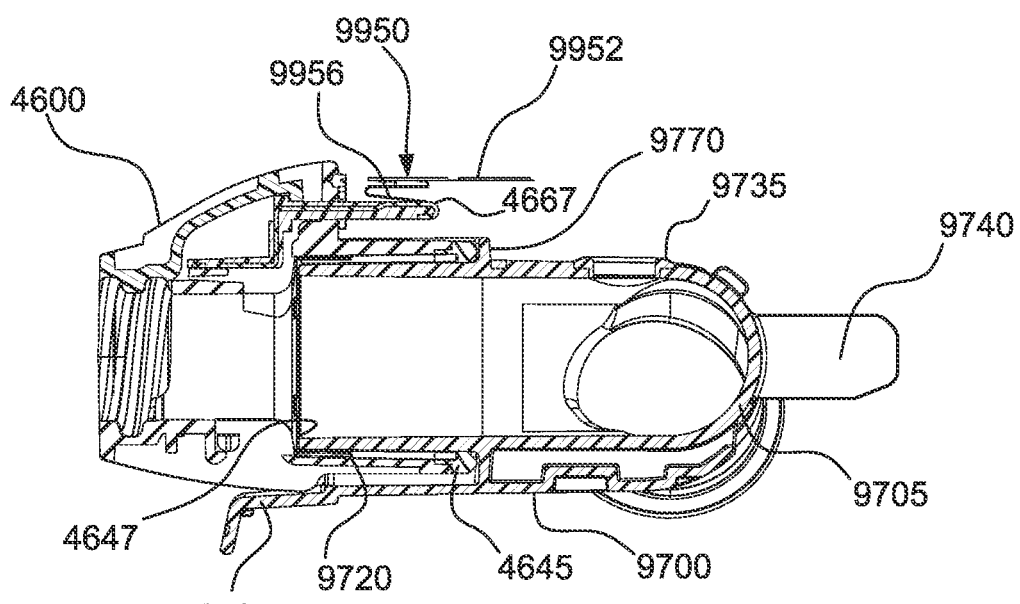

FIG. 130 is a cross-sectional view related to FIG. 129 showing the dock connector in a locked position.

Figure 131:
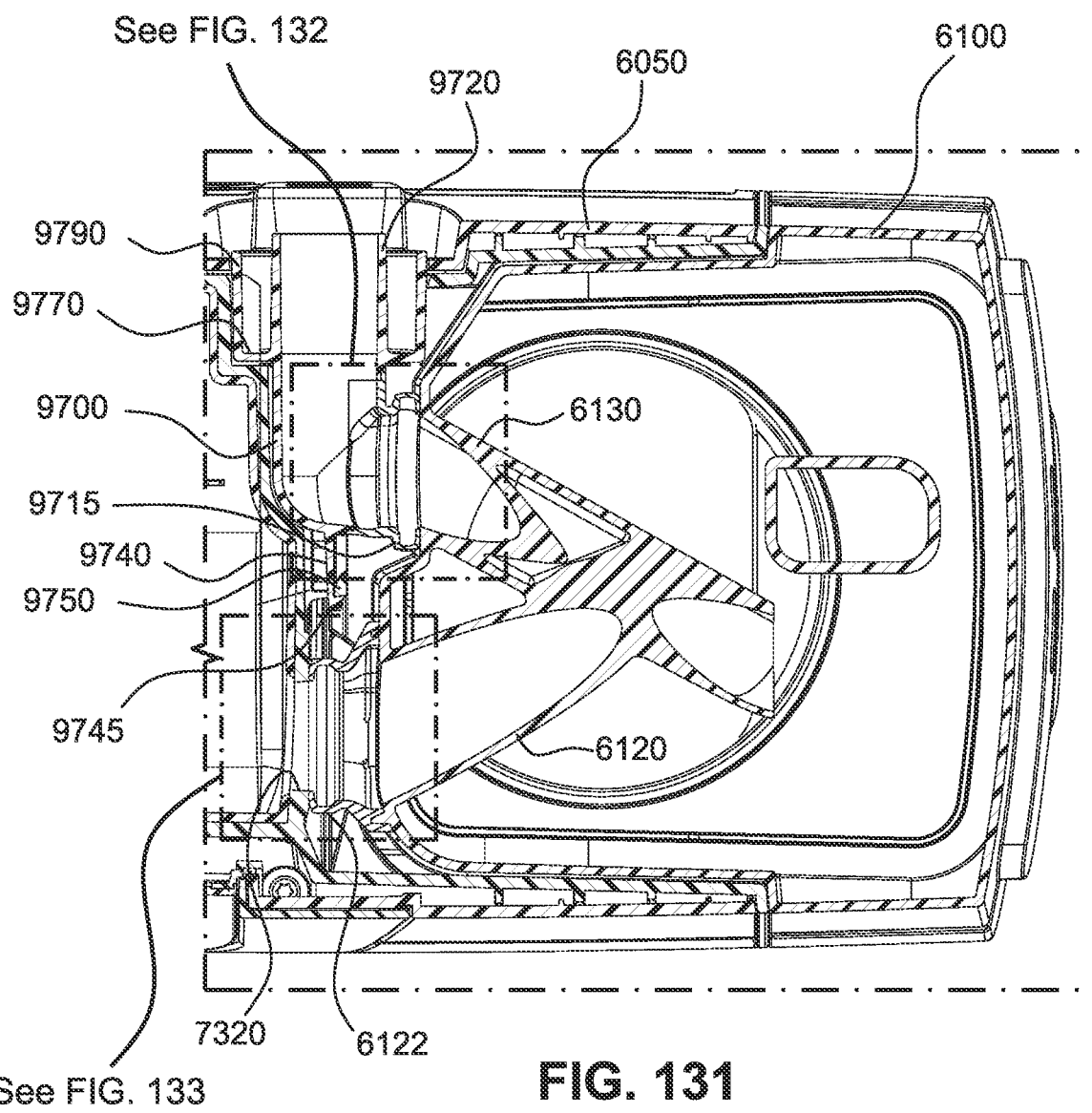

FIG. 131 is a cross-sectional view of the humidification portion of the integrated RPT device and humidifier of FIG. 79, taken along line 131-131 of FIG. 79.

Figure 132:
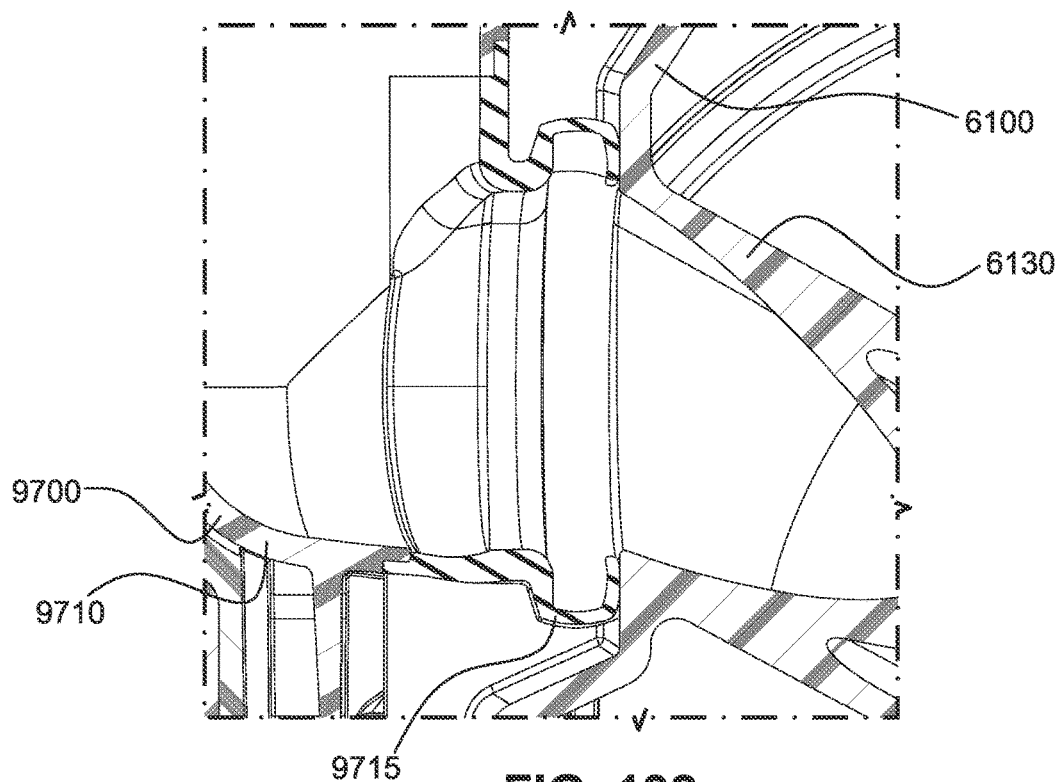

FIG. 132 is an enlarged view showing a portion of the integrated RPT device and humidifier of FIG. 131.

Figure 133:
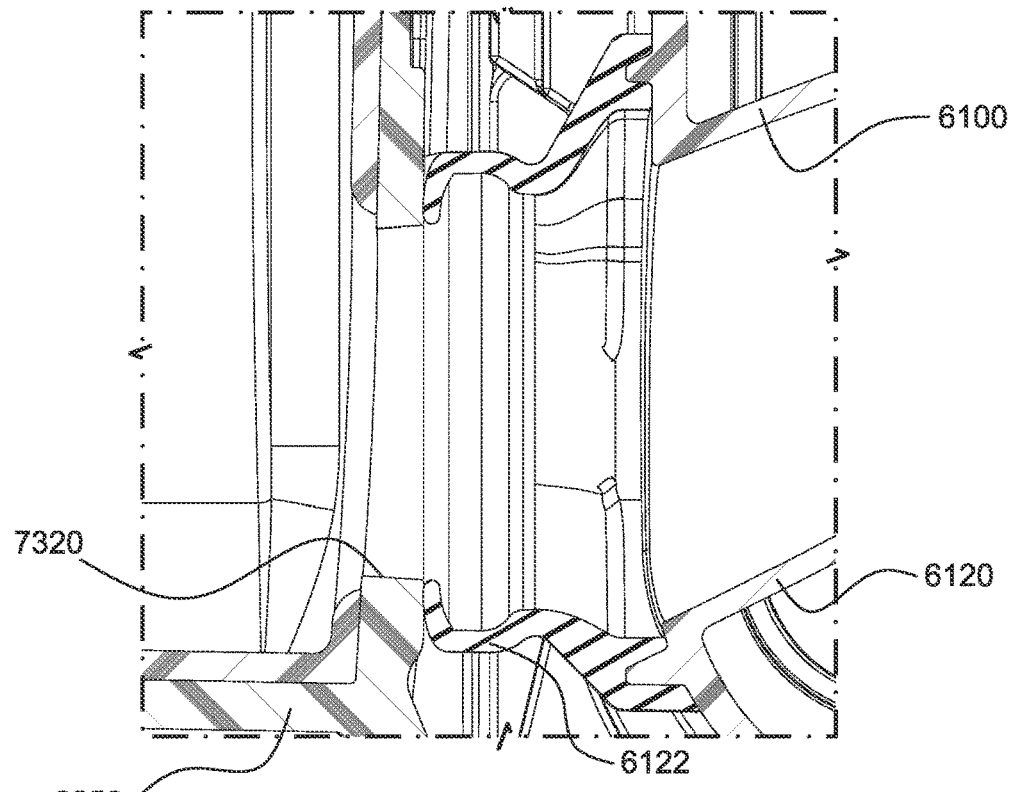

FIG. 133 is an enlarged view showing another portion of the integrated RPT device and humidifier of FIG. 131.

Figure 134:
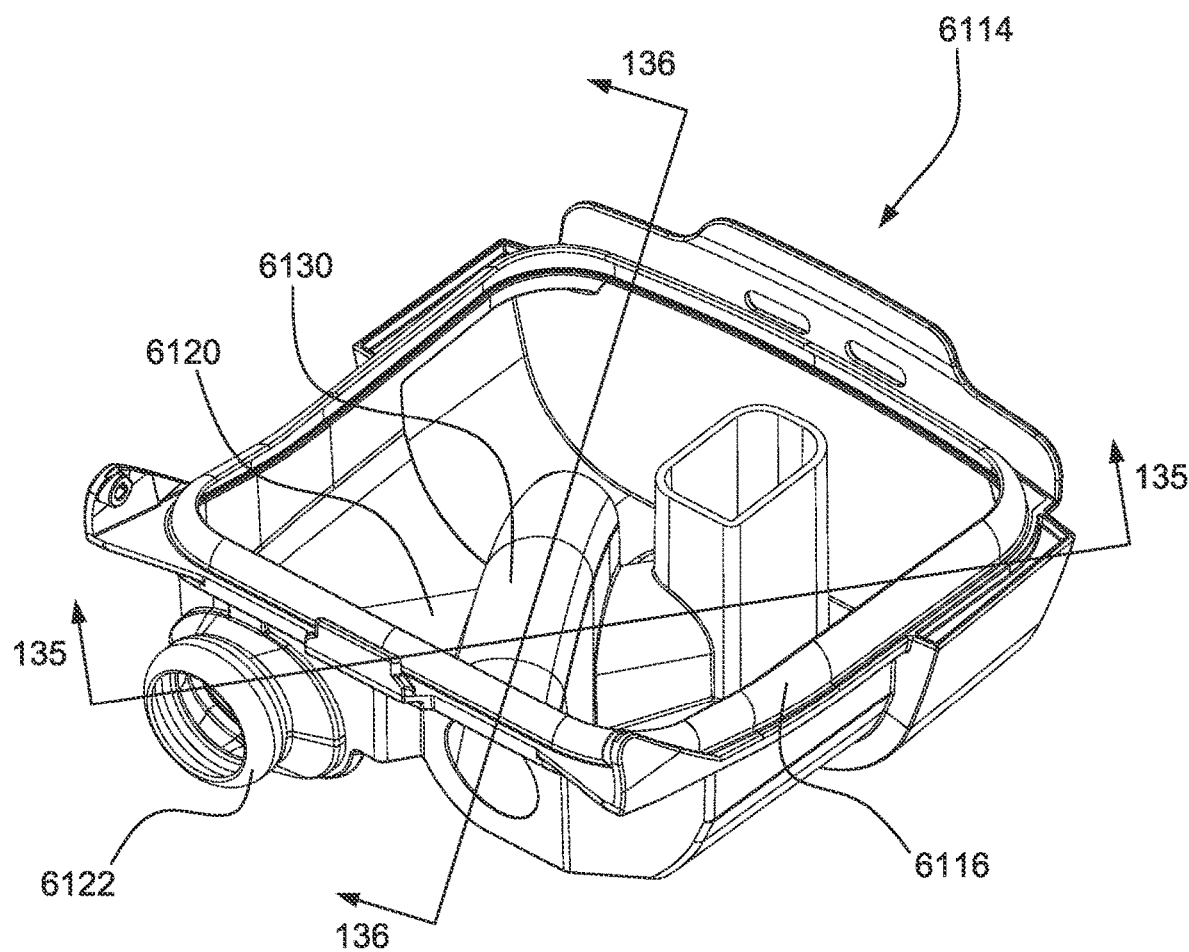

FIG. 134 is an inverted bottom perspective view of a lid of the water reservoir of FIG. 82.

Figure 135:
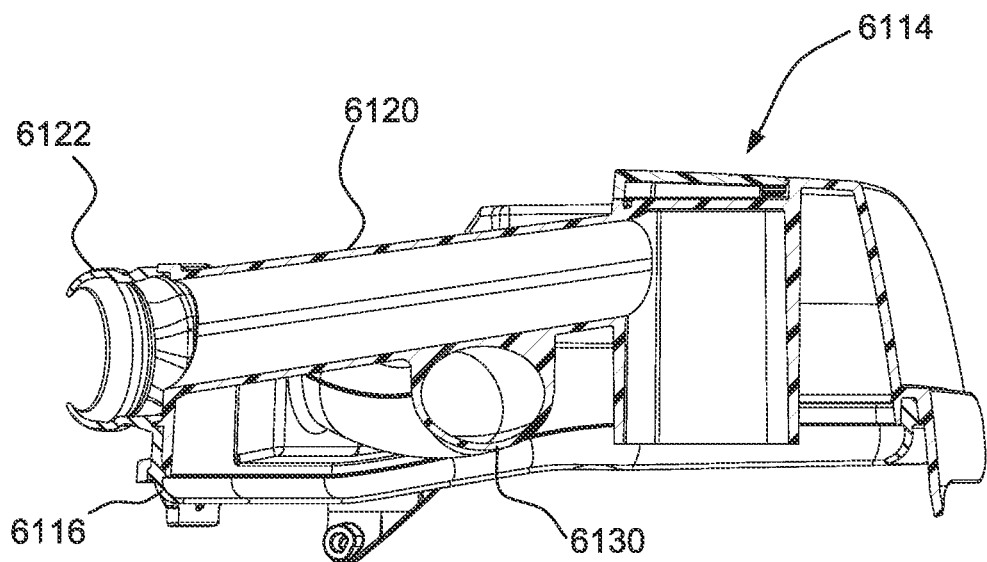

FIG. 135 is an inverted cross-sectional view of the lid of FIG. 134, taken along line 135-135 of FIG. 134.

Figure 136:
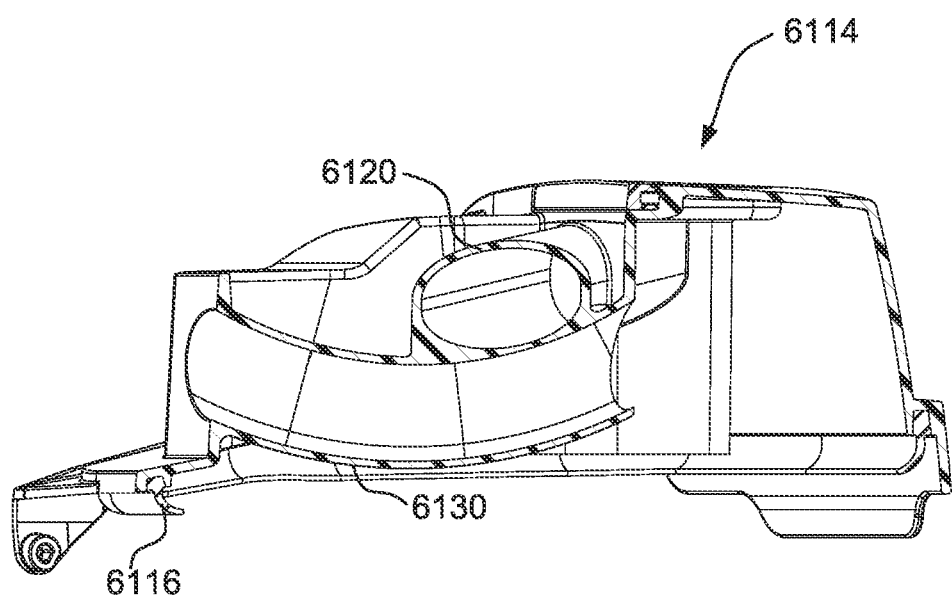

FIG. 136 is an inverted cross-sectional view of the lid of FIG. 134, taken along line 136-136 of FIG. 134.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Treatment Systems

Figure 1A:
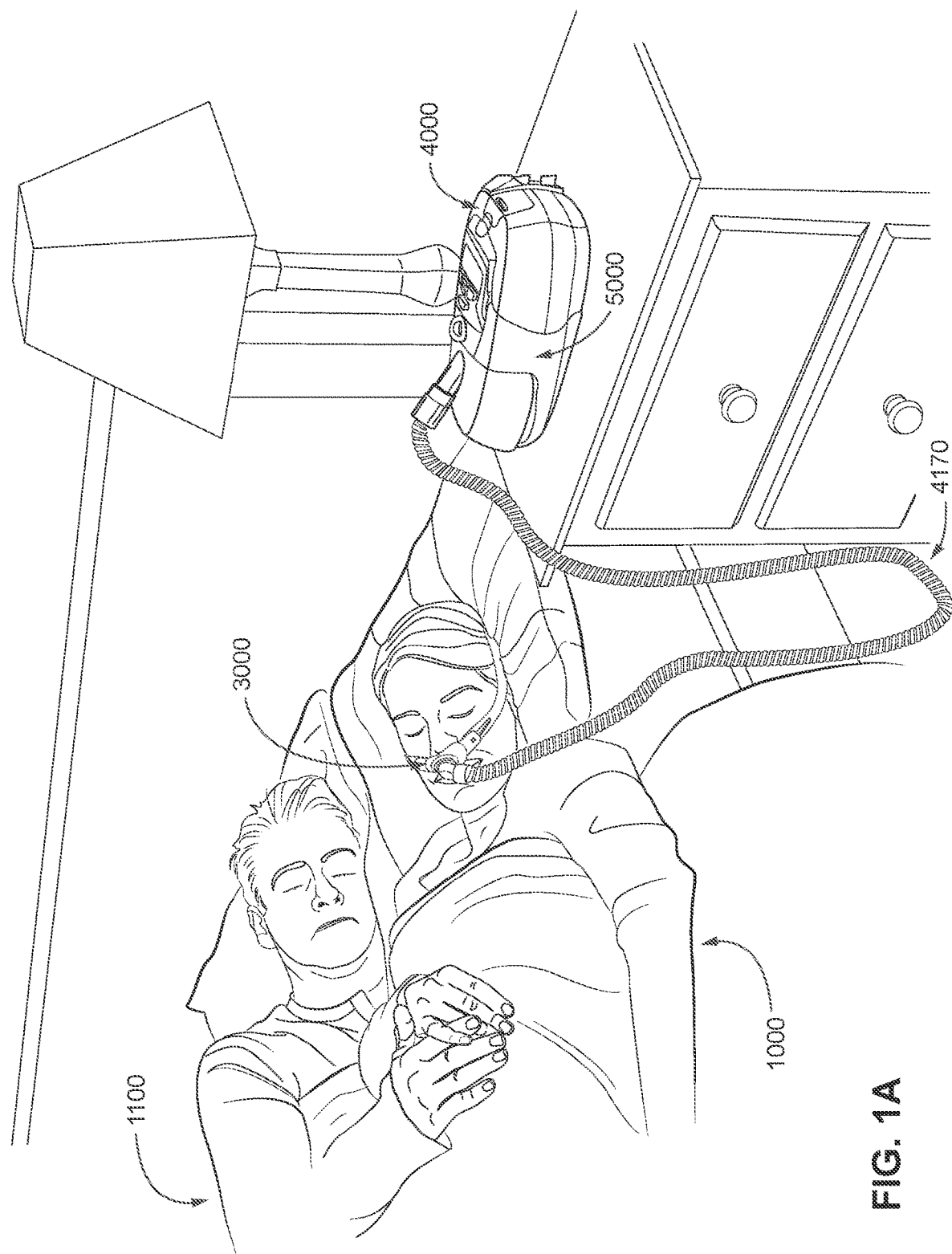
Figure 1C:
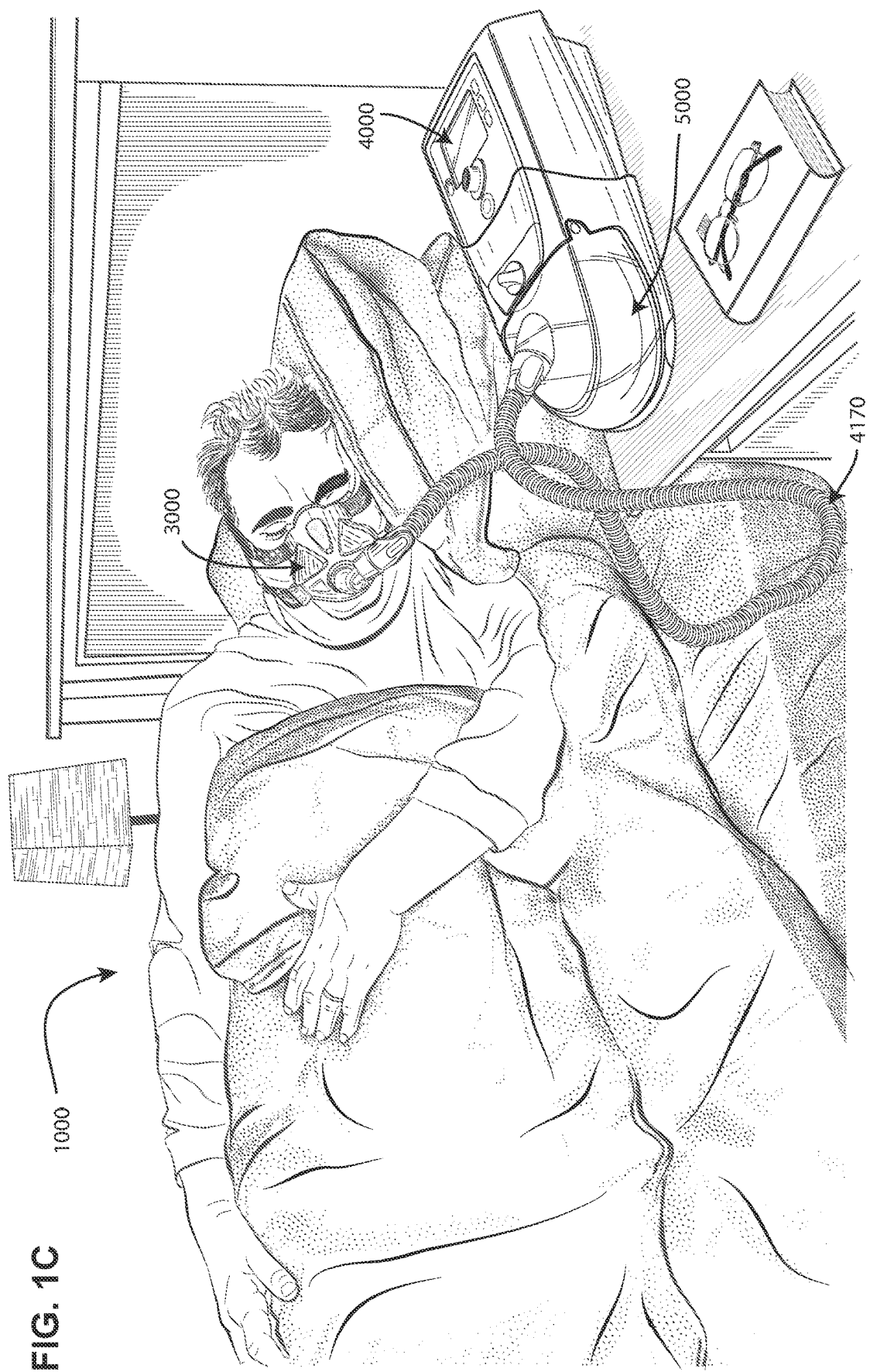
Figure 2A:
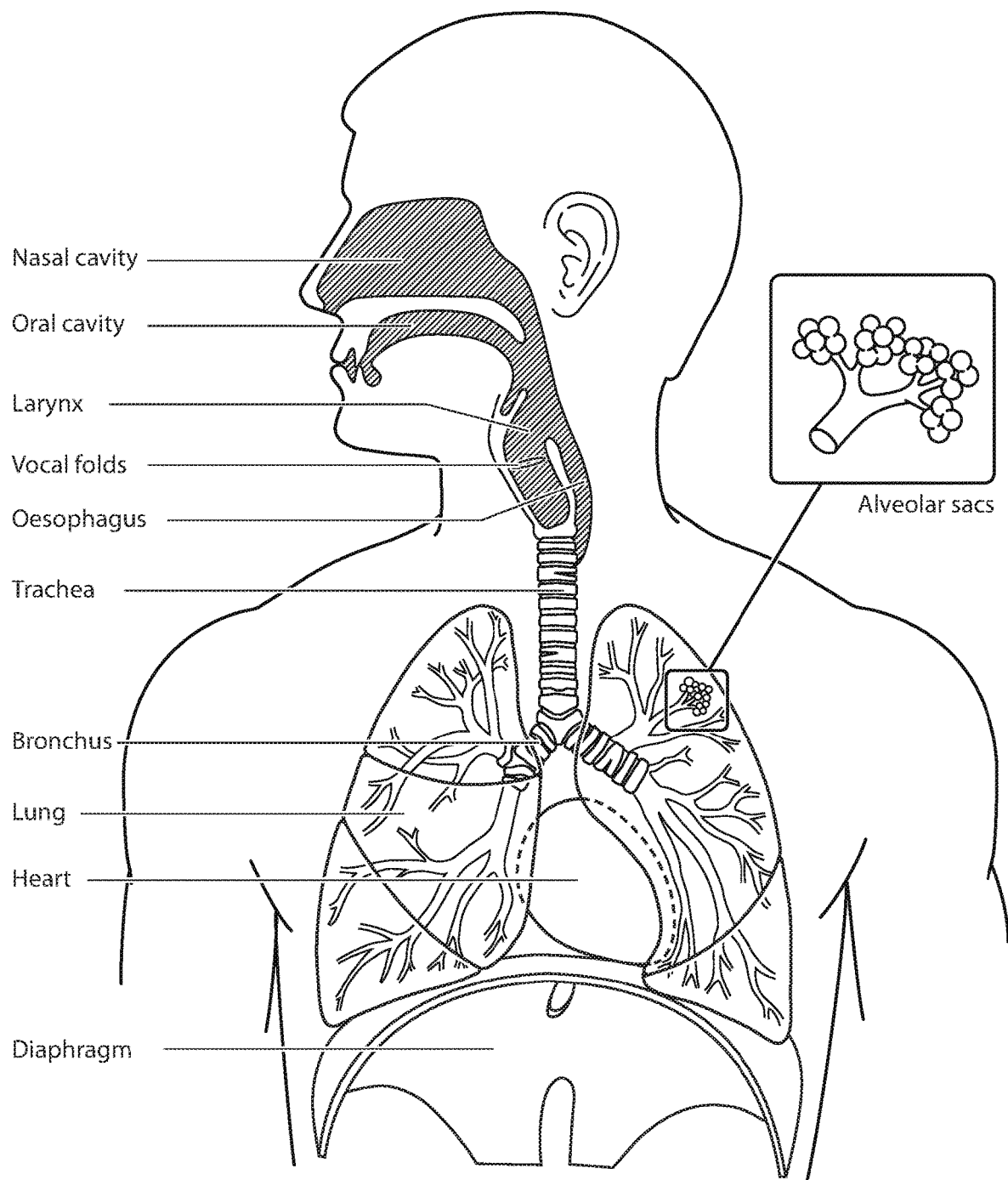
FIG. 2A shows an overview of a human respiratory system including the nasal and oral cavities, the larynx, vocal folds, oesophagus, trachea, bronchus, lung, alveolar sacs, heart and diaphragm.
Figure 2B:
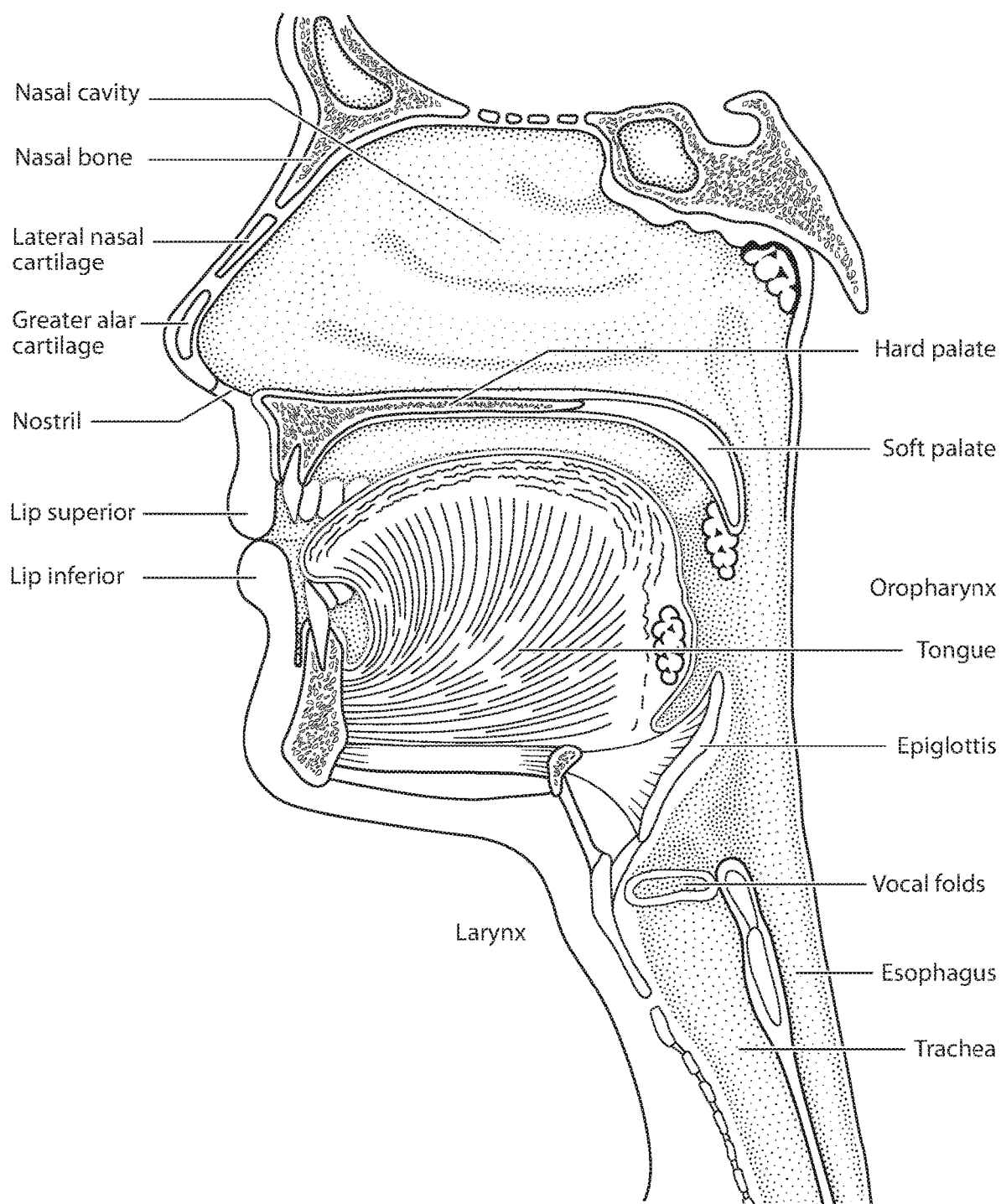
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

In one form, the present technology comprises an apparatus or device for treating a respiratory disorder. The apparatus or device may comprise an RPT device 4000 for supplying pressurised air to the patient 1000 via an air circuit 4170 to a patient interface 3000, e.g., see FIGS. 1A to 1C.

5.3 Patient Interface

FIG. 3A shows a non-invasive patient interface 3000 in accordance with one aspect of the present technology comprising the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 $cmH_2O$ with respect to ambient.

The patient interface 3000 in accordance with one form of the present technology is constructed and arranged to be able to provide a supply of air at a positive pressure of at least 10 $cmH_2O$ with respect to ambient.

The patient interface 3000 in accordance with one form of the present technology is constructed and arranged to be able to provide a supply of air at a positive pressure of at least 20 $cmH_2O$ with respect to ambient.

5.4 RPT Device

An exploded view of an RPT device 4000 in accordance with one aspect of the present technology is shown in FIG. 5A. An RPT device 4000 may comprise mechanical, pneumatic, and/or electrical components and be configured to execute one or more algorithms. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 $cmH_2O$, or at least 10 $cmH_2O$, or at least 20 $cmH_2O$.

The RPT device 4000 may include an external housing having one or more panel(s) such as a main panel 4010, a front panel 4012 and a side panel 4014. The RPT device 4000 may also comprise an outlet cap with a muffler 4124 as shown in FIGS. 5A and 5B. The outlet cap with a muffler 4124 may be removable and replaced with a water reservoir 5110 (see FIG. 5C). In such forms, the RPT device 4000 may be considered to include an integrated humidifier 5000. Thus, the RPT device 4000 may be used with or without humidification depending upon whether the water reservoir 5110 or the outlet cap with a muffler 4124 respectively is attached. Preferably the RPT device 4000 comprises a chassis 4016 that supports one or more internal components of the RPT device 4000. In one form the RPT device 4000 comprises a pressure generator 4140, which may be housed in a pneumatic block 4020 coupled to the chassis 4016.

Further examples and details of an exemplary RPT device are described in PCT Publication No. WO 2015/089582, which is incorporated herein by reference in its entirety.

The pneumatic path of the RPT device 4000 (e.g. shown in FIG. 5D) may comprise an inlet air filter 4112, an inlet muffler 4122, a pressure generator 4140 capable of supplying air at positive pressure (preferably a blower 4142) and an outlet muffler 4124 (or a water reservoir 5110 if humidification is required). One or more transducers 4270, such as pressure sensors and flow sensors may be included in the pneumatic path. The pneumatic path may also include anti-spill back valve 4160 to prevent water from the humidifier 5000 spilling back to the electrical components of the RPT device 4000.

As shown in FIG. 5E, the RPT device 4000 may have an electrical power supply 4210, one or more input devices 4220, a central controller 4230, a therapy device controller 4240, one or more protection circuits 4250, memory 4260, sensors/transducers 4270, data communication interface 4280 and one or more output devices 4290. Electrical components 4200 may be mounted on a single Printed Circuit Board Assembly (PCBA) 4202 (e.g., see FIG. 5A). In an alternative form, the RPT device 4000 may include more than one PCBA 4202.

5.4.1 RPT Device Mechanical & Pneumatic Components

An RPT device may comprise one or more of the following components in an integral unit. In an alternative form, one or more of the following components may be located as respective separate units.

5.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

5.4.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

5.4.1.3 Pressure Generator

In one form of the present technology, a pressure generator 4140 for producing a flow, or a supply, of air at positive pressure is a controllable blower 4142. For example the blower 4142 may include a brushless DC motor 4144 with one or more impellers. The impellers may be located in a volute. The blower may be capable of delivering a supply of air, for example at a rate of up to about 120 litres/minute, at a positive pressure in a range from about 4 $cmH_2O$ to about 20 $cmH_2O$, or in other forms up to about 30 $cmH_2O$. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

5.4.1.4 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to generate signals representing properties of the flow of air such as a flow rate, a pressure or a temperature at that point in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

5.4.1.4.1 Flow Rate Sensor

A flow rate sensor 4274 in accordance with the present technology may be based on a differential pressure transducer, for example, an SDP600 Series differential pressure transducer from SENSIRION.

In one form, a signal representing a flow rate from the flow rate sensor 4274 is received by the central controller 4230.

5.4.1.4.2 Pressure Sensor

A pressure sensor 4272 in accordance with the present technology is located in fluid communication with the pneumatic path. An example of a suitable pressure sensor is a transducer from the HONEYWELL ASDX series. An alternative suitable pressure sensor is a transducer from the NPA Series from GENERAL ELECTRIC.

In one form, a signal from the pressure sensor 4272 is received by the central controller 4230.

5.4.1.4.3 Motor Speed Transducer

In one form of the present technology a motor speed transducer 4276 is used to determine a rotational velocity of the motor 4144 and/or the blower 4142. A motor speed signal from the motor speed transducer 4276 may be provided to the therapy device controller 4240. The motor speed transducer 4276 may, for example, be a speed sensor, such as a Hall effect sensor.

5.4.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

5.4.2 RPT Device Electrical Components

5.4.2.1 Power Supply

A power supply 4210 may be located internal or external of the external housing 4010 of the RPT device 4000.

In one form of the present technology, power supply 4210 provides electrical power to the RPT device 4000 only. In another form of the present technology, power supply 4210 provides electrical power to both RPT device 4000 and humidifier 5000.

5.4.2.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form, the input device 4220 may be constructed and arranged to allow a person to select a value and/or a menu option.

5.4.2.3 Central Controller

In one form of the present technology, the central controller 4230 is one or a plurality of processors suitable to control an RPT device 4000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more transducers 4270, one or more input devices 4220, and the humidifier 5000.

The central controller 4230 may be configured to provide output signal(s) to one or more of an output device 4290, a therapy device controller 4240, a data communication interface 4280, and the humidifier 5000.

In some forms of the present technology, the central controller 4230 is configured to implement the one or more methodologies described herein, such as the one or more algorithms 4300 expressed as computer programs stored in a non-transitory computer readable storage medium, such as memory 4260. In some forms of the present technology, the central controller 4230 may be integrated with an RPT device 4000. However, in some forms of the present technology, some methodologies may be performed by a remotely located device. For example, the remotely located device may determine control settings for a ventilator or detect respiratory related events by analysis of stored data such as from any of the sensors described herein.

5.4.2.4 Clock

The RPT device 4000 may include a clock 4232 that is connected to the central controller 4230.

5.4.2.5 Therapy Device Controller

In one form of the present technology, therapy device controller 4240 is a therapy control module 4330 that forms part of the algorithms 4300 executed by the central controller 4230.

In one form of the present technology, therapy device controller 4240 is a dedicated motor control integrated circuit. For example, in one form a MC33035 brushless DC motor controller, manufactured by ONSEMI is used.

5.4.2.6 Protection Circuits

The one or more protection circuits 4250 in accordance with the present technology may comprise an electrical protection circuit, a temperature and/or pressure safety circuit.

5.4.2.7 Memory

In accordance with one form of the present technology the RPT device 4000 includes memory 4260, e.g., non-volatile memory. In some forms, memory 4260 may include battery powered static RAM. In some forms, memory 4260 may include volatile RAM.

Memory 4260 may be located on the PCBA 4202. Memory 4260 may be in the form of EEPROM, or NAND flash.

Additionally or alternatively, RPT device 4000 includes a removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms 4300.

5.4.2.8 Data Communication Systems

In one form of the present technology, a data communication interface 4280 is provided, and is connected to the central controller 4230. Data communication interface 4280 may be connectable to a remote external communication network 4282 and/or a local external communication network 4284. The remote external communication network 4282 may be connectable to a remote external device 4286. The local external communication network 4284 may be connectable to a local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such a remote external device 4286 may be accessible to an appropriately authorised person such as a clinician.

The local external device 4288 may be a personal computer, mobile phone, tablet or remote control.

5.4.2.9 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

5.4.2.9.1 Display Driver

A display driver 4292 receives as an input the characters, symbols, or images intended for display on the display 4294, and converts them to commands that cause the display 4294 to display those characters, symbols, or images.

5.4.2.9.2 Display

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

5.4.3 RPT Device Algorithms

As mentioned above, in some forms of the present technology, the central controller 4230 may be configured to implement one or more algorithms 4300 expressed as computer programs stored in a non-transitory computer readable storage medium, such as memory 4260. The algorithms 4300 are generally grouped into groups referred to as modules, e.g., see FIG. 5F.

5.4.3.1 Pre-Processing Module

A pre-processing module 4310 in accordance with one form of the present technology receives as an input a signal from a transducer 4270, for example a flow rate sensor 4274 or pressure sensor 4272, and performs one or more process steps to calculate one or more output values that will be used as an input to another module, for example a therapy engine module 4320.

In one form of the present technology, the output values include the interface or mask pressure Pm, the respiratory flow rate Qr, and the leak flow rate Ql.

In various forms of the present technology, the pre-processing module 4310 comprises one or more of the following algorithms: pressure compensation 4312, vent flow rate estimation 4314, leak flow rate estimation 4316, and respiratory flow rate estimation 4318.

5.4.3.1.1 Pressure Compensation

In one form of the present technology, a pressure compensation algorithm 4312 receives as an input a signal indicative of the pressure in the pneumatic path proximal to an outlet of the pneumatic block. The pressure compensation algorithm 4312 estimates the pressure drop through the air circuit 4170 and provides as an output an estimated pressure, Pm, in the patient interface 3000.

5.4.3.1.2 Vent Flow Rate Estimation

In one form of the present technology, a vent flow rate estimation algorithm 4314 receives as an input an estimated pressure, Pm, in the patient interface 3000 and estimates a vent flow rate of air, Qv, from a vent 3400 in a patient interface 3000.

5.4.3.1.3 Leak Flow Rate Estimation

In one form of the present technology, a leak flow rate estimation algorithm 4316 receives as an input a total flow rate, Qt, and a vent flow rate Qv, and provides as an output an estimate of the leak flow rate Ql. In one form, the leak flow rate estimation algorithm estimates the leak flow rate Ql by calculating an average of the difference between total flow rate Qt and vent flow rate Qv over a period sufficiently long to include several breathing cycles, e.g. about 10 seconds.

In one form, the leak flow rate estimation algorithm 4316 receives as an input a total flow rate Qt, a vent flow rate Qv, and an estimated pressure, Pm, in the patient interface 3000, and provides as an output a leak flow rate Ql, by calculating a leak conductance, and determining a leak flow rate Ql to be a function of leak conductance and pressure, Pm. Leak conductance is calculated as the quotient of low pass filtered non-vent flow rate equal to the difference between total flow rate Qt and vent flow rate Qv, and low pass filtered square root of pressure Pm, where the low pass filter time constant has a value sufficiently long to include several breathing cycles, e.g. about 10 seconds. The leak flow rate Ql may be estimated as the product of leak conductance and a function of pressure, Pm.

5.4.3.1.4 Respiratory Flow Rate Estimation

In one form of the present technology, a respiratory flow rate estimation algorithm 4318 receives as an input a total flow rate, Qt, a vent flow rate, Qv, and a leak flow rate, Ql, and estimates a respiratory flow rate of air, Qr, to the patient, by subtracting the vent flow rate Qv and the leak flow rate Ql from the total flow rate Qt.

5.4.3.2 Therapy Engine Module

In one form of the present technology, a therapy engine module 4320 receives as inputs one or more of a pressure, Pm, in a patient interface 3000, and a respiratory flow rate of air to a patient, Qr, and provides as an output one or more therapy parameters.

In one form of the present technology, a therapy parameter is a treatment pressure Pt.

In one form of the present technology, therapy parameters are one or more of an amplitude of a pressure variation, a base pressure, and a target ventilation.

In various forms, the therapy engine module 4320 comprises one or more of the following algorithms: phase determination 4321, waveform determination 4322, ventilation determination 4323, inspiratory flow limitation determination 4324, apnea/hypopnea determination 4325, snore determination 4326, airway patency determination 4327, target ventilation determination 4328, and therapy parameter determination 4329.

5.4.3.2.1 Phase Determination

In one form of the present technology, the RPT device 4000 does not determine phase.

In one form of the present technology, a phase determination algorithm 4321 receives as an input a signal indicative of respiratory flow rate, Qr, and provides as an output a phase $\Phi$ of a current breathing cycle of a patient 1000.

In some forms, known as discrete phase determination, the phase output $\Phi$ is a discrete variable. One implementation of discrete phase determination provides a bi-valued phase output $\Phi$ with values of either inhalation or exhalation, for example represented as values of 0 and 0.5 revolutions respectively, upon detecting the start of spontaneous inhalation and exhalation respectively. RPT devices 4000 that "trigger" and "cycle" effectively perform discrete phase determination, since the trigger and cycle points are the instants at which the phase changes from exhalation to inhalation and from inhalation to exhalation, respectively. In one implementation of bi-valued phase determination, the phase output $\Phi$ is determined to have a discrete value of 0 (thereby "triggering" the RPT device 4000) when the respiratory flow rate Qr has a value that exceeds a positive threshold, and a discrete value of 0.5 revolutions (thereby "cycling" the RPT device 4000) when a respiratory flow rate Qr has a value that is more negative than a negative threshold. The inhalation time Ti and the exhalation time Te may be estimated as typical values over many respiratory cycles of the time spent with phase $\Phi$ equal to 0 (indicating inspiration) and 0.5 (indicating expiration) respectively.

Another implementation of discrete phase determination provides a tri-valued phase output $\Phi$ with a value of one of inhalation, mid-inspiratory pause, and exhalation.

In other forms, known as continuous phase determination, the phase output $\Phi$ is a continuous variable, for example varying from 0 to 1 revolutions, or 0 to $2\pi$ radians. RPT devices 4000 that perform continuous phase determination may trigger and cycle when the continuous phase reaches 0 and 0.5 revolutions, respectively. In one implementation of continuous phase determination, a continuous value of phase $\Phi$ is determined using a fuzzy logic analysis of the respiratory flow rate Qr. A continuous value of phase determined in this implementation is often referred to as "fuzzy phase".

In one implementation of a fuzzy phase determination algorithm 4321, the following rules are applied to the respiratory flow rate Qr:

1. If the respiratory flow rate is zero and increasing fast then the phase is 0 revolutions.
2. If the respiratory flow rate is large positive and steady then the phase is 0.25 revolutions.
3. If the respiratory flow rate is zero and falling fast, then the phase is 0.5 revolutions.
4. If the respiratory flow rate is large negative and steady then the phase is 0.75 revolutions.
5. If the respiratory flow rate is zero and steady and the 5-second low-pass filtered absolute value of the respiratory flow rate is large then the phase is 0.9 revolutions.
6. If the respiratory flow rate is positive and the phase is expiratory, then the phase is 0 revolutions.
7. If the respiratory flow rate is negative and the phase is inspiratory, then the phase is 0.5 revolutions.
8. If the 5-second low-pass filtered absolute value of the respiratory flow rate is large, the phase is increasing at a steady rate equal to the patient's breathing rate, low-pass filtered with a time constant of 20 seconds.

The output of each rule may be represented as a vector whose phase is the result of the rule and whose magnitude is the fuzzy extent to which the rule is true. The fuzzy extent to which the respiratory flow rate is "large", "steady", etc. is determined with suitable membership functions. The results of the rules, represented as vectors, are then combined by some function such as taking the centroid. In such a combination, the rules may be equally weighted, or differently weighted.

In another implementation of continuous phase determination, the phase $\Phi$ is first discretely estimated from the respiratory flow rate Qr as described above, as are the inhalation time Ti and the exhalation time Te. The continuous phase $\Phi$ at any instant may be determined as the half the proportion of the inhalation time Ti that has elapsed since the previous trigger instant, or 0.5 revolutions plus half the proportion of the exhalation time Te that has elapsed since the previous cycle instant (whichever instant was more recent).

5.4.3.2.2 Waveform Determination

In one form of the present technology, the therapy parameter determination algorithm 4329 provides an approximately constant treatment pressure throughout a respiratory cycle of a patient.

In other forms of the present technology, the therapy control module 4330 controls the pressure generator 4140 to provide a treatment pressure Pt that varies as a function of phase $\Phi$ of a respiratory cycle of a patient according to a waveform template $\Pi(\Phi)$.

In one form of the present technology, a waveform determination algorithm 4322 provides a waveform template $\Pi(\Phi)$ with values in the range [0, 1] on the domain of phase values $\Phi$ provided by the phase determination algorithm 4321 to be used by the therapy parameter determination algorithm 4329.

In one form, suitable for either discrete or continuously-valued phase, the waveform template $\Pi(\Phi)$ is a square-wave template, having a value of 1 for values of phase up to and including 0.5 revolutions, and a value of 0 for values of phase above 0.5 revolutions. In one form, suitable for continuously-valued phase, the waveform template $\Pi(\Phi)$ comprises two smoothly curved portions, namely a smoothly curved (e.g. raised cosine) rise from 0 to 1 for values of phase up to 0.5 revolutions, and a smoothly curved (e.g. exponential) decay from 1 to 0 for values of phase above 0.5 revolutions. In one form, suitable for continuously-valued phase, the waveform template Π(Φ) is based on a square wave, but with a smooth rise from 0 to 1 for values of phase up to a "rise time" that is less than 0.5 revolutions, and a smooth fall from 1 to 0 for values of phase within a "fall time" after 0.5 revolutions, with a "fall time" that is less than 0.5 revolutions.

In some forms of the present technology, the waveform determination algorithm 4322 selects a waveform template Π(Φ) from a library of waveform templates, dependent on a setting of the RPT device. Each waveform template Π(Φ) in the library may be provided as a lookup table of values Π against phase values Φ. In other forms, the waveform determination algorithm 4322 computes a waveform template Π(Φ) "on the fly" using a predetermined functional form, possibly parametrised by one or more parameters (e.g. time constant of an exponentially curved portion). The parameters of the functional form may be predetermined or dependent on a current state of the patient 1000.

In some forms of the present technology, suitable for discrete bi-valued phase of either inhalation (Φ=0 revolutions) or exhalation (Φ=0.5 revolutions), the waveform determination algorithm 4322 computes a waveform template Π "on the fly" as a function of both discrete phase Φ and time t measured since the most recent trigger instant. In one such form, the waveform determination algorithm 4322 computes the waveform template Π(Φ, t) in two portions (inspiratory and expiratory) as follows:

$$\Pi(\Phi, t) = \begin{cases} \Pi_i(t), & \Phi = 0 \\ \Pi_e(t - T_i), & \Phi = 0.5 \end{cases}$$

where $\Pi_i(t)$ and $\Pi_e(t)$ are inspiratory and expiratory portions of the waveform template Π(Φ, t). In one such form, the inspiratory portion $\Pi_i(t)$ of the waveform template is a smooth rise from 0 to 1 parametrised by a rise time, and the expiratory portion $\Pi_e(t)$ of the waveform template is a smooth fall from 1 to 0 parametrised by a fall time.

5.4.3.2.3 Ventilation Determination

In one form of the present technology, a ventilation determination algorithm 4323 receives an input a respiratory flow rate Qr, and determines a measure indicative of current patient ventilation, Vent.

In some implementations, the ventilation determination algorithm 4323 determines a measure of ventilation Vent that is an estimate of actual patient ventilation. One such implementation is to take half the absolute value of respiratory flow rate, Qr, optionally filtered by low-pass filter such as a second order Bessel low-pass filter with a corner frequency of 0.11 Hz.

In other implementations, the ventilation determination algorithm 4323 determines a measure of ventilation Vent that is broadly proportional to actual patient ventilation. One such implementation estimates peak respiratory flow rate Qpeak over the inspiratory portion of the cycle. This and many other procedures involving sampling the respiratory flow rate Qr produce measures which are broadly proportional to ventilation, provided the flow rate waveform shape does not vary very much (here, the shapes of two breaths are taken to be similar when the flow rate waveforms of the breaths normalised in time and amplitude are similar). Some simple examples include the median positive respiratory flow rate, the median of the absolute value of respiratory flow rate, and the standard deviation of flow rate. Arbitrary linear combinations of arbitrary order statistics of the absolute value of respiratory flow rate using positive coefficients, and even some using both positive and negative coefficients, are approximately proportional to ventilation. Another example is the mean of the respiratory flow rate in the middle K proportion (by time) of the inspiratory portion, where 0<K<1. There is an arbitrarily large number of measures that are exactly proportional to ventilation if the flow rate shape is constant.

5.4.3.2.4 Determination of Inspiratory Flow limitation

In one form of the present technology, the central controller 4230 executes an inspiratory flow limitation determination algorithm 4324 for the determination of the extent of inspiratory flow limitation.

In one form, the inspiratory flow limitation determination algorithm 4324 receives as an input a respiratory flow rate signal Qr and provides as an output a metric of the extent to which the inspiratory portion of the breath exhibits inspiratory flow limitation.

In one form of the present technology, the inspiratory portion of each breath is identified by a zero-crossing detector. A number of evenly spaced points (for example, sixty-five), representing points in time, are interpolated by an interpolator along the inspiratory flow rate-time curve for each breath. The curve described by the points is then scaled by a scalar to have unity length (duration/period) and unity area to remove the effects of changing breathing rate and depth. The scaled breaths are then compared in a comparator with a pre-stored template representing a normal unobstructed breath, similar to the inspiratory portion of the breath shown in FIG. 6A. Breaths deviating by more than a specified threshold (typically 1 scaled unit) at any time during the inspiration from this template, such as those due to coughs, sighs, swallows and hiccups, as determined by a test element, are rejected. For non-rejected data, a moving average of the first such scaled point is calculated by the central controller 4230 for the preceding several inspiratory events. This is repeated over the same inspiratory events for the second such point, and so on. Thus, for example, sixty five scaled data points are generated by the central controller 4230, and represent a moving average of the preceding several inspiratory events, e.g., three events. The moving average of continuously updated values of the (e.g., sixty five) points are hereinafter called the "scaled flow rate", designated as Qs(t). Alternatively, a single inspiratory event can be utilised rather than a moving average.

From the scaled flow rate, two shape factors relating to the determination of partial obstruction may be calculated.

Shape factor 1 is the ratio of the mean of the middle (e.g. thirty-two) scaled flow rate points to the mean overall (e.g. sixty-five) scaled flow rate points. Where this ratio is in excess of unity, the breath will be taken to be normal. Where the ratio is unity or less, the breath will be taken to be obstructed. A ratio of about 1.17 is taken as a threshold between partially obstructed and unobstructed breathing, and equates to a degree of obstruction that would permit maintenance of adequate oxygenation in a typical patient.

Shape factor 2 is calculated as the RMS deviation from unit scaled flow rate, taken over the middle (e.g. thirty two) points. An RMS deviation of about 0.2 units is taken to be normal. An RMS deviation of zero is taken to be a totally flow—limited breath. The closer the RMS deviation to zero, the breath will be taken to be more flow limited.

Shape factors 1 and 2 may be used as alternatives, or in combination. In other forms of the present technology, the number of sampled points, breaths and middle points may differ from those described above. Furthermore, the threshold values can be other than those described.

5.4.3.2.5 Determination of Apneas and Hypopneas

In one form of the present technology, the central controller 4230 executes an apnea/hypopnea determination algorithm 4325 for the determination of the presence of apneas and/or hypopneas.

In one form, the apnea/hypopnea determination algorithm 4325 receives as an input a respiratory flow rate signal Qr and provides as an output a flag that indicates that an apnea or a hypopnea has been detected.

In one form, an apnea will be said to have been detected when a function of respiratory flow rate Qr falls below a flow rate threshold for a predetermined period of time. The function may determine a peak flow rate, a relatively short-term mean flow rate, or a flow rate intermediate of relatively short-term mean and peak flow rate, for example an RMS flow rate. The flow rate threshold may be a relatively long-term measure of flow rate.

In one form, a hypopnea will be said to have been detected when a function of respiratory flow rate Qr falls below a second flow rate threshold for a predetermined period of time. The function may determine a peak flow, a relatively short-term mean flow rate, or a flow rate intermediate of relatively short-term mean and peak flow rate, for example an RMS flow rate. The second flow rate threshold may be a relatively long-term measure of flow rate. The second flow rate threshold is greater than the flow rate threshold used to detect apneas.

5.4.3.2.6 Determination of Snore

In one form of the present technology, the central controller 4230 executes one or more snore determination algorithms 4326 for the determination of the extent of snore.

In one form, the snore determination algorithm 4326 receives as an input a respiratory flow rate signal Qr and provides as an output a metric of the extent to which snoring is present.

The snore determination algorithm 4326 may comprise the step of determining the intensity of the flow rate signal in the range of 30-300 Hz. Further, the snore determination algorithm 4326 may comprise a step of filtering the respiratory flow rate signal Qr to reduce background noise, e.g., the sound of airflow in the system from the blower.

5.4.3.2.7 Determination of Airway Patency

In one form of the present technology, the central controller 4230 executes one or more airway patency determination algorithms 4327 for the determination of the extent of airway patency.

In one form, the airway patency determination algorithm 4327 receives as an input a respiratory flow rate signal Qr, and determines the power of the signal in the frequency range of about 0.75 Hz and about 3 Hz. The presence of a peak in this frequency range is taken to indicate an open airway. The absence of a peak is taken to be an indication of a closed airway.

In one form, the frequency range within which the peak is sought is the frequency of a small forced oscillation in the treatment pressure Pt. In one implementation, the forced oscillation is of frequency 2 Hz with amplitude about 1 cmH$_2$O.

In one form, airway patency determination algorithm 4327 receives as an input a respiratory flow rate signal Qr, and determines the presence or absence of a cardiogenic signal. The absence of a cardiogenic signal is taken to be an indication of a closed airway.

5.4.3.2.8 Determination of Target Ventilation

In one form of the present technology, the central controller 4230 takes as input the measure of current ventilation, Vent, and executes one or more target ventilation determination algorithms 4328 for the determination of a target value Vtgt for the measure of ventilation.

In some forms of the present technology, there is no target ventilation determination algorithm 4328, and the target value Vtgt is predetermined, for example by hard-coding during configuration of the RPT device 4000 or by manual entry through the input device 4220.

In other forms of the present technology, such as adaptive servo-ventilation (ASV), the target ventilation determination algorithm 4328 computes a target value Vtgt from a value Vtyp indicative of the typical recent ventilation of the patient.

In some forms of adaptive servo-ventilation, the target ventilation Vtgt is computed as a high proportion of, but less than, the typical recent ventilation Vtyp. The high proportion in such forms may be in the range (80%, 100%), or (85%, 95%), or (87%, 92%).

In other forms of adaptive servo-ventilation, the target ventilation Vtgt is computed as a slightly greater than unity multiple of the typical recent ventilation Vtyp.

The typical recent ventilation Vtyp is the value around which the distribution of the measure of current ventilation Vent over multiple time instants over some predetermined timescale tends to cluster, that is, a measure of the central tendency of the measure of current ventilation over recent history. In one implementation of the target ventilation determination algorithm 4328, the recent history is of the order of several minutes, but in any case should be longer than the timescale of Cheyne-Stokes waxing and waning cycles. The target ventilation determination algorithm 4328 may use any of the variety of well-known measures of central tendency to determine the typical recent ventilation Vtyp from the measure of current ventilation, Vent. One such measure is the output of a low-pass filter on the measure of current ventilation Vent, with time constant equal to one hundred seconds.

5.4.3.2.9 Determination of Therapy Parameters

In some forms of the present technology, the central controller 4230 executes one or more therapy parameter determination algorithms 4329 for the determination of one or more therapy parameters using the values returned by one or more of the other algorithms in the therapy engine module 4320.

In one form of the present technology, the therapy parameter is an instantaneous treatment pressure Pt. In one implementation of this form, the therapy parameter determination algorithm 4329 determines the treatment pressure Pt using the equation $$Pt = A\Pi(\Phi, t) + P_0 \qquad (1)$$

where:
A is the amplitude,
$\Pi(\Phi, t)$ is the waveform template value (in the range 0 to 1) at the current value $\Phi$ of phase and t of time, and
$P_0$ is a base pressure.

If the waveform determination algorithm 4322 provides the waveform template $\Pi(\Phi, t)$ as a lookup table of values $\Pi$ indexed by phase $\Phi$, the therapy parameter determination algorithm 4329 applies equation (1) by locating the nearest lookup table entry to the current value $\Phi$ of phase returned by the phase determination algorithm 4321, or by interpolation between the two entries straddling the current value $\Phi$ of phase.

The values of the amplitude A and the base pressure $P_0$ may be set by the therapy parameter determination algorithm 4329 depending on the chosen respiratory pressure therapy mode in the manner described below.

5.4.3.3 Therapy Control Module

The therapy control module 4330 in accordance with one aspect of the present technology receives as inputs the therapy parameters from the therapy parameter determination algorithm 4329 of the therapy engine module 4320, and controls the pressure generator 4140 to deliver a flow of air in accordance with the therapy parameters.

In one form of the present technology, the therapy parameter is a treatment pressure Pt, and the therapy control module 4330 controls the pressure generator 4140 to deliver a flow of air whose mask pressure Pm at the patient interface 3000 is equal to the treatment pressure Pt.

5.4.3.4 Detection of Fault Conditions

In one form of the present technology, the central controller 4230 executes one or more methods 4340 for the detection of fault conditions. The fault conditions detected by the one or more methods 4340 may include at least one of the following:

Power failure (no power, or insufficient power)
Transducer fault detection
Failure to detect the presence of a component
Operating parameters outside recommended ranges (e.g. pressure, flow rate, temperature, $PaO_2$)
Failure of a test alarm to generate a detectable alarm signal.

Upon detection of the fault condition, the corresponding algorithm 4340 signals the presence of the fault by one or more of the following:

Initiation of an audible, visual &/or kinetic (e.g. vibrating) alarm
Sending a message to an external device
Logging of the incident

5.5 Air Circuit

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230. One example of an air circuit 4170 comprising a heated wire circuit is described in U.S. Pat. No. 8,733,349, which is incorporated herewithin in its entirety by reference.

5.5.1 Oxygen Delivery

In one form of the present technology, supplemental oxygen 4180 is delivered to one or more points in the pneumatic path, such as upstream of the pneumatic block 4020, to the air circuit 4170 and/or to the patient interface 3000.

5.6 Humidifier

5.6.1 Humidifier Overview

In one form of the present technology there is provided a humidifier 5000 (e.g., as shown in FIG. 5C) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

RPT Device and Humidifier

FIGS. 6A, 6B, 7, and 8A to 8D illustrate an integrated RPT device and humidifier 6000 according to an example of the present technology. As illustrated, the integrated RPT device and humidifier 6000 includes a reservoir dock 6050 structured and arranged to receive a water reservoir 6100 (also referred to as a humidifier tub or a humidifier reservoir). In the illustrated example, the integrated RPT device and humidifier 6000 comprises a humidifier that is integrated with an RPT device such that a pneumatic block 7100 of the RPT device comprises components that perform the function of the RPT device as well as components that perform the function of the humidifier. For example, as shown in FIG. 7, the reservoir dock 6050 is integrated with the pneumatic block 7100 of the RPT device to provide an integral unit, with the reservoir dock 6050 structured and arranged to receive the water reservoir 6100.

It should be appreciated that the humidifier (e.g., reservoir dock 6050) may be provided separately to the RPT device (e.g., pneumatic block 7100) in an alternative arrangement. In such arrangement, additional interfaces may be used to connect the humidifier (e.g., reservoir dock 6050) to the RPT device (e.g., pneumatic block 7100).

The RPT device comprises a blower supported within the pneumatic block 7100. The blower is structured and arranged for producing a flow, or a supply, of air at positive pressure, e.g., in the range of 2-50 $cmH_2O$. In an example, the blower may include a single stage design or a multi-stage design, e.g., two or more stage designs. The blower is operable to draw a supply of air into the pneumatic block 7100, e.g., through one or more intake openings in the pneumatic block, and into an inlet thereof (blower inlet), and provide a pressurized supply of air at an outlet (blower outlet). Examples and details of an exemplary blower are described in PCT Patent Application Publication No. WO 2013/020167, which is incorporated herein by reference in its entirety. The blower outlet is communicated with the humidifier, e.g., an inlet of the water reservoir 6100.

The pneumatic block 7100 includes a chassis assembly 7300, e.g., including a top chassis and a bottom chassis. The chassis assembly 7300 includes a chassis inlet 7310 (e.g., see FIG. 20E) and a chassis outlet 7320 (e.g., see FIGS. 20F and 21). In an example, an external housing 8002, including one or more panels and/or one or more user inputs/displays, may enclose the pneumatic block 7100, e.g., see FIGS. 6A and 6B. The chassis assembly 7300 supports and/or houses internal components of the pneumatic block 7100, e.g., the blower. The chassis assembly 7300 also supports a printed circuit board assembly (PCBA) 7600. The chassis assembly 7300 and internal components of the pneumatic block cooperate to form a pneumatic air flow path that extends from the chassis inlet 7310 to the blower inlet of the blower and from the blower outlet of the blower to the chassis outlet 7320.

The chassis outlet 7320 is adapted to communicate with the reservoir dock 6050 and an inlet of the water reservoir 6100 when the water reservoir is received in the reservoir dock 6050. The reservoir dock 6050 is also configured and arranged to allow communication between an outlet of the water reservoir 6100 and the air circuit 4170 as described in greater detail below.

Whilst most of the described examples are based on a description of the air circuit or air delivery tube being attachable to a water reservoir dock, it should be appreciated that in some air delivery systems there is no humidification and water reservoir present in the system. In this case, the air delivery tube is directly or indirectly connectable to a tube engagement dock of the RPT device. All of the above disclosure related to the water reservoir connecting dock is also applicable to the respective tube engagement of the RPT device in such cases.

Also, the RPT device and/or humidifier provides one form of connection or engagement port for connecting to the air circuit or air delivery tube 4170, i.e., the place where the air delivery tube 4170 engages with the RPT device and/or humidifier. In below described examples, the connection or engagement port may comprise the outlet tube 6130 (outlet) of the water reservoir 6100, the outlet of the outlet muffler 4124, the intermediate component 6700, or the intermediate component 9700, for example. The function of the connection or engagement port is to pass on pressurized air generated in the RPT device to the air delivery tube and the patient interface, and as such may be used with an RPT device with or without a humidifier. In examples, the connection or engagement port may also locate, secure and/or electrically connect to the air delivery tube. Also, it should be appreciated that the connection or engagement port may be located anywhere on the RPT device and/or humidifier, as long as it is communicated (e.g., via one or more intermediate connectors) with the pressurised flow source of the RPT device and/or the humidifier (e.g., water reservoir). For example, the connection or engagement port may form part of the water reservoir dock, or may be positioned elsewhere (i.e., not part of the water reservoir dock) and communicated with the water reservoir dock, water reservoir thereof or the pneumatic block of the RPT device.

5.6.2 Humidifier Components
5.6.2.1 Water Reservoir

FIGS. 6B and 9 show a water reservoir 6100 according to an example of the present technology. The water reservoir 6100 is configured to hold, or retain, a volume of liquid (e.g. water) to be evaporated for humidification of the flow of air. The water reservoir 6100 may be configured to hold a predetermined maximum volume of water in order to provide adequate humidification for at least the duration of a respiratory therapy session, such as one evening of sleep. Typically, the water reservoir is configured to hold several hundred millilitres of water, e.g. 300 millilitres (ml), 325 ml, 350 ml or 400 ml, although it is to be understood that other volumes of liquid may be utilised, e.g., at least 100 ml. In other forms, the humidifier may be configured to receive a supply of water from an external water source such as a building's water supply system.

In the illustrated example, the water reservoir 6100 includes a reservoir base 6112 (also referred to as a reservoir body, a humidifier tub base, or a humidifier tub body) and a reservoir lid 6114 (also referred to as a humidifier tub lid) removably coupled to the reservoir base 6112. A deformable seal may be provided to the reservoir lid and/or to the reservoir base, e.g., see deformable peripheral seal 6116 provided to periphery of reservoir lid 6114 in FIG. 19C.

When the reservoir lid 6114 is coupled to the reservoir base 6112, the seal 6116 is structured and arranged to engage between the lid 6114 and the base 6112 to seal the lid and the base and prevent egress of water from the water reservoir. The reservoir lid 6114 may be structured to be fully removable from the reservoir base 6112, e.g., for patient usability to clean the interior of the reservoir base and/or the reservoir lid. In an alternative example, the reservoir lid 6114 may be permanently attached to the reservoir base 6112.

According to one aspect, the water reservoir 6100 is configured to add humidity to a flow of air from the RPT device as the flow of air travels therethrough. In one form, the water reservoir 6100 may be configured to encourage the flow of air to travel in a tortuous path through the reservoir while in contact with the volume of water therein. For example, the water reservoir 6100 may comprise one or more flow elements, e.g., baffles, to encourage a tortuous flow path.

As described in more detail below, the water reservoir 6100 may be removably coupled with the reservoir dock 6050. In an example, insertion/removal of the water reservoir may be provided along a path extending in an anterior-posterior direction. In an alternative example, at least a portion of the path for insertion/removal of the water reservoir may extend in an inferior-superior direction, e.g., at least a portion of the path for insertion includes a slope or drop down into an operative position.

The water reservoir 6100 may also be configured to discourage egress of liquid therefrom, such as when the reservoir is displaced and/or rotated from its normal, working orientation, such as through any apertures and/or in between its sub-components. As the flow of air to be humidified by the humidifier is typically pressurised, the reservoir may also be configured to prevent losses in pneumatic pressure through leak and/or flow impedance.

Reservoir Base

As shown in FIG. 9, the reservoir base 6112 comprises a main body 6140 including a plurality of walls and a conductive portion 6150, typically provided to a bottom one of the walls to form a chamber or cavity to hold the volume of water.

The reservoir base 6112 is structured and arranged to engage or interface with the reservoir lid 6114. In an example as shown in FIG. 19C, the perimeter of the reservoir base 6112 provides surfaces arranged to engage or interface with a seal 6116 provided to the reservoir lid 6114, e.g., to prevent egress of water from the water reservoir.

The reservoir base 6112 may be structured and arranged to retain the reservoir lid 6114 to the reservoir base 6112, e.g., hinge arrangement and/or snap-fit locking tabs to releasably retain the reservoir lid to the reservoir base.

Conductive Portion

The conductive portion 6150 is configured to allow efficient transfer of heat from a heating element (e.g., heater plate 6080 of the reservoir dock 6050 shown in FIG. 6B) to the volume of liquid in the reservoir. In one form, the conductive portion may be arranged as a plate, although other shapes may also be suitable. All or a part of the conductive portion may be made of a thermally conductive material such as aluminium (e.g. approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

Conductive Portion Including Metal Plate and/or Thin Film

In an example, the conductive portion 6150 may comprise a metal plate, a thin, non-metallic film (also referred to as a film plate or film base), or a combined layered arrangement of a metal plate and a thin, non-metallic film. As described below, the conductive portion 6150 is configured to thermally couple with the heater plate 6080 of the reservoir dock 6050 so as to allow thermal transfer of heat from the heater plate 6080 to the volume of liquid in the water reservoir 6100.

FIGS. 10A to 10G show a reservoir base 6112M1 comprising a metal plate as the conductive portion 6150M according to an example of the present technology. In an example, the reservoir base 6112M1 comprises a two-part construction, i.e., only a main body 6140 and a metal conductive portion 6150M.

As illustrated, the main body 6140 comprises a plurality of walls and the metal conductive portion 6150M is provided to a bottom one of the walls to form the chamber to hold the volume of water. For example, the main body 6140 includes side walls 6142 extending around the perimeter of the main body 6140 and a bottom wall 6144 that joins the side walls 6142. The metal conductive portion 6150M is provided or otherwise incorporated into the bottom wall 6144 to form the chamber for holding water.

In an example, the metal thermo-conductive portion 6150M is provided as a separate and distinct structure from the main body 6140 and then secured or otherwise provided to the bottom wall 6144 in an operative position, e.g., the metal conductive portion 6150M comprises a pre-formed structure that is secured to the bottom wall 6144. In an example, the metal conductive portion 6150M comprises a metallic material, e.g., metal plate, and the main body 6140 comprises a plastic or thermoplastic polymer material, e.g., PC, ABS, copolyester. In an example, the conducive portion 6150M generally may have a uniform wall thickness of about 0.25-0.50 mm, e.g., 0.40 mm. For metal conductive portions, the wall thickness can be even larger, e.g., up to 1.5 mm. If a thin film is used instead (see description below regarding FIGS. 13A to 13C), a smaller thickness, such as 0.1-0.5 mm may be used.

In an example, the metal conductive portion 6150M may be pre-formed, and then insert molded to the plastic main body 6140. For example, the metal conductive portion is first formed into its working configuration by one or more metal-forming processes. The metal conductive portion or insert is then inserted into an injection mold for the main body prior to melt injection. During the injection process, the melt flows around the edges of the metal conductive portion and locks or connects the metal conductive portion to the main body as the melt solidifies.

As illustrated in FIG. 10G, the metal conductive portion 6150M may include a bottom wall or plate 6152M, a side wall 6154M extending around the perimeter of the plate 6152M, and an interfacing portion 6156M engaging with bottom wall 6144 to secure the metal conductive portion 6150M to the plastic main body 6140. In an alternative arrangement, the metal conductive portion 6150M may extend up to the peripheral side walls 6142 of the main body 6140, thus replacing the bottom wall 6144. In this case, interfacing portion 6156M may engage the side walls 6142 of the main body 6140.

As illustrated in FIG. 10G, the plate 6152M includes a first side 6152.1M adapted to form a bottom interior surface of the reservoir, the surface of the first side being exposed to the water. The second side 6152.2M of plate 6152M is opposite to the first side and is adapted to form a bottom exterior surface of the reservoir, which surface is exposed to the heater plate. Thus, the second side 6152.2M of the plate provides a contact surface structured and arranged to directly engage with the heater plate 6080.

In an example, the plate 6152M may comprise a preformed curvature or dome-shape, i.e., the second side 6152.2M provides a generally convex surface. When the water reservoir 6100 is inserted into the reservoir dock 6050, a bias may be provided between the water reservoir and the heater plate so that the curved plate 6152M will flatten, e.g., become substantially planar, so as to align or conform itself with the flat surface of the heater plate 6080. The flattening of the curved plate 6152M creates a bias between the plate 6152M and the heater plate 6080 to ensure good thermal contact and improve heat transfer between the heater plate and water within the water reservoir. In an example, the curvature of the plate may be formed by placing the metal conductive portion into a smaller opening in the bottom wall of the main body, e.g., smaller opening in the bottom wall compresses the metal conductive portion to form curvature in the plate.

In an alternative example, the plate 6152M may comprise a generally planar shape, i.e., pre-formed planar shape.

In the illustrated example, the metal conductive portion 6150M is configured such that the plane of plate 6152M is offset and generally parallel to the plane of bottom wall 6144 of the main body 6140, i.e., plate is inferior the bottom wall in the operational vertical orientation of the water reservoir. In an alternative example, the metal plate 6152M may be configured such that the plate is generally co-planar with the bottom wall 6144, i.e., thereby providing the reservoir base with substantially flat bottom surface. In another example, the metal plate 6152M may be configured to extend in more than one plane, e.g., the metal plate may provide a stepped arrangement as shown in FIG. 29.

In an example, the metal conductive portion 6150M may include a surface treatment, e.g., plasma surface treatment. For example, interior and/or exterior sides of the metal conductive portion, e.g., at least on its interfacing portion 6156M, may comprise nano-plasma particles on the metal surface.

In the illustrated example, the plate 6152M of the reservoir base 6112M1 includes a rectangular shape, e.g., corresponding to a shape of the heater plate 6080 within the reservoir dock 6050. However, it should be appreciated that the plate 6152M may comprise other suitable shapes, which may or may not correspond to a shape of the heater plate, e.g., circular, square, oval. For example, FIGS. 11A to 11C illustrate a reservoir base 6112M2 in which the metal plate 6152M of the metal conductive portion 6150M is circular. In alternative examples, the side wall extending around the perimeter of the plate and/or the interfacing portion may be longer to provide a deeper drawn metal conductive portion, e.g., see FIGS. 12A to 12C showing a reservoir base 6112M3 with a deeper drawn, rectangular-shaped, metal conductive portion 6150M.

FIGS. 13A to 13C show a reservoir base 6112F1 comprising a thin, non-metallic film as the conductive portion 6150F according to an example of the present technology. In an example, the reservoir base 6112F1 comprises a two-part construction, i.e., only a main body 6140 and a thin film conductive portion 6150F.

The thin film conductive portion 6150F can comprise a thermally conductive, non-metallic material, e.g., silicone, polycarbonate, or other thermoplastic or elastomeric materials, e.g., copolyester.

In an example, the thin film conductive portion 6150F may comprise a thickness of about 0.05 mm to 0.5 mm, e.g., 0.10 mm to 0.125 mm. In rare cases, thicker films, i.e., up to 1.5 mm, may be required. In an example, the thin film conductive portion 6150F may comprise a thickness equal or less than about 1 mm, e.g., 0.5 mm, less than about 0.5 mm, e.g., 0.40 mm, 0.375 mm, 0.25 mm, 0.175 mm, 0.125 mm.

As shown in FIGS. 13A to 13C, the main body 6140 of the reservoir base 6112F1 includes a bottom wall 6144 and side walls 6142 extending around the perimeter of the bottom wall 6144. In such an example, the thin film conductive portion 6150F can extend across a hole provided to the bottom wall 6144, and the thin film conductive portion 6150F is provided not only across the hole, but also over at least a portion of the remaining bottom wall 6144 to enhance the seal between them and ensure that the reservoir base does not leak water. The thin film conductive portion 6150F thus forms at least a portion of the bottom of the reservoir base to form the chamber to hold and prevent egress of water from the water reservoir. Also, e.g., for a better seal, the thin film conductive portion 6150F may not only overlap the opening in the bottom wall 6144 but also extend to cover at least portions of the side walls 6142 of the reservoir base.

In an example, the thin film conductive portion 6150F is provided as a separate and distinct structure from the main body 6140 and then secured or otherwise provided to the main body in an operative position, e.g., the thin film comprises a pre-formed structure that is secured to the main body. In an example, the main body 6140 comprises a plastic or thermoplastic polymer material, e.g., PC, ABS, copolyester.

In an example, the thin film conductive portion 6150F may be pre-formed, and then insert molded or otherwise attached (e.g., by using adhesive) to the plastic main body 6140. For example, the thin film conductive portion 6150F is first formed into its working configuration, e.g., by a vacuum forming process. The thin film conductive portion 6150F or insert may then be insert molded to the plastic main body 6140. A reference is provided to application WO 2018/094452, which is hereby incorporated by reference in its entirety.

Post-Molding Forming of Thin Film

When insert-moulding a thin film plate into a polycarbonate humidification tub base (also referred to as a water reservoir base), there may be problems with the geometry of the film. Usually, the film is preformed (e.g., stamped into a deep drawn step-wise shape) and then insert-moulded. However, when the mould cools down, tension in various location within the mould may lead to the film bending and distorting. This is further complicated by the fact that the thin film and the water reservoir base have different mechanical characteristics and coefficient of thermal expansion/shrinkage. Because of this, the film shape is difficult to control during the cooling process. One way to mitigate this problem is the following. Instead of pre-forming, forming the shape of the film after the moulding process (post—mould forming). This is to say that one can insert—mould the film as a flat film and post-form it into its drawn shape afterwards. It will still shrink during the moulding. However, when the shrinked/distorted film is post-formed—the forming process will tighten/straighten the film, allowing a tighter geometry control.

In the post-mould forming process, one starts with a film in some form (say a flat film). The film is a non-final form (say a flat configuration). The plastic can then be insert moulded around the flat film. After the plastic moulding, the film is again distorted. However, one can now use stamping, vacuum forming or thermal vacuum forming—in order to create a desired step-wise geometric shape. During the formation of this final geometry of the film, the film is stretched in a controlled way, allowing the formation of a very flat surface.

The process of vacuum forming is similar to that of moulding, since it usually involves temperature and pressure, although for some small geometry changes, pressure alone may be sufficient. For a good geometry control we need a good temperature control. For that purpose, during the step-wise geometry formation, we soften the film only and try not to soften the plastic tub surface around the film. Therefore, the chemical compositions of the tub and the film, the temperature and pressure for the post-forming, should be such that during the post-mould forming process only the film is softened, and not the tub. The shape does not have to be step wise—it can be any surface that has one or more dimples (tensioning region) that take the looseness out of the flat surface.

The technology can also be used in the manufacture of masks, LCD windows (for thin film coverage with antibacterial properties (the film will cover any gaps, edges that can collect bioburden). In one example, film can be used for manufacturing masks, i.e., for a disposable mask. A thin film is probably most suitable for forming the walls defining the plenum chamber of the mask. However, frames can also include a thin film body, with only the edges being formed of more rigid plastic attached to the seal. The geometry in a mask may be much more complex, e.g., tight control may be important. This can be done by post-forming. It is important to ensure a homogeneous junction between the film and the remaining surface.

When we require the processing of the thin film to be performed post-molding, there is a certain time that needs to pass after the process of moulding, in order for the film to be efficiently performed. This time may be relevant to the cooling of the moulded film, and/or the stage of the process of shrinkage associated with the cooling process. These two processes (the cooling and the shrinkage) are both non-linearly dependent on time and, whilst closely related, are still different processes. This is one clear advantage of the proposed process, which allows the film forming process to be performed in the same tool and setup as the insert-moulding process. This can bring substantial time and cost savings.

For a successful post-moulding forming of a thin film, it is important to follow a process that allows any significant dimensional change (such as one that occurs during the moulding of the plastic over the film) to stabilise, before the film formation. The intent is for the post forming to be completed at a stage where a sufficient cooling has already occurred so that the plastic is approaching dimensional stability. Thus a post-moulding forming may allow good dimensional control and dimensional stability of the formed thin film component.

Also—the process is suitable to anywhere where there is a window/opening in the part. The window allows the stamping tool to access the film and perform the post-mould forming step. An arrangement with a plurality of windows are used with a one or more large film portions, one or more of them arranged to cover more than one of the windows.

As illustrated in FIG. 13C, the thin film conductive portion 6150F includes a bottom wall or plate 6152F, a side wall 6154F extending around the perimeter of the plate 6152F, and an interfacing portion 6156F to secure the thin film conductive portion 6150F to the plastic main body 6140.

As illustrated in FIG. 13C, the plate 6152F includes a first side 6152.1F adapted to form a bottom interior surface of the reservoir, which surface is exposed to the water. The plate 6152F includes a second side 6152.2F, opposite to the first side, and, in some cases, adapted to form a bottom exterior surface of the reservoir, which surface is exposed to the heater plate. Thus, the second side 6152.2F of the plate provides a contact surface structured and arranged to directly engage with the heater plate 6080.

In an example, similar to a previous example described in relation to a metal thermo-conductive plate, the 6152F plate may comprise a pre-formed curvature or dome-shape, i.e., the second side 6152.2F provides a generally convex surface. When the water reservoir 6100 is inserted into the reservoir dock 6050, the water reservoir and the heater plate may be biased against each other so that the curved plate 6152F will flatten, e.g., become substantially planar, so as to align or conform itself with the flat surface of the heater plate 6080. The flattening of the curved plate 6152F creates a bias between the plate 6152F and the heater plate 6080 to ensure good thermal contact and improve heat transfer between the heater plate and water within the water reservoir. In an example, the curvature of the plate may be formed by placing the thin film conductive portion into a smaller opening in the bottom wall of the main body, e.g., smaller opening in the bottom wall compresses the thin film conductive portion to form curvature in the plate.

In an alternative example, the plate 6152F may comprise a generally planar shape, i.e., pre-formed planar shape.

In the illustrated example, the thin film conductive portion 6150F is configured such that the plate 6152F is offset and generally parallel to the bottom wall 6144 of the main body 6140, i.e., plate is inferior the bottom wall. In an alternative example, the thin film conductive portion 6150F may be configured such that the plate 6152F is generally co-planar with the bottom wall 6144, i.e., thereby providing the reservoir base with substantially flat bottom surface. In another example, the thin film conductive portion 6152F may be configured to extend in more than one plane, e.g., the thin film conductive portion may provide a stepped arrangement as shown in FIG. 29.

In an example, not shown, one or more ribs may be provided along the first side and/or second side of the thin film conductive portion 6150F, e.g., to add rigidity to the thin film conductive portion and/or to enhance force adapted to push the thin film conductive portion towards the heater plate.

In an example, a thin metallic layer (e.g., mesh) may be provided along the first side and/or second side of the thin film conductive portion 6150F, e.g., to improve thermal conductivity.

In the illustrated example, the plate 6152F of the reservoir base 6112F1 includes a rectangular shape, e.g., corresponding to a shape of the heater plate 6080 within the reservoir dock 6050. However, it should be appreciated that the plate 6152F may comprise other suitable shapes, which may or may not correspond to a shape of the heater plate, e.g., circular, square, oval. For example, FIGS. 14A to 14C illustrate a reservoir base 6112F2 in which the plate 6152F of the thin film conductive portion 6150F is circular.

FIGS. 15A to 15C show a reservoir base 6112MF1 comprising a combined layered arrangement of a metal plate and a thin, non-metallic film as the conductive portion 6150MF according to an example of the present technology. In an example, the reservoir base 6112MF1 comprises a three-part construction, i.e., a main body 6140, a metal conductive portion 6150M, and a thin film conductive portion 6150F.

The thin film conductive portion 6150F can comprise a thermally conductive, non-metallic material, e.g., silicone, polycarbonate, or other thermoplastic or elastomeric materials, e.g., copolyester.

In an example, the thin film conductive portion 6150F may comprise a thickness of about 0.05 mm to 1 mm, e.g., 0.10 mm to 0.125 mm. In an example, the thin film may comprise a thickness less than about 1 mm, e.g., 0.5 mm, less than about 0.5 mm, e.g., 0.40 mm, 0.375 mm, 0.25 mm, 0.175 mm, 0.125 mm.

In an example as shown in FIGS. 15B and 15C, the reservoir base 6112MF1 includes a bottom wall 6144 and side walls 6142 extending around the perimeter of the bottom wall 6144. In such an example, the thin film conductive portion 6150F not only covers the metal conductive portion 6150M, but also extends over at least a portion of the remaining bottom wall 6144. Such arrangement ensures that the connecting boundary between the metal conductive portion 6150M and the bottom wall 6144 is covered by the thin film conductive portion 6150F to enhance the water seal between them and ensure that the reservoir base does not leak water. For a better seal, the thin film conductive portion 6150F may not only cover the connecting boundary between the metal conductive portion 6150M and the bottom wall 6144, but also extend to cover at least portions of the side walls 6142 of the reservoir base. This is especially important in the case where the metal conductive portion 6150M covers the entire bottom wall 6144 and, possibly part of the side wall 6142, and the connecting boundary is actually between the metal conductive portion 6150M and the side wall 6142.

As illustrated, the thin film conductive portion 6150F includes a first side 6152.1F adapted to form a bottom interior surface of the reservoir, which surface is exposed to the water. The thin film conductive portion 6150F includes a second side 6152.2F, opposite to the first side, adapted to engage the metal conductive portion 6150M and bottom and side walls 6144, 6142 of the reservoir base. The metal conductive portion 6150M forms a bottom exterior surface of the reservoir, which surface is exposed to the heater plate 6080. Thus, the metal conductive portion 6150M provides a contact surface structured and arranged to directly engage with the heater plate 6080. One advantage of such an arrangement is that the metal thermo-conductive plate 6150M, which is much more scratch resistant, is the one exposed to the mechanical interaction with the heater plate 6080.

In an alternative example (not shown), the thin film conductive portion 6150F may be disposed on the other, external surface of the reservoir, with the metal conductive portion 6150M forming the inner (superior) surface that is on contact with the water content of the reservoir. An advantage of such an arrangement may be in that the chemical composition and stability of the thin film conductive portion in this case is less critical, e.g., the thin film conductive portion is not into contact with the water in the reservoir.

In an example, one or more ribs may be provided along the first side and/or second side of the thin film conductive portion 6150F, e.g., to add rigidity to the thin film and/or to enhance force adapted to push the thin film/metal plate towards the heater plate.

In an example, a metallic layer (e.g., mesh) may be provided along the first side and/or second side of the thin film conductive portion 6150F, e.g., to improve thermal conductivity.

In an example, the conductive portion 6150MF may include a shape corresponding to a shape of the heater plate 6080, e.g., for stability, more efficient thermal conductivity. For example, the conductive portion 6150MF and heater plate 6080 may include circular or non-circular shapes, e.g., rectangular, square, oval. In illustrated example, the conductive portion 6150MF includes a rectangular shape, e.g., corresponding to a shape of the heater plate 6080 within the reservoir dock 6050. FIGS. 16A to 16C show an alternative example in which reservoir base 6112MF2 includes a circular, conductive portion 6150MF. FIGS. 17A to 17C show a reservoir base 6112MF3 including a deeper drawn, rectangular-shaped, conductive portion 6150MF.

In an example, the thin film conductive portion 6150F and the metal conductive portion 6150M are provided as separate and distinct structures from the main body 6140 and then secured or otherwise provided to the main body 6140 in an operative position, e.g., the thin film conductive portion 6150F and the metal conductive portion 6150F comprise pre-formed structures that are secured to the main body 6140. In an example, the main body 6140 comprises a plastic or thermoplastic polymer material, e.g., PC, ABS, copolyester.

In an example, the thin film conductive portion 6150F may be pre-formed (e.g., vacuum formed), and then assembled to a pre-formed metal conductive portion 6150M (e.g., bonded, laminated, or simply engaged with one another). Then, the thin film/metal plate heat conducting assembly portion may be insert molded to the plastic main body 6140, i.e., bottom and side walls of main body 6140 injection molded to the thin film/metal plate assembly. In another example, the metal conductive portion 6150M can be separately insert molded to the main body 6140 and then the thin film conductive portion 6150F may be bonded to the metal conductive portion 6150M so as to cover at least the metal conductive portion 6150M, and preferably areas of the main body 6140 beyond the metal conductive portion 6150M, so as to ensure a reliable sealing of the contact boundary between the metal conductive portion 6150M with the main body 6140. Vacuum may be used to remove any air gap between the thin film conductive portion 6150F and metal conductive portion 6150M in any of the above examples. Also, bonding, e.g., adhesive, may be used between the thin film conductive portion 6150F and metal conductive portion 6150M, e.g., to maintain assembly and ensure good thermal conductivity.

In an example, the metal conductive portion 6150M and/or thin film conductive portion 6150F may comprise a pre-formed curvature or dome-shape, i.e., the inferior side of the metal conductive portion 6150M and/or thin film conductive portion 6150F provides a generally convex surface. When the water reservoir 6100 is inserted into the reservoir dock 6050, the curved metal plate/thin film will flatten, e.g., become substantially planar, so as to align or conform itself with the flat surface of the heater plate 6080. The flattening of the curved metal plate/thin film creates a bias between the metal plate/thin film and the heater plate to ensure good thermal contact and improve heat transfer between the heater plate and water within the water reservoir. In an example, the curvature of the metal plate/thin film may be formed by placing the metal plate/thin film into a smaller opening in the bottom wall of the main body, e.g., smaller opening in the bottom wall compresses the metal plate/thin film to form curvature in the metal plate/thin film.

In an alternative example, the metal plate/thin film may comprise a generally planar shape, i.e., pre-formed planar shape.

In the illustrated example, the metal plate/thin film is configured such that the metal plate/thin film is offset and generally parallel to the bottom wall of the main body, i.e., metal plate/thin film is inferior the bottom wall. In an alternative example, the metal plate/thin film may be configured such that the metal plate/thin film is generally co-planar with the bottom wall, i.e., thereby providing the reservoir base with substantially flat bottom surface. In another example, the metal plate/thin film may be configured to extend in more than one plane, e.g., the metal plate/thin film may provide a stepped arrangement as shown in FIG. 29.

The combination of the thin film conductive portion 6150F and the metal conductive portion 6150M may be advantageous in that the non-metallic properties of the thin film (e.g., thermoplastic or elastomeric material properties) provides corrosion protection (e.g., protection due to exposure to water) and an improved seal with the bottom wall (e.g., to form a sealed reservoir for the humidification water), while the metallic properties of the metal plate provide good thermal contact, rigidity, and durability, e.g., for multi-patient multi-use applications.

Reservoir Lid

As shown in FIGS. 18A, 18B, and 19A to 19G, the reservoir lid 6114 is configured to connect to the reservoir base 6112. The configuration may be arranged to allow the water reservoir to be convertible between an open configuration and a closed configuration. For example, the reservoir lid 6114 may be hingedly connected to the reservoir base 6112 by hinge pins. In an alternative example, the reservoir lid 6114 may include a plurality of resilient locking tabs adapted to interlock with the reservoir base 6112, e.g., with a snap-fit. In an example, a seal 6116 (e.g., see FIG. 19C) may be provided to the reservoir lid 6114, e.g., to prevent egress of water from the connecting boundary between the lid 6114 and the base 6112 of the water reservoir. In one form, the reservoir lid 6114 may be constructed from a bio-compatible material, such as a plastic or thermoplastic polymer, e.g., PC, ABS, copolyester, etc.

As shown in FIGS. 18A and 18B, the reservoir lid 6114 may comprise an inlet tube 6120 arranged to provide an inlet for receiving the flow of air into the water reservoir, and an outlet tube 6130 arranged to provide an outlet for delivering a flow of humidified air from the water reservoir.

When the reservoir lid 6114 is coupled to the reservoir base 6112, the inlet tube 6120 includes an outer (inlet) end 6124 arranged outside the chamber and an inner (outlet) end 6126 arranged inside the chamber. Likewise, the outlet tube 6130 includes an outer (outlet) end 6134 arranged outside the chamber and an inner (inlet) end 6136 arranged inside the chamber. Each of the inlet tube or the outlet tube (together with each tube's respective inlet and outlet) may be replaced by an opening in a wall of the reservoir lid.

In an example, an inlet seal 6122 is provided to the free outer (inlet) end of the inlet tube 6120 (see FIGS. 19A, 19B, 19D, and 21), and/or an outlet seal 6132 is provided to the free outer (outlet) end of the outlet tube 6130 (e.g., see FIG. 21). The fact that the inlet and outlet seals 6122, 6132 are a part of the water reservoir and not, say of the RPT device, allows seal replacement each time the water reservoir is replaced, i.e., which is useful feature, especially in the case of a disposable water reservoir. In an example, each seal comprises bellows-type arrangement that may provide a certain degree of decoupling between the two connecting parts. In an example, the inlet seal and outlet seal may be overmolded to the reservoir lid.

FIG. 80 illustrate an integrated RPT device and humidifier 6000 according to an example of the present technology similar to that illustrated in FIGS. 6A, 6B, 7 and 8A to 8D.

FIGS. 80, 85, 86 and 134-136 show a water reservoir 6100 and a reservoir lid 6114 according to another example of the present technology. In this example, an inlet seal 6122 (e.g., bellows-type arrangement) is provided to the free outer (inlet) end of the inlet tube 6120, while no seal is provided to the free outer (outlet) end of the outlet tube 6130. As discussed later in the text, instead, such a seal may be provided to the inlet of the intermediate element to which the outlet tube 6130 is attached. In use, when the water reservoir 6100 is removably coupled with the reservoir dock 6050, the inlet seal 6122 of the inlet tube 6120 (or inlet) of the water reservoir 6100 is structured and arranged to provide a face seal with the chassis outlet 7320 (dock inlet) of the reservoir dock 6050 (see FIGS. 100, 131 and 133), and the inlet seal 9715 of the intermediate component 9700 (described in greater detail below) is structured and arranged to provide a face seal with the outlet end of the outlet tube 6130 (or outlet) of the water reservoir 6100 (see FIGS. 131 and 132).

Also, in this example, the inlet seal 6122 may be overmolded to the reservoir lid 6114 along with the peripheral seal 6116 arranged to form a seal between the lid 6114 and the base 6112 in use (see FIG. 85), e.g., seals 6122, 6116 from integral, once-piece component of elastomeric material. That is, as shown in FIG. 85, the reservoir lid 6114 (including the inlet tube 6120 and the outlet tube 6130) may comprise a first part or base mold constructed of a relatively rigid material (e.g., thermoplastic polymer (e.g., PC, ABS)) and the inlet seal 6122 and the seal 6116 may comprise a second part or overmold constructed of a relatively soft material (e.g., thermoplastic elastomer (TPE) or silicone) that is provided (e.g., by overmolding) to the first part.

Further, as shown in 80 and 85, a thumb grip 6133 may be provided (e.g., mechanical interlock, snap-fit) to the top of the reservoir lid 6144 to facilitate manual manipulation of the water reservoir 6100 and/or interlocking of the water reservoir 6100 with the reservoir dock 6050. The thumb grip helps to align the reservoir 6100 upon insertion. It also facilitates gripping and squeezing the portion of the reservoir 6100 which extends outside of the RPT device and humidifier 6000 (e.g., see FIG. 79). Because of the deforming nature of the peripheral seal 6116, upon the user depressing the thumb grip (squeezing the reservoir 6100), the seal yields and reduces the transverse dimension of the water reservoir 6100. This reduces the friction during insertion or extraction of the water reservoir 6100 into/from the humidification dock, thus improving the overall user experience.

Spillback Protection

In an example, the water reservoir 6100 may be configured to discourage egress of liquid therefrom, such as when the water reservoir is displaced and/or rotated from its normal, working orientation.

In an example, as shown in FIGS. 19C to 19G, the inlet tube 6120 can include an outer (inlet) end 6124 arranged outside the chamber and an inner (outlet) end 6126 arranged inside the chamber. The inlet tube 6120 includes an inlet portion 6123 including the inlet end 6124 and an outlet portion 6125 including the outlet end 6126. The bottom of the water reservoir (e.g., the conductive portion 6150) includes a bottom surface defining a bottom plane that is substantially horizontal when the water reservoir is in the normal, working orientation (e.g., see FIG. 19C). As illustrated in FIGS. 19C to 19G, various portions of the inlet tube 6120 may extend in different directions, e.g., change direction at least at one point along its length. For example, the inlet portion 6123 extends in a plane that is substantially parallel to the bottom plane, while the outlet portion 6125 extends in a different direction (in this case the outlet portion 6125 extends in a plane that is substantially perpendicular to the bottom plane). Various twists and/or turns may be introduced in each portion (orientation) of the inlet tube 6120.

As shown in FIGS. 19C to 19G, the outlet tube 6130 can include an outer (outlet) end 6134 arranged outside the chamber and an inner (inlet) end 6136 arranged inside the chamber. Similar to the inlet tube, the outlet tube can also extend in different directions, e.g., change direction at least at one point along its length. Also similar, the outlet tube 6130 can include a vertical twist (a bend in the plane that is substantially perpendicular to the bottom plane) such that the outlet tube 6130 curves downwardly from the outlet end 6134 to the inlet end 6136, which allows the outlet tube 6130 to cross under the inlet portion 6123 of the inlet tube 6120. Further, the opening at the inlet end 6136 of the outlet tube 6130 is curved upwards to prevent spitting (which happens when water is pushed out of the outlet tube due to pressure and flow).

FIGS. 19D, 19H-1, 19H2, and 19I show a change in direction of the inlet and outlet tubes in the horizontal plane, while FIGS. 19C, 19E, and 19F show similar turns in vertical direction (the respective tube effectively moving closer to, or further away from, the bottom surface provided by the conductive portion 6150).

In an example, the outlet end 6126 of the inlet tube 6120 and the inlet end 6136 of the outlet tube 6130 may be arranged at or near the geometric center or centroid of the reservoir chamber.

The inlet tube 6120 and the outlet tube 6130 could be further arranged such that at least one (and preferably at least two) of:

a. the outer (inlet) end 6124 of the inlet tube 6120;
b. the inner (outlet) end 6126 of the inlet tube 6120;
c. the outer (outlet) end 6134 of the outlet tube 6130; and
d. the inner (inlet) end 6136 of the outlet tube 6130, is above a level of the predetermined maximum volume of water both when: (1) the water reservoir is in the working orientation and (2) the water reservoir is rotated by 90 degrees in at least one direction from the working orientation.

Depending on the arrangement and the horizontal and vertical location of the above mentioned inlets/outlets, in some examples the same at least one (or two) inlets/outlets will be elevated above the water level when the reservoir is turned at 90 degrees. In other arrangement, at least one (or two) inlets/outlets will be elevated above the water level in the operational configuration, while the other at least one (or two) inlets/outlets will be elevated above water when the reservoir is tilted at 90 degrees.

For example, FIG. 19C shows inlet end 6124, outlet end 6126, outlet end 6134 and inlet end 6136 all above the water level in the working orientation, FIG. 19D shows outlet end 6126 and outlet end 6134 above the water level when the water reservoir is rotated by 90 degrees front, and FIG. 19D shows inlet end 6124 and inlet end 6136 above the water level when the water reservoir is rotated by 90 degrees back. Also, FIG. 19G shows at least the outlet end 6126 above the water level when the water reservoir is rotated by 180 degrees. Such arrangement achieves spillback protection to discourage water from entering the inlet and outlet tubes of the water reservoir at various orientations. In addition, as shown in FIGS. 19C and 19I, in the operational configuration, the inlet tube 6120 is inclined so that its inlet 6124 is higher than its outlet end 6126. Because of that, when the water reservoir is returned to its operational configuration, after it has been filled in (and in the process having being rotated at various angles, including by at least 90 degrees in any direction), any water in the inlet tube trickles down back towards the outlet end (the water chamber) and not the inlet end (which is in the direction of the RPT device). This may prevent damage to electronics in the RPT device when the water reservoir is received in the reservoir dock.

As described above, the inlet tube 6120 and the outlet tube 6130 for the water reservoir can be curved and extend in different directions, e.g., curved in one or more planes. The curved tubes 6120, 6130 can allow more control and flexibility in positioning the tube inlets and outlets at a preferred location within the water reservoir, i.e., to improve the water spill protection of the tub. The curved tubes 6120, 6130 can allow for a better utilization of the space in the water reservoir and better integration of all reservoir elements as one whole, as well as for more flexibility in defining airlock features of the reservoir. In an example, the inlet tube 6120 and/or the outlet tube 6130 may also change its diameter along its length (e.g., see FIG. 19D), e.g., to provide flexibility to locate the tubes in the water reservoir.

As described above, the spillback feature involves the inlet and outlet tubes 6120, 6130 having their outlet end 6126/inlet end 6136 being located in the middle of the water reservoir (e.g., at or near the geometric center or centroid of the reservoir chamber), so that upon an accidental tumbling of the water reservoir in various angles, when the water reservoir still includes a certain amount of water, the level of that water stays mostly below the level of these centrally located outlet end 6126/inlet end 6136 of the inlet and outlet tubes 6120, 6130. This is where the curved shape of the tubes can help. In particular, if one of the tubes is directed so that its outlet end 6126/inlet end 6136 is located centrally to the water reservoir, the other tube may not simply extend below the first tube (and therefore move away from the central area of the water reservoir), but can be directed to bend below the first tube and then curve back to any desired level.

In alternative designs, the tubes may simply cross each other at different levels. Such a design can define two sides of the reservoir for which, when the reservoir is tilted on one of these sides, one of the inlet or the outlet tube is inclined upwardly, thus keeping the respective in-tub opening above the water level. In this case the other tube would be inclined downwardly and the in-tub opening may be exposed to the water, unless mitigation measures have been taken. The curved design of the present technology may mitigate this problem.

The curvature of the inlet tube 6120 and/or the outlet tube 6130 may be a shallow or a significant curvature. The curvature can also be in more than one plane, in order to optimize the inner space of the tub. The concept of curving the tubes may be further enhanced by introducing a second curvature, subsequent to the first one, which may change the direction, or at least the radius, of the first curvature. The premise behind such shapes is that they can introduce further resistance to a propagation of water in some direction. Thus, such consecutive "kinks" that extend in one or more planes/directions, can provide resistance in the respective one or more directions, and therefore protect against tumbling/rolling over/flipping of the reservoir. Of course, the benefit can be weighed against the complexity of the design and the resistance provided to the airflow.

Thus, curved tubes inside the reservoir may allow for an improved water spillage feature of the reservoir and better utilized space. This may allow for the reservoir to be internally optimized and the overall volume of the reservoir to be reduced. The improved overall efficiency allows to either fit more water or reduce the overall size of the reservoir. Instead of introducing a continuous curvature, similar results may also be achieved with the tube changing direction, at the desired point along its length, by way of a discrete angle.

In an example, the inlet tube 6120 and/or the outlet tube 6130 may be provided as a separate and distinct structure from the reservoir lid 6114 (e.g., see FIGS. 19H-1, 19H-2, and 19I described below) and then secured or otherwise provided to the reservoir lid 6114 in an operative position. Alternatively, the inlet tube 6120 and/or the outlet tube 6130 may be formed, e.g., molded, as a part of the reservoir lid 6114 or the reservoir base 6112 (e.g., see FIGS. 134-136 which show the inlet tube 6120 and the outlet tube 6130 formed as part of the reservoir lid 6114). In an example, the inlet tube 6120 and/or the outlet tube 6130 may comprise a different material (e.g., more flexible material) than the reservoir lid, e.g., silicone or TPE to facilitate bending into the desired configuration. Alternatively, the inlet tube 6120 and/or the outlet tube 6130 may comprise a similar material to the reservoir lid, e.g., polycarbonate.

For example, FIGS. 19H-1 and 19H-2 show a removable outlet tube arrangement for a water reservoir according to an example of the present technology. As illustrated, the removable outlet tube arrangement includes the outlet tube 6130 and a portion of the inlet tube 6120, e.g., an outlet end 6126 of the inlet tube 6120. In this example, the inlet portion 6123 and the outlet portion 6125 of the inlet tube 6120 may be formed, e.g., molded, as a part of the reservoir lid 6114. The removable outlet tube arrangement is formed as a separate and distinct structure from the reservoir lid 6114 and then secured or otherwise assembled to the reservoir lid 6114 to form complete inlet and outlet air paths. For example, the outlet end 6134 of the outlet tube 6130 is secured or otherwise anchored to a side wall of the reservoir lid 6114 and the outlet end 6126 is engaged or otherwise anchored to the end of the outlet portion 6125 of the inlet tube 6120. FIGS. 19A to 19G show the removable outlet tube arrangement secured to the reservoir lid 6114 in an operative position.

FIG. 19I shows an alternative example in which the inlet tube 6120 and the outlet tube 6130 comprise a removable inlet tube and outlet tube arrangement that is a separate and distinct structure from the reservoir lid 6114 and then secured or otherwise provided to the reservoir lid 6114 in an operative position.

Hinged Connection of Reservoir Lid to Reservoir Base

FIGS. 82 to 97 show a water reservoir 6100 including reservoir lid 6114 hingedly and removably coupled to the reservoir base 6112 according to an example of the present technology.

As illustrated, the water reservoir 6100 comprises a hinge joint between the lid 6114 and the base 6112 which allows the lid 6114 to hingedly move between an open position (see FIGS. 84 and 89) and a closed position (see FIGS. 82, 83, and 91).

In the illustrated example, each side of the lid 6114 includes a hinge arm 9100 with an inwardly extending hinge pin 9105 (see FIGS. 86 and 87). Each hinge pin 9105 is configured to engage with a respective open-ended slot or cavity 9200 provided on each side of the base 6112 (see FIGS. 86 and 88).

Each hinge pin 9105 (see FIG. 87) includes a segmented cylindrical shape comprising a cylindrical surface 9105c to provide hinged movement, and a flat surface 9105*f*—to facilitate engagement/disengagement of each hinge pin 9105 with/from a respective open-ended slot 9200 (see FIG. 88). That is, as shown in FIG. 90, the cross-section of each hinge pin 9105 represents a major segment of a circle.

Each open-ended slot 9200 provides a segmented cylindrical surface 9200*c* to provide hinged movement for a respective hinge pin 9105, and an open end or side 9200*o* providing an opening to facilitate engagement and disengagement of each slot 9200 with the respective hinge pin 9105 (see FIG. 88).

As shown in FIGS. 94 and 95, to assemble or engage the lid 6114 with the base 6112, the lid 6114 is oriented to align each hinge pin 9105 with a respective open-ended slot 9200, and then the lid 6114 is pushed towards the base 6112 (e.g., in a generally horizontal direction) until each hinge pin 9105 is pushed into a respective open-ended slot 9200 (e.g., with a snap-fit). Because of the flexibility of the opening of the slot 9200, the snap-fit engagement can be effected at any orientation of the hinge pin. However, an easier engagement and disengagement of the lid is effected if, as illustrated in FIG. 95, the flat surface 9105*f* of each hinge pin 9105 is oriented generally horizontally, which allows the smaller width (or diameter) of the major segment cross-section of the hinge pin 9105, which extends from the flat surface 9105*f* to the opposing cylindrical surface 9201*c*, to engage with the open end 9200*o* of the slot 9200, thereby allowing the hinge pin 9105 to pass relatively easy through the open end 9200*o* into the interior of the slot 9200. However, the smaller width of the major segment provided by each of the pair of hinge pins is larger than an opening of the open end or side of the respective one of the pair of slots, so that even when aligned, force has to be applied to lever the pair of hinge pins out of the pair of slots, by causing each opening to flex out and release a respective one of the pair of hinge pins.

Once assembled, the slots 9200 hingedly retain respective hinge pins 9105 to allow the lid 6114 to hingedly move between the open position (see FIGS. 89 and 90) and the closed position (see FIGS. 91 and 92).

As shown in FIGS. 82, 91, and 93, the lid 6114 includes a clip 9120 adapted to releasably interlock with one or more latches 9220 on the base 6112, e.g., with a snap-fit, to releasably retain or lock the lid 6114 to the base 6112 in the closed position. As illustrated, the clip 9120 includes at least one slot 9122, e.g., a pair of slots, adapted to receive a respective latch 9220. As shown in FIGS. 83 and 93, the free end of the clip 9120 includes a finger pull tab 9125 that is angled outwards from the base 6112 to be gripped by the user when the user wants to open the lid by disengaging the clip 9120. As shown in FIG. 93, a small gap G, e.g., 0.2 mm, may be provided between the bottom of each latch 9220 and the slot 9122 in clip 9120 in some embodiments, so that the latch 9220 is not under constant load when the lid is in the closed and locked position. However, in general, peripheral resilient supporting member 6096 pushes the lid, and therefore the bottom of each latch 9220, upwardly, thus removing any such gaps.

As shown in FIGS. 96 and 97, to disassemble or disengage the lid 6114 from the base 6112, the lid 6114 is over-extended or hingedly moved beyond the fully open position (i.e., further than the rotation stop provided by the stop member 9110). In the fully open position the smallest dimension of the segmented cross-section of the hinge pins is generally aligned with the opening 9200*o* in the respective slots. When the lid is pushed even further back, the stop member 9110 engaged with the side wall 9210 starts to act as a cantilever and push the hinge pins towards the opening 9200*o*. This causes the opening 9200*o* to flex and release the hinge pins 9105 out of respective slots 9200. The openings 9200*o* and the segmented cross-sections of the hinged pins are not strictly needed, as a continuous push backwards would eventually allow the stop member 9110 to lever the hinge pins out of the slots 9200, even without the openings or the segmented cross-section. However, having the openings and having the smaller width or diameter of the major segment provided by the hinge pins 9105 arranged at the open end 9200*o* of the slot 9200 when the lid 6114 is over-extended, does make the disengagement of the lid easier, i.e., the flat surface 9105*f* of the hinge pin 9105 reduces stress on the hinge when pulling or popping it out of the slot 9200. Also, providing the opening 9200*o* changes the location of accumulated stress. In particular, upon disengaging the lid by levering the hinge pins out of the slots 9200, stress is generally concentrated in the side portions 9100 of the lid. In contrast, when the openings 9200*o* are provided, upon disengaging the lid by levering the hinge pins out of the slots 9200, stress is generally concentrated in the portion of the tub base that defines the openings 9200*o*, as this portion has to flex and increase the side of the openings, for the hinge pins to be released and the lid to be disengaged.

As shown in FIGS. 86 and 97, the lid 6114 includes a stop member 9110 adapted to engage a side wall 9210 of the base 6112 when the lid 6114 reaches a fully open position, e.g., allows the lid 6114 to rest in the fully open position. In an example, the lid 6114 may be oriented slightly less than 90 degrees from the base 6112 when in the fully open position, e.g., about 80-90 degrees. In this position, the lid is well balanced so that it does not fall forward to close the tub, whilst at the same time it does not weigh back on the tub so as to tilt it sidewise.

In an alternative example, the positions of the hinge pin 9105 and the slot 9200 may be switched, e.g., the hinge pin 9105 may be provided to the base 6112 and the slot 9200 may be provided to the lid 6114.

5.6.2.2 Reservoir Dock

In the example illustrated in FIG. 20A, the reservoir dock 6050 is provided to the chassis assembly 7300 of the RPT device and configured and arranged to receive the water reservoir 6100. In some arrangements, the reservoir dock 6050 may comprise a locking feature such as a locking lever or tab, configured to retain the water reservoir 6100 in the reservoir dock 6050.

The reservoir dock 6050 includes a main body forming a cavity to receive the water reservoir 6100. As best shown in FIGS. 20F and 21, a rear wall of the reservoir dock 6050 comprises the chassis outlet 7320 (also referred to as a dock inlet) structured and arranged to receive a pressurized flow of air from the outlet of the RPT device for delivery to the water reservoir 6100. The reservoir dock 6050 may also include a dock outlet 6090 structured and arranged to connect to or otherwise interface with either the air delivery tube 4170 or an intermediate component that then connects to the air delivery tube 4170. In an example of the present technology, the reservoir dock 6050 may allow the air delivery tube 4170 to form a direct, pneumatic connection with the water reservoir 6100 so that the pressurized flow of air that has been humidified in the water reservoir 6100 is delivered directly from the water reservoir 6100 to the air delivery tube 4170.

The main body of the reservoir dock 6050 comprises a plurality of walls and a heating element (e.g., heater plate

6080) provided to a bottom one of the walls to form the cavity to receive the water reservoir 6100.

Water Reservoir to Reservoir Dock Connection

In use, the water reservoir 6100 is removably coupled with the reservoir dock 6050 by inserting the water reservoir 6100 into the reservoir dock 6050. In the case where the water reservoir is arranged for direct engagement (pneumatic seal) with the air delivery conduit 4170, when the water reservoir 6100 is coupled to the reservoir dock 6050 (e.g., see FIG. 21), the inlet seal 6122 of the inlet tube 6120 (or inlet) of the water reservoir 6100 is structured and arranged to provide a face seal with the chassis outlet 7320 (dock inlet) of the reservoir dock 6050. Similarly, the outlet seal 6132 of the outlet tube 6130 (or outlet) of the water reservoir 6100 is structured to provide a face seal with the air circuit or air delivery tube 4170, e.g., to prevent losses in pneumatic pressure through leak. In the illustrated example, the water reservoir 6100 is structured and arranged to form a direct, pneumatic seal with the air delivery conduit 4170, completely bypassing the RPT device and the reservoir dock 6050. The reservoir dock 6050 facilitates this direct connection, but is not part of it. The connections other than the pneumatic connection, can be effected between the delivery tube and the water reservoir dock. For example, the air delivery tube can be structured and arranged to form a releasable mechanical/locking connection and/or an electrical connection with the water reservoir dock. The releasable mechanical (locking) connection can comprise a snap-fit connection.

Removing the RPT device and the reservoir dock 6050 from the air delivery path eliminates the presence of an internally located coupling component between the water reservoir 6100 and the air delivery conduit 4170. This eliminates the need to disassemble and sterilize such coupling component, thus making sterilization much easier. In this way, when preparing the device for a different user, the water reservoir 6100 is the only component of the RPT device which needs to be replaced or sterilized.

When the water reservoir 6100 is inserted into the reservoir dock 6050 and it reaches the operative position, the conductive portion 6150 of the water reservoir 6100 aligns with and thermally contacts the heater plate 6080 of the reservoir dock 6050 to allow heat transfer from the heater plate 6080 to the water in the water reservoir 6100, e.g., surface of the conductive portion 6150 engages or contacts surface of the heater plate 6080. A biasing mechanism may be introduced that presses the water reservoir and the heater plate towards each other, thus varying the level of thermal contact between the conductive portion and the heater plate. In one example, a spring element provided to the water reservoir, the reservoir dock and/or the heater plate may be arranged to bias the water reservoir and the heater plate towards each other to increase contact pressure and improve thermal contact.

The chassis outlet 7320 (dock inlet), e.g., shown in FIG. 21, is configured to receive the pressurized flow of air from the blower of the RPT device, and to pass on the flow of air into the water reservoir 6100 via the inlet tube 6120 of the water reservoir 6100. Humidity (i.e., water vapour) is added to the flow of air as the air travels through the water reservoir 6100, and the humidified flow of air exits the water reservoir through the outlet tube 6130. Air flows directly from the outlet tube 6130 and into the air delivery tube 4170 to deliver the flow of humidified air to the patient.

Guiding structures for Insertion/Removal

In an example, an outer side portion of the water reservoir 6100 provides a dock engagement portion structured and arranged to interface and engage a reservoir engagement portion of the reservoir dock 6050. In an example, the water reservoir 6100 and reservoir dock 6050 may include guiding structures to facilitate insertion, removal, and alignment of the water reservoir 6100 with the reservoir dock 6050.

For example, as shown in FIG. 6B, opposing sides of the water reservoir 6100 along the dock engagement portion may include guiding surfaces (e.g. provided by guide rails 6200) arranged to engage corresponding guiding surfaces (e.g., provided by a guide slot 6060) along the reservoir engagement portion of the reservoir dock 6050 to guide the water reservoir 6100 into the reservoir dock 6050.

In an example, as shown in FIG. 6B, the water reservoir 6100 may be inserted/removed (e.g., by sliding or push/pull only) along a path extending in a lateral direction (i.e., anterior-posterior direction) into and out of the cavity of the reservoir dock 6050.

In an alternative example, at least a portion of the path for insertion/removal of the water reservoir may extend in an inferior-superior direction, e.g., at least a portion of the path for insertion of the water reservoir into the dock includes a slope, such as an elevation or drop down, into the operative position.

For example, the guiding structures of the water reservoir 6100 and reservoir dock 6050 may be structured and arranged to provide an initial horizontal or sloped insertion of the water reservoir with a subsequent drop down in the last section into the operative position. In an example, the reservoir dock may provide a sloping surface with an internal edge located on the bottom surface of the dock that has to be cleared by the water reservoir before it can be dropped down to its operative position. The cleared edge and/or the drop down itself may effectively lock the water reservoir into the operative position. Further locking features may also be used. Such "push and drop" configuration includes movement of the tub that has components in both a horizontal and a vertical direction. The optional inclusion of the edge ensures that during insertion of the water reservoir into the reservoir dock, the base of the water reservoir engages a single edge or a small surface, as opposed to being dragged over a much larger surface. This reduces any wear and potential damage to the heater plate. A spring element may be arranged (e.g., between the reservoir dock and the water reservoir) to increase contact pressure between the water reservoir and the heater plate, e.g., to improve thermal contact between the base plate of the reservoir and the heater plate of the dock.

FIGS. 25A to 27B show a guiding structure to facilitate insertion, removal, and alignment of the water reservoir 6100 with the reservoir dock 6050 according to an example of the present technology. In the illustrated example, the engagement path for insertion/removal of the water reservoir 6100 extends in an anterior-posterior direction and in an inferior-superior direction, i.e., the engagement path includes both horizontal and vertical components.

In the illustrated example, each side of the reservoir dock 6050 includes a guide slot 6060 configured to receive a respective guide protrusion or pin 6250 on each side of the water reservoir 6100. As illustrated, each guide slot 6060 includes a generally horizontal section 6060H extending in anterior-posterior direction leading to a drop down section 6060D that slopes downwardly from the generally horizontal section 6060H in an inferior direction.

As shown in FIGS. 28A to 28C, the reservoir dock 6050 includes a recessed heating element 6085 configured to engage the conductive portion 6150 of the water reservoir 6100 so as to allow thermal transfer of heat from the heating element 6085 to the volume of liquid in the water reservoir 6100. As illustrated, the chassis assembly forming the reservoir dock 6050 includes a recessed opening adapted to receive the heating element 6085 (e.g., a heat generating component such as an electrically resistive heating track). The recessed opening is formed at least in part by a front ledge 7350 of the chassis assembly at the front or open end of the reservoir dock 6050 and a rear ledge 7360 of the chassis assembly at the rear or interior of the reservoir dock 6050. The heating element 6085 is firmly fixed or retained in place via a retainer plate 6095 configured and arranged to sandwich the heating element 6085 against the chassis assembly, e.g., against at least the front and rear ledges 7350, 7360 of the chassis assembly. In an example, the heating element 6085 may comprise a gasket 6086, e.g., silicone bead, along its perimeter to seal the heating element 6085 within the recessed opening of the chassis assembly.

The conductive portion 6150, e.g., metal plate, of the water reservoir 6100 may include a stepped arrangement in which the conductive portion 6150 extends in more than one plane. In an example, e.g., see FIG. 29, the conductive portion 6150 includes a first, heat conducting portion 6150.1 that extends in a first plane, and a second portion 6150.2 that extends in a second plane that is offset in a superior direction from the first plane. Each of the more than one plane may, but does not have to, extend in a horizontal plane (with reference to the water reservoir's operational configuration).

The above recessed configuration of the reservoir dock 6050 and water reservoir 6100 allows the water reservoir 6100 to drop down onto the heating element 6085 into its operative position. Specifically, the guide pins 6250 of the water reservoir 6100 are engaged within respective guide slots 6060 of the reservoir dock 6050 as the water reservoir 6100 is inserted into the reservoir dock 6050 (e.g., see FIGS. 25B and 26A). The generally horizontal section 6060H of the guide slots 6060 guide the water reservoir into the reservoir dock, i.e., in an anterior direction. As the water reservoir 6100 is guided along the generally horizontal section 6060H of the guide slots 6060, the first, heat conducting portion 6150.1 of the conductive portion 6150 of the water reservoir 6100 engages and slides along the upper guide surface 7355 of the front ledge 7350 supporting the heating element 6085 (e.g., see FIG. 27A). When the water reservoir 6100 reaches the drop down section 6060D of the guide slots 6060, the first, heat conducting portion 6150.1 of the water reservoir 6100 also clears the internal edge of the front ledge 7350, which allows the water reservoir 6100 and the first, heat conducting portion 6150.1 thereof to drop down into engagement with the heating element 6085 (e.g., see FIGS. 25A, 26B, and 27B). That is, the stepped arrangement of the conductive portion 6150 of the water reservoir 6100 is configured to allow the first, heat conducting portion 6150.1 to drop down into engagement with the recessed heating element 6085 while the second (usually not heat-conducting) portion 6150.2 drops down into engagement with the front ledge 7350 (e.g., see FIG. 27B). Such drop down engagement configuration effectively locks the water reservoir 6100 in an operative position, i.e., the front ledge 7350 provides a guide surface 7355 and also allows the water reservoir 6100 to engage therebehind to lock the water reservoir 6100 in position and prevent unintended release, e.g., during treatment, when the entire system is under pressure which may push the water reservoir out of its operational configuration. In the illustrated example, the first, heat conducting portion 6150.1 of the water reservoir 6100 is sized to substantially fill the recessed space provided by the recessed heating element 6085 (e.g., see FIG. 27B), e.g., to prevent any horizontal movement.

As the water reservoir 6100 slides across the front ledge 7350 during engagement, as opposed to along the heating element 6085, the engagement portion of the bottom surface of the water reservoir 6100, which could include either one or both of the heated plate and the remaining of the bottom wall of the reservoir, engages over a much smaller surface of the bottom of the dock, thus reducing wear and potential damage to the water reservoir 6110 (i.e., its conductive portion 6150) and the heater plate. Moreover, as the water reservoir 6100 drops down onto the heating element 6085 into its operative position, as opposed to sliding across the heating element 6085, in some configurations the heating element 6085 may be provided without a heater plate (also referred to as a wear plate or skid plate, e.g., formed of hard metallic material) along its upper or superior surface to protect the heating element 6085. That is, such engagement configuration allows the conductive portion 6150 of the water reservoir 6100 to directly engage the heating element 6085 such that heat is directly transferred from the heating element 6085 to the volume of liquid in the water reservoir 6100, i.e., thereby improving thermal conductivity as heat does not need to pass through a heater plate or skid plate. Such an arrangement can also be more cost effective.

In the illustrated example of FIGS. 27A and 27B, the upper wall portion of the reservoir dock includes a spring-loaded latch 6300 arranged to increase contact pressure between the water reservoir 6100 and the fixed heating element 6085, e.g., to improve thermal contact. As illustrated, when the water reservoir 6100 reaches its operative position, the spring-loaded latch 6300 is arranged to resiliently engage the top of the water reservoir 6100 to bias the water reservoir 6100 downwards and into the fixed heating element 6085 (e.g. see FIG. 27B. For removal, the water reservoir 6100 can be forced against the downwards pressure of the spring-loaded latch 6300 until it reaches the generally horizontal section 6060H of the guide slots 6060 for removal.

It should be appreciated that downwards force may be provided to the water reservoir 6100 in other suitable manners. For example, the guide slots of the reservoir dock may include springs or other biasing members arranged to provide downwards force, e.g., onto the guide pins of the water reservoir. In another example, the chassis assembly may comprise a hinged lid adjacent the reservoir dock configured to be moved down into engagement with the water reservoir after insertion of the water reservoir to provide downwards force. In yet another example, the chassis assembly may comprise a plunger-type element adjacent the reservoir dock configured to be pressed into engagement with the water reservoir after insertion of the water reservoir to provide downwards force.

In an alternative example, the water reservoir 6100 and the reservoir dock 6050 may be arranged such that the water reservoir 6100 can first drop down into engagement with the heating element 6085 and then can be further slid along the heating element 6085 into engagement with the spring-loaded latch 6300. In this example, as shown in FIGS. 30 to 32B, each guide slot 6060 includes an additional, generally horizontal section 6060H2 extending from the drop down section 6060D. Also, the first, heat conducting portion 6150.1 of the conductive portion 6150 of the water reservoir 6100 may be reduced in size such that the first, heat conducting portion 6150.1 does not fill the recessed space provided by the recessed heating element 6085, e.g., to allow horizontal movement. In use, when the water reservoir 6100 reaches the drop down section 6060D of the guide slots 6060, the first, heat conducting portion 6150.1 of the water reservoir 6100 clears the internal edge of the front ledge 7350 and drops down into engagement with the heating element 6085. Then, the water reservoir 6100 can be further slid into the reservoir dock 6050 along the additional, generally horizontal section 6060H2 until the water reservoir 6100 is slid under and into engagement with the spring-loaded latch 6300 (e.g., see FIG. 32B). For removal, the water reservoir 6100 can be moved horizontally out of engagement with the spring-loaded latch 6300 along the additional, generally horizontal section 6060H2 until it reaches the drop down section 6060D, where the water reservoir 6100 can then be pulled up and out of the reservoir dock 6050 along the drop down section 6060D and the generally horizontal section 6060H without pressure from the spring-loaded latch 6300.

FIGS. 80, 81, 91, and 98-101 show a guide arrangement to facilitate insertion, alignment, and engagement of the water reservoir 6100 with the reservoir dock 6050 according to another example of the present technology.

In the illustrated example, the water reservoir 6100 includes a pair of guiding or biasing rails 6200. As illustrated, each of the pair of guiding rails 6200 is provided to a respective one of opposing sides of the base 6112 of the water reservoir 6100. When the water reservoir 6100 is inserted into the reservoir dock 6050, each of the pair of guiding rails 6200 is configured to engage with a respective one of a pair of guide slots 6060 provided to the opposite sides of reservoir dock 6050 to guide coupling of the water reservoir 6100 into the reservoir dock 6050.

Each of the pair of guiding rails 6200 includes an upper (with reference to the operational orientation of the device) edge providing an upwardly oriented surface 9300, and each of the pair of guide slots 6060 includes an upper edge providing a downwardly oriented surface 9400 (see FIGS. 81, 98, and 99). When the water reservoir 6100 is inserted into the reservoir dock 6050, the guide slots 6060 are arranged to receive the rails 6200 and guide the insertion of the water reservoir 6100 within the dock 6050. Apart from this guiding function, there is an additional biasing function provided by the guide slots 6060. In particular, the upwardly oriented surfaces 9300 of the rails 6200 are configured to, at least in the last portion of their axial movement along the indicated arrow in FIG. 81, engage and be pushed or forced downwardly by respective downwardly oriented surfaces 9400 of the slots 6060. This downward pressure forces or depresses the water reservoir 6100 downwardly to, in its operational configuration, enhance abutment of its heat conductive portion 6150 with the heater plate 6080 of the heating assembly 6075 provided at the bottom of the reservoir dock 6050 (see FIGS. 98 and 99).

Each of the pair of guiding rails 6200 may include one or more engagement tabs 9315 (e.g., a single engagement tab as shown in FIGS. 81, 82, and 89) extending from its upwardly oriented surface 9300 configured to engage the downwardly oriented surface 9400 of a respective slot 6060, which engagement enhances displacement of the water reservoir 6100 towards the heating assembly 6075, and thereby enhancing abutment with the heater plate 6080 of the heating assembly 6075. Instead on the upwardly oriented surface 9300, the tab may be located on the associated downward oriented surface 9400. The provision of such a tab on one of the engagement surfaces between the rails 6200 and the slots 6060 ensures a smaller friction, as instead of the entire surface, only the area of a single tab is mechanically engaged with the opposing surface. This makes for a smoother insertion or retraction of the water reservoir 6100 into or out of the dock 6050, improving the user experience.

In the illustrated example, the leading side or edge of the water reservoir 6100 also includes one or more biasing edges or tabs 9320 (e.g., a pair of biasing tabs as shown in FIG. 80) configured to engage underneath a respective one of one or more abutment edges 9450 (e.g., a pair of abutment edges as shown in FIG. 112) provided to a rear wall of the reservoir dock 6050 (underneath the chassis outlet 7320 and the dock outlet 6090). Such an engagement locks the front end of the water reservoir 6100, when fully inserted inside the dock 6050, as well as biases downwardly the water reservoir 6100 in order to enhance abutment of its conductive portion 6150 with the heater plate 6080 of the heating assembly 6075 provided at the bottom of the reservoir dock 6050 (see FIGS. 100 and 101).

That is, the downward push of the slots 6060 onto respective rails 6200 (which are located at an intermediate to rear portion of the water reservoir 6100, with the front end being the end arranged to firstly engage with reservoir dock 6050) is complimented by a downward push exerted by the abutment edges 9450 onto respective biasing tabs 9320 at the front or leading side of the water reservoir 6100. The abutment edges 9450 engage the upwardly oriented surface 9325 of respective biasing tabs 9320 (see FIG. 101) close to the end of the engagement process, when the water reservoir 6100 is almost fully inserted into the reservoir dock 6050. At this point, the pair of biasing tabs 9320 is pushed under respective ones of the abutment edges 9450, which abutment edges 9450 are oriented generally horizontally. The abutment engagement is configured and arranged to balance the upwardly directed biasing force provided by the heating assembly 6075 provided at the bottom of the reservoir dock 6050 (e.g., see FIG. 98). As described in more detail below, the heater plate 6080 of the heating assembly 6075 is suspended over a resilient sealing and supporting member 9500, which is structured and arranged to bias the heater plate 6080 upwardly against the conductive portion 6150 of the water reservoir 6100 when the water reservoir 6100 is inserted into the reservoir dock 6050. Thus, the upward biasing force provided by the resilient sealing and supporting member 9500 pushes from underneath the heater plate 6080, which pushes the water reservoir 6100, which abuts the rails 6200 against respective slots 6060 and abuts the biasing tabs 9320 against respective abutment edges 9450. Such arrangement ensures sufficient contact of the conductive portion 6150 of the water reservoir 6100 with the heater plate 6080 of the water reservoir 6100.

In the illustrated example, the slots 6060 and the abutment edges 9450 are arranged to be generally horizontal (e.g., generally parallel to the heater plate 6080), which arrangement allows the water reservoir 6100 to be inserted/removed (e.g., by sliding or push/pull only) along a path extending in a lateral direction (i.e., anterior-posterior direction) into and out of the cavity of the reservoir dock 6050. However, in alternative examples, at least a portion of the slots 6060 and/or the abutment edges 9450 may include a slope, such that at least a portion of the path for insertion/removal may extend in an inferior/superior direction.

Also, as shown in FIG. 102, the lid 6114 of the water reservoir 6100 includes one or more retention protrusions 6115 (e.g., a pair of retention protrusions as shown in FIG. 80 and FIG. 85) structured and arranged to releasably engage respective dock locking edges or locking recesses 6051 in the reservoir dock 6050 to releasably lock and retain the water reservoir 6100 in an operative position within the reservoir dock 6050, i.e., each protrusion 6115 engages behind the forward end forming the recess 6051. The protrusions 6115 may include a taper to facilitate engagement of the protrusions 6115 into respective recesses 6051. To release, the water reservoir 6100 may be compressed (i.e., by depressing the lid 6114 against the base 6112) to compress the deformable seal 6116 and allow the protrusions 6115 to lower or drop beneath the forward end of the recess 6051. Such a locking arrangement ensures that the positive pressure inside the assembled RPT device, when in its operational configuration, does not push the water reservoir backwards and out of operational engagement with the reservoir dock 6050, thus ensuring a reliable operation of the device.

Retaining Feature

In an example, as shown in FIGS. 33A to 33F, the water reservoir 6100 may comprise a latch 6400 configured to releasably engage with a recessed slot 6055 in the reservoir dock 6050 to releasably retain the water reservoir 6100 in an operative position within the reservoir dock 6050. Such a locking arrangement prevents the water reservoir from disengaging from the dock, which in some arrangements, the water reservoir may be encouraged to do by the relatively high operational pressure within the dock during the operation of the device.

In the illustrated example, the latch 6400 is provided as a separate and distinct structure from the water reservoir 6100 and then secured or otherwise provided to the water reservoir 6100 in an operative position, e.g., the latch 6400 comprises a pre-formed structure that is secured to the reservoir lid 6114, or to other portions of the water reservoir 6100. In an example, the latch 6400 comprises a plastic or thermoplastic polymer material.

As shown in FIGS. 33E and 33F, the latch 6400 includes a locking lever 6402, a lid connector 6404, and support members 6406 to resiliently support the locking lever 6402 to the lid connector 6404.

As shown in FIG. 33G, the reservoir lid 6114 includes a recess 6260 to receive the latch 6400. Each side of the recess 6260 includes a rail 6262, and a bottom of the recess includes a locking tab 6264. Each rail 6262 forms a slot configured to receive a respective side of the lid connector 6404. The lid connector 6404 is guided by the rails 6262 into the recess 6260 until the slotted end 6405 of the lid connector 6404 engages behind the locking tab 6264 to secure the latch 6400 to the reservoir lid 6114 in an operative position, e.g., see FIGS. 33C and 33D.

The locking lever 6402 includes a retaining protrusion 6403 at one end of the locking lever 6402 and a finger/thumb grip 6407 at the other end of the locking lever 6402. The locking lever 6402 is supported by the resilient support members 6406 such that the retaining protrusion 6403 is resiliently biased to a locked position.

When the water reservoir 6100 reaches an operative position in the reservoir dock 6050, the retaining protrusion 6403 of the latch 6400 is configured and arranged to engage over and behind the forward ledge forming the recessed slot 6055 in the reservoir dock 6050, e.g., see FIG. 33B. The retaining protrusion 6403 includes a taper to facilitate engagement of the retaining protrusion 6403 into the recessed slot 6055. This connection releasably secures the water reservoir 6100 to the reservoir dock 6050. The finger/thumb grip 6407 can be manually depressed to pivot the locking lever 6402 and hence the retaining protrusion 6403 against the external bias of members 6406 and into an unlocked position, i.e., retaining protrusion 6403 pivoted out of the recessed slot 6055 to allow the water reservoir 6100 to be removed from the reservoir dock 6050.

Air Delivery Tube to Reservoir Dock Connection

In an example, e.g., as shown in FIGS. 20A, and 23A to 24B, the air delivery tube 4170 includes a tube portion 4500, a dock connector/cuff 4600 (outlet connector) to connect the air delivery tube 4170 to the reservoir dock 6050 and/or the water reservoir 6100, and a patient interface connector/cuff 4700 (inlet connector) to connect the air delivery tube 4170 to the patient interface 3000.

In an example, the dock connector 4600 is structured and arranged to form a mechanical and electrical connection with the reservoir dock 6050 and to form a pneumatic connection with the water reservoir 6100 and/or with the reservoir dock 6050. These connections locate and secure the air delivery tube 4170 to the reservoir dock 6050 or the water reservoir 6100, provide electrical power, information and control signals to the heating element and transducers associated with the air delivery tube 4170, and allow humidified, pressurized gas to flow from the water reservoir 6100 to the patient interface 3000. During the engagement of the air delivery tube 4170 with the water reservoir 6100 and the reservoir dock 6050, the connections may be formed simultaneously or in series, e.g., one of the mechanical, pneumatic or electrical connections may be completed before others.

The dock connector 4600 of the air delivery tube 4170 includes a retention feature that provides a fixed, non-rotatable connection with the dock outlet 6090 of the reservoir dock 6050.

In one example, as shown in FIGS. 23A and 23B, the retention feature of the dock connector 4600 includes a pair of resilient, quick release pinch arms 4610, i.e., cantilevered spring arms or pinch buttons. Each of the spring or pinch arms 4610 may include a barbed end or tab structured to provide a snap-fit connection with the dock outlet 6090. In an example, the dock outlet 6090 may include locking members, e.g., slots, structured and arranged to receive a respective barbed end of the pinch arms 4610.

The free end of the dock connector 4600 includes an outwardly extending flange or lip 4620 surrounding the tube opening. The flange or lip 4620 provides a generally planar contact surface 4625. When the dock connector 4600 is connected to the dock outlet 6090, the free end of the dock connector 4600 and contact surface 4625 thereof protrudes into the cavity of the reservoir dock 6050 to allow engagement with the outlet tube 6130 of the water reservoir 6100, e.g., as shown in FIG. 22C.

In the example of FIGS. 23A and 23B, the dock connector 4600 of the air delivery tube 4170 includes a longitudinal axis A1 (e.g., aligned with the axis of the tube, which may also be the axis of engagement/disengagement with the dock outlet 6090), and a contact surface 4625 arranged along an axis A2 that extends at an angle to the longitudinal axis A1, e.g., 45°. Such arrangement orients the contact surface 4625 for engagement with the water reservoir 6100 as described below.

FIGS. 20A and 24A to 24B show an air delivery tube 4170 including a dock connector 4600 according to alternative example of the present technology. As illustrated, each side of the dock connector 4600 includes a retaining protrusion 4615 structured to provide a snap-fit connection with the dock outlet 6090.

In an example, as best shown in FIGS. 20A to 20C, 20K, and 20L, the dock outlet 6090 may include a locking arrangement 6600 to receive and releasably retain the air delivery tube 4170 in an operative position within the dock outlet 6090. As illustrated, the locking arrangement 6600 includes a button portion 6605 and locking arms 6610 extending from the button portion 6605. Each locking arm 6610 includes a locking tab 6615 arranged to engage a respective retaining protrusion 4615 of the dock connector 4600. The locking arrangement 6600 is supported adjacent the dock outlet 6090 such that the locking arms 6610 and locking tabs 6615 thereof are resiliently biased to a locked position.

When the dock connector 4600 of the air delivery tube 4170 is inserted into the respective dock opening 6091 and reaches an operative position in the dock outlet 6090 of the reservoir dock 6050, the retaining protrusions 4615 of the dock connector 4600 are configured and arranged to engage over and behind respective locking tabs 6615 of the locking arrangement 6600, e.g., see FIG. 20K. In some arrangements, the dock connector 4600 of the air delivery tube 4170 may have to be inserted into the respective dock opening 6091 and rotated, in order to effect this locking engagement with the locking arrangement 6600. Each retaining protrusion 4615 and/or each locking tab 6615 may include a taper to facilitate engagement into a locked position. This connection releasably secures the air delivery conduit 4170 to the reservoir dock 6050, e.g., see FIGS. 20D to 20H. As shown in FIG. 20L, the button portion 6605 can be manually depressed to resiliently flex the locking arms 6610 and locking tabs 6615 thereof against biasing to an unlocked position, i.e., locking tabs 6615 moved laterally outwardly out of engagement with the retaining protrusions 4615 of the dock connector 4600 to allow the air delivery conduit 4170 to be removed from the dock outlet 6090 of the reservoir dock 6050.

Once the connection is established, the retaining features provided by the dock connector 4600/locking arrangement 6600, as well as the non-circular engagement profile provided by the dock opening 6091 of the dock outlet 6090 (see FIG. 20C) and the dock connector 4600, provides a fixed, non-rotatable connection of the air delivery conduit 4170 to the dock outlet 6090.

The free end of the dock connector 4600 includes an outwardly extending flange or lip 4620 surrounding the tube opening, e.g., see FIGS. 20A, 20G, 20I, and 20J. The flange or lip 4620 provides a contact surface 4625. When the dock connector 4600 is connected to the dock outlet 6090, the free end of the dock connector 4600 and contact surface 4625 thereof protrudes into the cavity of the reservoir dock 6050 to allow engagement with the water reservoir 6100, e.g., see FIGS. 20F to 20H.

Similar to the above example, the contact surface 4625 of the dock connector 4600 shown in FIGS. 20A and 24A to 24B is arranged along an axis that extends at an angle to the longitudinal axis of the tube, e.g., 45°.

Water Reservoir/Air Delivery Tube—Direct Engagement Under 45°

A direct, pneumatic connection between the water reservoir 6100 and the air delivery conduit 4170 was already discussed above. In the illustrated example of FIGS. 18A and 18B, the water reservoir 6100 includes an axis A1 (e.g., aligned with the direction of insertion/removal), and the outer end of the outlet tube 6130 (or outlet) and the outlet seal thereof is arranged along an axis A2 that extends at an angle to the axis A1, e.g., 45°. As described above in relation to FIGS. 23A and 23B, the dock connector 4600 of the air delivery tube 4170 includes an axis A1 (e.g., aligned with direction of insertion/removal of the air delivery tube 4170), and a contact surface 4625 of the dock connector 4600 is arranged along an axis A2 that extends at an angle to the axis A1, e.g., 45°.

When the air delivery tube 4170 is engaged with the water reservoir 6100 and/or the dock outlet 6090 of the reservoir dock 6050, the outlet tube 6130 (or outlet) and outlet seal 6132 of the water reservoir 6100 is structured to sealingly engage or interface against the contact surface 4625 along the free end of the dock connector 4600 of the air delivery tube 4170, e.g., see FIGS. 21 and 22A to 22C. Such engagement provides a face seal between the water reservoir 6100 and the dock connector 4600 to seal the outlet flow path that allows humidified air to flow out of the water reservoir 6100 and into the air delivery tube 4170 for delivery to the patient interface 3000.

The engagement profile of the outlet tube 6130 (and outlet seal 6132) and contact surface 4625, e.g., at 45°, allows the water reservoir 6100 to be removed from the reservoir dock 6050 while the air delivery tube 4170 remains attached to the dock outlet 6090. Similarly, this 45° angle allows the air delivery tube 4170 to be disengaged from the dock, without the need for the water reservoir 6100 to be removed from the reservoir dock 6050 outlet 6090. Thus, the insertion and removal of the water reservoir 6100 may be independent of the connection of the air delivery tube 4170 to the dock outlet 6090, i.e., water reservoir 6100 and air delivery tube 4170 may be engaged/disengaged with the reservoir dock 6050 independently.

It should be appreciated that the outlet tube 6130 (and outlet seal 6132) and the contact surface 4625 may be arranged at other suitable angles for direct contact with one another.

In an alternative example, the air delivery tube 4170 may not directly contact the reservoir dock 6050. Instead, a tube adaptor may be provided to interconnect an air delivery tube 4170 to the reservoir dock 6050. The tube adaptor may include a dock connector end for connection to the reservoir dock 6050 and a tapered/ISO (standardized) end for connection to an air delivery tube 4170. The tube adaptor may include a lockout feature to prevent removal of the air delivery tube 4170 from the tube adaptor when the tube adaptor is connected to the dock outlet 6090 of the reservoir dock 6050.

Data Collection

In an example, the air delivery tube 4170 may include a plurality of wires helically wound around the axis of the air delivery tube 4170 (e.g., along the tube portion 4500 of the air delivery conduit 4170), e.g., configured to heat air in the air delivery tube and/or transmit signal from one or more transducers (e.g., temperature sensor, flow sensor) to a controller of the RPT device.

In an example, the air delivery tube 4170 may comprise four wires, e.g., two wires for powering one or more heating elements and two wires for connecting a temperature sensor/transducer. However, it should be appreciated that other numbers of wires may be used, e.g., two wires, three wires, or five or more wires.

In an example (e.g., see FIGS. 23B and 24A), the dock connector 4600 of the air delivery tube 4170 includes a contact assembly 4650 including contacts 4655 that, in use, are engaged with respective contacts provided to the reservoir dock 6050 to form electrical connections with the reservoir dock at the dock outlet to provide electrical power and/or control signal transmission. In an example, the contacts 4655 of the dock connector 4600 may be joined to respective wires running along the air delivery tube 4170. In an alternative example, the at least some of the contacts 4655 are not related to the wires running along the air delivery tube 4170, but are characterised by their own independent and/or unique electrical characteristics (e.g., resistance, conductance, etc.). Such independent and/or unique electrical characteristics may be used for identifying one or more elements of the tube/patient interface system, or of characteristics of these elements.

In an example, the dock outlet 6090 of the reservoir dock 6050 includes a contact assembly 6800 in communication with electrical power and electrical signalling within the reservoir dock, e.g., the PCBA 7600. In an example, the contact assembly 6800 includes contacts 6805 corresponding to the number of contacts 4655 provided to the dock connector 4600 of the air delivery tube 4170, e.g. four contacts as shown in FIGS. 20B, 20C, 20H to 20J. In an example, as shown in FIGS. 20H to 20J, each of the contacts 6805 comprises a spring loaded pin (e.g., pogo-pin). In use, the spring loaded pins 6805 will resiliently deflect during engagement with the dock connector 4600 to maintain contact with respective contacts 4655 of the dock connector 4600. In the illustrated example (e.g., see FIG. 20J), the contact assembly 6800 also includes contacts 6810 (e.g., spring loaded pins) arranged to engage the PCBA 7600. The contacts 6805, 6810 are supported by a support member 6815 configured to orient the contacts 6805 substantially perpendicular to the contacts 6810.

Because each contact 4655, or combination of contacts, in the contact assembly 4650 of the air delivery tube 4170 may have unique electrical characteristic, in an example, the contact assembly 4650 of the air delivery tube 4170 may be used as an identifier of various parameters of the air delivery tube 4170 and/or the patient interface. For example, the contact assembly 4650 may be configured to provide identification of the type of air delivery tube 4170 (e.g., non-heated tube, heated tube, tube with heat and moisture exchanger (HME), tube unknown), size of air delivery tube (e.g., 15 mm, 19 mm), presence and type of HME, type of patient interface connected to tube, etc. The data from identification may be communicated and used by a controller, e.g., to optimize operation of the RPT device, humidifier, to facilitate data collection, etc. For example, the controller may be configured to recognize a unique identifying feature provided by the contact assembly 4650 so that the controller can recognize the specific characteristics of the air delivery tube 4170 coupled to the reservoir dock 6050, and therefore the controller can automatically configure the RPT device and/or humidifier to optimize operation.

In an example, the dock connector 4600 may include a tapered support protrusion 4630 (e.g., see FIGS. 20A, 20M, and 20N). When the dock connector 4600 of the air delivery tube 4170 is connected to the dock outlet 6090 of the reservoir dock 6050, the tapered support protrusion 4630 is adapted to be arranged adjacent to or in contact with one or more tapered support protrusions 6850 provided to the dock outlet 6090 as best shown in FIGS. 20M and 20N. The tapered support protrusions 4630, 6850 provide an interface between the dock connector 4600 and the dock outlet 6090 to maintain the dock connector 4600 in generally perpendicular relation to the front face of the dock outlet 6090, e.g., interface prevents the dock connector 4600 from sagging or tilting downwardly away from the dock outlet 6090. For example, the interface between the dock connector 4600 and the dock outlet 6090 may counteract force applied by the contact assembly 6800 to the dock connector 4600 which tends to force the dock connector 4600 downwardly, e.g., force applied by spring loaded pins of the contact assembly 6800 are offset from the axis of the dock connector 4600 which may force the dock connector 4600 at a downward angle away from the dock outlet 6090.

Bayonet-Style Connection and Intermediate Component

FIGS. 43 to 78 illustrate an alternative example for connecting the air delivery tube 4170 to the reservoir dock 6050 and the water reservoir 6100. In this example, an intermediate component 6700 is removably coupled to the reservoir dock 6050. The intermediate component 6700 is configured to pneumatically connect the water reservoir 6100 to the air delivery tube 4170 so that the pressurized flow of air that has been humidified in the water reservoir 6100 can be delivered from the water reservoir 6100, via the intermediate component 6700, to the air delivery tube 4170. Also, in this example, the dock connector 4600 of the air delivery tube 4170 is structured and arranged to form a bayonet-style connection with the reservoir dock 6050, which mechanically and/or electrically connects the air delivery tube 4170 with the reservoir dock 6050. That is, the bayonet-style connection locates and secures the air delivery tube 4170 to the reservoir dock 6050 and/or provides electrical power, information and control signals to the heating element and transducers associated with the air delivery tube 4170.

Intermediate Component

As shown in FIGS. 43, 46, 49, 57, and 58, the intermediate component 6700 is provided to the dock outlet 6090 of the reservoir dock 6050 to pneumatically connect the water reservoir 6100 to the air delivery tube 4170. In the illustrated example, the intermediate component 6700 is removably coupled to the reservoir dock 6050 so that the intermediate component 6700 can be disassembled for cleaning, sterilization and/or replacement, e.g., for multi-patient multi-use (MPMU) applications.

As shown in FIGS. 53-56, the intermediate component 6700 comprises a tubular portion 6705 including an inlet end 6710 adapted to interface with the water reservoir 6100 and an outlet end 6720 adapted to interface with the air delivery tube 4170. The intermediate component 6700 also comprises retention and alignment features structured and arranged to align the intermediate component 6700 with the reservoir dock 6050 and provide a removable, non-rotatable connection with the reservoir dock 6050. In addition, the intermediate component 6700 comprises a port 6730, e.g., a pressure port for inserting a sensor for measuring air pressure at the dock outlet 6090. The port 6730 includes a port seal 6735 to provide a sealing interface between a sensor, e.g., pressure sensor, and the intermediate component 6700.

In the illustrated example, e.g., see FIG. 56, the tubular portion 6705 (including the inlet end 6710 and the outlet end 6720) along with the retention and alignment features comprise a first part or base mold constructed of a relatively rigid material (e.g., thermoplastic polymer (e.g., PC, ABS)) and the port seal 6735 comprises a second part or overmold constructed of a relatively soft material (e.g., thermoplastic elastomer (TPE) or silicone) that is provided (e.g., by overmolding) to the first part. Thus, the intermediate component 6700 provides a substantially rigid construction, e.g., for durability for MPMU applications.

In the illustrated example, the inlet end 6710 is arranged at an angle to the outlet end 6720, e.g., the axis of the inlet end is arranged at about 90° with respect to the axis of the outlet end. However, it should be appreciated that other suitable angles are possible, e.g., the axis of the inlet end is arranged at about 45° with respect to the axis of the outlet end.

The free end of the inlet end 6710 includes a flange or lip 6712 surrounding the tube opening. The flange or lip 6712 provides a contact surface 6715. When the water reservoir 6100 is coupled to the reservoir dock 6050, the outlet seal 6132 of the outlet tube 6130 (or outlet) of the water reservoir 6100 is structured to engage and provide a face seal with the contact surface 6715 of the inlet end 6710. In an alternative embodiment, the seal between the outlet tube 6130 (or outlet) of the water reservoir 6100 and the contact surface 6715 of the inlet end 6710 may be an integral part of the inlet end 6710, or may be a sealing portion independent from either the outlet tube 6130 or the inlet end 6710. In the illustrated example, the contact surface 6715 comprises a taper into the tube opening, e.g., to enhance sealing and prevent leak.

The outlet end 6720 may comprise an ISO taper, e.g., 22 mm outer diameter ISO taper, for coupling to the air delivery conduit 4170.

In regards to retention and alignment features, the intermediate component 6700 includes a pair of resilient pinch arms 6740, i.e., cantilevered spring arms. Each of the spring or pinch arms 6740 may include a barbed end or tab 6745 structured to provide a snap-fit connection with respective locking members, e.g., protrusions 6750, provided within the cavity of the reservoir dock 6050 as shown in FIG. 46. The intermediate component 6700 also includes a guide rail 6760 structured and arranged to assist in correct alignment and insertion of the intermediate component 6700 into the reservoir dock 6050 by engagement with a corresponding guide slot 6755 extending into the cavity of the reservoir dock 6050 as shown in FIGS. 46, 50 and 52. Further, the intermediate component 6700 includes a flange 6770 arranged between the inlet end 6710 and the outlet end 6720 to assist in locating or positioning the intermediate component 6700 in the reservoir dock 6050 by abutting a flange or wall provided to the reservoir dock 6050, e.g., flange acts as a stop during insertion as shown in FIG. 72. The flange 6770 of intermediate component 6700 may include one or more cut-outs or recesses 6772, e.g., to accommodate fasteners or projections along the flange or wall provided to the reservoir dock 6050 as shown in FIGS. 57 and 58.

When the intermediate component 6700 is inserted into the dock opening 6091 of the reservoir dock 6050, the intermediate component 6700 is oriented to engage its guide rail 6760 with the guide slot 6755 which correct aligns and guides the intermediate component 6700 into an operative position. Also, the dock opening 6091 and/or an opening 6919 provided by the locking and contact assembly 6900 at the dock opening 6091 includes a non-circular profile to facilitate correct orientation of the intermediate component 6700 during insertion as shown in FIG. 63. When the intermediate component 6700 reaches an operative position, the barbed ends or tabs 6745 of the spring or pinch arms 6740 are configured and arranged to engage over and/or behind respective protrusions 6750, e.g., see FIG. 46. Each barbed end 6745 and/or each protrusion 6750 may include a taper to facilitate engagement into the operative position. In an example, the engagement of the spring or pinch arms 6740 with the protrusion 6750 may provide sensory feedback, e.g., audible click, to indicate correction connection. This snap-fit connection releasably secures the intermediate component 6700 to the reservoir dock 6050. To disengage the intermediate component 6700, the spring or pinch arms 6740 can be manually depressed towards one another (e.g., with or without a tool) to resiliently flex the spring or pinch arms 6740 and barbed ends 6745 thereof against biasing to an unlocked position, i.e., barbed ends 6745 moved out of engagement with the protrusion 6750 to allow the intermediate component 6700 to be removed from the reservoir dock 6050.

Once the connection is established, the cooperating retention and alignment features provided by the intermediate component 6700/reservoir dock 6050 provides a removable, non-rotatable connection of the intermediate component 6700 to the dock outlet 6090 of the reservoir dock 6050. Also, once connected, the spring or pinch arms 6740 of the intermediate component 6700 are lockingly engaged within the cavity of the reservoir dock 6050, e.g., to prevent removal of the intermediate component 6700 when the water reservoir 6100 is received in the reservoir dock 6050.

When the intermediate component 6700 is connected to the dock outlet 6090 of the reservoir dock 6050, the inlet end 6710 and contact surface 6715 thereof protrudes into the cavity of the reservoir dock 6050 to allow engagement with the outlet seal 6132 of the outlet tube 6130 (or outlet) of the water reservoir 6100, e.g., see FIG. 46. Likewise, the outlet end 6720 of the intermediate component 6700 extends within, and/or protrudes out, of the cavity of the reservoir dock 6050 to allow engagement with the air delivery tube 4170, e.g., see FIG. 43. Further, the port 6730 of the intermediate component 6700 is oriented, e.g., upwardly as shown in FIG. 57, to interface with the sensor associated with the PCBA.

Bayonet-Style Locking and Contact Assembly

As shown in FIGS. 43-52, a locking and contact assembly 6900 is provided to the dock outlet 6090 of the reservoir dock 6050 to mechanically and electrically connect the reservoir dock 6050 to the air delivery tube 4170. In the illustrated example, the locking and contact assembly 6900 comprises a bayonet-style connection structured and arranged to locate and secure the air delivery tube 4170 to the reservoir dock 6050 and form mechanical, pneumatic and electrical (both power and control signals) connections.

As shown in FIGS. 59-62, the locking and contact assembly 6900 includes a base 6910, an (electrical) contact assembly 6950 provided to the base, and a cover 6970 provided to the base 6910 to enclose at least a portion of the contact assembly 6950.

The base 6910 includes a rear wall 6912 that is secured, e.g., via one or more fasteners, to one or more walls surrounding the dock opening 6091 so as to secure the base 6910 at the dock outlet 6090 of the reservoir dock 6050. As shown in FIG. 63, the rear wall 6912 includes an opening 6915, e.g., non-circular, that aligns with the dock opening 6091 to allow insertion and connection of the intermediate component 6700 as mentioned above, e.g., a non-circular opening 6915 adapted to receive non-circular profile of the intermediate component 6700. Further, as mentioned above, the rear wall 6912 provides a stop for the intermediate component 6700 during assembly, e.g., at least a portion of the flange 6770 of the intermediate component 6700 may abut the rear wall 6912 as shown in FIG. 72.

The base 6910 includes an annular side wall 6920 that projects outwardly from the rear wall 6912. When the intermediate component 6700 is connected to the reservoir dock 6050, the outlet end 6720 of the intermediate component 6700 and the annular side wall 6920 cooperate to form a channel 6780 for receiving the air delivery tube 4170. A retaining wall 6930 projects radially outwardly from the annular side wall 6920 along a portion of the perimeter of the annular side wall, e.g., along a portion of the superior side of the annular side wall. With reference to FIG. 57, a gap is provided in the annular side wall 6920 along a portion of the perimeter of the annular side wall which forms a recess 6940 that leads into the channel 6780. The recess 6940 is adjacent to, and disposed counter-clockwise from, the retaining wall 6930. As described below, the recess 6940 and retaining wall 6930 are configured and arranged so that a portion of the dock connector 4600 of the air delivery tube 4170 may be inserted into the recess 6940 and then rotated clockwise, to move behind retaining wall 6930, to effect a locking engagement between the air delivery tube and the dock.

Additional retention and alignment features, e.g., recesses and/or grooves, are provided to the annular side wall 6920 along its perimeter that are structured and arranged to interact with corresponding features on the dock connector 4600 of the air delivery tube 4170 during engagement as discussed below.

As shown in FIGS. 60-62, the electrical contact assembly 6950 is supported by the base 6910 adjacent the retaining wall 6930. The contact assembly 6950 is in communication with electrical power and electrical signalling within the reservoir dock 6050, e.g., the PCBA 7600. As illustrated, the contact assembly 6950 includes a support member 6952 and a plurality of contacts 6955, e.g., four contacts, supported by the support member 6952. Each of the contacts 6955 comprises a spring arm 6956 (as best seen in FIG. 61) that is biased away from the support member 6952. In use, when the tube engages with the dock, the spring arms 6956 will resiliently deflect during engagement with the dock connector 4600 to maintain contact with respective contacts of the dock connector 4600. The contact assembly 6950 also includes an electrical connector 6958, e.g., flexible circuit board (FCB), flexible printed circuits (FPC) and/or flexible flat cables (FFC), to electrically connect the contacts 6955 to the PCBA 7600 (see FIG. 62).

The superior side of the base 6910 includes a contact support structure 6960 (FIG. 62) structured and arranged to support and retain the support member 6952 of the contact assembly 6950 (FIG. 61), which supports the contacts 6955 of the contact assembly 6950 radially outwardly of the annular side wall 6920 and axially inwardly of the retaining wall 6930. The cover 6970 is secured to the superior side of the base 6910 to enclose at least the support member 6952 and contacts 6955 (see FIG. 60). The electrical connector 6958 protrudes from the base 6910, e.g., through one or more slots in the base, to connect to the PCBA 7600 (FIG. 62).

Dock Connector

As shown in FIGS. 43-45, the dock connector 4600 of the air delivery tube 4170 is structured to form a pneumatic connection with the intermediate component 6700 and form a mechanical and electrical connection with the locking and contact assembly 6900 provided to the reservoir dock 6050.

In the illustrated example, the dock connector 4600 includes a tubular base portion 4640 and a locking and contact assembly 4660 provided to the base portion 4640.

As shown in FIGS. 64-68, the tubular base portion 4640 includes a radial lip seal 4645 that protrudes into the opening of the base portion 4640. The radial lip seal 4654, in its relaxed, undeformed shape, provides an internal diameter that is smaller than the external diameter of the outlet end 6720 of the intermediate component 6700 with which the dock connector pneumatically engages. For example, the internal diameter provided by the radial lip seal 4645 may be less than about 22 mm (e.g., about 19-21 mm or less) for use with an outlet end 6720 comprising a 22 mm outer diameter ISO taper. In use, the radial lip seal 4645 is structured to resiliently deform upon engagement with the outlet end 6720 of the intermediate component 6700 so as to provide a pneumatic connection with the intermediate component 6700, e.g., radial lip seal 4645 forms a gas tight seal against the exterior surface of the outlet end 6720 of the intermediate component 6700. As illustrated, the radial lip seal 4645 extends at an angle towards the interior of the base portion 4640 to provide a lead in for aligning and engaging the dock connector 4600 with the intermediate component 6700. Also, a stop surface 4647 (see FIG. 66) within the base portion 4640 provides a stop to prevent the intermediate component 6700 from being inserting further into the dock connector 4600.

The base portion 4640 includes a tapered protrusion 4642 that protrudes outwardly from the base portion 4640 (see FIG. 64) adjacent the locking and contact assembly 4660. The tapered protrusion 4642 provides a thumb and/or finger grip to facilitate manual manipulation and connection of the dock connector 4600 with the intermediate component 6700 and the locking and contact assembly 6900 provided to the reservoir dock 6050.

Further, the base portion 4640 includes resilient retaining bumps 4644 along opposing sides thereof. As described below, the retaining bumps 4644 are structured and arranged to interact with retention and alignment features, e.g., recesses and/or grooves, provided to the base 6910 of the locking and contact assembly 6900 on the reservoir dock 6050 during engagement.

In the illustrated example, as shown in FIG. 68, the base portion 4640 may comprise a base 4640bs (e.g., comprising one or more parts) constructed of a relatively rigid material (e.g., thermoplastic polymer (e.g., polypropylene (PP), polycarbonate (PC), and Acrylonitrile butadiene styrene (ABS)) and an overmold 4640ov constructed of a relatively soft material (e.g., thermoplastic elastomer (TPE) or silicone) that is provided (e.g., by overmolding) to the base 4640bs. As illustrated, the relatively rigid base 4640bs may form the structural shape for the tubular base portion 4640 including the tapered protrusion 4642 and resilient retaining bumps 4644 while the relatively soft overmold 4640ov forms the exterior for the tubular base portion 4640 along with the radial lip seal 4645.

As shown in FIG. 64, the locking and contact assembly 4660 includes a retaining portion 4665, a support arm 4662 to support the retaining portion 4665 in spaced relation from the base portion 4640, and a contact assembly 4666 provided to the retaining portion 4665. As described below, the retaining portion 4665 is structured and arranged to be rotated behind the retaining wall 6930 provided to the locking and contact assembly 6900 on the reservoir dock 6050 to axially lock the dock connector 4600 in a locked position. The contact assembly 4666 includes contacts 4667 that, in use, are arranged to engage with respective contacts 6955 provided to the locking and contact assembly 6900 on the reservoir dock 6050 to form electrical and control signal connections with the reservoir dock 6050. The contacts 4667 are arranged along the retaining portion 4665 to form the electrical and signal connections as the dock connector 4600 is rotated into the locked position. An electrical connector 4668, e.g., flexible circuit board (FCB), flexible printed circuits (FPC) and/or flexible flat cables (FFC), electrically connects the contacts 4667 to respective wires running along the air delivery tube 4170 and/or circuit elements. The fact that, as shown in FIG. 64, the contact tracks extend in a circumferential direction allows them to initiate and maintain the electrical connection, whilst the dock connector 4600 is being rotated within the locking and contact assembly 6900.

Engagement of Dock Connector with Reservoir Dock

FIGS. 43-45 and 69-78 illustrate engagement of the dock connector 4600 of the air delivery tube 4170 with the reservoir dock 6050. As shown in FIG. 43, the dock connector 4600 is oriented to align its locking and contact assembly 4660 with the recess 6940 provided by the locking and contact assembly 6900 on the reservoir dock 6050. The dock connector 4600 is then pushed towards the reservoir dock 6050 so that the outlet end 6720 of the intermediate component 6700 extends into the opening of the base portion 4640 and the radial lip seal 4645 engages and resiliently deforms against the exterior surface of the outlet end 6720. The radial lip seal 4645 of the dock connector 4600 engages and slides along the exterior surface of the outlet end 6720 of the intermediate component 6700 as the dock connector 4600 is pushed further towards the reservoir dock 6050 into an unlocked, engaged position.

As shown in FIGS. 44 and 69-72, when the dock connector 4600 reaches the unlocked, engaged position, the base portion 4640 of the dock connector 4600 is received within the channel 6780 formed by the base 6910 and the intermediate component 6700, and the locking and contact assembly 4660 of the dock connector 4600 is received within the recess 6940. In an example, the forward end of the base portion 4640 may engage the flange 6770 of the intermediate component 6700 and/or the stop surface 4647 within the base portion 4640 may engage the free end of the outlet end 6720 to prevent the dock connector 4600 from inserting further into the locking and contact assembly 6900.

Further, when the dock connector 4600 reaches the unlocked, engaged position, the retaining bumps 4644 of the dock connector 4600 are oriented to engage within respective recesses provided to the annular side wall 6920 of the base 6910, e.g., one of the bumps 4644 engages within a closed, elongated recess 6922 and the other of the bumps 4644 engages within an open-ended recess 6924. The friction forces keeping the bumps inside the engagement grooves may be calibrated to be sufficient to maintain the tube inside in this engaged, but unlocked configuration when the device is under operational pressure. Thus, in this configuration, there may be a full operational pneumatic engagement between the tube and the dock. However, mechanically the engagement is uncompleted. Also, the tube and the dock are not in electrical communication in this configuration.

As shown in FIGS. 45 and 73-78, the dock connector 4600 is rotated in a clockwise direction from the unlocked, engaged position into a locked position which locks the dock connector 4600 to the reservoir dock 6050 and forms electrical and control signal connections with the reservoir dock 6050. When the dock connector 4600 reaches the locked position, the retaining portion 4665 is rotated over the annular side wall 6920 and behind the retaining wall 6930 provided to the locking and contact assembly 6900 which prevents the dock connector 4600 from being pulled axially outwardly from the reservoir dock 6050. Also, the contacts 4667 along the retaining portion 4665 are rotated into engagement with respective spring arms 6956 of the contact 6955 provided to the locking and contact assembly 6900 which forms the electrical and control signal connections with the reservoir dock 6050.

Further, when the dock connector 4600 reaches the locked position, the one bump 4644 rotates within the closed, elongated recess 6922 and the other bump 4644 rotates out of the open-ended recess 6924 and into an adjacent open-ended recess 6926. Such engagement of the bumps 4644 within respective recesses provides retention, provides alignment features, and provides tactile feedback during engagement. In addition, the locking and contact assembly 6900 may include a stop wall 6935 (see FIG. 70) arranged to engage the locking and contact assembly 4660 of the dock connector 4600 when the dock connector 4600 reaches the locked position to prevent further rotation of the dock connector 4600, e.g., see FIG. 74.

In this example, connection of the dock connector 4600 with the reservoir dock 6050 is configured so that the pneumatic connection is completed prior to the electrical and mechanical connections. In another example, the electrical, pneumatic and mechanical connections may be formed simultaneously, either when the dock connector is rotated into the locked position, or by removing the rotational functionality from the connection.

To allow removal of the air delivery conduit 4170 from the reservoir dock 6050, the dock connector 4600 can be rotated in a counter-clockwise direction from the locked position into the un-locked, engaged position. This rotates the locking and contact assembly 4660 of the dock connector 4600 into the recess 6940 provided by the locking and contact assembly 6900. Such rotation disengages the dock connector 4600 electrically from the reservoir dock 6050 and allows the dock connector 4600 to be pulled outwardly away from the reservoir dock 6050 for disengagement.

Straight Plug-In Connection and Intermediate Component

FIGS. 110 to 133 illustrate an alternative example of engagement between the dock connector 4600 of air delivery tube 4170 and the humidification tub 6100. The arrangement involves a different configuration of the intermediate component 9700 for connecting the air delivery tube 4170 to the reservoir dock 6050 and the water reservoir 6100, as best seen in FIGS. 116-120. In this example, the intermediate component 9700 is removably coupled to the reservoir dock 6050 and is configured to pneumatically connect the water reservoir 6100 to the air delivery tube 4170 so that the pressurized flow of air that has been humidified in the water reservoir 6100 can be delivered from the water reservoir 6100, via the intermediate component 9700, to the air delivery tube 4170. Also, in this example, the intermediate component 9700 is configured to also releasably mechanically/lockingly connect to the air delivery tube 4170, which locates and releasably retains the air delivery tube 4170 to the reservoir dock 6050. Further, the arrangement is such that, whilst the air delivery tube 4170 is mechanically locked and pneumatically engaged with the intermediate component 9700, it can also form an electrical connection with the reservoir dock 6050. This electrical connection provides electrical power, information and control signals to the heating element and transducers associated with the air delivery tube 4170. Each two of the following connections; locking mechanical engagement, the pneumatic engagement and the electrical engagement can be effected sequentially or substantially simultaneously. If the engagements are effected sequentially, the specific order in which they are effected can vary. In one example, during the connection of the air delivery tube to the intermediate component, the pneumatic engagement me be effected first, followed by the substantially simultaneous engagement of the mechanical/locking and the electrical engagements. In another example, the locking mechanical engagement, the pneumatic and the electrical engagement can be effected substantially simultaneously upon connecting the air delivery tube to the intermediate component.

In the example described above in relation to FIGS. 43-78, the dock connector 4600 pneumatically seals with the intermediate component 6700 and mechanically connects (locks) with the reservoir dock 6050. In contrast in this later example shown in FIGS. 110 to 133, the dock connector 4600 of the air delivery tube 4170 forms both a pneumatic seal and a mechanical (locking) connection with the intermediate component 9700 in the example of FIGS. 110-133. By combining the pneumatic and mechanical connections into one component, the dimensional tolerances can improve, which may make the dock connector 4600 more reliable and easier to manufacture, and may also allow reduction in the size of the dock connector 4600.

Intermediate Component

As shown in FIGS. 110, 112, 113, and 115A, the intermediate component 9700 is provided to, and mechanically engaged with, the dock outlet 6090 of the reservoir dock 6050 to pneumatically connect the water reservoir 6100 to the air delivery tube 4170 and mechanically connect the air delivery tube 4170 to the reservoir dock 6050. In the illustrated example, the intermediate component 9700 is removably coupled to the reservoir dock 6050 so that the intermediate component 9700 can be disassembled for cleaning, sterilization and/or replacement, e.g., for multi-patient multi-use (MPMU) applications.

As shown in FIGS. 113 and 116-120, the intermediate component 9700 comprises a tubular portion 9705 including an inlet end 9710 and an outlet end 9720. The inlet end 9710, best shown in FIG. 120, is provided with an inlet seal 9715 adapted to interface with the water reservoir 6100, and the outlet end 9720 is adapted to interface with the air delivery tube 4170. The tubular portion 9705 also comprises retention and alignment features structured and arranged to align the intermediate component 9700 with the reservoir dock 6050 and provide a removable, non-rotatable connection with the reservoir dock 6050. In addition, the tubular portion 9705 comprises a port 9730 (best shown in FIG. 120), e.g., for communicating with a sensor (e.g., pressure sensor) and/or a microphone. In the illustrated example, the port 9730 is provided with a port seal and/or membrane 9735 to provide a sealing interface and/or cover between the port 9730 and a chassis opening 7380 (see FIG. 115C3) associated with the sensor and/or microphone. In an alternative example, the port 9730 may not include a port seal or membrane. Further, the intermediate component 9700 comprises retention features structured and arranged to provide a removable connection with the dock connector 4600 of the air delivery tube 4170.

In the illustrated example (e.g., see FIG. 120), the tubular portion 9705 (including the inlet end 9710, the outlet end 9720, and retention and alignment features) comprise a first part or base mold constructed of a relatively rigid material (e.g., thermoplastic polymer (e.g., PC, ABS)) and the inlet seal 9715 and the port seal 9735 comprise a second part or overmold constructed of a relatively soft material (e.g., thermoplastic elastomer (TPE) or silicone) that is provided (e.g., by overmolding) to the first part. The spatial separation of the soft components from the remaining hard material components of the intermediate component 9700 in FIG. 120 is only for illustrative purposes—in practice the soft material components can be permanently attached to respective rigid components and the configuration of FIG. 119 could be an integral intermediate component 9700 that cannot be dissembled into the individual components shown in FIG. 120.

In the illustrated example, the inlet end 9710 and inlet seal 9715 thereof are arranged at an angle to the outlet end 9720, e.g., the axis of the opening at the inlet seal 9715 is arranged at about 90° with respect to the axis of the opening at the outlet end 9720 (see FIG. 119). However, it should be appreciated that other suitable angles are possible, e.g., the axis of the inlet seal 9715 is arranged at about 45° with respect to the axis of the outlet end 9720.

When the water reservoir 6100 is coupled to the reservoir dock 6050, the inlet seal 9715 of the intermediate component 9700 is structured and arranged to engage and provide a face seal against a contact surface along the outlet end of the outlet tube 6130 (or outlet) of the water reservoir 6100 (see FIGS. 131 and 132). Such engagement seals the outlet flow path that allows humidified air to flow out of the water reservoir 6100 and into the intermediate component 9700 for delivery to the air delivery tube 4170. As illustrated, the inlet seal 9715 may comprise a bellows-type arrangement that is resiliently compressible to provide a certain degree of decoupling between the intermediate component 9700 and the water reservoir 6100.

In an alternative embodiment, the soft and/or flexible material seal between the outlet tube 6130 (or outlet) of the water reservoir 6100 and the intermediate component 9700 may be an integral part of the outlet tube 6130, or may be a sealing portion independent from either the outlet tube 6130 or the intermediate component 9700.

The outlet end 9720 (e.g., see FIG. 115C3) may comprise an ISO taper, e.g., 22 mm outer diameter ISO taper, for coupling to the air delivery conduit 4170.

In regards to retention and alignment features to align and retain the intermediate component 9700 to the reservoir dock 6050, the intermediate component 9700 includes a resilient pinch arm 9740 (e.g. see FIGS. 116-118), i.e., a cantilevered spring arm. The spring or pinch arm 9740 may include a barbed end or tab 9745 structured to provide a snap-fit connection with a locking member, e.g., cross-bar 9750, provided within the cavity of the reservoir dock 6050 (see FIGS. 112 and 114). The intermediate component 9700 may also include a guide rail 9760 (along a lower side of the intermediate component 9700) and a guide rib 9761 (along a forward, upper side of the intermediate component 9700) structured and arranged to assist in correct alignment and insertion of the intermediate component 9700 into the reservoir dock 6050 by engagement with corresponding guide slots 9755 extending into the cavity of the reservoir dock 6050 (e.g., see FIGS. 114, 115B, 116, 117).

Further, the intermediate component 9700 includes a flange 9770 (e.g. see FIG. 116) arranged between the inlet end 9710 and the outlet end 9720 to assist in locating and/or positioning the intermediate component 9700, and more particular limiting the insertion depth of the intermediate component 9700 in the reservoir dock 6050. Flange 9770 does that by abutting a wall provided to the reservoir dock 6050, e.g., flange acts as a stop during insertion as shown in FIGS. 115C3 and 115E. As shown in FIGS. 115D, 115E, and 120, one or more bumpers 9775 (e.g., constructed of thermoplastic elastomer ((TPE) or silicone) can be provided to soften abutment of the flange 9770 with the dock wall during insertion, and absorb vibrations in use. Apart from minimising the vibration of the intermediate component 9700, the flexible nature of the bumpers ensures that, once they are depressed, there is a resultant spring force that pushes backwards the barbed tab 9745 and ensures that the tab is in a constant locking engagement with the cross-bar 9750. This minimises any vibrations in the locking engagement between barbed tab 9745 and the cross-bar 9750, as well as the likelihood of disengagement. In the illustrated example, a first bumper 9775 is provided to an upper side of the intermediate component 9700, and a second bumper 9775 is provided to a lower side of the intermediate component 9700 (see FIGS. 115D and 115E). In an example, the bumpers 9775 may be attached to the dock wall or overmolded to the tubular portion 9705 along with the inlet seal 9715 and the port seal 9735 (see FIG. 120).

In regards to retention features to retain the dock connector 4600 of the air delivery tube 4170 to the intermediate component 9700, the intermediate component 9700 includes a part-annular side wall 9790 (see FIG. 120) that projects outwardly from the flange 9770 along the outlet end 9720. As illustrated in FIG. 120, the outlet end 9720 and the part-annular side wall 9790 cooperate to form an annular channel 9780 for receiving the air delivery tube 4170. Each of the opposing inner sides of the part-annular side wall 9790 includes a hole or recess 9792 adapted to receive a respective retaining bump 4644 (see FIG. 123) provided to the dock connector 4600 of the air delivery tube 4170 during engagement. In the illustrated example, a gap is provided in the part-annular side wall 9790 (along a superior side thereof—see FIG. 120) to accommodate and facilitate the electrical connection of the dock connector 4600 of the air delivery tube 4170.

Also, the intermediate component 9700 includes a lower tab 9795 (e.g. FIG. 120) that projects outwardly and downwardly from the part-annular side wall 9790 along a portion of the perimeter of the part-annular side wall 9790 (along an inferior side thereof). The lower tab 9795 may act as a finger or push tab to facilitate insertion or retraction of the intermediate component 9700 into/from the reservoir dock 6050. In addition, the lower tab 9795 may be configured and arranged to cover or hide one or more fasteners 9799 (e.g., (screws) or edges between outer shroud and chassis components of the integrated RPT device and humidifier 6000 (see FIGS. 110 and 113).

When the intermediate component 9700 is inserted into the dock opening 6091 of the reservoir dock 6050, the intermediate component 9700 is oriented to engage its guide rail 9760 and guide rib 9761 with respective guide slots 9755 which correctly aligns and guides the intermediate component 9700 into an operative position (e.g., see FIG. 113). Also, the dock opening 6091 and the part-annular side wall 9790 of the intermediate component 9700 include non-circular profiles to facilitate correct orientation of the intermediate component 9700 during insertion.

The dimensions and the interaction between the intermediate component 9700 and the reservoir dock 6050 may also be so arranged that the dock opening 6091 of the reservoir dock 6050, which opening receives the intermediate component 9700, may be of a cross-section that is slightly larger than that of the intermediate component 9700 (e.g., see FIG. 115C1). Closer to the end of the insertion path (e.g., see FIG. 115C2), however, there may be one or more bumpers, e.g. bumper 9751 and/or bumper 9752, providing elevation or bumper point(s) that elevates an interior edge, or surface, 9758 of the intermediate component 9700 (e.g., along the pinch arm 9740 and guide rail 9760) so that the entire front end of the intermediate element 9700 is lifted. Because of that, the port seal 9735 may be moved into, or be made ready for, a sealing engagement with chassis opening 7380. Further insertion of the intermediate component can then bring a portion of the intermediate element into an abutment engagement with a respective portion of the chassis opening, preventing further insertion. At this point the port seal 9735 of the port 9730 is moved into the sealing engagement with the chassis opening 7380 (e.g., see FIG. 115C3), or is arranged to preserve the sealing engagement, if such an engagement had already been formed. As shown in FIG. 115C, the tab 9795 may include a rib or bumper 9753 providing an additional elevation or bumper point arranged to interface with the dock. The above described arrangement would minimise the friction during insertion of the intermediate element into the dock opening 6091, whilst still ensuring the sealing engagement between the port seal 9735 and the chassis opening 7380 in the engaged configuration. Because of the large forces that may be applied to the intermediate element 9700 during use, more than one bumper points may be used (such as elevation points at bumpers 9751 and 9753, or elevation points at bumpers 9751, 9752 and 9753) for increased stability. The inclusion of such multiple support/elevation points may help ensuring a robust and consistent seal at 9730 even where the patient may pull on the tube during therapy. Additionally, the robust support of the intermediate element enables easier attachment and removal of attached tubes to the intermediate element.

When the intermediate component 9700 reaches an operative position, the barbed end or tab 9745 of the spring or pinch arm 9740 is configured and arranged to engage under and behind the cross-bar 9750, e.g., see FIG. 112. The barbed end 9745 and/or the cross-bar 9750 may include a taper to facilitate engagement into the operative position. In an example, the engagement of the spring or pinch arm 9740 with the cross-bar 9750 may provide sensory feedback, e.g., audible click, to indicate correction connection. This snap-fit connection releasably secures the intermediate component 9700 to the reservoir dock 6050. To disengage the intermediate component 9700, the spring or pinch arm 9740 can be manually depressed towards the back of the reservoir dock 6050 (e.g., with or without a tool). Such pressure resiliently flexes the spring or pinch arm 9740 and barbed end 9745 into an unlocked position, i.e., where barbed end 9745 is moved out of engagement with the cross-bar 9750 to allow the intermediate component 9700 to be removed from the reservoir dock 6050.

Once the intermediate component 9700 is inserted and locked into the dock opening 6091 of the reservoir dock 605, the cooperating retention and alignment features provided by the intermediate component 9700/reservoir dock 6050 provides a removable, non-rotatable connection of the intermediate component 9700 to the dock outlet 6090 of the reservoir dock 6050. Also, once connected, the spring or pinch arm 9740 of the intermediate component 9700 is lockingly engaged within the cavity of the reservoir dock 6050, e.g., to prevent removal of the intermediate component 9700 when the water reservoir 6100 is received in the reservoir dock 6050.

When the intermediate component 9700 is connected to the dock outlet 6090 of the reservoir dock 6050, the inlet seal 9715 thereof protrudes into the cavity of the reservoir dock 6050 to allow engagement with the outlet tube 6130 (or outlet) of the water reservoir 6100 (see FIG. 112 and FIG. 131). Likewise, the outlet end 9720, along with the part-annular side wall 9790 and holes 9792 thereof, extends within and/or protrudes out of the cavity of the reservoir dock 6050 to allow engagement with the air delivery tube 4170, e.g., see FIGS. 110 and 115A. Further, the port 9730 and port seal 9735 thereof, are oriented, e.g., upwardly as shown in FIG. 115C3, to interface with the chassis opening 7380 associated with the sensor and/or microphone.

Electrical Connection

As shown in FIGS. 110, 115A, 121, and 122, an electrical contact assembly 9950 is provided to the dock outlet 6090 of the reservoir dock 6050 to electrically connect the reservoir dock 6050 to the air delivery tube 4170 and form electrical (both power and control signal) connections.

As best shown in FIGS. 121 and 122, the contact assembly 9950 is supported by the reservoir dock 6050 along a superior side of the dock opening 6091 at the dock outlet 6090 of the reservoir dock 6050. The contact assembly 9950 is in communication with electrical power and electrical signalling within the reservoir dock 6050, e.g., the PCBA 7600. As illustrated, the contact assembly 9950 includes a support member 9952 and a plurality of contacts 9955, e.g., four contacts, supported by the support member 9952. Each of the contacts 9955 can comprise a spring arm 9956 (as best seen in FIG. 122) that is biased away from the support member 9952. In use, when the dock connector 4600 of the air delivery tube 4170 engages with the reservoir dock 6050, the spring arms 9956 will resiliently deflect during engagement with the dock connector 4600 to maintain contact with respective contacts 4667 of the dock connector 4600. The contact assembly 9950 also includes an electrical connector 9958, e.g., flexible circuit board (FCB), flexible printed circuits (FPC) and/or flexible flat cables (FFC), to electrically connect the contacts 9955 to the PCBA 7600 (see FIG. 122).

As shown in FIGS. 110 and 115A, an external housing or outer shroud 8050 (enclosing the chassis assembly 7300 and reservoir dock 6050) provides a cover or enclosure for the contact assembly 9950, and forms a socket or opening 9980 leading to the contacts 9955 (female connector) for engagement with respective contacts of the dock connector 4600 (male connector).

Dock Connector

As shown in FIGS. 110-111, the dock connector 4600 of the air delivery tube 4170 is structured to form a pneumatic and mechanical connection with the intermediate component 9700 and form an electrical connection with the contact assembly 9950 provided to the reservoir dock 6050.

In the illustrated example, the dock connector 4600 includes a tubular base portion 4640 and a contact assembly 4661 provided to the base portion 4640 (see FIG. 110).

As shown in FIGS. 123-126, the tubular base portion 4640 includes a radial lip seal 4645 that protrudes into the inlet opening of the base portion 4640. The radial lip seal 4654, in its relaxed, undeformed shape, provides an internal diameter that is smaller than the external diameter of the outlet end 9720 (FIG. 115A) of the intermediate component 9700 with which the dock connector pneumatically engages. For example, the internal diameter provided by the radial lip seal 4645 may be less than about 22 mm (e.g., about 19-21 mm or less) for use with an outlet end 9720 comprising a 22 mm outer diameter ISO taper. In use, the radial lip seal 4645 is structured to resiliently deform upon engagement with the outlet end 9720 of the intermediate component 9700 so as to provide a pneumatic connection with the intermediate component 9700, e.g., radial lip seal 4645 forms a gas tight seal around and against the exterior surface of the outlet end 9720 of the intermediate component 9700. As best shown in FIG. 125, the radial lip seal 4645 extends at an angle towards the interior of the base portion 4640 to provide a lead in for aligning and engaging the dock connector 4600 with the intermediate component 9700. Also, a stop surface 4647 (see FIG. 125) within the base portion 4640 provides a stop to prevent the intermediate component 9700 from being inserted further into the dock connector 4600.

A tapered protrusion 4642 protrudes outwardly from the base portion 4640 (see FIG. 123) adjacent the contact assembly 4661. The tapered protrusion 4642 provides a thumb and/or finger grip to facilitate manual manipulation and connection of the dock connector 4600 with the intermediate component 9700 and the contact assembly 9950 provided to the reservoir dock 6050. As shown in FIG. 111, the tapered protrusion 4642 may include an alignment marking that is configured and arranged to align with an alignment marking provided to the reservoir dock 6050 when the air delivery tube 4170 is connected to the reservoir dock 6050, to ensure correct alignment and proper connection of the dock connector 4600 of the air delivery tube 4170 to the reservoir dock 6050 in use.

Further, as best shown in FIG. 123, the base portion 4640 includes a resilient retaining bump 4644 on each of the opposing sides of the base portion 4640. As described below, the retaining bumps 4644 are structured and arranged to interact with respective holes 9792 provided to the intermediate component 9700 during engagement, so as to retain the dock connector 4600 in operational engagement with the intermediate component 9700 and, thus, with the entire RPT device 6000.

As shown in FIG. 123, the contact assembly 4661 (lead frame) includes a support portion 4665 and a plurality of contacts 4667, e.g., four contacts, included along a front side of the support portion 4665. As illustrated, the support portion 4665 includes a step-shaped configuration to support the contacts 4667 in spaced relation from the base portion 4640. The contacts 4667 are arranged to engage with respective contacts 9955 provided to the contact assembly 9950 on the reservoir dock 6050 to form electrical and control signal connections with the reservoir dock 6050. In the illustrated example, the contacts 4667 are arranged as a male connector configured to form the electrical and signal connections when inserted into engagement with the contacts 9955 arranged as a female connector on the reservoir dock 6050, i.e., straight or direct plug-in connection. The support portion 4665 provides an electrical connector to electrically connect the contacts 4667 to respective wires running along the air delivery tube 4170 and/or circuit elements.

As shown in FIG. 123, the tracks of the contacts 4667 are elevated (spaced away from the main body of the cuff) and extend in an axial direction which allows them to initiate and maintain the electrical connection when the dock connector 4600 is inserted into the socket 9980 in which the contacts 9955 are arranged. However, it should be appreciated that the support portion and/or the contacts may have alternative configurations and arrangements, e.g., depending on the interface arrangement or connection mechanism provided at the dock outlet 6090 of the reservoir dock 6050.

In the illustrated example, as shown in FIG. 126, the dock connector 4600 may comprise a base assembly 4680 (including a base 4682 and a cover 4684) that supports the contact assembly 4661 (lead frame). In an example, the contact assembly 4661 may first be engaged or interlocked with the base 4682, and then the cover 4684 may be clipped onto or otherwise engaged with the base 4682 to securely support and retain the contact assembly 4661 in an operative position. The base assembly 4680 is constructed of a relatively rigid material (e.g., thermoplastic polymer (e.g., PP, PC, ABS)) and an overmold 4690 constructed of a relatively soft material (e.g., thermoplastic elastomer (TPE) or silicone) is provided (e.g., by overmolding) to the base assembly 4680. As illustrated, the relatively rigid base assembly 4680 may form the structural shape for the tubular base portion 4640, the tapered protrusion 4642, and resilient retaining bumps 4644 while the relatively soft overmold 4690 forms the soft exterior for the tubular base portion 4640 and the tapered protrusion 4642 and forms the radial lip seal 4645.

Engagement of Dock Connector with Reservoir Dock

FIGS. 110-111 and 127-130 illustrate engagement of the dock connector 4600 of the air delivery tube 4170 with the reservoir dock 6050. As shown in FIG. 110, the dock connector 4600 is oriented to align its contact assembly 4661 with the socket 9980 leading to the contact assembly 9950 on the reservoir dock 6050. The dock connector 4600 is then pushed axially towards the reservoir dock 6050 so that the outlet end 9720 of the intermediate component 9700 extends into the opening of the base portion 4640 and the radial lip seal 4645 engages and resiliently deforms against the exterior surface of the cylindrical outlet end 9720. The radial lip seal 4645 of the dock connector 4600 engages and slides along the exterior surface of the outlet end 9720 of the intermediate component 9700 as the dock connector 4600 is pushed further towards the reservoir dock 6050 until it reaches a locked position, wherein the contact assembly 4661 extends into the socket 9980 to engage the contacts 4667 with respective spring arms 9956 of the contacts 9955 which forms the electrical and control signal connections with the reservoir dock 6050 (see FIGS. 111 and 129-130).

Moreover, when the dock connector 4600 reaches the locked position, the base portion 4640 of the dock connector 4600 is received within the channel 9780 formed by the intermediate component 9700 and the retaining bumps 4644 are configured and arranged to engage within respective holes 9792 provided to the part-annular side wall 9790 of the intermediate component 9700 to releasably retain the dock connector 4600 in the locked position under operational pressure (see FIGS. 127-128). Such engagement of the retaining bumps 4644 within respective holes 9792 may provide tactile feedback during engagement. In the locked position, the dock connector 4600 is pneumatically and mechanically engaged with the intermediate component 9700 and electrically connected to the electrical contacts of the reservoir dock 6050.

Also, as shown in FIGS. 123, 125 and 126, the dock connector 4600 may include one or more internal ribs 4648 configured to engage along the exterior surface of the outlet end 9720 of the intermediate component 9700 to help locate and align the dock connector 4600 with respect to the intermediate component 9700.

In an example, the forward end of the base portion 4640 may engage the flange 9770 of the intermediate component 9700 and/or a stop surface 9647 within the base portion 4640 may engage the free end of the outlet end 9720 of the intermediate component 9700. The abutment prevents the dock connector 4600 from inserting further into the socket 9980 and the intermediate component 9700 and acts as a stop during insertion (see FIGS. 127-130).

In an example, connection of the dock connector 4600 with the reservoir dock 6050 is configured so that the pneumatic connection is completed prior to the electrical and mechanical connections. In an example, the electrical and mechanical connections may be formed simultaneously following the pneumatic connection, or the electrical and mechanical connections may be formed in series following the pneumatic connection. In another example, the pneumatic, electrical, and mechanical connections may be formed simultaneously when the dock connector is inserted into the locked position.

To remove the air delivery conduit 4170 from the reservoir dock 6050, the dock connector 4600 may be pulled outwardly away from the reservoir dock 6050 with sufficient force to release the retaining bumps 4644 from respective holes 9792.

Tube Identification Examples

FIG. 35A shows a schematic view of a dock and a tube connection in accordance with one form of the present technology. The dock outlet 6090 may include a contact assembly 6800 that can be coupled to a corresponding contact assembly 4172 of the tube 4170 via four connections. The dock outlet 6090 may be mechanically and electrically coupled to the tube 4170.

As shown in FIG. 35A, the contact assembly 6800 includes four connections that are coupled to processing circuitry, e.g., PCBA 7600. Two of the connections (Heater+ and Heater−) are coupled to a heater control circuit and two of the connections (+SENSOR and −SENSOR) are coupled to a sensing circuit. In some examples, the +SENSOR and −SENSOR connections may be coupled to an NTC sensor. In some examples, the sensing circuit may also be connected to the connections (Heater+ and Heater−). The heater control circuit and the sensing circuit may be included in the humidifier, e.g., PCBA 7600.

The heater control circuit may supply power to heating element in the tube 4170 via a switch (e.g., a transistor). The heater control circuit may control the duration, voltage, and/or frequency and/or period of Pulse Width Modulation (PWM) signal supplied to the heating elements in the tube 4170.

The sensing circuit may be configured to receive signal(s) from a transducer (e.g., negative temperature coefficient (NTC) thermistor) disposed in the tube 4170, indicative of the operation of the heating elements in the tube 4170. The transducer may be disposed at the mask proximal end) of the tube.

For example, the sensing circuit may measure voltage and/or current of the transducer to determine the operating characteristics (e.g., temperature) of the heating elements. The heater control circuit may control the heating elements based on the signals received by the sensing circuit and the settings sets for the heating tube 4170. Other sensors disposed anywhere in the tube, i.e., humidity sensors, may also be connected in a similar way.

The sensing circuit may automatically identify the type of tube 4170 connected to the dock 6050. The type of tube that is connected to the dock 6050 may be determined by the sensing circuit based on unique electrical characteristic(s) provided by active and/or passive components in the tube 4170 via one or more of the four electrical connectors 6805. Based on the indicated type of tube 4170 connected to the dock, a controller may change the operating parameter of the system. For example, different heating control settings may be provided for different tubes (e.g., non-heated tube, heated tube, tube with heat and moisture exchanger (HME), tube unknown). In some example, the settings may be modified based on the size of the identified air delivery tube (e.g., 15 mm, 19 mm), presence and type of HME, type of patient interface connected to tube, etc. The type of tube that is connected to the dock 6050 may be determined by the sensing circuit based on unique electrical characteristic(s) provided by active and/or passive components in the tube 4170 via one or more of the four connectors.

As shown in FIG. 35A, the tube 4170 includes four connections for coupling to respective four connections in the contact assembly 6800. The connections in the tube may be solid pins (as shown in FIG. 24A), but are not so limited. In some examples, the connections may be provided by, for example, leadframe terminals. In one example, when the tube 4170 is connected to the dock, solid pins in one of the devices connect to corresponding pogo pins in the other device (e.g., see FIG. 20J).

As shown in FIG. 35A, a first circuit element 8022 is coupled to two pins in tube 4170 and a second circuit element 8024 is coupled to two other pins in the tube 4170. While single circuit elements are shown in FIG. 35A, first and/or circuit elements may include a plurality of active and/or passive circuit elements.

The first circuit element 8022 may include the heater elements in the tube 4170 and/or one or more other elements. The first circuit element 8022 may represent the resistance of the heater elements.

The second circuit element 8024 may include a sensor in the form of a thermistor formed of a Negative Temperature Coefficient (NTC) material. The parameters of the second circuit element 8024 (e.g., resistance) may change with a change of tube temperature. The sensing circuit may be configured to sense the temperature of the tube 4170 by monitoring changes in the parameters of the second circuit element 8024.

FIG. 35B shows circuit diagram of the dock and tube connection in accordance with one form of the present technology. The first circuit element 8022 in FIG. 35A may be represented by two resistors 5R (with approximately 5 ohms) coupled to the Heater+ and Heater− connections. This is associated with the fact that the heating wire usually comprises one or more (usually two) copper wires connected sequentially to each other and having a total resistance of about 10 ohms. The combined length of wire extends from the dock coupling end of the tube to the mask coupling end of the tube and back to the dock coupling end of the tube. The second circuit element 8024 in FIG. 35A may be represented by a thermistor and two resistors 5R coupled to the NTC+ and NTC− connections. The thermistor in FIG. 35A may be selected based on the type of air tube. A 10 k thermistor may be provided in a 15 mm air tube, a 100 k thermistor may be provided in a 19 mm air tube, and an open circuit may be provided in a passive air tube.

The heating wires 8022 are usually distributed along the length of the tube and the sensor 8024 is usually positioned at the mask end of the tube. Thus, both the heating wires and the sensor connecting wires extend the length of the tube.

The first and second circuit elements may be used by the sensing circuit to identify the type of tube connected to the dock 6050. In some examples, unique electrical characteristic of one or more contact pins may be used to identify parameters of the tube. The different resistance values provided by the first and second circuit elements may allow for the control circuit in the humidifier to determine the type of tube that is connected and which control parameters to use for the operation of the system. The sensing circuit may measure the resistance of the first circuit element and/or the second circuit element to determine the type of tube. Alternatively, further electrical pins (in addition to the four pins illustrated in FIGS. 35 and 36) may be included in the dock connector 4600 of the air delivery tube 4170, which are associated with a unique characteristic (such as electrical resistance) and may be used to indicate parameters such as the type, as well as other characteristics associated with the tube.

As an example, the different type of tubes may include: (1) a 4-wire 15 mm heated tube may provide a Heater Wire resistance of 2×5R and a NTC resistance value at 25° C. is 10 K; (2) a 4-wire 19 mm heated tube may provide a Heater Wire resistance is 2×5R and NTC resistance value at 25° C. is 100 K; and (3) a passive non-heated tube may be provided with a standard ISO-taper.

Thus the detection of the connected tube type is performed by measuring the second circuit element (e.g., NTC) and the first circuit element (e.g., Heater Wire) resistance combinations (in cases (1) and (2) above), detecting the electrical characteristics of one or more independent pins or a combination of such, or detecting the open circuit on both pairs of connections (case (3) above).

The system may also be configured to automatically detect a single fault conditions in the connected active tube, for example short or open circuit on any of the four tube wires, as well as the non-legit value (partial crack) of the Heater Wire, as well as cross-short circuit between the tube wires.

Examples of the present technology provides not only for direct coupling of a tube to the dock, but also for an electrical adapter. While such an adaptor may allow the connection to the dock of different types of heated wire tube, its main purpose is to facilitate the coupling to the dock of a passive air tube capable of operating with or without HME passive humidifier at the proximal end. The two main applications for using such adapter are: (a) allowing the mechanical connection of passive air tubes to the dock and (b) providing the means for the system to detect the passive air tube.

FIG. 36 shows a schematic view of a dock and a tube connection in accordance with the above discussed form of the present technology. As shown in FIG. 36, the contact assembly 6800 of the dock may be coupled to a passive tube 4170 via an adapter 8020. The adaptor 8020 provides an electrical connection, which is generally not present in the passive tube 4170, to the contact assembly 6800 of the dock. In one example, the tube 4170 may provide a mechanical connection to the dock 6050 and the tube adaptor 8020 may provide the electrical connection. In some examples, the tube adaptor 8020 may also mechanically couple to the dock. FIGS. 24A-24B illustrate a mechanical connection of the tube 4170 and a tube adaptor 8020 in accordance with one form of the present technology.

In some examples, the adaptor 8020 may be part of a contact assembly. The adaptor 8020 may be manufactured as an integral part of the tube 4170 or be removable from the tube 4170. In this manner air tubes that do not have electrical components, such as heating elements and/or sensors, may be provided with circuit elements to identify the kind of air tube that is connected to the dock 6050.

In contrast to FIG. 35A including the first and second circuit elements 8022 and 8024 in the tube 4170, the example shown in FIG. 36 includes the first and second circuit elements 8022 and 8024 in the adapter. Only in this case these circuit elements do not represent the resistance of a heater wire and of a NTC sensor/transducer, but include simple resistors that are detected by the controller in order to identify the connection of a passive tube to the system. As shown schematically in FIGS. 24A-B, the first and second circuit elements 8022 and 8024 may be provided in a housing including the connections. The first and second circuit elements 8022 and 8024 may directly connect to the connections provided in the adaptor 8020. In one example, the first circuit element 8022 includes a single resistor which is directly coupled to two of the connections in the adapter of the tube, and the second circuit element 8024 includes a single resistor which is directly coupled to two other connections in the adapter of the tube. In some examples, the adaptor 8020 may be provided outside of the tube and/or surrounding the tube. In this example, the first and second circuit elements are provided on the external surface of the tube and/or the tube connector.

The first and second circuit elements in the adapter allow for the sensing circuit in the humidifier to determine the type of tube connected to the dock 6050. This is different from the example in FIG. 35A, where characteristics of circuitry including the heating element and/or the sensor (e.g., provided in the tube) are used to determine the type of type connected to the system. Because of that, the value of the first and second circuit elements in this example of a passive tube needs to be selected so that it is outside of the range of values that would be expected from first and second circuit elements of the active tube in FIG. 35A. As would be discussed below, the specific electrical characteristics (i.e., resistance) of the NTC element has to be considered in working environment where it may spread over a broad range of values.

FIG. 37 shows a schematic view of a tube NTC resistance variations over different temperatures for a 100 k thermistor (usually used with a 19 mm heated tube) and a 10 k thermistor (usually used with a 15 mm heated tube). The 100 k thermistor and a 10 k thermistor may correspond to the thermistor that may be included in the second circuit element 8024 shown in FIG. 35A. The present technology is based on using the resistor connected to NTC terminals of an adaptor, which is distinctly different from that of the real NTC resistances at legitimate areas of operation. As seen in FIG. 37, the area between approximately 27 Kohm and 51 K is not used by the 10 k and 100 k NTC during normal operation, so the resistor used in the tube (or adaptor as discussed below) can be selected to be at 36 K or thereabout. Accordingly, when a tube with an adaptor having a second circuit element 8024 resistance value of 36 k is connected, the system will know that the tube is not the 15 mm tube using the 10 k thermistor nor the 19 mm tube using the 100 k thermistor. Whilst such atypical value resistance was described above as indicating the use of a passive tube with an adaptor, the specific resistance of one or more electrical pins may be used to indicate a variety of other parameters associated with the tube or even the mask, in a tube-mask system. Such parameters may include the presence or absence of HME in the tube/mask, the type of mask attached to the tube (nasal or full face) etc.

To reduce the possibility of the false detection (in case, for example, when 15 mm heated tube is exposed to the sun and gets heated to 50° C. and then gets immediately connected to the dock), the first circuit element 8022 is used in the adapter, which connects the Heater+ and Heater− terminals together through the resistance of a predetermined value (e.g., approximately 1 Kohm). A 1 kohm resistance can conduct maximum 24 mA of current (at 100% PWM) which is only dissipating 0.6 W power but is enough to be reliably measured by dock subsystem circuit.

Using two circuit elements (e.g., resistors) as described above in the adapter practically eliminates the possibility of misdetection of the connected tube while keeping the system safe. Using the resistors provides for a low cost identification system with accurate identification. Other circuit elements (e.g., resistors, capacitors etc.) may be provided in parallels and/or series with the first and/or second circuit elements to provide characteristics that are distinct from characteristics of other circuits used for identification.

FIG. 38 shows a schematic view of a dock and a tube connection in accordance with another form of the present technology. The example shown in FIG. 38 is similar to the example shown in FIG. 36, but only uses a single circuit element (e.g., 36 K resistor) in the adapter to reduce the cost of goods in the adapter. In this example, in addition to reducing the number of circuit elements, the number of connections in the adapter are also decreased. The reliability of the detection may be somewhat diminished, as the combination of 36 K value of NTC and open circuit of the Heater wire may also represent the situation of either double fault in the tube (NTC partial crack on NTC wire+open circuit on heater wire) or the case of the contaminated NTC terminals with the passive tube connected mechanically via ISO taper.

FIG. 39 shows a dock and a tube connection in accordance with another form of the present technology. In this example, a part of the PWM which is provided to the heating elements, is "injected" into the NTC detection circuit. This signal is detected by the microcontroller via the comfort subsystem NTC measurement circuit. Because the detected signal is distinctly different from all standard modes of operation of other tubes discussed above, this example may present the best detectability. However, this configuration may be undesirable in some implementations because it uses the undesirable functional interaction between two different parts of the circuitry (+24 PWM heating and +3V3 NTC detection) that logically should not be functionally connected together.

While the above examples of the present technology have been described with reference to a four wire system, the examples are not so limited. The examples of the present technology may be applied to systems with other number of wires, e.g., two wires, three wires, or five or more wires. Also, whilst the above embodiments were mostly described with respect to detecting the type (size) of tube attached to the system, the variation in electrical parameter values described in relation to FIGS. 35-39, may be used to not only indicate various parameters associated with the tube (e.g. the type (heated/non-heated) and size (15 mm or 19 mm)) but also of parameters associated with the mask used. For example, the variation in electrical parameters may be used to indicate one or more of the following mask parameters; the type of the mask attached to the tube (nasal or full face), the mask size (small, medium, large), the presence or absence of HME in the tube or the mask etc.

Wire Cross-Talk

As noted above, the air delivery tube 4170 according to an example of the present technology may comprise four wires, e.g., two wires for heating elements and two wires for a transducer, e.g., negative temperature coefficient (NTC) thermistor used as a temperature sensor. It should be noted that NTC is only one of a plurality of different types of temperature sensors known to a skilled addressee.

An aspect of the present technology relates to reducing or eliminating cross-talk between wires, e.g., to enhance accuracy of the signal transmission provided by the NTC thermistor.

FIG. 40 shows a schematic view of a tube with a four wire circuit coupled to a dock in accordance with one form of the present technology. In the four wire circuit, resistors 9010 and 9012 represent resistance of the one or more heating element/s and resistors 9020 and 9022 represent the resistance of the wires coupled to a sensor 9030. FIG. 40 is a schematic representation and the fact that two set of resistors 910 and 912 are shown does not necessarily mean that there are two or more heater wires. A single continuous heating wire or more than two wires may also be used in the discussed heated tubes. For example, the two-wire arrangement shown in FIG. 40 has four connections formed between the dock and the tube. PWM and GND connections are coupled to the heating element/s and VH and VL are coupled to the sensor 9030. The capacitance elements C shown in FIG. 40 are not actual capacitors, but represent the distributed parasitic capacitive coupling between two wires (i.e. between the heater wire 9010 and the resistor wire 9020) located in close proximity.

For the heating element/s, the power is supplied via connections PWM and GND and may be regulated by a Pulse Width Modulator (PWM). The PWM signal creates an AC signal. Certain settings (e.g., pulse frequency) of the PWM signal may cause the heating element wires to move/vibrate (which can be audible) due to electromagnetics (EM). To prevent hearing the movement of the wires, the pulse frequencies of the PWM signal may be set at and/or above a predetermined value (e.g., at or above 20 KHz).

The sensor 9030 may be a transducer (e.g., a negative temperature coefficient (NTC) thermistor) disposed in the tube 4170 for measuring the heat in the tube 4170. As discussed above, the sensor 9030 may have different characteristics (e.g., nominal resistance values of 10 K or a 100 k) to identify different types of tubes. At room temperature the sensor 9030 may have a resistance value (e.g., tens of K Ohms) that is significantly larger than a resistance of wires (e.g., 5 Ohms) connected to the sensor. 9030.

As shown schematically in FIG. 42, voltage Vsense is provided to the sensor 9030. The voltage is provided by the microcontroller via a divider network comprising a first resistor RHigh and a second resistor RLow. The sensor 9030 is coupled with the two resistors RLow and RHigh so that, upon failure of one of the wires, the system can detect which wire failed. A DC voltage is applied to the divider network for detecting the operating parameters of the sensor 9030 and/or failure of one of the wires. The combination of measured voltages at the VLow and VHigh terminals would indicate to a skilled addressee whether an NTC wire is shortened with another NTC wire, or with a heater wire, and also with which exactly heater wire. For example, an NTC wire shortened with an NTC wire the microcontroller will measure a zero voltage difference. On the other hand, if the NTC wire has short-circuited with a PWM heater wire, the measured voltage difference will be larger than Vsense (the Vsense DC voltage is usually about 3.3V, whilst the PWM AC voltage is about 24V).

In operation, when the PWM pulse is turned on, the PWM wires are capacitively connected (see capacitors C in FIG. 40) to the wires of the sensor 9030. The AC signal penetrates through the parasitic (inherent) capacitors into the sensor 9030 wires. FIG. 41 shows a signal diagram of a PWM signal that may be applied to the heating elements (Signal (A) or (B)) and the portions of the PWM induced signal that may be observed in the sensing circuit (Signal (C)).

The signal at VH (V high) and VL (V low) points is provided to the microcontroller configured to subtract the V low from the V high. The difference between the V low and V high indicates the resistance of the sensor 9030. The microprocessor is configured to track the changes in resistance of the sensor 9030 due to changes in the temperature of the tube 4170 and determine operation setting for components of the system (e.g., heating elements in the tube 4170).

The probing of the sensor 9030 (e.g., by a microprocessor) may be timed at intervals that are not synchronized with the PWM signal. In some examples, the probing of the sensor 9030 is slower than the period of the PWM signal. In some instances, the probing period may be several seconds. The probing period may change depending on the circumstances. For example, in some instances the probing may be constant, whilst in others, a probing of several seconds may be used for the time periods when it is detected that there is no tube connected to the dock, however a shorter period, or even a continuous monitoring, may be used once it is detected that there is a tube connected to the device. As discussed above, the signal for probing the sensor 9030 is provided as a DC signal.

Because of the slow probing of the sensor 9030, the sensing circuit can catch different portion of the fast PWM induced signal (see graph (c) of FIG. 41). The induced signal may be 10-20 percent of the voltage of the sensor 9030 signal. The setting of the PWM signal and changes in the PWM signal may affect the accuracy of the measurement based on the voltage of the sensor 9030 signal. The temperature error caused in the sensing circuitry may be up to 5 degrees (in a measured range of 5 to 40 degrees).

To address these issues, in accordance with one form of the present technology, high pass electrical filters are provided between the NTC output Vhigh and Vlow points and ground, to remove the high frequency components of the signal (those of PWM frequency and above) in the circuitry including the sensor 9030. As shown in FIG. 42, a first high pass filter HPF1 is coupled to the RHigh resistor and ground, and a second high pass filter HPF2 is coupled to the Rlow resistor and ground. Alternatively, or in addition to the above, low pass electrical filters (e.g., LPF3 and/or LPF4) can be provided between the NTC output Vhigh and Vlow points and the microcontroller. As shown in FIG. 42, a first low pass filter LPF1 is coupled to the RHigh resistor and connection VH-Lpf and a second low pass filter LPF2 is coupled to the Rlow resistor and the connection VL-Lpf. Each filter may be formed as a single component (i.e., a capacitor) or a combination of active (i.e., operational amplifiers) and/or passive (resistor/capacitors) electronic components. For example, when a large capacitor (tens of nF) is used for each of LPF1 and LPF2, the cross-talk between the wires of the heated tube and the sensor is largely mitigated even without the use of LPF3 and/or LPF4. However, if smaller capacitors (i.e., tens of nF) are used instead for LPF1 and LPF2, these two filters are now more useful for removing external interferences of larger frequencies, but may not mitigate the cross-talk efficiently. This can be compensated with the introduction of LPF3 and LPF4 which may be configured to filter frequencies near the frequencies of the pulse width modulated power signal and frequencies higher than the frequencies of the pulse width modulated power signal.

The sensor 9030 supply (for the divider) Vsense can be turned on and off to detect if the tube 4170 connected. When the tube 4170 is not connected, the supply to the sensor 9030 can be turned off. Turning off the supply may reduce corrosion in the connections.

In accordance with one form of the present technology, the sensor 9030 supply (for the divider) Vsense is generally turned off, but is turned on and off periodically to detect if the tube 4170 is connected. When it is detected that the tube 4170 is not connected, the supply to the sensor 9030 is turned off again. Turning off the supply may reduce corrosion in the connections in the humid environment in which they may be operating. During the short periods the tube is intermittently turned on, the check on whether the tube has been attached, is conducted by probing Vhigh and Vlow. If Vhigh=Vsense and Vlow=0, the tube is not connected. If the tube has been connected, because of the voltage divider defined by RH and RL, Vhigh and Vlow change to respective voltages that are within a predetermined range. When the tube is detected, Vsense is switched on permanently and VH and VL are used to measure the temperature.

The turning on and off of Vsense may be controlled to happen at intervals that are greater than the period of the PWM signal applied to the heating elements. In one example, the frequency of the PWM signal may be 20 KHz (T=50 μs) and the Vsense is turned on and off every 1, 2, or 3 seconds (1 to 0.333 Hz). If other, including non-periodical, time ranges are employed for the intermittent turning on of Vsense, to effect the probing for the connection of the heated tube, they are likely to be of similar frequency range. Therefore, the filter may be configured to filter out the cross-talk (20 KHz), but keep the 1 second transients from the on and off operation, and any fast changes in the sensor 9030 (e.g., an open window). In one example, the filter may be configured to filter out everything above several Hz. In other examples the filter may filter everything above any one chosen frequency in the frequency range of 1 to 100 Hz.

5.6.2.3 Water Level Indicator

The water reservoir 6100 may comprise a water level indicator. In some forms, the water level indicator may provide one or more indications to a user such as the patient 1000 or a care giver regarding a quantity of the volume of water in the water reservoir. The one or more indications provided by the water level indicator may include an indication of a maximum of a predetermined volume of water, as well as any portions thereof, such as 25%, 50% or 75%, or volumes such as 200 ml, 300 ml or 400 ml.

In an example, a heating element may be internally suspended within the water reservoir 6100, e.g., heating element provided within chamber of water reservoir 6100 to directly heat water rather than heat water via heat transfer through conductive portion 6150 of water reservoir 6100. In an example, the heating element may be vertically suspended by the reservoir lid 6114.

In the above example, the heating element may be subdivided or partitioned into vertically distributed zones/sections. Each of the zones/sections may be controlled independently to independently switch on/off and control the temperature of each of the zones/sections and to deactivate when not heating (i.e., when water level has dropped and an upper portion of the heater is no longer in contact with water). This can lead to an efficient use of energy to only heat the zones/sections that are in contact with water. Also, each of the zones/sections may be associated with a respective sensor. The distribution in vertical direction of a number of sensors (such as NTC-type sensors) allows detecting the water level to provide an indication to the patient regarding a quantity of the volume of water in the water reservoir, e.g., without the patient having to directly view the water level in the water reservoir. Such arrangement may allow the use of a water reservoir having non-transparent side walls, e.g., non-clear plastic or metal side walls, as the water level does not need to be directly viewed through a side wall of the water reservoir.

In some cases, the heating element may include a PCB with printed resistive tracks. Such an arrangement allows for easy partitioning of the track, thus defining different heating zones. A vertically orientated distributed temperature sensor or a number of discrete sensors, may be used to indicate if a level is inside water or not.

5.6.2.4 Humidifier Transducer(s)

The humidifier 5000 may comprise one or more humidifier transducers (sensors) 5210 instead of, or in addition to, transducers 4270 described above. Humidifier transducers 5210 may include one or more of an air pressure sensor 5212, an air flow rate transducer 5214, a temperature sensor 5216, or a humidity sensor 5218 as shown in FIG. 5G. A humidifier transducer 5210 may produce one or more output signals which may be communicated to a controller such as the central controller 4230 and/or the humidifier controller 5250. In some forms, a humidifier transducer may be located externally to the humidifier 5000 (such as in the air circuit 4170) while communicating the output signal to the controller.

5.6.2.4.1 Pressure Transducer

One or more pressure transducers 5212 may be provided to the humidifier 5000 in addition to, or instead of, a pressure sensor 4272 provided in the RPT device 4000.

5.6.2.4.2 Flow Rate Transducer

One or more flow rate transducers 5214 may be provided to the humidifier 5000 in addition to, or instead of, a flow rate sensor 4274 provided in the RPT device.

5.6.2.4.3 Temperature Transducer

The humidifier 5000 may comprise one or more temperature transducers 5216. The one or more temperature transducers 5216 may be configured to measure one or more temperatures such as of the heating element 5240 and/or of the flow of air downstream of the humidifier outlet. In some forms, the humidifier 5000 may further comprise a temperature sensor 5216 to detect the temperature of the ambient air.

5.6.2.4.4 Humidity Transducer

In one form, the humidifier 5000 may comprise one or more humidity sensors 5218 to detect a humidity of a gas, such as the ambient air. The humidity sensor 5218 may be placed towards the humidifier outlet in some forms to measure a humidity of the gas delivered from the humidifier 5000. The humidity sensor may be an absolute humidity sensor or a relative humidity sensor.

5.6.2.5 Heating Element

As shown in FIGS. 6B, 20A and other figures, a heater plate 6080 is used to transfer heat to the water reservoir. In the illustrated example, the heater plate may form a part of the reservoir dock 6050, and may be located on or near the base of the reservoir dock. At least the top layer of the heater plate comprises a hard scratch resistant surface that may be formed, for example, of a nickel chrome alloy, stainless steel or anodised aluminium. The heater plate may transfer heat from a heating element. The heating element may comprise a heat generating component such as an electrically resistive heating track. One suitable example of a heating element is a layered heating element such as one described in the PCT Patent Application Publication No. WO 2012/171072, which is incorporated herewith by reference in its entirety.

FIGS. 34A to 34C show a heating assembly 6075 according to an example of the present technology. In the illustrated example, the heating assembly 6075 includes a heater plate 6080, a heating element 6085, and a thermal pad 6088 (e.g., thermo-conductive rubber or ceramic pad) arranged between the heater plate 6080 and the heating element 6085. The heating assembly 6075 may further comprise a support structure 6089 structured and arranged to support the heater plate/thermal pad/heating element at the bottom of the reservoir dock 6050. In the illustrated example, the support structure 6089 includes a peripheral resilient supporting member 6096 and a base plate 6097 to support the resilient supporting member 6096 at the bottom of the reservoir dock 6050. As illustrated, in addition to the resilient supporting member 6096 (e.g., constructed of an elastomeric material (e.g., silicone)), one or more support cones 6098 (e.g., see FIGS. 34A and 34C) or tubes (e.g., see FIGS. 103 and 104) may also be used to resiliently support the heater plate/thermal pad/heating element.

The thermal pad is preferably made by a pliable or compliant thermo-conductive material and is arranged between the heater plate 6080 and the heating element 6085 (e.g., engages or sticks (e.g., bonds) to both the heater plate and the heating element). In this arrangement, the thermal pad can fill the air gaps or spaces between heater plate 6080 and the heating element 6085, which enhances thermal conductivity from the heating element 6085 to the heater plate 6080. As both the heater plate 6080 and the heating element 6085 typically include planar surfaces made of a hard material, any small imperfections on the surfaces may cause air gaps between these two surfaces. Having the pliable layer between these surfaces helps with removing such air gaps and improving the thermal conductivity of the system.

FIGS. 81, 98, 100, and 103-109 show a heating assembly 6075 according to another example of the present technology. In the illustrated example, the heating assembly 6075 (e.g., see FIG. 103) includes a heater plate or wear plate 6080, a heating element or heater 6085, and a thermal pad 6088 (e.g., thermo-conductive rubber or ceramic pad) arranged between the heater plate 6080 and the heating element 6085 (see FIG. 103). The heating assembly 6075 further comprises a support structure 6089 structured and arranged to support the heater plate/thermal pad/heating element at the bottom of the reservoir dock 6050 (see FIG. 103).

The support structure 6089 includes a resilient sealing and supporting member 9500 and a base plate 9600 to support the resilient sealing and supporting member 9500 at the bottom of the reservoir dock 6050 (see FIG. 104). As described below, the resilient sealing and supporting member 9500 (e.g., constructed of an elastomeric material (e.g., silicone)) resiliently suspends the heater plate/thermal pad/heating element assembly within the reservoir dock 6050 so that the heater plate is be biased upwardly by the resilient sealing and supporting member 9500 against the conductive portion 6150 of the water reservoir 6100 when the water reservoir 6100 is inserted in the reservoir dock 6050. The bias keeps the heater plate 6080 and the conductive portion 6150 pressed against each other to enhance thermal conductivity between them.

In the illustrated example, the base plate 9600 (e.g., constructed of a plastic or thermoplastic polymer material) comprises a continuous interior base surface 9610 and a peripheral flange 9620 that extends upwards and outwards (directions applicable when the integrated RPT device and humidifier 6000 are in an operational configuration) from the base surface 9610. As best shown in FIG. 106, the peripheral flange 9620 is configured and arranged to extend up and over a base wall 8005 that forms an opening at the bottom of the integrated RPT device and humidifier 6000, and to form a removable or non-removable connection (e.g., via a plurality of connection stakes 9622—see FIG. 104) with an inner wall 6052 (see FIGS. 106, 108, 109) of the reservoir dock 6050. In the illustrated example, the exterior base surface 9612 of the base plate 9600 forms an outer, exterior surface of the integrated RPT device and humidifier 6000 (see FIG. 106).

In some examples, the resilient sealing and supporting member 9500 is laid down over a flat base surface 9610. In another example (see FIGS. 104 and 106), raised tracks 9615 may be provided to the base surface 9610 of the base plate 9600, which tracks 9615 are configured to align and laterally support at least the one or more resilient hollow tubes 9520 of the resilient sealing and supporting member 9500 on the base plate 9600. The resilient hollow tubes 9520 will be described in more detail further in the text. In some cases, tracks 9615 are configured to align and laterally support the entire resilient sealing and supporting member 9500 on the base plate 9600. Also, as described in more detail below, one or more drain holes or cut-outs 9625 (e.g., 9 drain holes as shown in FIG. 104) are provided along the perimeter of the peripheral flange 9620 to allow drainage of water that may collect in the base plate 9600 during use.

The resilient sealing and supporting member 9500 comprises a resilient peripheral lip 9510 and one or more resilient hollow tubes 9520 (e.g., hollow cylinders) distributed within the space bounded by the resilient peripheral lip 9510. In the illustrated example, the peripheral lip 9510 and the hollow tubes 9520 comprise a one-piece molded construction (of an elastomeric material (e.g., silicone)), e.g., with one or more intermediate connectors 9530 to interconnect the peripheral lip 9510 and the hollow tubes 9520. Also, a wire or cable guide 9540 can be provided to the peripheral lip 9510 to accommodate one or wires or cables that electrically connect the heater 6085 to the PCBA 7600.

When provided to the base plate 9600, the peripheral lip 9510 is configured to extend on the inner side of the peripheral flange 9620 in a substantially upward (with respect to the operation configuration of the device) direction (see FIG. 106), with some possible slight outward flaring in the upper portion of the flange. In an example, the peripheral lip 9510 may extend concentrically to the peripheral flange 9620 (see FIG. 103). Each of the hollow tubes 9520 includes one end supported by the base surface 9610 and an opposite end configured to engage the heater 6085 when the heating assembly 6075 is assembled to the reservoir dock 6050 (see FIG. 106). The resilient sealing and supporting member 9500 may be either removably, or permanently attachable to the base surface 9610 of the base plate 9600, e.g., by way of adhesive, over-molding, etc.

In the illustrated example, each of the hollow tubes 9520 includes an axis that is generally vertically oriented, i.e., generally perpendicular to the generally horizontally oriented and planar base surface 6882 of the base 6880. In the illustrated example, the resilient sealing and supporting member 9500 comprises 4 hollow tubes 9520, however it should be appreciated that more or less hollow tubes may be provided. In an example, each of the hollow tubes 9520 may include a height of about 7-8 mm, an internal diameter of about 7 mm, and a wall thickness of about 1 mm, however other suitable dimensions, which may depend on the number of cylinders used, are also possible.

The heater plate or wear plate 6080 (see FIG. 81) is arranged within an opening provided to a bottom wall 6053 of the reservoir dock 6050, which arranges the heater plate 6080 within the dock cavity for engagement with the conductive portion 6150 of the water reservoir 6100 in use. The heater plate 6080 (e.g., constructed (e.g., stamped) of a metallic material (e.g., stainless steel having uniform wall thickness of about 0.15 mm)) comprises a base 6880 and a skirt 6885 extending around the perimeter of the base 6880 (see FIGS. 103 and 106).

The base 6880 includes a first side that forms an exterior or base surface 6882 adapted to engage the conductive portion 6150 of the water reservoir 6100 in use. A second side of the base 6880 forms an interior surface 6884 engaged with the thermal pad 6088 (see FIG. 106). As illustrated, the base 6880 comprises a generally planar shape configured to extend substantially horizontally when the integrated RPT device and humidifier 6000 is in an operational configuration.

The skirt 6885 may be horizontal (a simple extension of the base 6880), but is preferably sloped or angled generally downwardly and generally outwardly with respect to the base 6880. The skirt can, thus, be formed by a single portion extending downwardly and outwardly from the base 6880. In the illustrated example, the skirt 6885 includes a vertical portion 6885*v* that extends substantially vertically with respect to the base 6880, which leads to a horizontal portion 6885*h* that extends in a substantially horizontal plane to that of the base 6880 (see FIGS. 103 and 106).

When assembled to the reservoir dock 6050 (with the water reservoir 6100 removed), the resilient sealing and supporting member 9500 resiliently supports the heater plate 6080 (along with the heater 6085 and the thermal pad 6088) such that the base 6880 protrudes through the opening in the bottom wall 6053 and the horizontal portion 6885$h$ of the skirt 6885 engages underneath the bottom wall 6053 which provides a hard stop to retain the heater plate 6080 within the opening (see FIG. 106).

More specifically, as best shown in FIG. 106, the heater 6085 and the thermal pad 6088 are arranged within a pocket of the heater plate 6080 formed by the base 6880 and the vertical portion 6885$v$ of the skirt 6885. One side of the heater 6085 is engaged with the hollow tubes 9520 within the boundaries of the peripheral lip 9510, and the opposite side of the heater 6085 is engaged with the thermal pad 6088 which engages the interior surface 6884 of the base 6880. Instead of all hollow tubes 9520 being engaged with the heater 6085, some or all of the supporting members (in this case—vertical hollow tubes 9520) may be engaged directly with the interior surface 6884 of the base 6880. Further, the peripheral lip 9510 of the resilient sealing and supporting member 9500 engages underneath the horizontal portion 6885$h$ of the skirt 6885 of the heater plate 6080. As a result of this configuration, the heater plate 6080 is supported in two ways, i.e., along its periphery (the horizontal portion 6885$h$) by the peripheral lip 9510, and along its central base 6880 by the hollow tubes 9520.

In an example, the thermal pad 6088 may include only one side that is sticky, e.g., thermal pad 6088 includes an adhesive on one side to stick to the heater 6085 and an opposite side that is not sticky that engages the heater plate 6080. A non-sticky thermal pad can also be used, as the hollow tubes 9520 can be designed to apply continuous pressure that keeps thermal contact between components within the thermal pad 6088. As a result, the thermal pad/heater may move within the pocket of the heater plate 6080, however even when moved, the heater plate/thermal pad/heater will remain supported by the hollow tubes 9520. As noted above, the thermal pad 6088 is configured to fill the air gaps or spaces between heater plate 6080 and the heating element 6085, which enhances thermal conductivity from the heating element 6085 to the heater plate 6080.

The resilient sealing and supporting member 9500 provides the heater plate/thermal pad/heater with a spring-like resistance to any downward pressure (which is in axial direction for the hollow tubes 9520) applied by the water reservoir 6100 to the heater plate 6080 when the water reservoir 6100 is inserted into the reservoir dock 6050. Such a resistance provides a constant upward spring bias to the heater plate 6080 that allows a good mechanical and thermal contact between the heater plate 6080 and the conductive portion 6150 of the water reservoir 6100 when the water reservoir is in its operating configuration. Such good mechanical and thermal contact a more efficient operation of the device.

The specific configuration of the vertically oriented hollow tubes 9520 supporting the heater plate 6080 ensures a more linear resilient response to downward pressure applied to the base 6880 of the heater plate 6080 by the inserted water reservoir 6100. This compares favorably to the case of a solid-structured resilient supporting members that, if depressed beyond a certain limit, may provide a very strong resistance to any further deflection of the heater plate 6080. Such strong resistance may cause a high friction and make insertion of a water reservoir 6100 difficult for the user.

FIGS. 105 and 106 show the heating assembly 6075 when the water reservoir 6100 is removed from the reservoir dock 6050, and FIGS. 107 and 108 show the heating assembly 6075 when the water reservoir 6100 is inserted into the reservoir dock 6050. As illustrated, when the water reservoir 6100 is inserted into the reservoir dock 6050, the resilient sealing and supporting member 9500 is so configured that, when depressed, it resiliently deflects (e.g., the peripheral lip 9510 curls along its length and the side wall of each hollow tube 9520 buckles radially outwardly), which resilient deflection provides the upward biasing force to bias the heater plate 6080 upwardly against the conductive portion 6150 of the water reservoir 6100. The biasing force biases the heater plate 6080 (via thermal pad 6088) to the conductive portion 6150 of the water reservoir 6100. This leads to an improved mechanical and thermal contact between the heater plate 6080 and the conductive portion 6150, thus enhancing the overall humidification performance. As mentioned earlier in the text, the mechanics of the vertically oriented flexible hollow tube 9520 buckling under pressure (applied by the inserted water reservoir) ensures a more linear resilient response, which may provide for a relatively smooth insertion of the water reservoir into the water reservoir dock. This is especially useful when a water reservoir with a vertical dimension at the upper end of the dimensional tolerance, is inserted in the dock. Even though an increased pressure is applied vertically on the resilient member in this case, because the heater plate 6080 is deflected further down by the slightly larger vertical dimension of the tub, the relatively linear response of the buckled tubes may ensure a relatively minor increase in the resistance to the insertion of the tub.

In an example, the normal displacement of the heater plate 6080 caused by the insertion of the water reservoir 6100 is about 1-2 mm (i.e. how much the heater plate 6080 is pushed down from its rest or stopped position in FIGS. 105-106 when the water reservoir 6100 is inserted). Displacement is at least greater than 0 mm to ensure interference of the heater plate 6080 with the conductive portion 6150 of the water reservoir 6100. In an example, the resilient sealing and supporting member 9500 may include a nominal pre-load when the water reservoir 6100 is removed from the reservoir dock 6050. In an example, the pre-load and/or the displacement may be adjusted by the edge height or thickness of the bottom wall 6053 of the dock 6050 which provides a stop or end of travel for the heater plate 6080.

In an example, as shown in FIG. 104, in one or more of the tubes, the top edge (adjacent the heater 6085) of each of the hollow tubes 9520 may include one or more edge cut-outs 9550 which form air-bleed apertures to allow the release of air (from the interior of each hollow tube) when each of the hollow tubes 9520 are depressed or deflected when the water reservoir 6100 is inserted into the reservoir dock 6050. In an alternative example, the wall of one or more of the hollow tubes 9520 may include one or more holes to provide air-bleed aperture(s) for the release of air when the tubes are under pressure. The function of the edge cut-out/s or opening/s in the tube wall is to ensure an equalisation of pressure to maintain a consistent spring force function. During a depression of the heater plate, for example during insertion of the water reservoir, the volume within the vertical tube/s will be compressed, forcing air to move outside the cylindrical shape. This creates a risk of a vacuum being formed inside any one hollow tube. Since each tube essentially acts as a spring, the formation of vacuum in a tube may change the reaction force applied by the tube to the heater, and therefore, to the heated base of the humidification reservoir. The formation of (potentially) different degrees of vacuum in one or more tubes (springs), can cause various response pressure to be applied to different points across the surface of the heater. This can potentially cause various degrees of thermal contact between the heater and the water reservoir base, across the area of the heater/base, which may result in a reduction in humidification performance. The inclusion of cut-outs or openings in the side wall of the cylinders can minimise the variation in the hollow tubes spring force, resulting in better humidification performance.

As shown in FIG. 109, the heater plate 6080 and the resilient sealing and supporting member 9500 are arranged so that any water spilled inside the cavity of the reservoir dock 6050 is sealed out of the peripheral lip 9510 and prevented from reaching the space on the inner side of the peripheral lip 9510, where the heater 6085 is located. Moreover, the spilled water may leak through the drain holes 9625 (see FIG. 104) along the perimeter of the base plate 9600 and be released onto an underlying supporting surface (e.g., bedside table).

That is, with reference to FIGS. 107 to 109, the peripheral lip 9510 resiliently engages underneath the horizontal portion 6885h of the skirt 6885 and forms a seal along the perimeter of the heater plate 6080. When water from the heater reservoir 6100 spills inside the cavity of the reservoir dock 6050, it will pass through the small gap 6890 between the heater plate 6080 and the bottom wall 6053 of the dock 6050 and into a reservoir 6891 formed between the peripheral lip 9510 and the peripheral flange 9620 of the base plate 9600 (see FIG. 109). Such trapped water in the reservoir 6891 can then flow through the drain holes 9625 along the perimeter of the peripheral flange 9620, and through the small gap 6892 between the base wall 8005 and the base plate 9600, to allow drainage onto the underlying supporting surface (see FIG. 109).

It should be noted that any references in the above description to horizontal, vertical, downward and upward directions are meant to apply with respect to an operational configuration of the integrated RPT device and humidifier 6000.

5.6.2.6 Humidifier Controller

According to one arrangement of the present technology, a humidifier 5000 may comprise a humidifier controller 5250 as shown in FIG. 5G. In one form, the humidifier controller 5250 may be a part of the central controller 4230. In another form, the humidifier controller 5250 may be a separate controller, which may be in communication with the central controller 4230.

In one form, the humidifier controller 5250 may receive as inputs measures of properties (such as temperature, humidity, pressure and/or flow rate), for example of the flow of air, the water in the reservoir 5110 and/or the humidifier 5000. The humidifier controller 5250 may also be configured to execute or implement humidifier algorithms and/or deliver one or more output signals.

As shown in FIG. 5G, the humidifier controller 5250 may comprise one or more controllers, such as a central humidifier controller 5251, a heated air circuit controller 5254 configured to control the temperature of a heated air circuit 4171 and/or a heating element controller 5252 configured to control the temperature of a heating element 5240.

5.7 Breathing Waveforms

FIG. 4 shows a model typical breath waveform of a person while sleeping. The horizontal axis is time, and the vertical axis is respiratory flow rate. While the parameter values may vary, a typical breath may have the following approximate values: tidal volume Vt 0.5 L, inhalation time Ti 1.6 s, peak inspiratory flow rate Qpeak 0.4 L/s, exhalation time Te 2.4 s, peak expiratory flow rate Qpeak −0.5 L/s. The total duration of the breath, Ttot, is about 4 s. The person typically breathes at a rate of about 15 breaths per minute (BPM), with Ventilation Vent about 7.5 L/min. A typical duty cycle, the ratio of Ti to Ttot, is about 40%.

5.8 Glossary

For the purposes of the present technology disclosure, in certain forms of the present technology, one or more of the following definitions may apply. In other forms of the present technology, alternative definitions may apply.

5.8.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including $cmH_2O$, $g\text{-}f/cm^2$ and hectopascal. 1 $cmH_2O$ is equal to 1 $g\text{-}f/cm^2$ and is approximately 0.98 hectopascal. In this specification, unless otherwise stated, pressure is given in units of $cmH_2O$.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.8.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

5.8.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 $cmH_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

5.8.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:

(i) Flattened: Having a rise followed by a relatively flat portion, followed by a fall.

(ii) M-shaped: Having two local peaks, one at the leading edge, and one at the trailing edge, and a relatively flat portion between the two peaks.

(iii) Chair-shaped: Having a single local peak, the peak being at the leading edge, followed by a relatively flat portion.

(iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:
(i) a 30% reduction in patient breathing for at least 10 seconds plus an associated 4% desaturation; or
(ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume Vt may be defined as equal to either quantity. In practice the tidal volume Vt is estimated as some combination, e.g. the mean, of the inspiratory volume Vi and the expiratory volume Ve.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.8.3 Ventilation

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired mask pressure which the ventilator will attempt to achieve at a given time.

End expiratory pressure (EEP): Desired mask pressure which the ventilator will attempt to achieve at the end of the expiratory portion of the breath. If the pressure waveform template $\Pi(\Phi)$ is zero-valued at the end of expiration, i.e. $\Pi(\Phi)=0$ when $\Phi=1$, the EEP is equal to the EPAP.

Inspiratory positive airway pressure (IPAP): Maximum desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

5.8.4 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.8.5 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector atp points away from the surface. In some examples we describe the surface from the point of view of an imaginary small person standing upright on the surface.

5.8.5.1 Curvature in One Dimension

The curvature of a plane curve atp may be described as having a sign (e.g. positive, negative) and a magnitude (e.g. 1/radius of a circle that just touches the curve atp).

Positive curvature: If the curve atp turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve atp is a straight line, the curvature will be taken to be zero (if the imaginary small person leaves the pointp, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

5.8.5.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures atp are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.8.5.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix. A typical human right ear comprises a helix, which is a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule, or alternatively by a left-hand rule.

Osculating plane: The plane containing the unit tangent vector and the unit principal normal vector.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path).

With reference to the right-hand rule, a space curve turning towards the direction of the right-hand binormal may be considered as having a right-hand positive torsion. A space curve turning away from the direction of the right-hand binormal may be considered as having a right-hand negative torsion (e.g. a left-hand helix).

Equivalently, and with reference to a left-hand rule, a space curve turning towards the direction of the left-hand binormal may be considered as having a left-hand positive torsion (e.g. a left-hand helix). Hence left-hand positive is equivalent to right-hand negative.

5.8.5.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3G, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. In a yet another example, a conduit may comprise a one-dimension hole (e.g. at its entrance or at its exit), and a two-dimension hole bounded by the inside surface of the conduit. See also the two dimensional hole through the structure shown in FIG. 3I, bounded by a surface as shown.

5.9 Other Remarks

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.10 Reference Signs List

| Feature Item | Number |
|---|---|
| patient | 1000 |
| bed partner | 1100 |
| patient interface | 3000 |
| seal-forming structure | 3100 |
| plenum chamber | 3200 |
| positioning and stabilizing structure | 3300 |
| vent | 3400 |
| connection port | 3600 |
| forehead support | 3700 |
| RPT device | 4000 |
| main panel | 4010 |
| front panel | 4012 |
| side panel | 4014 |
| chassis | 4016 |
| pneumatic block | 4020 |
| air filter | 4110 |
| inlet air filter | 4112 |
| outlet air filter | 4114 |
| mufflers | 4120 |
| inlet muffler | 4122 |
| outlet muffler | 4124 |
| pressure generator | 4140 |
| blower | 4142 |
| motor | 4144 |
| anti-spill back valve | 4160 |
| air circuit | 4170 |
| air circuit | 4171 |
| supplemental oxygen | 4180 |
| electrical components | 4200 |
| PCBA | 4202 |
| power supply | 4210 |
| input device | 4220 |
| central controller | 4230 |
| clock | 4232 |
| therapy device controller | 4240 |
| protection circuits | 4250 |
| memory | 4260 |
| transducer | 4270 |
| pressure sensor | 4272 |
| flow rate sensor | 4274 |
| motor speed transducer | 4276 |
| data communication interface | 4280 |
| remote external communication network | 4282 |
| local external communication network | 4284 |
| remote external device | 4286 |
| local external device | 4288 |
| output device | 4290 |
| display driver | 4292 |
| display | 4294 |
| algorithms | 4300 |
| pre-processing module | 4310 |
| pressure compensation algorithm | 4312 |
| vent flow rate estimation algorithm | 4314 |
| leak flow rate estimation algorithm | 4316 |
| respiratory flow rate estimation algorithm | 4318 |
| therapy engine module | 4320 |
| phase determination algorithm | 4321 |
| waveform determination algorithm | 4322 |
| ventilation determination algorithm | 4323 |
| inspiratory flow limitation determination algorithm | 4324 |
| apnea/hypopnea determination algorithm | 4325 |
| snore determination algorithm | 4326 |
| airway patency determination algorithm | 4327 |
| target ventilation determination algorithm | 4328 |
| therapy control module | 4330 |
| method | 4340 |
| tube portion | 4500 |
| dock connector | 4600 |
| pinch arms | 4610 |

-continued

| Feature Item | Number |
|---|---|
| retaining protrusion | 4615 |
| lip | 4620 |
| contact surface | 4625 |
| support protrusion | 4630 |
| base portion | 4640 |
| base | 4640bs |
| overmold | 4640ov |
| protrusion | 4642 |
| bumps | 4644 |
| lip seal | 4645 |
| stop surface | 4647 |
| internal rib | 4648 |
| contact assembly | 4650 |
| contacts | 4655 |
| locking and contact assembly | 4660 |
| contact assembly | 4661 |
| support arm | 4662 |
| support portion | 4665 |
| contact assembly | 4666 |
| contacts | 4667 |
| electrical connector | 4668 |
| base assembly | 4680 |
| base | 4682 |
| cover | 4684 |
| overmold | 4690 |
| patient interface connector | 4700 |
| humidifier | 5000 |
| humidifier reservoir | 5110 |
| humidifier transducer | 5210 |
| pressure transducer | 5212 |
| flow rate transducer | 5214 |
| temperature transducer | 5216 |
| humidity sensor | 5218 |
| heating element | 5240 |
| humidifier controller | 5250 |
| central humidifier controller | 5251 |
| heating element controller | 5252 |
| air circuit controller | 5254 |
| integrated RPT device and humidifier | 6000 |
| reservoir dock | 6050 |
| locking recess | 6051 |
| inner wall | 6052 |
| bottom wall | 6053 |
| slot | 6055 |
| guide slots | 6060 |
| heating assembly | 6075 |
| heater plate | 6080 |
| heating element | 6085 |
| gasket | 6086 |
| thermal pad | 6088 |
| support structure | 6089 |
| dock outlet | 6090 |
| opening | 6091 |
| retainer plate | 6095 |
| supporting member | 6096 |
| base plate | 6097 |
| support cone | 6098 |
| water reservoir | 6100 |
| reservoir base | 6112 |
| reservoir lid | 6114 |
| retention protrusion | 6115 |
| seal | 6116 |
| inlet tube | 6120 |
| inlet seal | 6122 |
| inlet portion | 6123 |
| inlet end | 6124 |
| outlet portion | 6125 |
| outlet end | 6126 |
| outlet tube | 6130 |
| outlet seal | 6132 |
| thumb grip | 6133 |
| outlet end | 6134 |
| inlet end | 6136 |
| main body | 6140 |
| side walls | 6142 |
| bottom wall | 6144 |
| conductive portion | 6150 |

-continued

| Feature Item | Number |
|---|---|
| guide rails | 6200 |
| guide pins | 6250 |
| recess | 6260 |
| rails | 6262 |
| locking tab | 6264 |
| latch | 6300 |
| latch | 6400 |
| locking lever | 6402 |
| protrusion | 6403 |
| lid connector | 6404 |
| slotted end | 6405 |
| support members | 6406 |
| finger tab | 6407 |
| locking arrangement | 6600 |
| button portion | 6605 |
| locking arms | 6610 |
| locking tabs | 6615 |
| intermediate component | 6700 |
| tubular portion | 6705 |
| inlet end | 6710 |
| flange | 6712 |
| contact surface | 6715 |
| outlet end | 6720 |
| port | 6730 |
| port seal | 6735 |
| spring arms | 6740 |
| barbed end | 6745 |
| protrusion | 6750 |
| guide slot | 6755 |
| guide rail | 6760 |
| flange | 6770 |
| cut-outs | 6772 |
| channel | 6780 |
| contact assembly | 6800 |
| contacts | 6805 |
| contacts | 6810 |
| support member | 6815 |
| support protrusions | 6850 |
| base | 6880 |
| base surface | 6882 |
| interior surface | 6884 |
| skirt | 6885 |
| vertical portion | 6885v |
| horizontal portion | 6885h |
| gap | 6890 |
| reservoir | 6891 |
| gap | 6892 |
| locking and contact assembly | 6900 |
| base | 6910 |
| rear wall | 6912 |
| opening | 6915 |
| side wall | 6920 |
| recess | 6922 |
| recess | 6924 |
| recess | 6926 |
| retaining wall | 6930 |
| stop wall | 6935 |
| recess | 6940 |
| contact assembly | 6950 |
| support member | 6952 |
| contacts | 6955 |
| spring arm | 6956 |
| electrical connector | 6958 |
| contact support structure | 6960 |
| cover | 6970 |
| drop down section | 6060D |
| horizontal section | 6060H |
| horizontal section | 6060H2 |
| thin film conductive portion | 6150F |
| metal conductive portion | 6150M |
| thin film plate | 6152F |
| metal plate | 6152M |
| thin film side wall | 6154F |
| metal side wall | 6154M |
| thin film interfacing portion | 6156F |
| metal interfacing portion | 6156M |
| reservoir base with thin film | 6112F1 |

| Feature Item | Number |
|---|---|
| reservoir base with thin film | 6112F2 |
| reservoir base with metal | 6112M1 |
| reservoir base with metal | 6112M2 |
| reservoir base with metal | 6112M3 |
| reservoir base with metal/thin film | 6112MF1 |
| reservoir base with metal/thin film | 6112MF2 |
| reservoir base with metal thin film | 6112MF3 |
| metal/thin film conductive portion | 6150MF |
| pneumatic block | 7100 |
| chassis assembly | 7300 |
| chassis inlet | 7310 |
| chassis outlet | 7320 |
| front ledge | 7350 |
| guide surface | 7355 |
| rear ledge | 7360 |
| chassis opening | 7380 |
| PCBA | 7600 |
| external housing | 8002 |
| base wall | 8005 |
| adaptor | 8020 |
| first circuit element | 8022 |
| second circuit element | 8024 |
| shroud | 8050 |
| resistor | 9010 |
| resistor | 9012 |
| resistor | 9020 |
| resistor | 9022 |
| sensor | 9030 |
| hinge arm | 9100 |
| hinge pin | 9105 |
| cylindrical surface | 9105c |
| flat surface | 9105f |
| stop member | 9110 |
| clip | 9120 |
| slot | 9122 |
| tab | 9125 |
| slot | 9200 |
| cylindrical surface | 9200c |
| open side | 9200o |
| side wall | 9210 |
| latch | 9220 |
| upwardly oriented surface | 9300 |
| tab | 9315 |
| tab | 9320 |
| upwardly oriented surface | 9325 |
| downwardly oriented surface | 9400 |
| abutment edge | 9450 |
| sealing and supporting member | 9500 |
| peripheral lip | 9510 |
| hollow tube | 9520 |
| intermediate connector | 9530 |
| wire guide | 9540 |
| air bleed indentation | 9550 |
| base plate | 9600 |
| interior base surface | 9610 |
| exterior base surface | 9612 |
| tracks | 9615 |
| peripheral flange | 9620 |
| stakes | 9622 |
| drain hole | 9625 |
| intermediate component | 9700 |
| tubular portion | 9705 |
| inlet end | 9710 |
| inlet seal | 9715 |
| outlet end | 9720 |
| port | 9730 |
| port seal | 9735 |
| pinch arm | 9740 |
| barbed end | 9745 |
| cross-bar | 9750 |
| bumper | 9751 |
| bumper | 9752 |
| bumper | 9753 |
| guide slot | 9755 |
| surface | 9758 |
| guide rail | 9760 |
| guide rib | 9761 |

| Feature Item | Number |
|---|---|
| flange | 9770 |
| bumper | 9775 |
| channel | 9780 |
| side wall | 9790 |
| hole | 9792 |
| tab | 9795 |
| fastener | 9799 |
| contact assembly | 9950 |
| support member | 9952 |
| contacts | 9955 |
| spring arm | 9956 |
| socket | 9980 |

The invention claimed is:

1. A medical treatment apparatus for providing a supply of pressurized breathable gas to a patient in a pressure range suitable for treatment of a respiratory disorder, the apparatus comprising:
a flow generator configured to pressurize the supply of pressurized breathable gas in the pressure range;
a water reservoir including a cavity structured to hold a volume of water to humidify the supply of pressurized breathable gas, the water reservoir including a water reservoir inlet and a water reservoir outlet, the water reservoir inlet including an integrated water reservoir inlet seal; and
a water reservoir dock structured and arranged to receive the water reservoir in an operative position, the water reservoir dock including a dock inlet arranged to, in use, supply pressurized gas to the inlet of the water reservoir, and a dock outlet to, in use, receive the supply of breathable gas with added humidity from the water reservoir, the dock outlet including a dock seal to sealingly engage with the water reservoir outlet only when the water reservoir is received in the water reservoir dock.

2. The medical treatment apparatus of claim 1, wherein the dock inlet includes an aperture surrounded by a flat surface configured to sealingly engage the water reservoir inlet seal when the water reservoir is received in the water reservoir dock.

3. The medical treatment apparatus of claim 1, wherein the water reservoir outlet includes an aperture surrounded by a flat surface that sealingly engages the dock seal when the water reservoir is received in the water reservoir dock.

4. The medical treatment apparatus of claim 1, wherein each of the dock seal and the water reservoir inlet seal includes a bellows that forms a face seal against a respective flat surface.

5. The medical treatment apparatus of claim 1, wherein the water reservoir includes a lid, a base and a water reservoir seal that seals between the lid and the base.

6. The medical treatment apparatus of claim 1, further comprising an air delivery tube configured to pass the flow of breathable gas that has been humidified in the water reservoir to a patient interface, wherein the dock seal is permanently affixed to an intermediate component of a tubular form, the intermediate component further comprising an external tube connector to which the air delivery tube is removably connectable.

7. The medical treatment apparatus of claim 5, wherein the water reservoir inlet seal is integrally overmoulded on the lid.

8. The medical treatment apparatus of claim 1, wherein the water reservoir comprises a first material that is relatively rigid compared to a second material forming the water reservoir inlet seal.

9. The medical treatment apparatus of claim 1, wherein the dock seal is removably attached to a rear wall forming a recess of the water reservoir dock.

10. The medical treatment apparatus of claim 1, wherein the dock seal is affixed to an intermediate component of a tubular shape, the intermediate component further comprising an external tube connector to which an air delivery tube is removably connectable.

11. The medical treatment apparatus of claim 10, wherein the intermediate component is removably attached to the water reservoir dock.

12. The medical treatment apparatus of claim 1, further comprising a chassis supporting a blower of the flow generator, the chassis at least partly forming the water reservoir dock such that the flow generator and the water reservoir dock are integrated, the water reservoir dock including a recess in which the water reservoir is at least partly received, the water reservoir being engaged with the water reservoir dock by horizontally sliding the water reservoir at least partly into the recess of the water reservoir dock.

13. A medical treatment apparatus for providing a supply of pressurized breathable gas to a patient in a pressure range suitable for treatment of a respiratory disorder, the apparatus comprising:
a flow generator configured to pressurize the supply of pressurized breathable gas in the pressure range;
a water reservoir including a cavity structured to hold a volume of water to provide water vapor to humidify the supply of pressurized breathable gas, the water reservoir including a water reservoir inlet and a water reservoir outlet;
a water reservoir dock structured and arranged to at least partially receive the water reservoir in an operative position, the water reservoir dock including a dock inlet arranged to, in use, supply the pressurized breathable gas to the inlet of the water reservoir, and a dock outlet configured to, in use, receive the supply of breathable gas with added humidity from the water reservoir outlet,
a first seal between the dock inlet and the water reservoir inlet; and
a second seal between the water reservoir outlet and the dock outlet;
wherein at least one of the first seal and the second seal is supported solely by the water reservoir inlet or outlet, and
wherein the water reservoir inlet includes the first seal, and wherein the water reservoir outlet does not have the second seal affixed thereto.

14. The medical treatment apparatus of claim 13, wherein the dock inlet includes an aperture surrounded by a flat surface configured to sealingly engage the first seal when the water reservoir is received in the water reservoir dock, and wherein the water reservoir outlet includes an aperture surrounded by a flat surface that sealingly engages the second seal when the water reservoir is received in the water reservoir dock.

15. The medical treatment apparatus of claim 14, wherein each of the first seal and the second seal includes a bellows that forms a face seal against the respective flat surfaces.

16. The medical treatment apparatus of claim 13, wherein the water reservoir includes a lid, a base and a water reservoir seal that seals between the lid and the base.

17. The medical treatment apparatus of claim 16, wherein the lid includes the water reservoir inlet and the first seal.

18. The medical treatment apparatus of claim 13, wherein the water reservoir comprises a first material that is relatively rigid compared to a second material forming the first seal that is overmolded to the first material.

19. The medical treatment apparatus of claim 13, further comprising an air delivery tube configured to pass the flow of breathable gas that has been humidified in the water reservoir to a patient interface, wherein the second seal is permanently affixed to an intermediate component in a tubular form, the intermediate component further comprising an external tube connector to which the air delivery tube is removably connectable.

20. The medical treatment apparatus of claim 19, wherein the intermediate component is removably attached to the water reservoir dock.

21. The medical treatment apparatus of claim 13, further comprising a chassis supporting a blower of the flow generator, the chassis at least partly forming the water reservoir dock such that the flow generator and the water reservoir dock are integrated, the water reservoir dock including a recess in which the water reservoir is partly received, the water reservoir being engaged with the water reservoir dock by horizontally sliding the water reservoir into the recess of the water reservoir dock.

22. A medical treatment apparatus for providing a supply of pressurized breathable gas to a patient in a pressure range suitable for treatment of a respiratory disorder, the apparatus comprising:
a flow generator configured to pressurize the supply of pressurized breathable gas in the pressure range;
a water reservoir including a cavity structured to hold a volume of water to provide water vapor to humidify the supply of pressurized breathable gas, the water reservoir including a water reservoir inlet and a water reservoir outlet;
a water reservoir dock structured and arranged to at least partially receive the water reservoir in an operative position, the water reservoir dock including a dock inlet arranged to, in use, supply the pressurized breathable gas to the inlet of the water reservoir, and a dock outlet configured to, in use, receive the supply of breathable gas with added humidity from the water reservoir outlet,
a first seal between the dock inlet and the water reservoir inlet; and
a second seal between the water reservoir outlet and the dock outlet;
wherein at least one of the first seal and the second seal is supported solely by the water reservoir inlet or outlet, and
wherein the second seal is removably attached to a rear wall forming a recess of the water reservoir dock.

23. A medical treatment apparatus for providing a supply of pressurized breathable gas to a patient in a pressure range suitable for treatment of a respiratory disorder, the apparatus comprising:
a flow generator configured to pressurize the supply of pressurized breathable gas in the pressure range;
a water reservoir including a cavity structured to hold a volume of water to provide water vapor to humidify the supply of pressurized breathable gas, the water reservoir including a water reservoir inlet and a water reservoir outlet;
a water reservoir dock structured and arranged to receive the water reservoir in an operative position, the water reservoir dock including a dock inlet configured to, in use, supply the breathable gas to the water reservoir inlet of the water reservoir, and a dock outlet configured to, in use, receive the supply of breathable gas with added humidity from the water reservoir outlet, a first seal between the dock inlet and the water reservoir inlet; and a second seal between the water reservoir outlet and the dock outlet;

wherein one of the water reservoir inlet and the water reservoir outlet includes the first seal or the second seal affixed thereto, respectively, and the other of the water reservoir inlet and the water reservoir outlet does not include the first or second seal affixed thereto, respectively.

24. The medical treatment apparatus of claim 23, wherein the water reservoir inlet includes the first seal affixed thereto, and only the dock outlet supports the second seal, and wherein the water reservoir comprises a first material that is relatively rigid compared to a second material forming the first seal that is overmolded to the first material, wherein the dock inlet includes an aperture surrounded by a flat surface configured to sealingly engage the first seal when the water reservoir is received in the water reservoir dock, and wherein the water reservoir outlet includes an aperture surrounded by a flat surface that sealingly engages the second seal when the water reservoir is received in the water reservoir dock, and wherein the water reservoir includes a lid, a base and a water reservoir seal that seals between the lid and the base.

\* \* \* \* \*